United States Patent
Schmidhalter et al.

(10) Patent No.: US 8,471,248 B2
(45) Date of Patent: Jun. 25, 2013

(54) ELECTROLUMINISCENT METAL COMPLEXES WITH DIBENZO[F,H] QUINOXALINES

(75) Inventors: Beat Schmidhalter, Bubendorf (CH); Thomas Schäfer, Liestal (CH); Peter Murer, Oberwil (CH); Kristina Bardon, Waldshut (DE); Stephan Allenbach, Sisseln (CH); Andrea Ricci, Basel (CH)

(73) Assignee: BASF SE, Ludwigshafen (DE)

( * ) Notice: Subject to any disclaimer, the term of this patent is extended or adjusted under 35 U.S.C. 154(b) by 356 days.

(21) Appl. No.: 12/864,877

(22) PCT Filed: Feb. 2, 2009

(86) PCT No.: PCT/EP2009/051109
§ 371 (c)(1),
(2), (4) Date: Dec. 1, 2010

(87) PCT Pub. No.: WO2009/100991
PCT Pub. Date: Aug. 20, 2009

(65) Prior Publication Data
US 2011/0089407 A1   Apr. 21, 2011

(30) Foreign Application Priority Data
Feb. 12, 2008 (EP) ..................... 08151313

(51) Int. Cl.
*H01L 35/24* (2006.01)
(52) U.S. Cl.
USPC .................... 257/40; 257/E51.001
(58) Field of Classification Search
USPC .......................... 257/40, E51.001
See application file for complete search history.

(56) References Cited

U.S. PATENT DOCUMENTS

| 2006/0144262 A1 | 7/2006 | Koong |
| 2007/0216288 A1 | 9/2007 | Lin |
| 2008/0122350 A1 | 5/2008 | Sakata |
| 2008/0149923 A1 | 6/2008 | Ohsawa |
| 2009/0062560 A1 | 3/2009 | Pretot |
| 2009/0140643 A1 | 6/2009 | Ohsawa |
| 2010/0108994 A1 | 5/2010 | Schaefer |

FOREIGN PATENT DOCUMENTS

| CN | 1810817 A | 8/2006 |
| CN | 1837325 A | 9/2006 |
| EP | 1939208 A1 | 7/2008 |
| JP | 2005298483 A | 10/2005 |
| KR | 20060079625 A | 7/2006 |
| TW | 588572 B | 5/2004 |
| WO | 2005/049762 A | 6/2005 |

OTHER PUBLICATIONS

English Language Abstract of CN1810817 Printed on Oct. 25, 2010.
English Language Abstract of CN1837325 Printed on Oct. 25, 2010.
English Language Abstract of TW588572 Printed on Oct. 25, 2010.
English Language Abstract of JP2005298482 Printed on Oct. 25, 2010.
Liu et al., Advanced Functional Materials, vol. 16, No. 11, 2006.
Chang et al., Chemical Phsics Letters, vol. 418, No. 1-3, 2006.
Duan et al., Advanced Materials vol. 15, No. 3, 2003.
English Language Abstract of KR20060036670 Dated Oct. 25, 2010.

*Primary Examiner* — Anthony Ho
(74) *Attorney, Agent, or Firm* — Tyler A. Stevenson

(57) ABSTRACT

This invention relates to electroluminescent metal complexes of the formula (I), or (II), a process for their preparation, electronic devices comprising the metal complexes and their use in electronic devices, especially organic light emitting diodes (OLEDs), as oxygen sensitive indicators, as phosphorescent indicators in bioassays, and as catalysts.

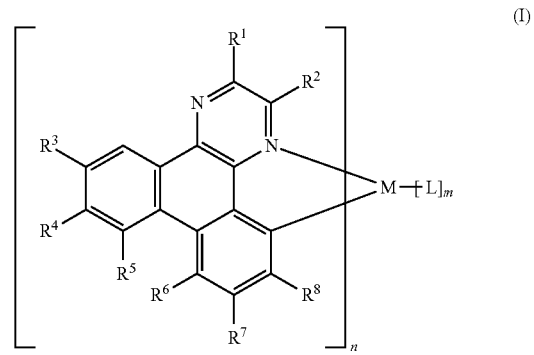

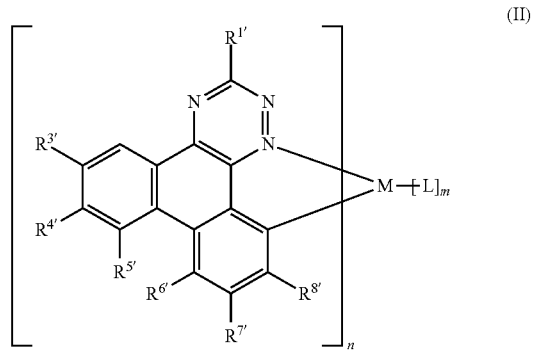

14 Claims, No Drawings

ELECTROLUMINISCENT METAL COMPLEXES WITH DIBENZO[F,H] QUINOXALINES

This invention relates to electroluminescent metal complexes with dibenzo[f,h]quinoxalines, a process for their preparation, electronic devices comprising the metal complexes and their use in electronic devices, especially organic light emitting diodes (OLEDs), as oxygen sensitive indicators, as phosphorescent indicators in bioassays, and as catalysts.

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, in U.S. Pat. Nos. 5,247,190, 5,408,109 and EP-A-443 861. Complexes of 8-hydroxyquinolate with trivalent metal ions, particularly aluminum, have been extensively used as electroluminescent components, as has been disclosed in, for example, U.S. Pat. No. 5,552,678.

Burrows and Thompson have reported that fac-tris(2-phenylpyridine) iridium can be used as the active component in organic light-emitting devices. (Appl. Phys. Lett. 1999, 75, 4.) The performance is maximized when the iridium compound is present in a host conductive material. Thompson has further reported devices in which the active layer is poly(N-vinyl carbazole) doped with fac-tris[2-(4',5'-difluorophenyl)pyridine-$C^{'2}$,N]iridium(III). (Polymer Preprints 2000, 41(1), 770.)

JP2005298483 describes an iridium complex, such as, for example,

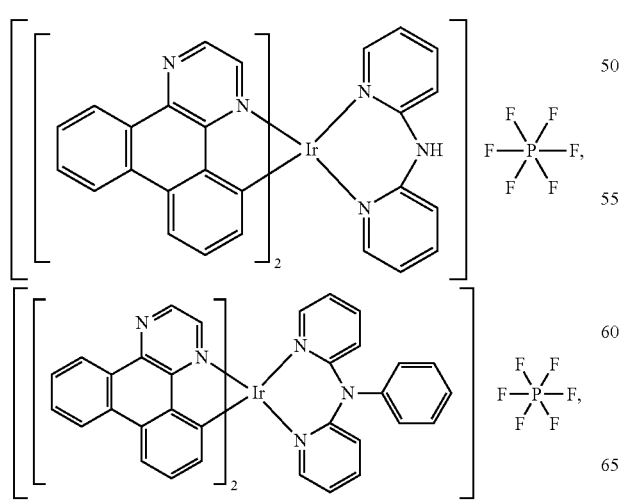

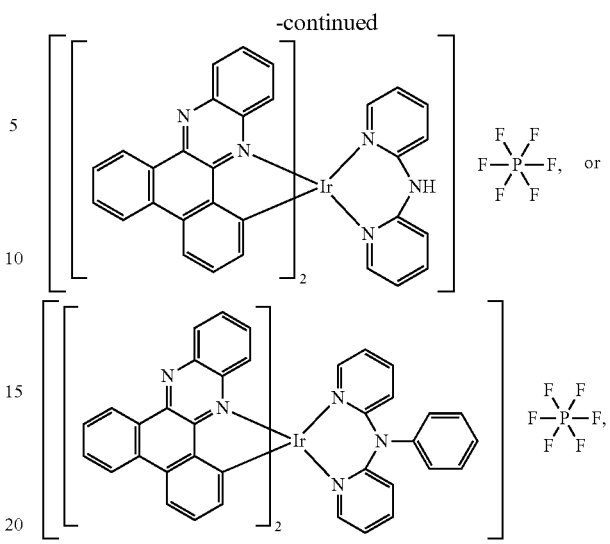

which can be used for the luminous element and is also suitable for an organic electroluminescent element material, an electrochemiluminescent (ECL) element material, a luminescence sensor, a photosensitizer, a display, etc., its preparation method and a luminous material.

KR20060079625 relates to phosphorescent red-emitting iridium complexes, such as, for example,

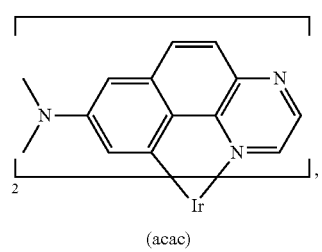

and organic electroluminescent device comprising same. Z. Liu et al, Adv. Funct. Mat. 2006, 16, 1441, describe the use of the complexes

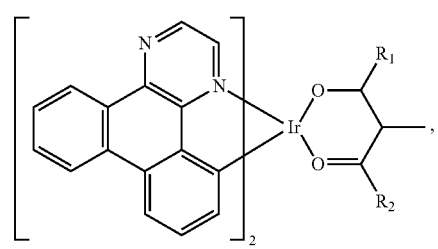

wherein $R^1$ is t-butyl and $R^2$ is

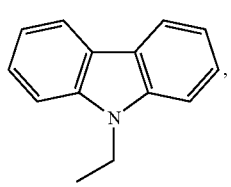

or $R^1$ is t-butyl and $R^2$ is

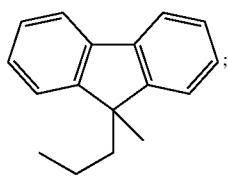 [SMILES: CCCC1(C)c2ccccc2-c2ccccc21]

for highly efficient non-doped organic light emitting diodes.

J.-P. Duan et al., Adv. Mat. 2003, 15, 224, describe the use of the complexes

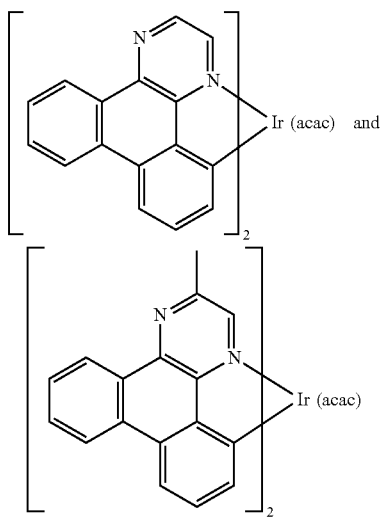

as orange-red emitters in an OLED.

KR20060036670 relates to phosphorescent iridium complexes and organic electroluminescent devices comprising the same. The following phosphorescent iridium complexes are explicitly disclosed

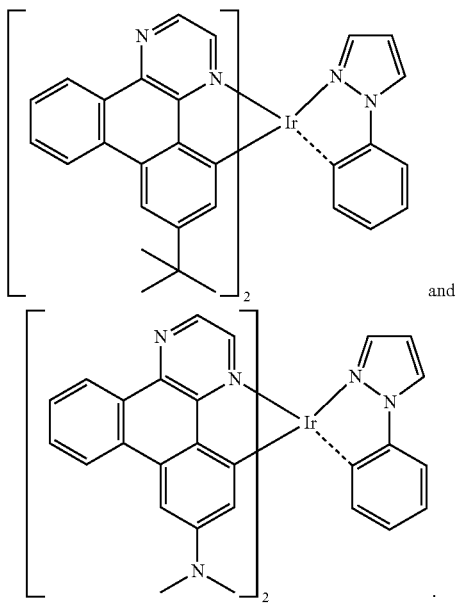

EP1939208A1, which enjoys an earlier priority than the present invention, but has been published after the priority date of the present invention, is directed to an organometallic complex having a structure represented by the general formula

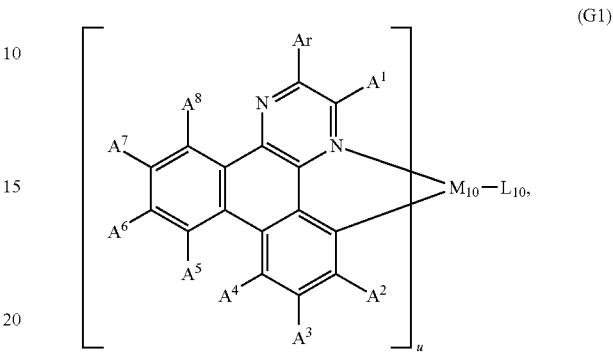

(G1)

wherein Ar represents an aryl group having 6 to 25 carbon atoms;

$A^1$ represents any one of hydrogen, an alkyl group having 1 to 4 carbon atoms, and an alkoxy group having 1 to 4 carbon atoms;

$A^2$ to $A^8$ each represent any one of hydrogen, an alkyl group having 1 to 4 carbon atoms, an alkoxy group having 1 to 4 carbon atoms, and a halogen group;

$M_{10}$ represents a metal of Group 9 elements and Group 10 elements;

$L_{10}$ represents a monoanionic ligand; and u is 2 when the metal is a Group 9 element, and u is 1 when the metal is a Group 10 element.

WO2005049762 relates to a light-emitting device comprising at least a substrate, an anode, a light-emitting layer and a cathode whereby the light-emitting layer contains an iridium complex IrL3 and whereby at least two ligands L are a dibenzoquinoline. WO2005049762 relates in particular to the complexes Ir(dibenzo[f,h]quinoline)$_2$(pentane-2,4-dionate) and Ir(dibenzo[f,h]quinoline)$_3$ which emit light with a wavelength of $\lambda_{max}$=545 nm and $\lambda_{max}$=595 nm respectively:

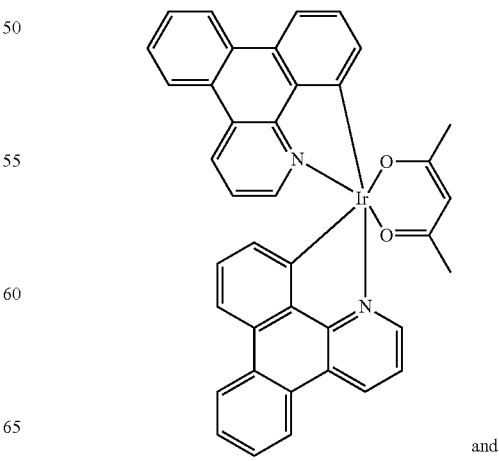

and

-continued

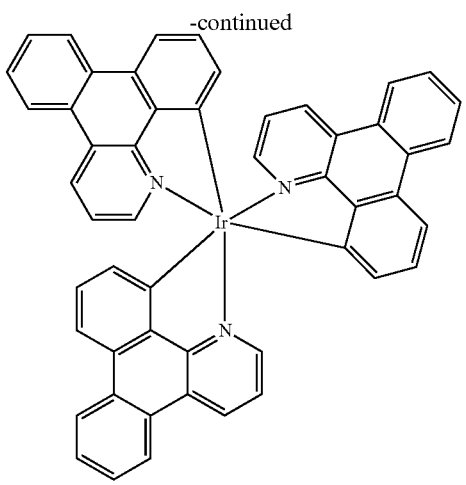

However, there is a continuing need for electroluminescent compounds, especially orange, or red emitters, having improved performance, such as for example, compounds having high emission efficiency, excellent vaporizability, thermal stability, processing stability, high charge carrier mobilities, low turn-on voltage and high temperature stability of the emission color.

Accordingly the present invention is directed to compounds (metal complexes) of the formula

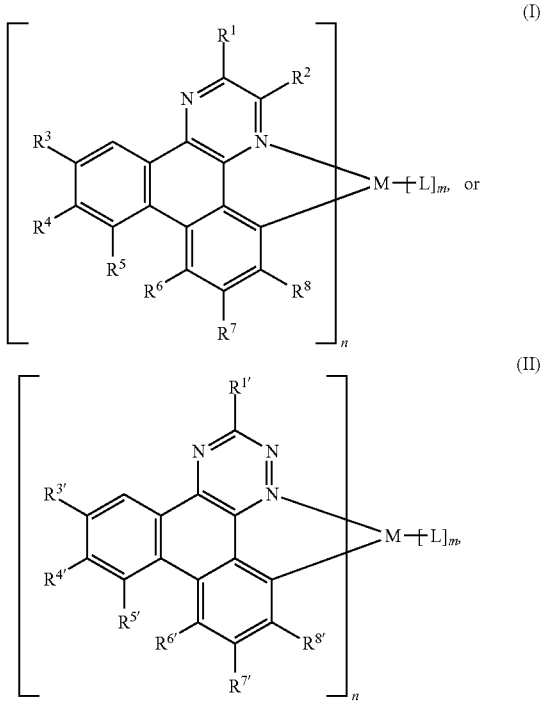

wherein
$R^1$, $R^2$ and $R^{1'}$ are independently of each other H, $C_1$-$C_{18}$alkyl, $C_1$-$C_{18}$alkyl which is substituted by E and/or interrupted by D, $C_1$-$C_{18}$perfluoroalkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$arylalkyl, CN,

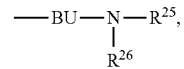

—CO—$R^{28}$, or
$R^1$ and $R^2$ together form a ring,
$R^3$, $R^8$, $R^{3'}$ and $R^{8'}$ are independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$arylalkyl, CN, or —CO—$R^{28}$,

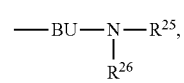

—$NR^{25}R^{26}$, —$SR^{29}$, or $Si(R^{30})_3$,
$R^4$, $R^7$, $R^{4'}$ and $R^{7'}$ are independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$arylalkyl, CN, or —CO—$R^{28}$,

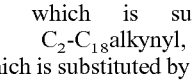

—$NR^{25}R^{26}$, —$SR^{29}$, or $Si(R^{30})_3$,
$R^5$, $R^6$, $R^{5'}$ and $R^{6'}$ are independently of each other H, $C_1$-$C_{18}$alkyl, $C_1$-$C_{18}$alkyl which is substituted by E and/or interrupted by D, $C_1$-$C_{18}$ perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$arylalkyl, CN, or —CO—$R^{28}$,

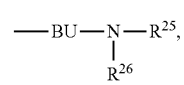

—$NR^{25}R^{26}$, —$SR^{29}$, $Si(R^{30})_3$,
$R^{25}$ and $R^{26}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or
$R^{25}$ and $R^{26}$ together with the nitrogen atom to which they are bonded form a heteroaromatic ring, or ring system, which may optionally be substituted;
BU is a bridging unit,
D is —CO—; —COO—; —S—; —SO—; —$SO_2$—; —O—; —$NR^{25'}$—; —$SiR^{30}R^{31}$—; —$POR^{32}$—; —$CR^{23}$=$CR^{24}$—; or —C≡C—;

E is —OR$^{28}$; —SR$^{28}$; —NR$^{25'}$R$^{26'}$; —COR$^{28}$; —COOR$^{27}$; —CONR$^{25'}$R$^{26'}$; —CN; or halogen; G is E, C$_1$-C$_{18}$alkyl, C$_1$-C$_{18}$alkyl which is interrupted by D, C$_1$-C$_{18}$ perfluoroalkyl, C$_1$-C$_{18}$alkoxy, or C$_1$-C$_{18}$alkoxy which is substituted by E and/or interrupted by D, or C$_2$-C$_{18}$alkenyl, R$^{23}$, R$^{24}$, R$^{25'}$ and R$^{26'}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—;

R$^{27}$ and R$^{28}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{29}$ is H; C$_6$-C$_{18}$aryl; C$_6$-C$_{18}$aryl, which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R$^{30}$ and R$^{31}$ are independently of each other C$_1$-C$_{18}$alkyl, C$_6$-C$_{18}$aryl, or C$_6$-C$_{18}$aryl, which is substituted by C$_1$-C$_{18}$alkyl, and R$^{32}$ is C$_1$-C$_{18}$alkyl, C$_6$-C$_{18}$aryl, or C$_6$-C$_{18}$aryl, which is substituted by C$_1$-C$_{18}$alkyl, M is Pd, Rh, or Re, especially Pt, or Ir,
L is a mono-, or bi-dentate ligand,
if L is a monodentate ligand,
m is 0, or 2, and n is 1, or 2, if M is Pd, or Pt,
m is 0, 2, or 4, and n is 1, 2, or 3, if M is Rh, Ir or Re,
if L is a bidentate ligand,
m is 0, or 1, and n is 1, or 2, if M is Pd, or Pt,
m is 0, 1, or 2, and n is 1, 2, or 3, if M is Rh, Ir or Re,
with the proviso that at least one of R$^1$, R$^2$, R$^3$, R$^8$, R$^4$, R$^7$, R$^5$ and R$^6$ is different from H and the further proviso that

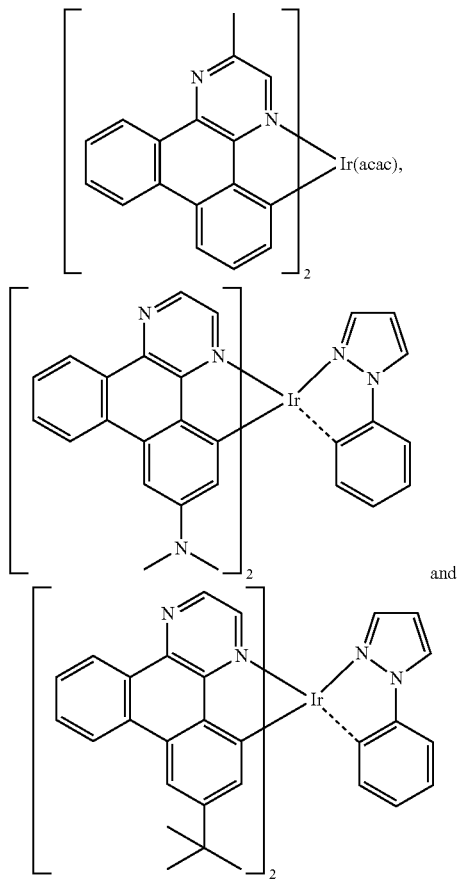

are excluded; and with the further proviso that organometallic complexes having a structure represented by the general formula

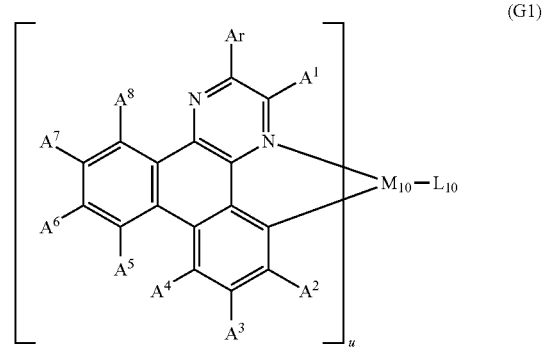

(G1)

are excluded,
wherein Ar represents an aryl group having 6 to 25 carbon atoms;
A$^1$ represents any one of hydrogen, an alkyl group having 1 to 4 carbon atoms, and an alkoxy group having 1 to 4 carbon atoms;
A$^2$ to A$^8$ each represent any one of hydrogen, an alkyl group having 1 to 4 carbon atoms, an alkoxy group having 1 to 4 carbon atoms, and a halogen group;
M$_{10}$ represents a metal of Group 9 elements and Group 10 elements;
L$_{10}$ represents a monoanionic ligand; and
u is 2 when the metal is a Group 9 element, and u is 1 when the metal is a Group 10 element.

The compounds of the present invention are preferably orange, or red emitters having a λ$_{max}$ above about 520 nm, especially above about 560 nm and very especially above about 600 nm. The dibenzo[f,h]quinoxaline compound or compounds should have a colour coordinate of between about (0.62, 0.37) and about (0.68, 0.32), especially a colour coordinate of between about (0.63, 0.34) and about (0.68, 0.32), very especially a NTSC coordinate of about (0.65, 0.35) or (0.68, 0.32).

According to the present invention the metal complex comprise at least a dibenzo[f,h]-quinoxaline ligand, i.e. it may comprise two or three or more dibenzo[f,h]quinoxaline ligands.

The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, Ma$_3$b$_3$, having octahedral geometry, in which the three "a" groups are all adjacent, i.e. at the corners of one triangular face of the octahedron. The term "meridional" is intended to mean one isomer of a complex, Ma$_3$b$_3$, having octahedral geometry, in which the three "a" groups occupy three positions such that two are trans to each other, i.e. the three "a" groups sit in three coplanar positions, forming an arc across the coordination sphere that can be thought of as a meridion. The phrase "adjacent to" when used to refer to layers in a device, does not necessarily mean that one layer is immediately next to another layer. The term "photoactive" refers to any material that exhibits electroluminescence and/or photosensitivity.

The metal complexes of the present invention are characterized in that at least one ligand is derived from a dibenzo[f,h]quinoxaline compound. Suitable dibenzo[f,h]quinoxalines, or intermediates thereof, are known or can be produced according to known procedures. The synthesis of suitable dibenzo[f,h]quinoxaline and intermediates thereof is, for example, described in J.-P. Duan et al., Adv. Mat. 2003, 15, 224 and WO2006/097419, as well as the references cited therein.

The metal M is selected from Ir, Rh and Re as well as Pt and Pd, wherein Pt and Ir are most preferred.

Preferably, at least one of $R^3$, $R^8$, $R^4$, $R^7$, $R^5$ and $R^6$ is different from H, in particular $R^3$ and $R^8$ or $R^4$ and $R^7$ or $R^5$ and $R^6$ are different from H. More preferably $R^3$ and $R^8$ or $R^4$ and $R^7$ are different from H, most preferably $R^4$ and $R^7$ are different from H.

Preferably at least one of the substituents $R^3$ and $R^8$ or $R^4$ and $R^7$ or $R^5$ and $R^6$ is different from H. More preferably at least one of the substituents $R^3$ and $R^8$ or $R^4$ and $R^7$ is different from H, most preferably at least one of the substituents $R^4$ and $R^7$ is different from H.

In one embodiment of the present invention at least one of the substituents $R^3$, $R^8$, $R^4$ and $R^7$ is $C_1$-$C_{18}$alkyl, $C_1$-$C_{18}$alkyl which is substituted by E and/or interrupted by D.

In one embodiment of the present invention at least one of the substituents $R^3$, $R^8$, $R^4$ and $R^7$ is a group

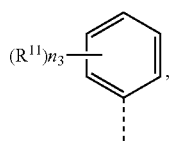

wherein $n_3$ is 0, or an integer 1, 2, 3, 4, or 5, $R^{11}$ can be same, or different in each occurrence and is $C_1$-$C_{25}$alkyl, $C_1$-$C_{25}$alkoxy, or $NR^{25}R^{26}$. Preferably $R^3$ and $R^8$ or $R^4$ and $R^7$ are a group

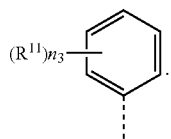

More preferably $R^4$ and $R^7$ are a group

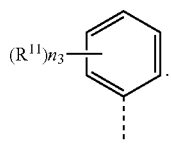

In one embodiment of the present invention at least one of the substituents $R^3$, $R^8$, $R^4$ and $R^7$ is a group —$NR^{25}R^{26}$, wherein $R^{25}$ and $R^{26}$ are independently of each other especially phenyl, naphthyl, anthryl, biphenylyl, 2-fluorenyl, phenanthryl, or perylenyl, which can optionally be substituted, such as

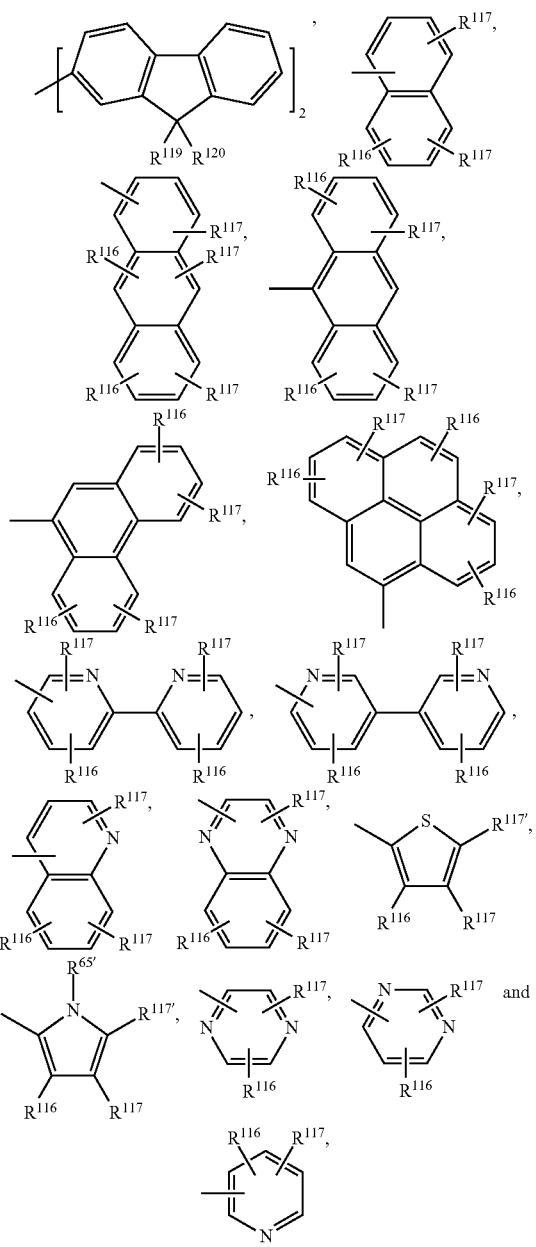

or $R^{25}$ and $R^{26}$ together with the nitrogen atom to which they are bonded form a heteroaromatic ring, or ring system, such as

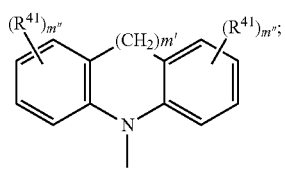

m' is 0, 1, or 2;
m" can be the same or different at each occurence and is 0, 1, 2, or 3, especially 0, 1, or 2, very especially 0 or 1;
$R^{41}$ can be the same or different at each occurence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —$NR^{45}$—, —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is H, a $C_1$-$C_{25}$alkyl group, a $C_4$-$C_{18}$cycloalkyl group, in which one or more carbon atoms which are not in neighbourhood to each other could be replaced by —$NR^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ is H, a $C_1$-$C_{25}$alkyl group, or a $C_4$-$C_{18}$cycloalkyl group, $R^{116}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or substituents $R^{116}$, $R^{117}$ and $R^{117'}$, which are adjacent to each other, can form a ring, $R^{119}$ and $R^{129}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =$CR^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{126}$ and $R^{127}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—, —COO—, —S—, —SO—, —$SO_2$—, —O—, —$NR^{65}$—, —Si$R^{70}R^{71}$—, —PO$R^{72}$—, —$CR^{63}$=$CR^{64}$—, or —C≡C—, and E is —O$R^{69}$, —S$R^{69}$, —$NR^{65}R^{66}$, —CO$R^{68}$, —COO$R^{67}$, —CON$R^{65}R^{66}$, —CN, or halogen, G is E, or $C_1$-$C_{18}$alkyl, $R^{63}$, $R^{64}$, $R^{65}$ and $R^{66}$ are independently of each other H; $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—; or $R^{65}$ and $R^{66}$ together form a five or six membered ring, $R^{67}$ and $R^{68}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{69}$ is H; $C_6$-$C_{18}$aryl; $C_6$-$C_{18}$aryl, which is substituted by $C_1$-$C_{18}$alkyl, $C_1$-$C_{18}$alkoxy; $C_1$-$C_{18}$alkyl; or $C_1$-$C_{18}$alkyl which is interrupted by —O—, $R^{70}$ and $R^{71}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{72}$ is $C_1$-$C_{18}$alkyl, $C_6$-$C_{18}$aryl, or $C_6$-$C_{18}$aryl, which is substituted by $C_1$-$C_{18}$alkyl.

BU is a bridging unit, such as

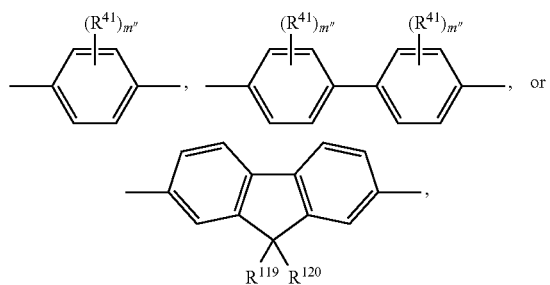

wherein $R^{119}$, $R^{120}$, $R^{41}$ and m″ are as defined above.

In a preferred embodiment of the present invention $R^{25}$ and $R^{26}$ are independently of each other

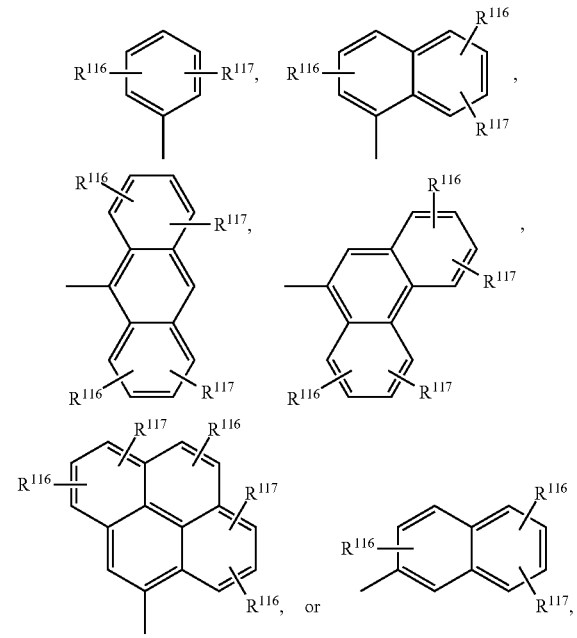

$R^{116}$ and $R^{117}$ are independently of each other $C_1$-$C_{25}$alkyl, which may optionally be interrupted by —O—, or $C_1$-$C_{25}$alkoxy.

Examples of

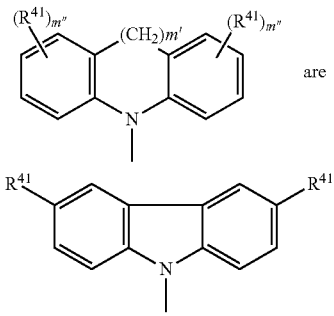

($R^{41}$ is H, or $C_1$-$C_8$alkyl), and

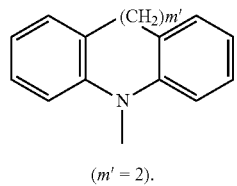

($m' = 2$).

Examples of groups

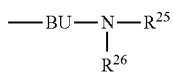

are shown below:

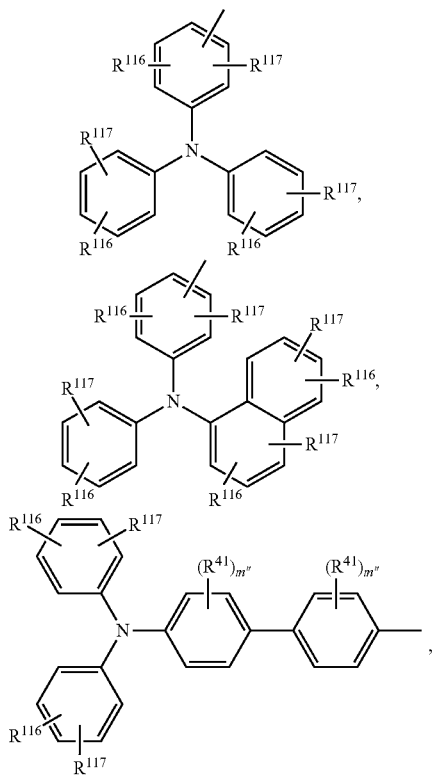

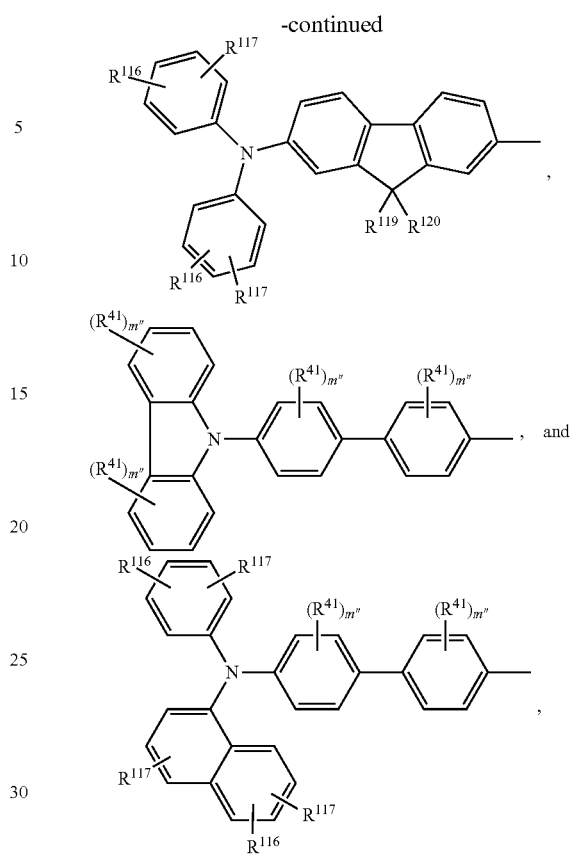

wherein $R^{41}$, $R^{116}$, $R^{117}$, $R^{119}$, $R^{120}$ and m" are as defined above.

Compounds of the formula I, or II are preferred, wherein $R^1$, $R^{1'}$ and $R^2$ are independently of each other H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G,

or CN, or
$R^1$ and $R^2$ together form a group

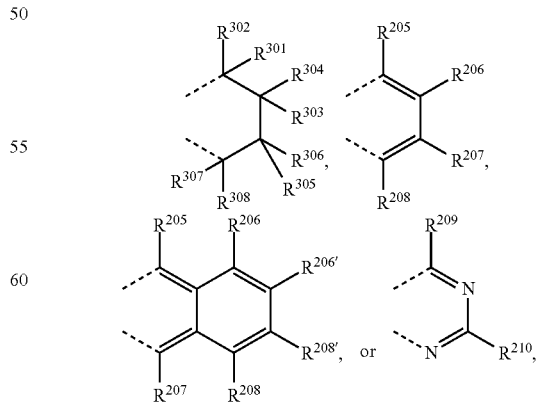

$R^{206'}$, $R^{208'}$, $R^{205}$, $R^{206}$, $R^{207}$, $R^{208}$, $R^{209}$ and $R^{210}$ and $R^{210}$ are independently of each other H, $C_1$-$C_{18}$alkyl, $C_1$-$C_{18}$alkoxy, or $C_6$-$C_{24}$aryl, $C_6$-$C_{24}$aryl which is substituted by $C_1$-$C_{18}$alkyl or $C_1$-$C_{18}$alkoxy;

$R^{301}$, $R^{302}$, $R^{303}$, $R^{304}$, $R^{305}$, $R^{306}$, $R^{307}$ and $R^{308}$ are independently of each other H, or $C_1$-$C_{18}$alkyl, $R^3$, $R^8$, $R^{3'}$ and $R^{8'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy, $C_1$-$C_{18}$alkoxy which is substituted by E and/or interrupted by —O—, $C_7$-$C_{25}$arylalkyl, CN, or —NR$^{25}$R$^{26}$;

$R^4$, $R^7$, $R^{4'}$ and $R^{7'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy which is substituted by E and/or interrupted by —O—, $C_7$-$C_{25}$arylalkyl, CN, —NR$^{25}$R$^{26}$;

$R^5$, $R^6$, $R^{5'}$ and $R^{6'}$ are H, $R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together with the nitrogen atom to which they are bonded form a heteroaromatic ring system

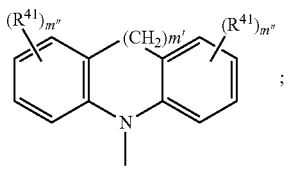
;

m", m' and $R^{41}$ are as defined below;

E is —OR$^{26}$; —SR$^{29}$; —NR$^{25'}$R$^{26'}$, CN, or F; G is E, CF$_3$, $C_1$-$C_{18}$alkyl, or $C_2$-$C_{18}$alkenyl, M is Pd, Rh, or Re, especially Pt, or Ir, L is a bidentate ligand, m is 0, or 1, and n is 1, or 2, if M is Pd, or Pt, m is 0, 1, or 2, and n is 1, 2, or 3, if M is Rh, Ir or Re, and $R^{29}$; $R^{29'}$; $R^{25'}$ and $R^{26'}$ are as defined in claim 1, with the proviso that at least one of $R^3$, $R^8$, $R^4$ and $R^7$ is different from H. More preferably $R^3$ and $R^8$, or $R^4$ and $R^7$ are different from H, most preferably $R^4$ and $R^7$ are different from H.

In a preferred embodiment the present invention is directed to compounds having a structure (Va), (Vb), (Vc), (VIa), (VIb), or (VIc) below:

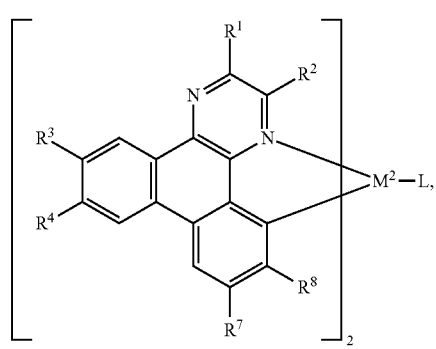
(Va)

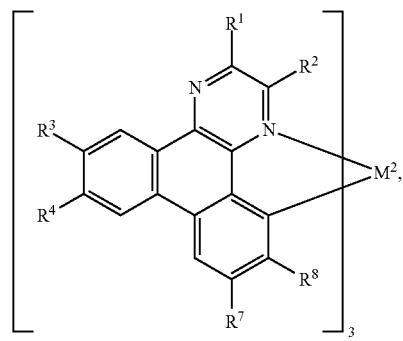
(Vb)

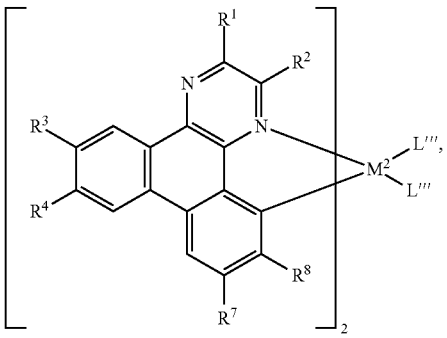
(Vc)

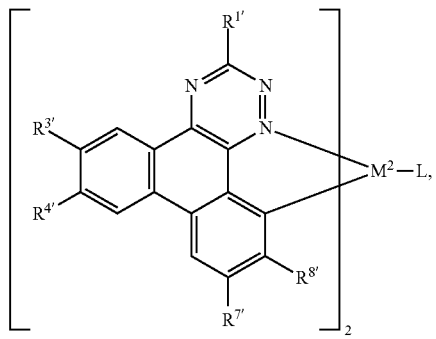
(VIa)

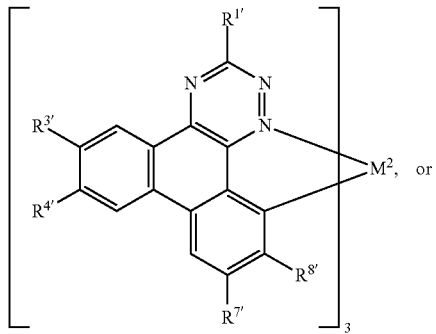
(VIb)

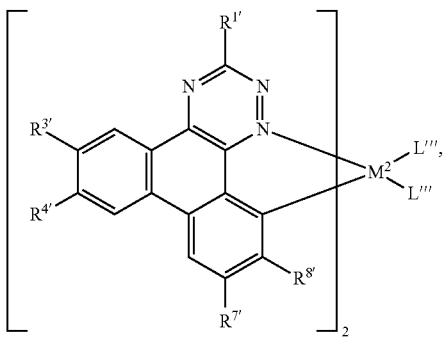
(VIc)

wherein
$R^1$, $R^{1'}$ and $R^2$ are independently of each other H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or CN, $R^3$, $R^8$, $R^{3'}$ and $R^{8'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy, $C_1$-$C_{18}$alkoxy which is substituted by E and/or interrupted by —O—, $C_7$-$C_{25}$arylalkyl, CN, or —NR$^{25}$R$^{26}$;

$R^4$, $R^7$, $R^{4'}$ and $R^{7'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy which is substituted by E and/or interrupted by —O—, $C_7$-$C_{25}$arylalkyl, CN, —NR$^{25}$R$^{26}$;

$R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or $R^{25}$ and $R^{26}$ together with the nitrogen atom to which they are bonded form a heteroaromatic ring system

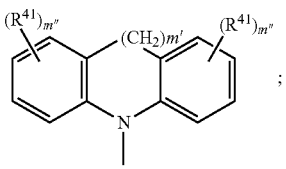

m' is 0, 1, or 2;
m" can be the same or different at each occurence and is 0, 1, 2, or 3, especially 0, 1, or 2, very especially 0 or 1;
$R^{41}$ can be the same or different at each occurence and is Cl, F, CN, N($R^{45}$)$_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —NR$^{45}$—, —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is H, a $C_1$-$C_{25}$alkyl group, a $C_4$-$C_{18}$cycloalkyl group, in which one or more carbon atoms which are not in neighbourhood to each other could be replaced by —NR$^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45''}$ is H, a $C_1$-$C_{25}$alkyl group, or a $C_4$-$C_{18}$cycloalkyl group,
E is —OR$^{29}$; —SR$^{29}$; —NR$^{25'}$R$^{26'}$, CN, or F; G is E, CF$_3$, $C_1$-$C_{18}$alkyl, or $C_2$-$C_{18}$alkenyl,
$R^{29}$; $R^{29'}$; $R^{25'}$ and $R^{26'}$ are as defined in claim 1,
$M^2$ is Rh, or Re, especially Ir,
L is a bidentate ligand, and
L''' is a monodentate ligand, or
a compound of claim 1 having a structure (VIIa), (VIIb), (VIIIa), or (VIIIb) below:

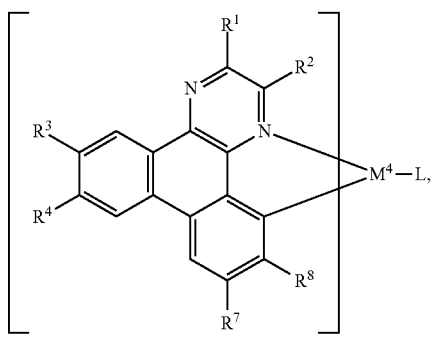
(VIIa)

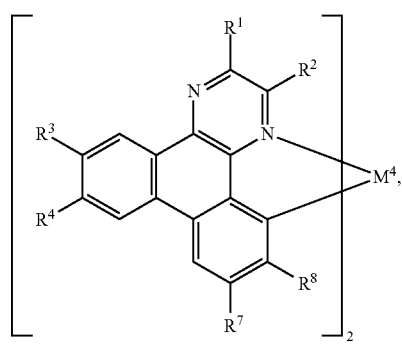
(VIIb)

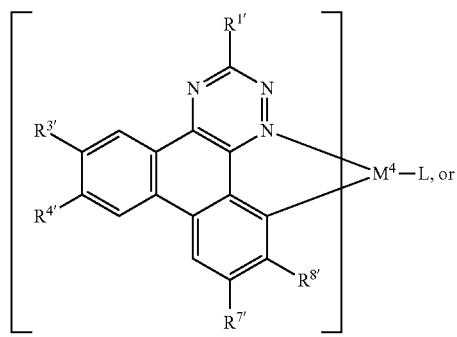
(VIIIa)

-continued

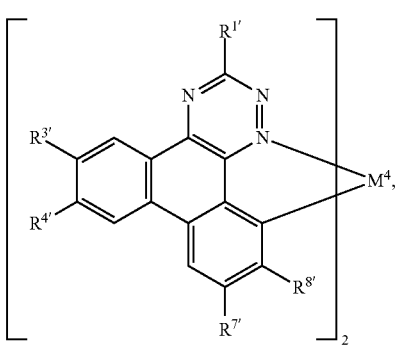
(VIIIb)

wherein $M^4$ is Pd, or Pt, and L, $R^1$, $R^2$, $R^{1'}$, $R^3$, $R^4$, $R^{3'}$, $R^{4'}$, $R^7$, $R^8$, $R^{7'}$ and $R^{8'}$ are as defined above.
$R^2$ is H,
$R^1$ and $R^{1'}$ H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G,

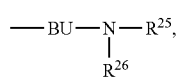

or CN,
$R^3$, $R^8$, $R^{3'}$ and $R^{8'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by $C_1$-$C_{18}$alkyl, or $C_1$-$C_{18}$alkoxy; $C_1$-$C_{18}$alkyl; or $C_1$-$C_{18}$alkoxy which are interrupted by —O—; $C_1$-$C_{18}$alkoxy, or $C_1$-$C_{18}$alkoxy which is interrupted by —O—; or —$NR^{25}R^{26}$;
$R^4$, $R^7$, $R^{4'}$ and $R^{7'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by $C_1$-$C_{18}$alkyl, or $C_1$-$C_{18}$alkoxy; $C_1$-$C_{18}$alkyl, or $C_1$-$C_{18}$alkoxy which are interrupted by —O—; $C_1$-$C_{18}$alkoxy, or $C_1$-$C_{18}$alkoxy which is interrupted by —O—; or —$NR^{25}R^{26}$;
$R^{25}$ and $R^{26}$ are independently of each other; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkoxy which are interrupted by —O—; or
$R^{25}$ and $R^{26}$ together with the nitrogen atom to which they are bonded form a heteroaromatic ring system

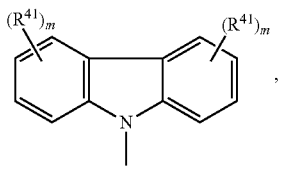

wherein G, $R^{41}$ and m are as defined above;
$M^4$ is Pd, especially Pt,
$M^2$ is Ir, and
L is a bidentate ligand.
Monodentate ligands are preferably monoanionic. Such ligands can have O or S as coordinating atoms, with coordinating groups such as alkoxide, carboxylate, thiocarboxylate, dithiocarboxylate, sulfonate, thiolate, carbamate, dithiocarbamate, thiocarbazone anions, sulfonamide anions, and the like. In some cases, ligands such as β-enolates can act as monodentate ligands. The monodentate ligand can also be a coordinating anion such as halide, nitrate, sulfate, hexahaloantimonate, and the like. Examples of suitable monodentate ligands are shown below:

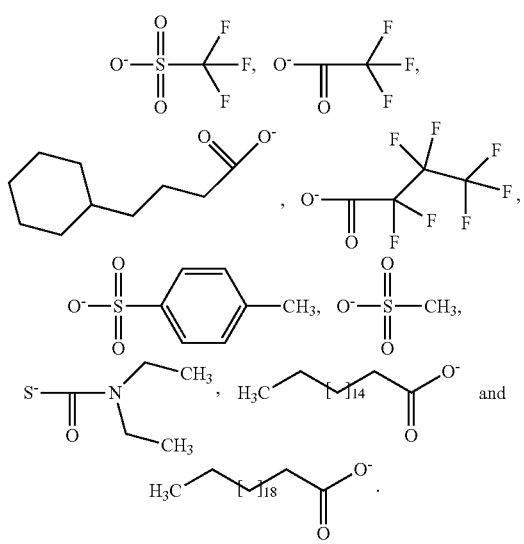

The monodentate ligands are generally available commercially.
In a preferred embodiment of the present invention the ligand is a (monoanionic) bidentate ligand. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands).
Examples of such bidentate ligands L are

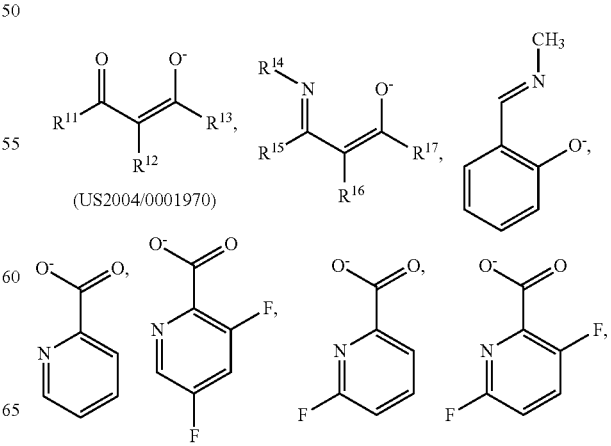

(US2004/0001970)

-continued
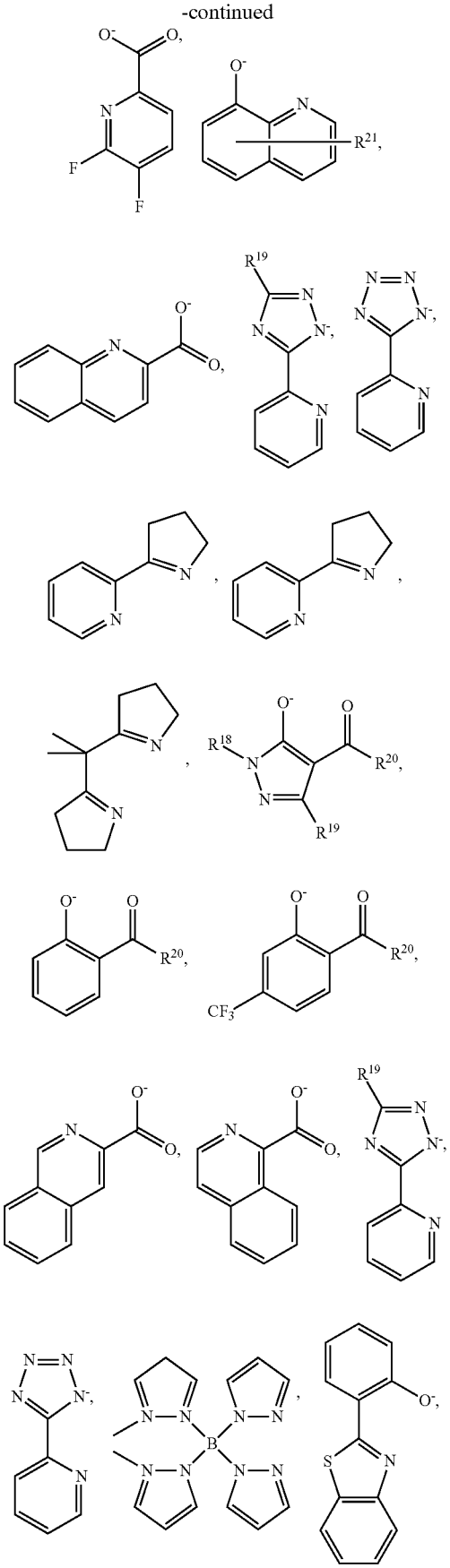
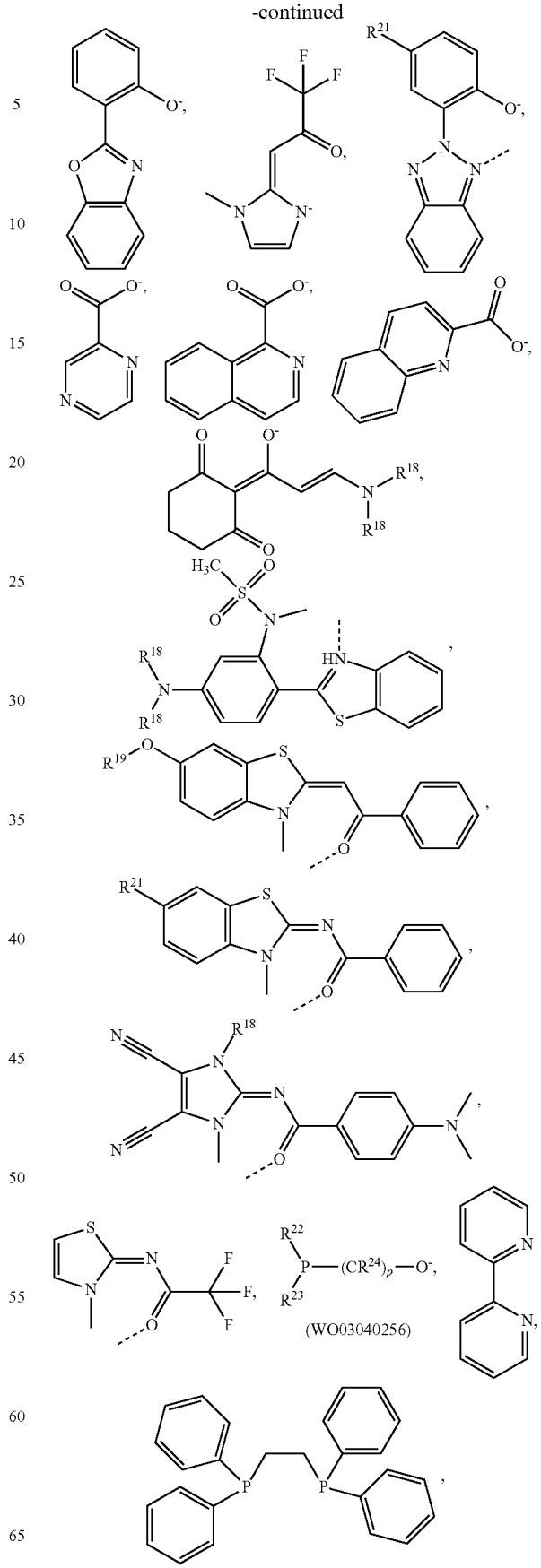

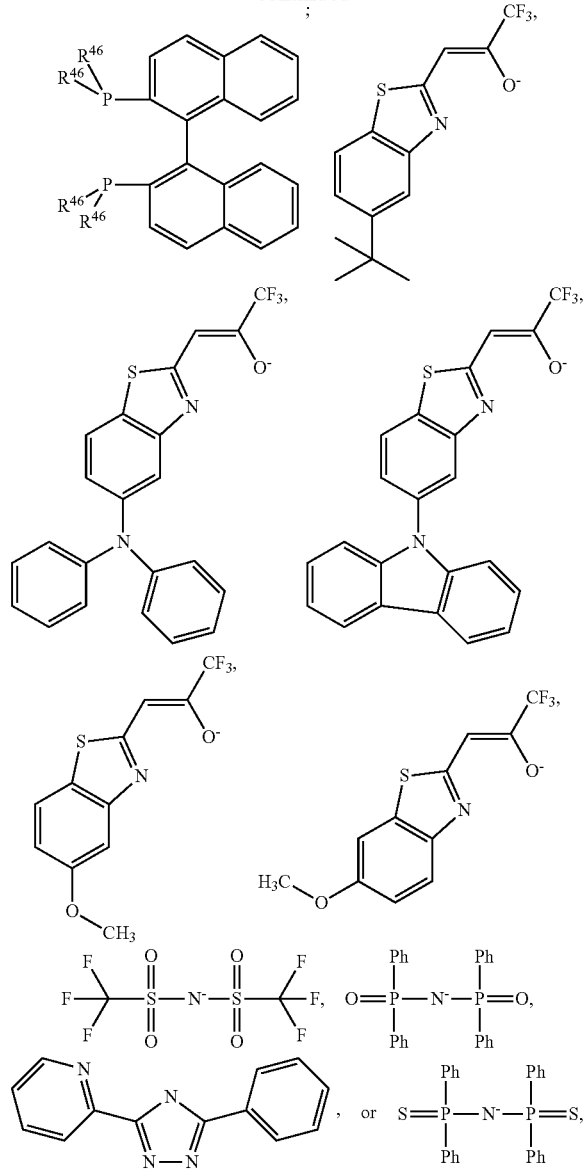

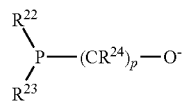

wherein
R[11] and R[15] are independently of each other hydrogen, $C_1$-$C_8$alkyl, $C_6$-$C_{18}$aryl, $C_2$-$C_{10}$heteroaryl, or $C_1$-$C_8$ perfluoroalkyl,
R[12] and R[16] are independently of each other hydrogen, $C_6$-$C_{18}$aryl, or $C_1$-$C_8$alkyl, and
R[13] and R[17] are independently of each other hydrogen, $C_1$-$C_8$alkyl, $C_6$-$C_{18}$aryl, $C_2$-$C_{10}$heteroaryl, $C_1$-$C_8$ perfluoroalkyl, or $C_1$-$C_8$alkoxy, and
R[14] is $C_1$-$C_8$alkyl, $C_6$-$C_{10}$aryl, or $C_7$-$C_{11}$aralkyl,
R[18] is $C_6$-$C_{10}$aryl,
R[19] is $C_1$-$C_8$alkyl, $C_1$-$C_8$ perfluoroalkyl,
R[20] is $C_1$-$C_8$alkyl, or $C_6$-$C_{10}$aryl,
R[21] is hydrogen, $C_1$-$C_8$alkyl, or $C_1$-$C_8$alkoxy, which may be partially or fully fluorinated,
R[22] and R[23] are independently of each other $C_q(H+F)_{2q+1}$, or $C_6(H+F)_5$, R[24] can be the same or different at each occurrence and is selected from H, or $C_q(H+F)_{2q+1}$,
q is an integer of 1 to 24, p is 2, or 3, and
R[46] is $C_1$-$C_8$alkyl, $C_6$-$C_{18}$aryl, or $C_6$-$C_{18}$aryl, which is substituted by $C_1$-$C_8$alkyl.

Examples of suitable phosphino alkoxide ligands

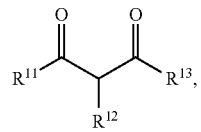

(WO03040256)

are listed below:
3-(diphenylphosphino)-1-oxypropane [dppO]
1,1-bis(trifluoromethyl)-2-(diphenylphosphino)-ethoxide [tfmdpeO].
Examples of particularly suitable compounds HL,

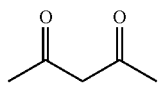

from which the ligands L are derived, include

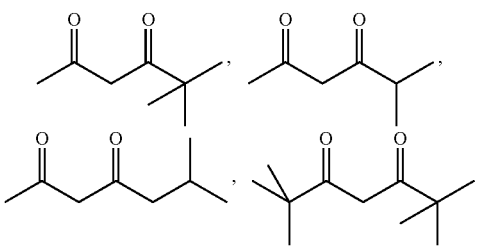

(2,4-pentanedionate [acac]), (2,2,6,6-tetramethyl-3,5-heptanedionate [TMH]),

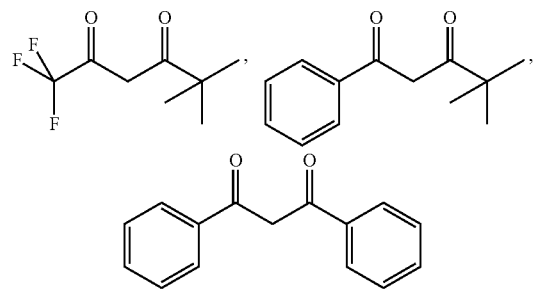

(1,3-diphenyl-1,3-propanedionate [DI]),

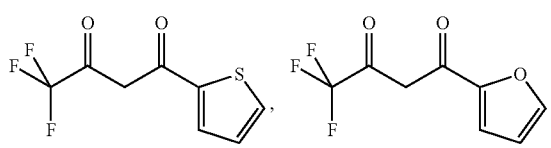

(4,4,4-trifluoro-1-(2-thienyl)-1,3-butanedionate [TTFA]),

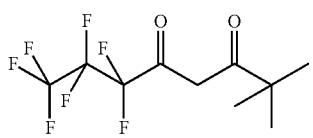 [SMILES: CC(C)(C)C(=O)CC(=O)C(F)(F)C(F)(F)C(F)(F)F]

(7,7-dimethyl-1,1,1,2,2,3,3-heptafluoro-4,6-octanedionate [FOD]),

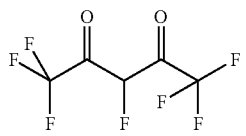 [SMILES: O=C(C(F)C(=O)C(F)(F)F)C(F)(F)F]

(1,1,1,3,5,5,5-heptafluoro-2,4-pentanedionate [F7acac]),

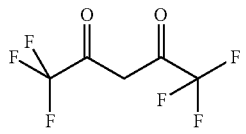 [SMILES: O=C(CC(=O)C(F)(F)F)C(F)(F)F]

(1,1,1,5,5,5-hexafluoro-2,4-pentanedionate [F6acac]),

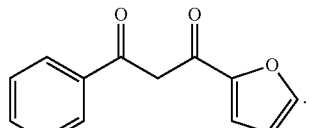

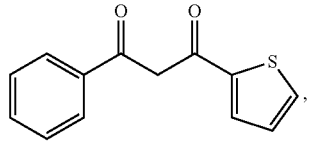

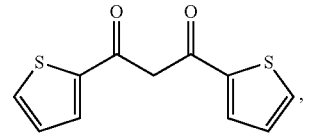

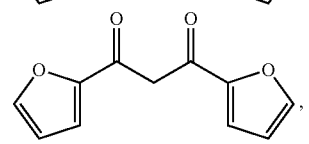

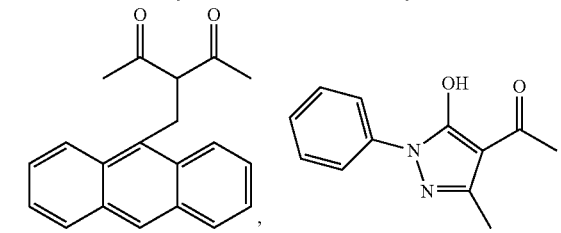

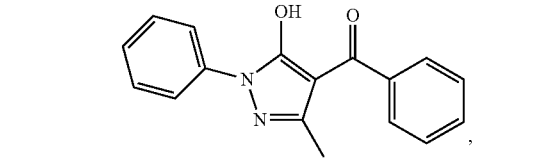

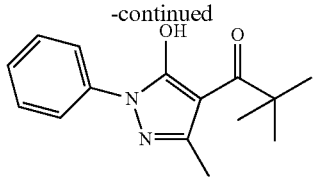

(1-phenyl-3-methyl-4-i-butyryl-pyrazolinonate [FMBP]),

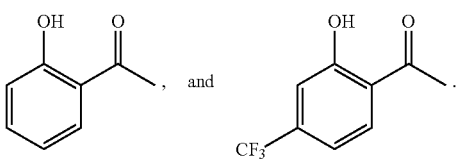

The hydroxyquinoline parent compounds, HL, can be substituted with groups such as alkyl or alkoxy groups which may be partially or fully fluorinated. In general, these compounds are commercially available. Examples of suitable hydroxyquinolinate ligands, L, include:

8-hydroxyquinolinate [8hq]
2-methyl-8-hydroxyquinolinate [Me-8hq]
10-hydroxybenzoquinolinate [10-hbq]

In a further embodiment of the present invention the bidentate ligand L is a ligand of formula

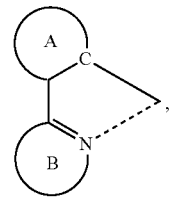

wherein the ring A,

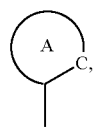

represents an optionally substituted aryl group which can optionally contain heteroatoms, the ring B,

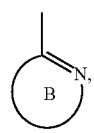

represents an optionally substituted nitrogen containing aryl group, which can optionally contain further heteroatoms, or the ring A may be taken with the ring B binding to the ring A to form a ring.

The preferred ring A includes a phenyl group, a substituted phenyl group, a naphthyl group, a substituted naphthyl group, a furyl group, a substituted furyl group, a benzofuryl group, a substituted benzofuryl group, a thienyl group, a substituted thienyl group, a benzothienyl group, a substituted benzothienyl group, and the like. The substitutent on the substituted phenyl group, substituted naphthyl group, substituted furyl group, substituted benzofuryl group, substituted thienyl group, and substituted benzothienyl group include $C_1$-$C_{24}$alkyl groups, $C_2$-$C_{24}$alkenyl groups, $C_2$-$C_{24}$alkynyl groups, aryl groups, heteroaryl groups, $C_1$-$C_{24}$alkoxy groups, $C_1$-$C_{24}$alkylthio groups, a cyano group, $C_2$-$C_{24}$acyl groups, $C_1$-$C_{24}$alkyloxycarbonyl groups, a nitro group, halogen atoms, alkylenedioxy groups, and the like.

In said embodiment the bidentate ligand

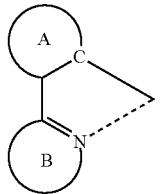

is preferably a group of formula

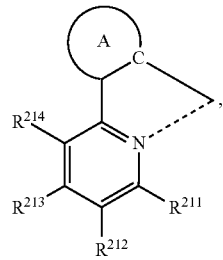

wherein $R^{211}$, $R^{212}$, $R^{213}$, and $R^{214}$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^{211}$, $R^{212}$, $R^{213}$, and $R^{214}$ may be substituted; or $R^{213}$ and $R^{214}$ or $R^{212}$ and $R^{213}$ are a group of formula

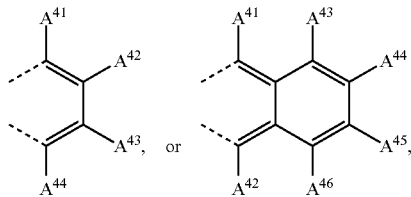

wherein $A^{41}$, $A^{42}$, $A^{43}$, $A^{44}$, $A^{45}$, and $A^{46}$ are as defined above.

Examples of preferred classes of such bidentate ligands L are compounds of the formula

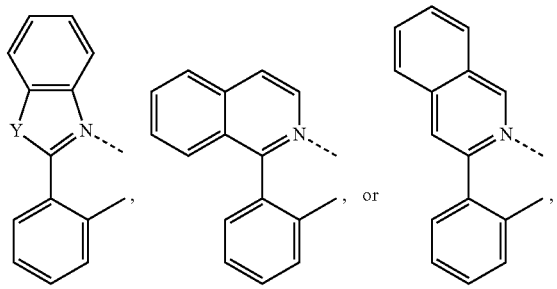

especially

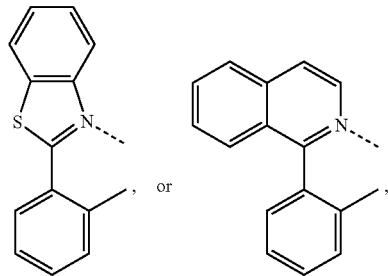

wherein Y is S, O, $NR^{200}$, wherein $R^{200}$ is $C_1$-$C_4$alkyl, $C_2$-$C_4$alkenyl, optionally substituted $C_6$-$C_{10}$aryl, especially phenyl, —$(CH_2)_r$—Ar, wherein Ar is an optionally substituted $C_6$-$C_{10}$aryl, especially

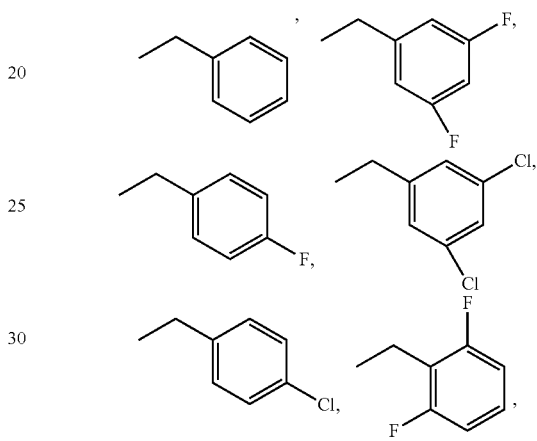

a group —$(CH_2)_{r'}X^{20}$, wherein r' is an integer of 1 to 5, $X^{20}$ is halogen, especially F, or Cl; hydroxy, cyano, —O—$C_1$-$C_4$alkyl, di($C_1$-$C_4$alkyl)amino, amino, or cyano; a group —$(CH_2)_{r'}$—OC(O)$(CH_2)_{r''}CH_3$, wherein r is 1, or 2, and r" is 0, or 1;

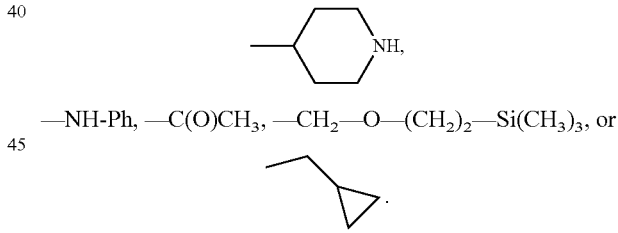

—NH-Ph, —C(O)$CH_3$, —$CH_2$—O—$(CH_2)_2$—Si$(CH_3)_3$, or

Another preferred class of ligands L is described in WO06/000544, of which the following can advantageously be used according to the present invention:

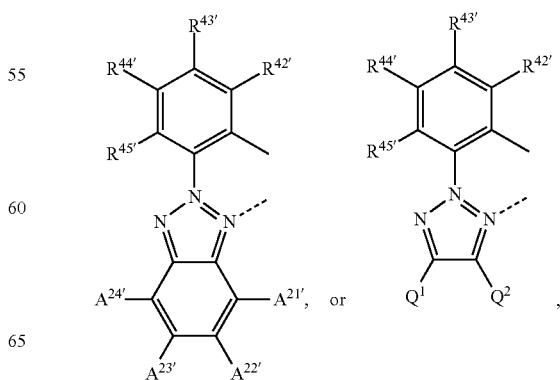

wherein
Q¹ and Q² are independently of each other hydrogen, $C_1$-$C_{24}$alkyl, or $C_6$-$C_{18}$aryl, $A^{21'}$ is hydrogen,
$A^{22'}$ is hydrogen, or $C_6$-$C_{10}$aryl,
$A^{23'}$ is hydrogen, or $C_6$-$C_{10}$aryl,
$A^{24'}$ is hydrogen, or
$A^{23'}$ and $A^{24'}$, or $A^{23'}$ and $A^{24'}$ together form a group

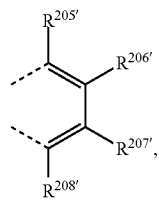

wherein $R^{205'}$, $R^{206'}$, $R^{207'}$ and $R^{208'}$ are independently of each other H, or $C_1$-$C_8$alkyl,
$R^{42'}$ is H, F, $C_1$-$C_4$alkyl, $C_1$-$C_8$alkoxy, or $C_1$-$C_4$ perfluoroalkyl,
$R^{43'}$ is H, F, $C_1$-$C_4$alkyl, $C_1$-$C_8$alkoxy, $C_1$-$C_4$ perfluoroalkyl, or $C_6$-$C_{10}$aryl,
$R^{44'}$ is H, F, $C_1$-$C_4$alkyl, $C_1$-$C_8$alkoxy, or $C_1$-$C_4$ perfluoroalkyl, and
$R^{45'}$ is H, F, $C_1$-$C_4$alkyl, $C_1$-$C_8$alkoxy, or $C_1$-$C_4$ perfluoroalkyl.

Another preferred class of bidentate ligands L is a compound of formula

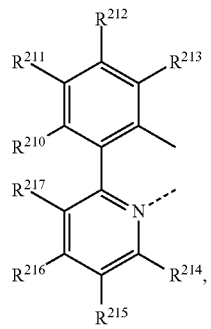

wherein $R^{214}$ is hydrogen, halogen, especially F, or Cl; $C_1$-$C_4$alkyl, $C_1$-$C_4$perfluoroalkyl, $C_1$-$C_4$alkoxy, or optionally substituted $C_6$-$C_{10}$aryl, especially phenyl,
$R^{215}$ is hydrogen, halogen, especially F, or Cl; $C_1$-$C_4$alkyl, $C_1$-$C_4$ perfluoroalkyl, optionally substituted $C_6$-$C_{10}$aryl, especially phenyl, or optionally substituted $C_6$-$C_{10}$ perfluoroaryl, especially $C_6F_5$,
$R^{216}$ is hydrogen, $C_1$-$C_4$alkyl, $C_1$-$C_4$ perfluoroalkyl, optionally substituted $C_6$-$C_{10}$aryl, especially phenyl, or optionally substituted $C_6$-$C_{10}$ perfluoroaryl, especially $C_6F_5$,
$R^{217}$ is hydrogen, halogen, especially F, or Cl; nitro, cyano, $C_1$-$C_4$alkyl, $C_1$-$C_4$ perfluoroalkyl, $C_1$-$C_4$alkoxy, or optionally substituted $C_6$-$C_{10}$aryl, especially phenyl,
$R^{210}$ is hydrogen,
$R^{211}$ is hydrogen, halogen, especially F, or Cl; nitro, cyano, $C_1$-$C_4$alkyl, $C_1$-$C_4$alkoxy, $C_2$-$C_4$alkenyl, $C_1$-$C_4$ perfluoroalkyl, —O—$C_1$-$C_4$ perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$ perfluoroaryl, especially $C_6F_5$, $R^{212}$ is hydrogen, halogen, especially F, or Cl; nitro, hydroxy, mercapto, amino, $C_1$-$C_4$alkyl, $C_2$-$C_4$alkenyl, $C_1$-$C_4$ perfluoroalkyl, $C_1$-$C_4$alkoxy, —O—$C_1$-$C_4$ perfluoroalkyl, —S—$C_1$-$C_4$alkyl, tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, and
$R^{213}$ is hydrogen, nitro, cyano, $C_1$-$C_4$alkyl, $C_2$-$C_4$alkenyl, $C_1$-$C_4$ perfluoroalkyl, —O—$C_1$-$C_4$perfluoroalkyl, tri($C_1$-$C_4$alkyl)silanyl, or optionally substituted $C_6$-$C_{10}$aryl, especially phenyl.

Specific examples of bidentate ligands L are the following compounds (X-1) to (X-57):

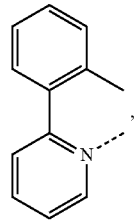
(X-1)

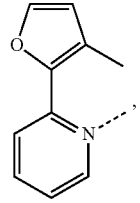
(X-2)

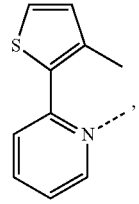
(X-3)

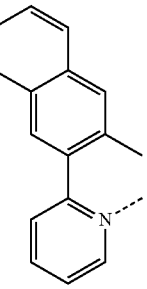
(X-4)

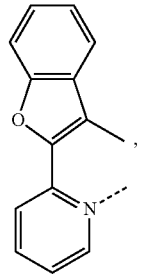
(X-5)

-continued
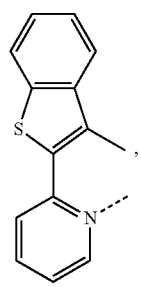
(X-6)
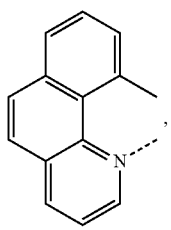
(X-7)
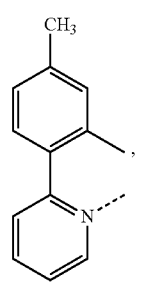
(X-8)
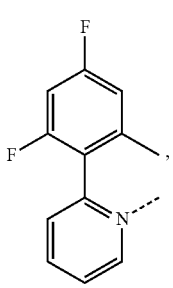
(X-9)
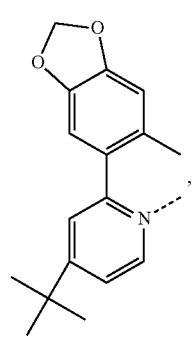
(X-10)
-continued
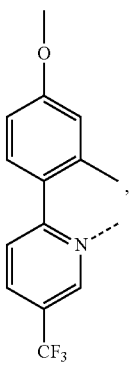
(X-11)
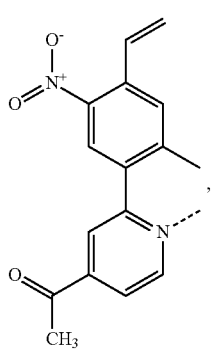
(X-12)
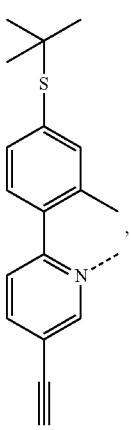
(X-13)
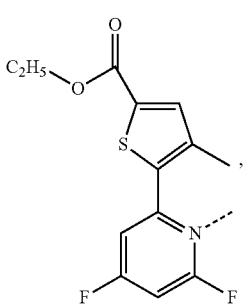
(X-14)

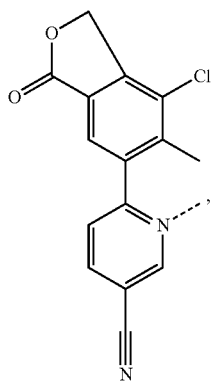 (X-15)
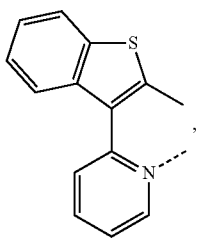 (X-16)
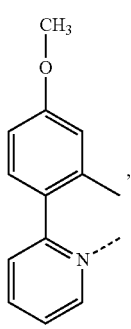 (X-17)
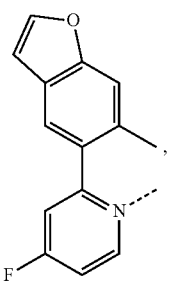 (X-18)
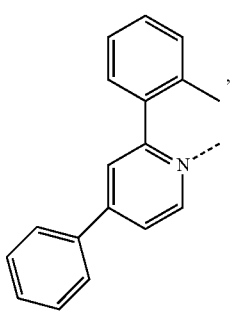 (X-19)
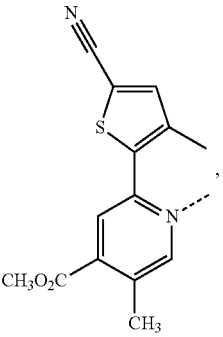 (X-20)
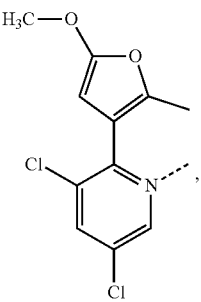 (X-21)
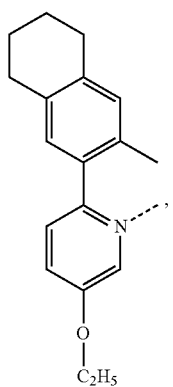 (X-22)
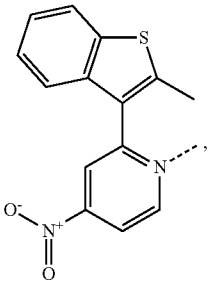 (X-23)
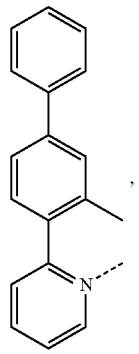 (X-24)

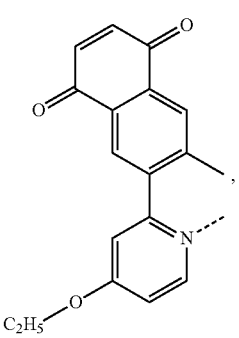 (X-25)
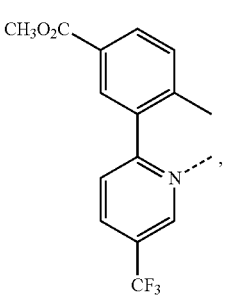 (X-26)
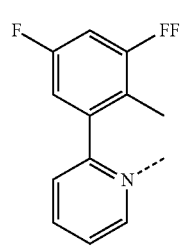 (X-27)
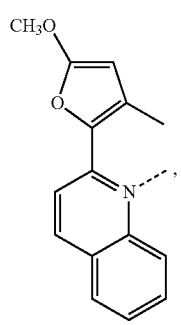 (X-28)
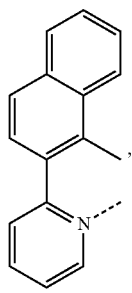 (X-29)
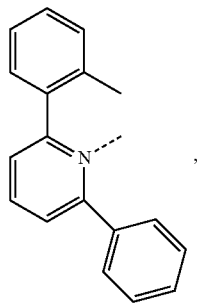 (X-30)
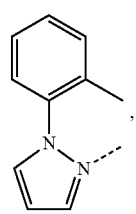 (X-31)
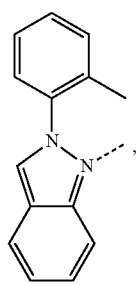 (X-32)
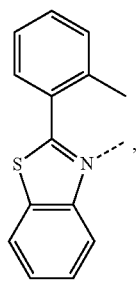 (X-33)
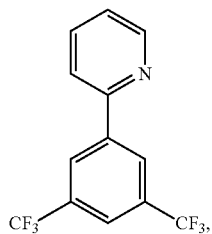 (X-34)
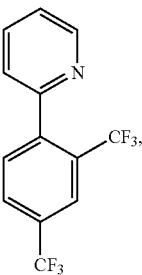 (X-35)

-continued
(X-36) 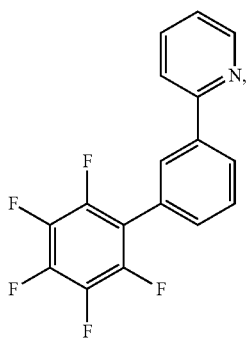
(X-37) 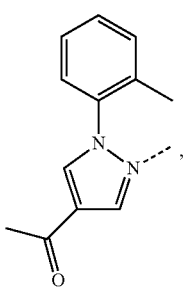
(X-37) 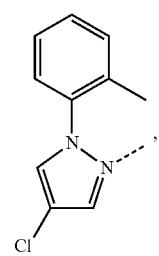
(X-38) 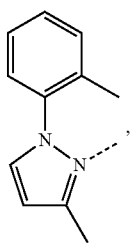
-continued
(X-39) 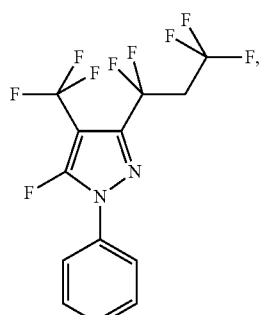
(X-40)
(X-41)
(X-42) 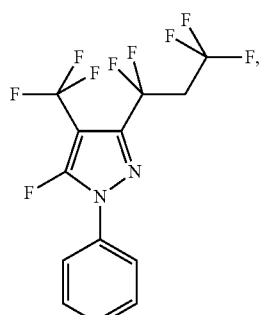
(X-43) 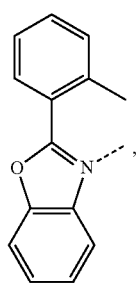

(X-44) 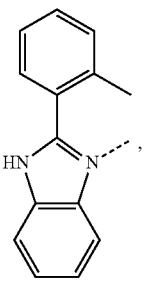
(X-45) 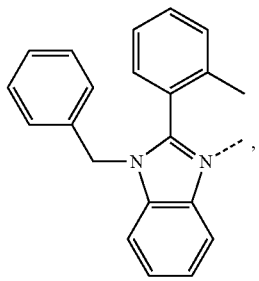
(X-46) 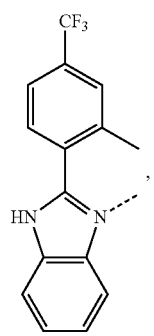
(X-47) 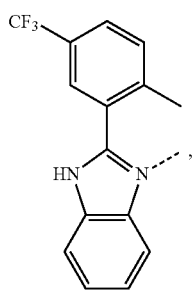
(X-48) 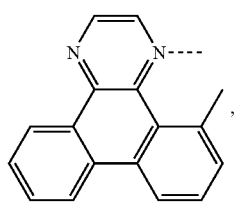
(X-49) 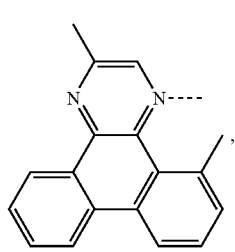
(X-50) 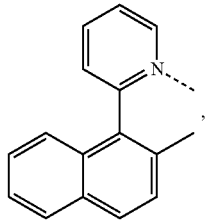
(X-51) 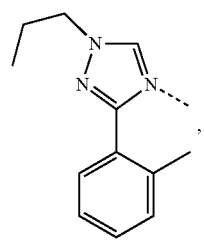
(X-52) 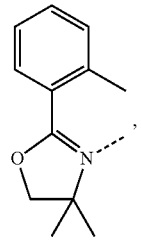
(X-53) 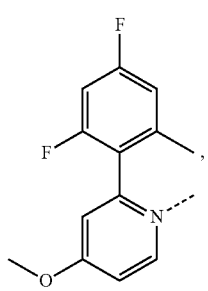
(X-54) 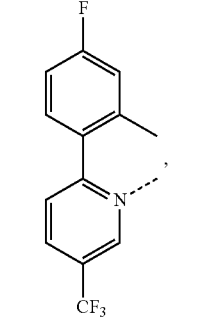
(X-55) 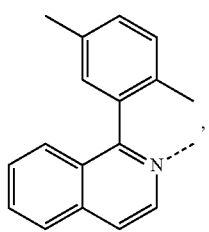

-continued

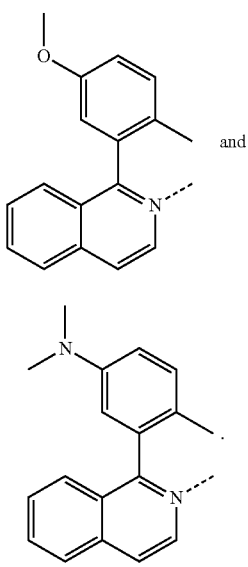

(X-56)

and (X-57)

In case of the metal complex $(L^a)_2IrL'$ three isomers can exist.

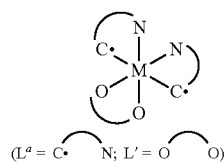

$(L^a = C \cdot\frown N; L' = O \frown O)$

In some cases mixtures of isomers are obtained. Often the mixture can be used without isolating the individual isomers. The isomers can be separated by conventional methods, as described in A. B. Tamayo et al., J. Am. Chem. Soc. 2003, 125, 7377-7387.

The at present most preferred ligands L are listed below:

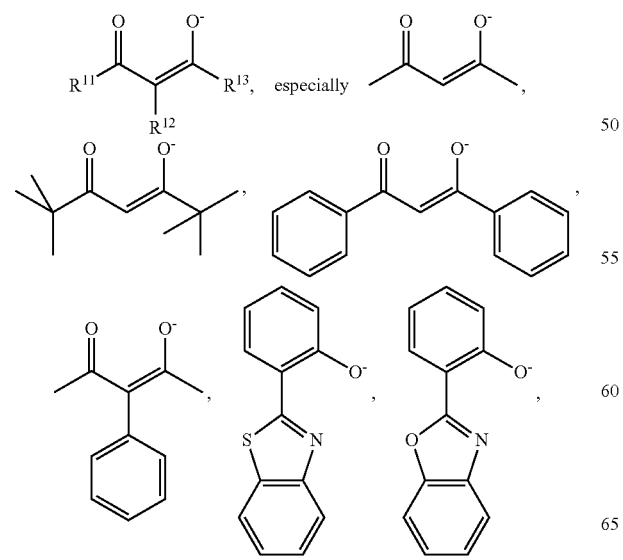

-continued

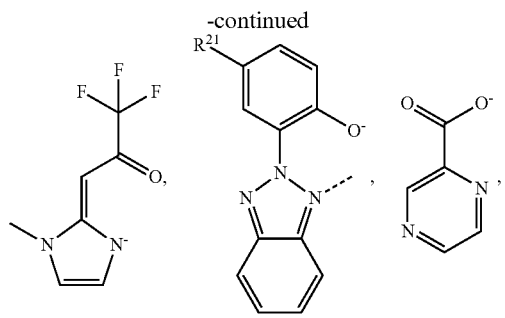

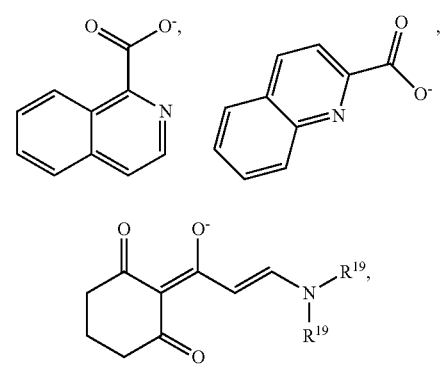

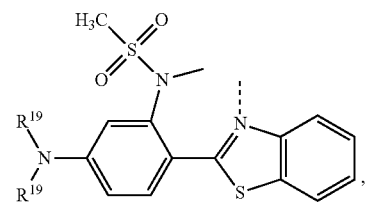

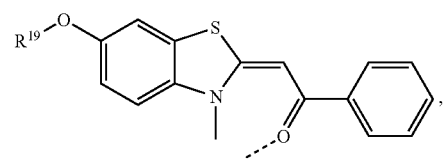

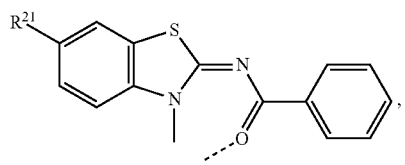

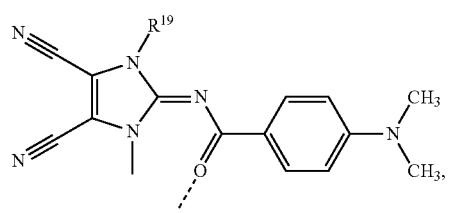

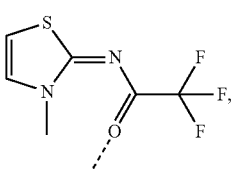

(X-1) 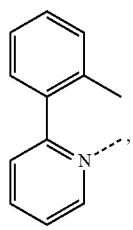

(X-4) 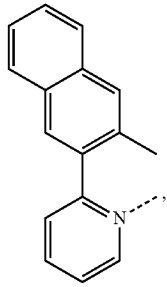

(X-6) 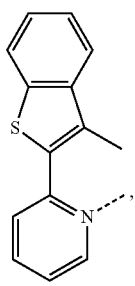

(X-29) 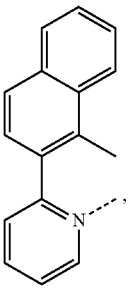

(X-48) 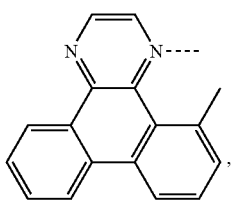

(X-49) 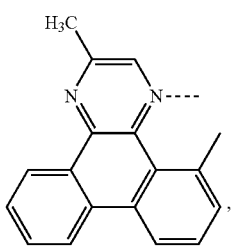

(X-50) 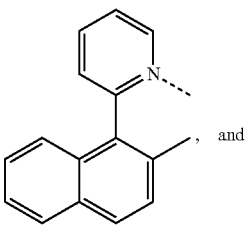
, and (X-51) 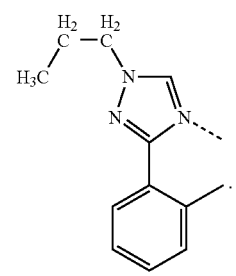

In a preferred embodiment the present invention is directed to compounds of formula Va, or Vb, wherein $M^2$ is Rh, or Re, especially Ir, $R^1$ and $R^2$ are independently of each other H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or CN, or $R^1$ and $R^2$ together form a group

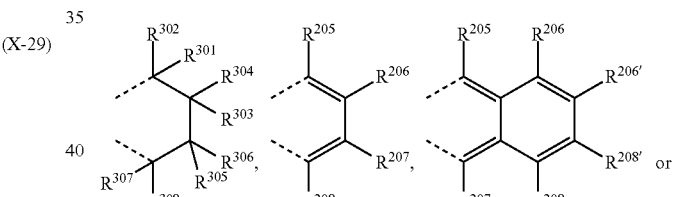

$R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkoxy, or $C_6$-$C_{24}$aryl, $C_6$-$C_{24}$aryl which is substituted by $C_1$-$C_{18}$alkyl or $C_1$-$C_{18}$alkoxy; $R^{301}$, $R^{302}$, $R^{303}$, $R^{304}$, $R^{305}$, $R^{306}$, $R^{307}$ and $R^{308}$ are independently of each other H, or $C_1$-$C_{18}$alkyl, $R^3$, $R^8$, $R^{3'}$ and $R^{8'}$ are independently of each other H, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy, $C_1$-$C_{18}$alkoxy which is substituted by E and/or interrupted by —O—, $C_7$-$C_{25}$arylalkyl, CN, or —NR$^{25}$R$^{26}$;

$R^4$ and $R^7$ are independently of each other H, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy which is substituted by E and/or interrupted by —O—, $C_7$-$C_{25}$arylalkyl, CN, —NR$^{25}$R$^{26}$;

$R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

E is —$OR^{29}$; —$SR^{29}$; —$NR^{25'}R^{26'}$, —$CF_3$, —CN, F; G is E, $C_1$-$C_{18}$alkyl, or $C_2$-$C_{18}$alkenyl, and L is a bidentate ligand.

In a particularly preferred embodiment $R^1$ is H, $C_1$-$C_{10}$alkyl, cyclohexyl, which can optionally be substituted by one to three $C_1$-$C_4$alkyl groups, phenyl, which may be substituted one to five times by F, such as

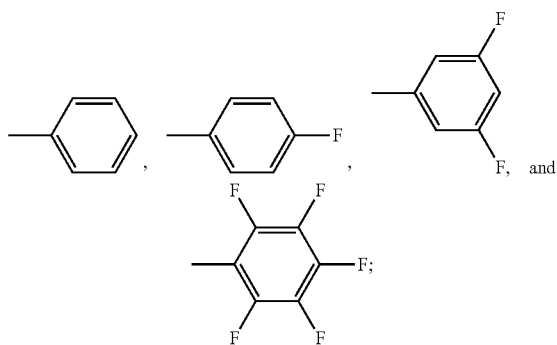

$CF_3$, such as

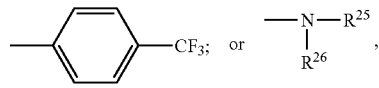

such as

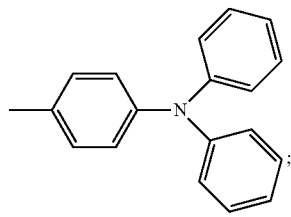 [SMILES: Cc1ccc(N(c2ccccc2)c2ccccc2)cc1]

and $R^2$ is H, $CH_3$.

In said embodiment compounds are even more preferred, wherein $R^4$ and $R^7$ are independently of each other H, $C_6$-$C_{24}$aryl, $C_6$-$C_{24}$aryl which is substituted by G, $C_1$-$C_{18}$alkoxy which may be interrupted by —O—, or —$NR^{25}R^{26}$.

In said embodiment the compounds of formula

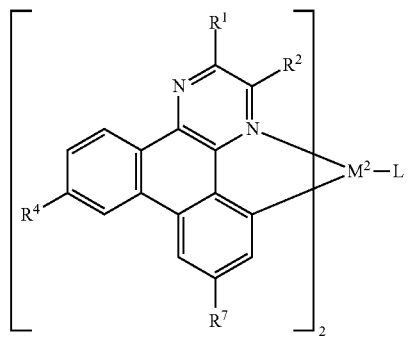

are most preferred, wherein $M^2$ is Ir,
$R^1$ is H, $C_1$-$C_{18}$alkyl, cyclohexyl, which can optionally be substituted by one to three $C_1$-$C_4$alkyl groups,

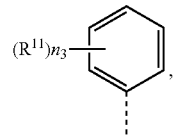

wherein $n_3$ is 0, or an integer 1, 2, 3, 4, or 5, especially 0, 1, 2, or 5, $R^{11}$ can be same, or different in each occurrence and is $C_1$-$C_{25}$alkyl, $C_1$-$C_{25}$alkoxy, —$NR^{25}R^{26}$, F, or $CF_3$,
$R^2$ is H, or $CH_3$,
$R^4$ and $R^7$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_1$-$C_{18}$alkoxy which may be interrupted by —O—, or —$NR^{25}R^{26}$;
$R^{25}$ and $R^{26}$ are independently of each other

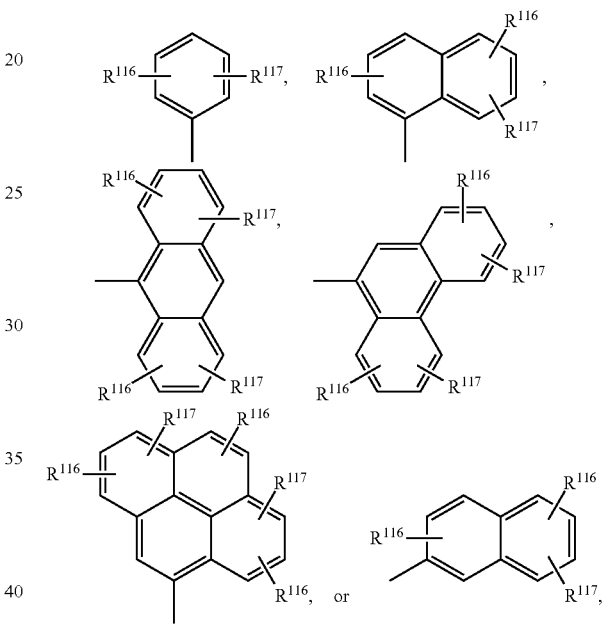

$R^{116}$ and $R^{117}$ are independently of each other $C_1$-$C_{25}$alkyl, which may optionally be interrupted by —O—, or $C_1$-$C_{25}$alkoxy; or $R^{25}$ and $R^{26}$ together with the nitrogen atom to which they are bonded form a group of formula

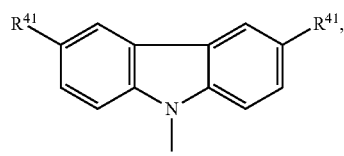

$R^{41}$ is H, $C_1$-$C_{25}$alkyl, and
L is

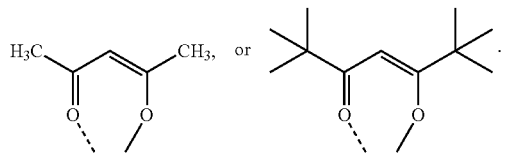

In another preferred embodiment the present invention is directed to compounds of formula VIIIa, or VIIb, wherein $M^4$ is Pd, especially Pt, $R^1$ and $R^2$ are independently of each other H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or CN, or $R^1$ and $R^2$ together form a group

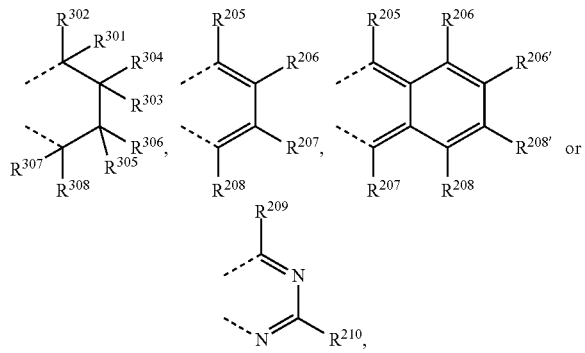

$R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkoxy, or $C_6$-$C_{24}$aryl, $C_6$-$C_{24}$aryl which is substituted by $C_1$-$C_{18}$alkyl or $C_1$-$C_{18}$alkoxy;

$R^{301}$, $R^{302}$, $R^{303}$, $R^{304}$, $R^{305}$, $R^{306}$, $R^{307}$ and $R^{308}$ are independently of each other H, or $C_1$-$C_{18}$alkyl, $R^3$, $R^8$, $R^{3'}$ and $R^{8'}$ are independently of each other H, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy, $C_1$-$C_{18}$alkoxy which is substituted by E and/or interrupted by —O—, $C_7$-$C_{25}$arylalkyl, CN, or —NR$^{25}$R$^{26}$;

$R^4$ and $R^7$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy which is substituted by E and/or interrupted by —O—, $C_7$-$C_{25}$arylalkyl, CN, —NR$^{25}$R$^{26}$;

$R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

E is —OR$^{29}$; —SR$^{29}$; —NR$^{25}$R$^{26'}$; G is E, $C_1$-$C_{18}$alkyl, or $C_2$-$C_{18}$alkenyl, and L is a bidentate ligand.

In said embodiment compounds are even more preferred, wherein $R^4$ and $R^7$ are independently of each other H, $C_6$-$C_{24}$aryl, $C_6$-$C_{24}$aryl which is substituted by G, $C_1$-$C_{18}$alkoxy which may be interrupted by —O—, or —NR$^{25}$R$^{26}$.

In said embodiment the compounds of formula

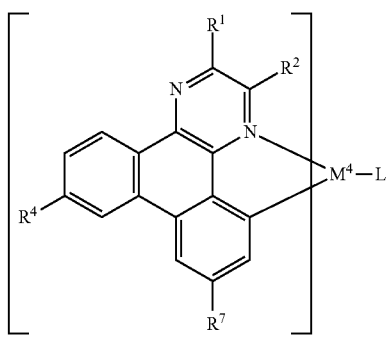

are even more preferred, wherein $M^4$ is Pt, $R^1$ is H, $C_1$-$C_{18}$alkyl, cyclohexyl, which can optionally be substituted by one to three $C_1$-$C_4$alkyl groups,

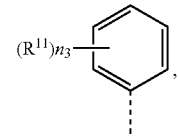

wherein $n_3$ is 0, or an integer 1, 2, 3, 4, or 5, especially 0, 1, 2, or 5, $R^{11}$ can be same, or different in each occurrence and is $C_1$-$C_{25}$alkyl, $C_1$-$C_{25}$alkoxy, or NR$^{25}$R$^{26}$, F, or CF$_3$, $R^2$ is H, $R^4$ and $R^7$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_1$-$C_{18}$alkoxy which may be interrupted by —O—, or —NR$^{25}$R$^{26}$;

$R^{25}$ and $R^{26}$ are independently of each other

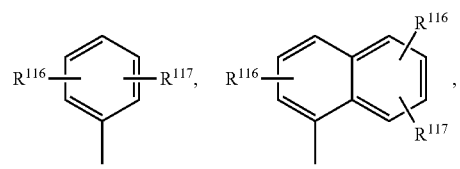

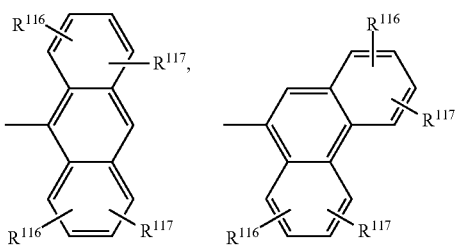

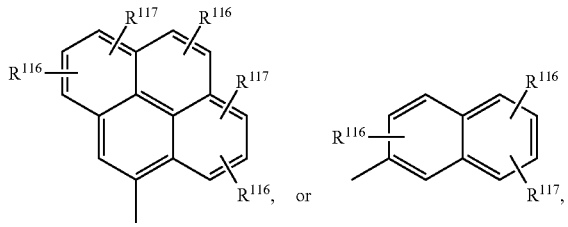

$R^{116}$ and $R^{117}$ are independently of each other $C_1$-$C_{25}$alkyl, which may optionally be interrupted by —O—, or $C_1$-$C_{25}$alkoxy; or $R^{25}$ and $R^{26}$ together with the nitrogen atom to which they are bonded form a group of formula

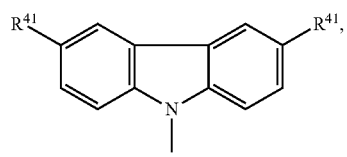

$R^{41}$ is H, or $C_1$-$C_{25}$alkyl, and

L is

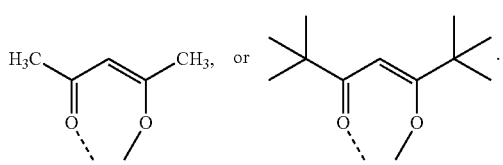

Preferences for the bidentate ligand L are given above, wherein the following ligands L are advantageously used:

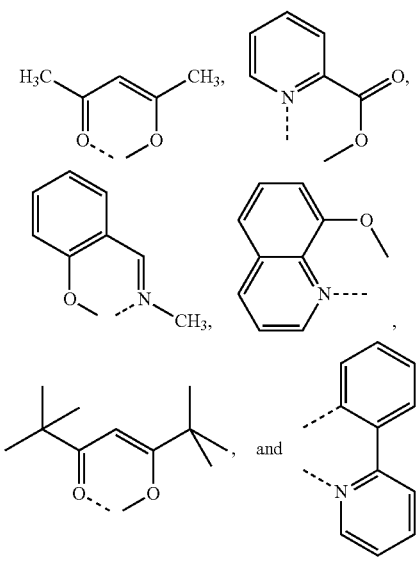

Higher preference is given to

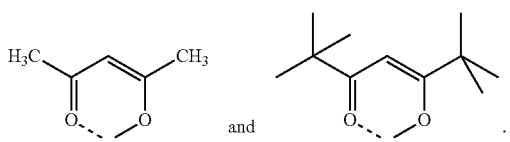

Even higher preference is given to

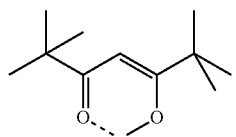

The metal complexes of the present invention are preferably non-ionic (uncharged).

If $R^1$ and $R^2$ together form a ring, they are preferably a group

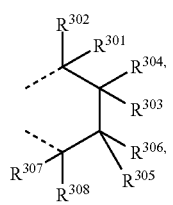

wherein $R^{301}$, $R^{302}$, $R^{303}$, $R^{304}$, $R^{305}$, $R^{306}$, $R^{307}$ and $R^{308}$ are independently of each other H, or $C_1$-$C_8$alkyl, especially H.

Compounds are preferred, wherein at least one of the substituents $R^1$, $R^4$ and $R^7$ (especially $R^1$, $R^4$ or $R^7$; or $R^4$ or $R^7$) is a functional group having charge transport properties, in particular hole transport properties. Examples of substituents having hole transport properties are —$NR^{25}R^{26}$, or $C_6$-$C_{24}$aryl, such as phenyl, 1-, or 2-naphthyl, which is substituted by —$NR^{25}R^{26}$, wherein $R^{25}$ and $R^{26}$ are as defined above, and are preferably independently of each other

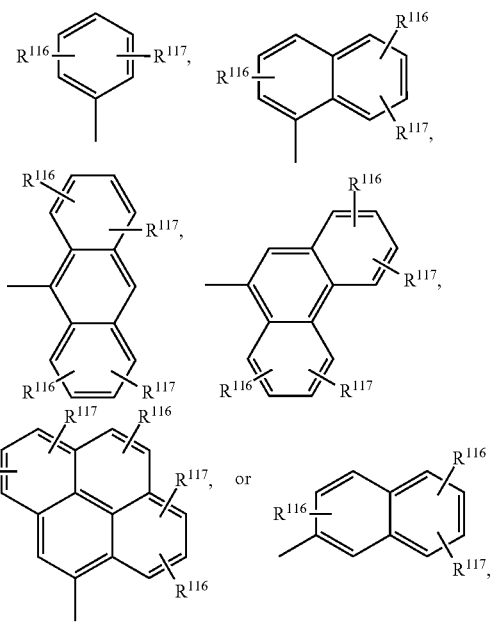

wherein $R^{116}$ and $R^{117}$ are independently of each other $C_1$-$C_{25}$alkyl, which may optionally be interrupted by —O—, or $C_1$-$C_{25}$alkoxy; or $R^{25}$ and $R^{26}$ together with the nitrogen atom to which they are bonded form a group of formula

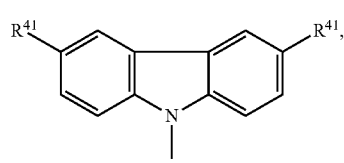

$R^{41}$ is H, or $C_1$-$C_{25}$alkyl.

In a particularly preferred embodiment the present invention is directed to compounds of formula

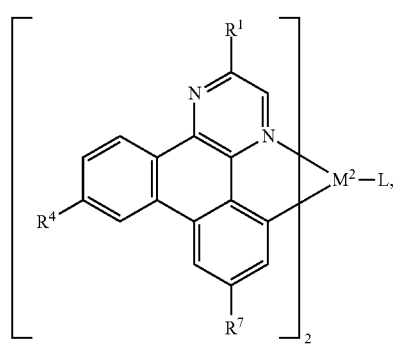

wherein $M^2$ is iridium, $R^1$ is H, cyclohexyl, which can optionally be substituted by one to three $C_1$-$C_4$alkyl groups, $C_1$-$C_{18}$alkyl,

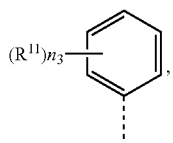

wherein $n_3$ is 0, or an integer 1, 2, 3, 4, or 5, especially 0, 1, 2, or 5, $R^{11}$ can be same, or different in each occurrence and is $C_1$-$C_{25}$alkyl, $C_1$-$C_{25}$alkoxy, —$NR^{25}R^{26}$, F, or $CF_3$, $R^4$ and $R^7$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_1$-$C_{18}$alkoxy, which may be interrupted by —O—, or —$NR^{25}R^{26}$;

$R^{25}$ and $R^{26}$ are independently of each other

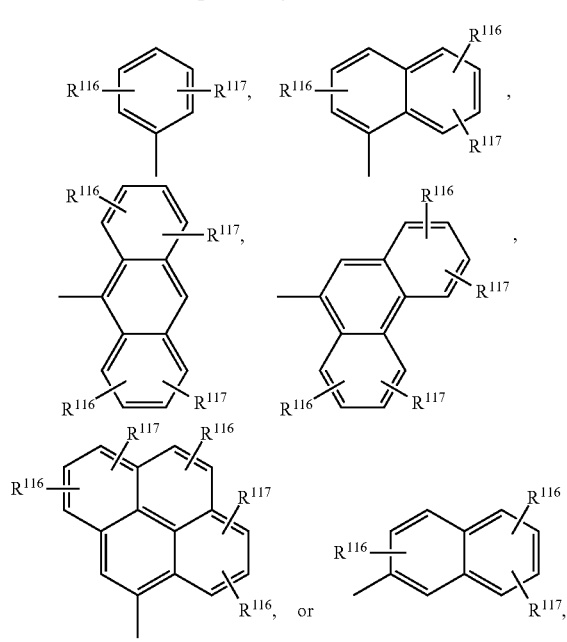

$R^{116}$ and $R^{117}$ are independently of each other $C_1$-$C_{25}$alkyl, which may optionally be interrupted by —O—, or $C_1$-$C_{25}$alkoxy; or $R^{25}$ and $R^{26}$ together with the nitrogen atom to which they are bonded form a group of formula

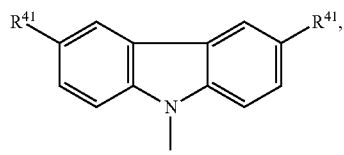

$R^{41}$ is H, or $C_1$-$C_{25}$alkyl, and L is as defined above. In said embodiment compounds are more preferred, wherein $R^1$ is H, $C_1$-$C_{18}$alkyl,

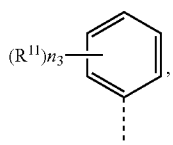

and $R^4$ and $R^7$ are independently of each other H, $C_6$-$C_{24}$aryl, $C_6$-$C_{24}$aryl which is substituted by G, $C_1$-$C_{18}$alkoxy, which may be interrupted by —O—, or —$NR^{25}R^{26}$. In said embodiment compounds of formula

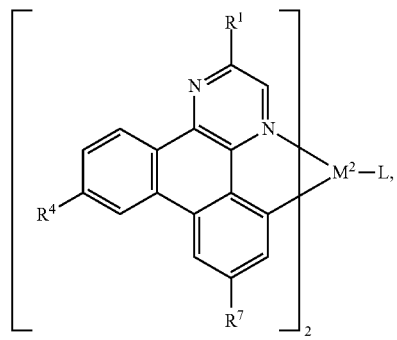

wherein $R^1$ is H, $C_1$-$C_{18}$alkyl,

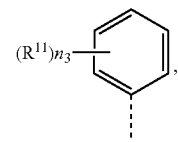

and $R^4$ and $R^7$ are independently of each other phenyl, 1-, or 2-naphthyl, which is substituted by —$NR^{25}R^{26}$; or —$NR^{25}R^{26}$, are even more preferred.

If a mixture of two isomers of mono-substituted dibenzoquinoxaline ligands

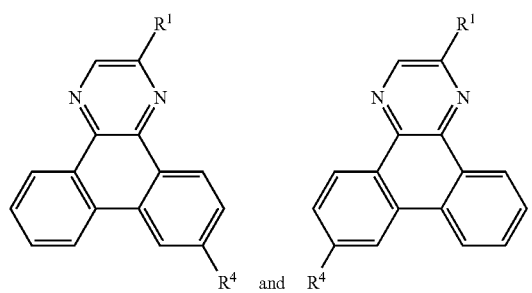

in which $R^1$ is, for example, H, $CH_3$, 2-ethylhexyl, cyclohexyl, which can optionally be substituted by one to three $C_1$-$C_4$alkyl groups, or phenyl, and $R^4$ is, for example, a substituted phenyl, is employed, said isomers coordinate in two ways to iridium, i.e.

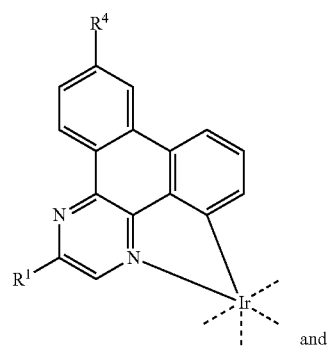

and

-continued

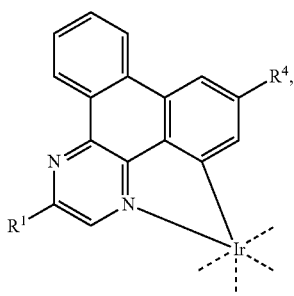

and isomers of iridium complexes are obtained.

In a particularly preferred embodiment the present invention is directed to compounds of formula LIr(L$^a$)$_2$, or Ir(L$^a$)$_3$, wherein L$^a$ is a group of formula

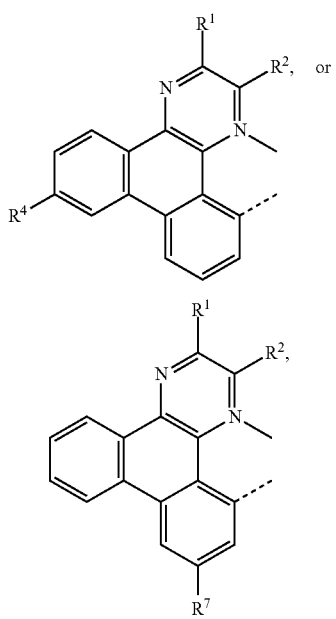

wherein R$^1$ is H, C$_1$-C$_{18}$alkyl, cyclohexyl, which can optionally be substituted by one to three C$_1$-C$_4$alkyl groups,

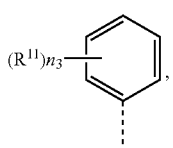

wherein n$_3$ is 0, or an integer 1, 2, 3, 4, or 5, especially 0, 1, 2, or 5, R$^{11}$ can be same, or different in each occurrence and is C$_1$-C$_{25}$alkyl, C$_1$-C$_{25}$alkoxy, —NR$^{25}$R$^{26}$, F, or CF$_3$, R$^2$ is H, or CH$_3$, R$^4$ and R$^7$ are independently of each other H, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by —NR$^{25}$R$^{26}$, C$_1$-C$_{18}$alkoxy which may be interrupted by —O—, or —NR$^{25}$R$^{26}$;

R$^{25}$ and R$^{26}$ are independently of each other

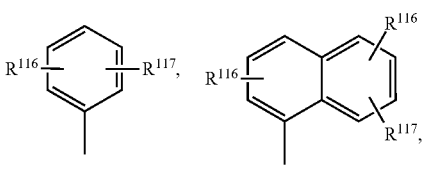

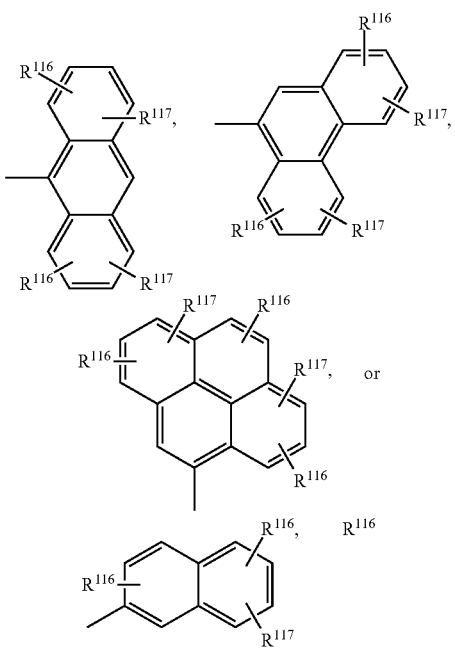

and R$^{117}$ are independently of each other C$_1$-C$_{25}$alkyl, which may optionally be interrupted by —O—, or C$_1$-C$_{25}$alkoxy; or R$^{25}$ and R$^{26}$ together with the nitrogen atom to which they are bonded form a group of formula

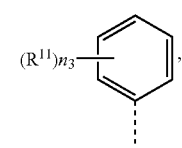

R$^{41}$ is H, or C$_1$-C$_{25}$alkyl, and L is as defined above. In said embodiment ligands L$^a$ are even more preferred, wherein R$^1$ is H, C$_1$-C$_{18}$alkyl,

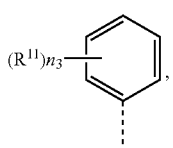

R$^2$ is H, or CH$_3$, and R$^4$ and R$^7$ are independently of each other H, C$_6$-C$_{24}$aryl, C$_6$-C$_{24}$aryl which is substituted by G, C$_1$-C$_{18}$alkoxy, which may be interrupted by —O—, or —NR$^{25}$R$^{26}$. In said embodiment ligands L$^a$ are even more preferred, wherein $R^1$ is $C_1$-$C_{18}$alkyl, $R^2$ is H, or $CH_3$, and $R^4$ and $R^7$ are independently of each other

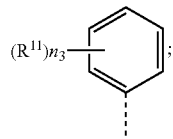

or $R^1$ is

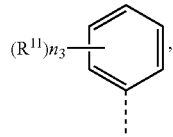

and $R^4$ and $R^7$ are independently of each other

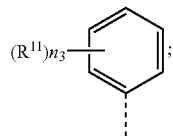

or $R^1$ is H, $C_1$-$C_{18}$alkyl,

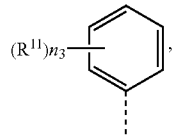

and $R^4$ and $R^7$ are independently of each other phenyl, which is substituted by —$NR^{25}R^{26}$; or —$NR^{25}R^{26}$. In said embodiment ligands $L^a$ are even more preferred wherein $R^2$ is H.

In a particularly preferred embodiment the present invention is directed to compounds of formula

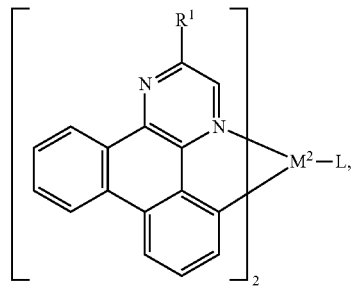

wherein $M^2$ is iridium, $R^1$ is $NR^{25}R^{26}$, or

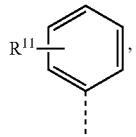

$R^{11}$ is —$NR^{25}R^{26}$, $R^{25}$, $R^{26}$ and L are as defined above.

In a particularly preferred embodiment the present invention is directed to compounds of formula

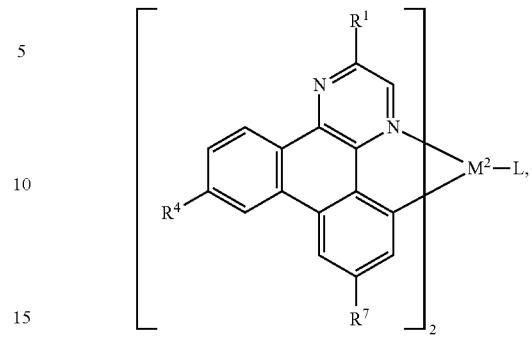

wherein $M^2$ is iridium, $R^1$ is H, $C_1$-$C_{18}$alkyl, cyclohexyl, which can optionally be substituted by one to three $C_1$-$C_4$alkyl groups,

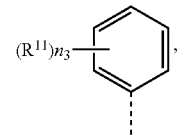

wherein $n_3$ is 0, or an integer 1, 2, 3, 4, or 5, especially 0, 1, 2, or 5, $R^{11}$ can be same, or different in each occurrence and is $C_1$-$C_{25}$alkyl, $C_1$-$C_{25}$alkoxy, —$NR^{25}R^{26}$, F, or $CF_3$,
$R^4$ and $R^7$ are independently of each other —$SR^{29}$, wherein $R^{29}$ is $C_1$-$C_{18}$alkyl, and $R^{25}$, $R^{26}$ and L are as defined above.

A compound of formula Vb, wherein $R^1$ is phenyl, and $R^2$, $R^3$, $R^4$, $R^7$ and $R^8$ are H is not comprised by the present invention.

In a particularly preferred embodiment the present invention is directed to compounds of formula

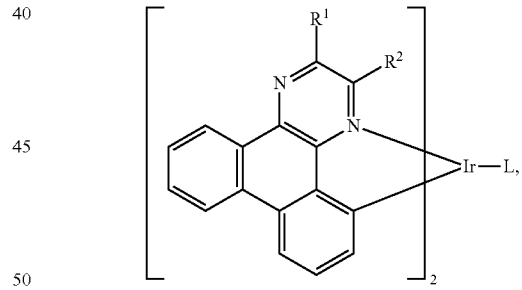

wherein $R^1$ is $C_2$-$C_{10}$alkyl, such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, cyclohexyl, which can optionally be substituted by one to three $C_1$-$C_4$alkyl groups, $R^2$ is H, or $CH_3$, and L is

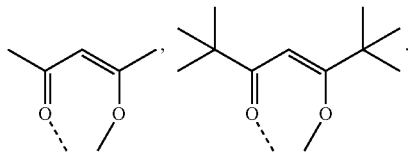

In said embodiment compounds of formula

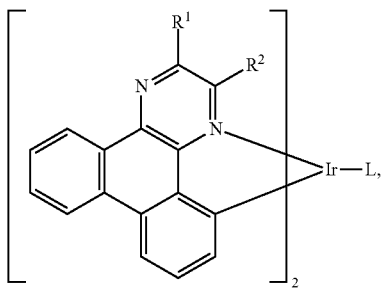

are even more preferred, wherein L is

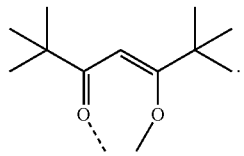

In said embodiment compounds of formula

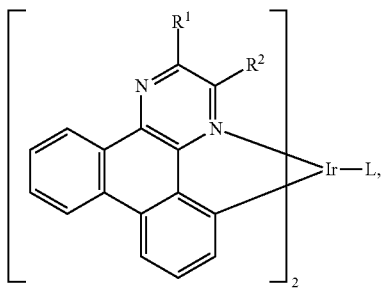

are even more preferred, wherein $R^2$ is H. Said compounds are very well vaporizable and are characterized by an excellent thermal stability and vaporizability, and high efficiency.

Examples of specific compounds of formula Va are compounds A-1 to A-176, compounds B-1 to B-176, C-1 to C-95, compounds D-1 to D-95 and compounds E-1 to E-36 (see claim 6). Special emphasis among them is given to compounds A-1 to A-4, A-17 to A-22, A-35 to A-40, A-53 to A-58, A-71 to A-76, A-89 to A-94, A-107 to A-112, A-125 to A-130, A-143 to A-151, A-163 to A-165, A-167 to A-172, and A-174 to A-176; and B-1 to B-4, B-17 to B-22, B-35 to B-40, B-53 to B-58, B-71 to B-76, B-89 to B-94, B-107 to B-112, B-125 to B-130, B-143 to B-151, B-156, B-163 to B-165, B-167 to B-172, and B-174 to B-176; and C-1, C-2, C-9 to C-12, C-19 to C-21, C-28 to C-30, C-37 to C-39, C-46 to C-48, C-55 to C-57, C-64 to C-66, C-70 to C-79, C82 to C-84, C-86 to C-91, and C-93 to C-95; and D-1, D-2, D-9 to D-12, D-19 to D-21, D-28 to D-30, D-37 to D-39, D-46 to D-48, D-55 to D-57, D-64 to D-66, D-70 to D-84, D-86 to D-91, and D-93 to D-95; and E-1 to E-6, E-10 to E-15, and E-28 to E-33. More preferred compounds are A-1, A-19, A-37, A-55, A-73, A-91, A-109, A-127, A-143, A-145, A-147, A-149, and A-151; and B-1, B-19, B-37, B-55, B-73, B-91, B-109, B-127, B-143, B-145, B-147, B-149, B-151, B-156, B-163 to B-165, B-167 to B-172, and B-174 to B-176; and C-1, C-10, C-20, C-29, C-37, C-38, C-46, C-47, C-56, C-64, C-65, and C-73 to C-79; and D-1, D-9, D-10, D-19, D-20, D-28, D-29, D-37, D-38, D-46, D-47, D-55, D-56, D-64, D-65, and D-73 to D-95; and E-1, E-5, E-6, E-10, E-14, E-15, E-19, E-23, E-24, E-28, E-32, and E-33. Most preferred are compounds A-1, B-1, C-1, D-1, C-79, D-79, C-81, D-81, A-151 and B-151.

The metal complexes of the present invention can be prepared according to usual methods known in the prior art. A convenient one-step method for preparing iridium metal complexes of formula $Ir(L^a)_3$

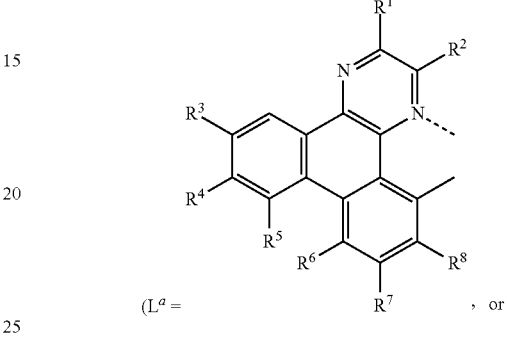

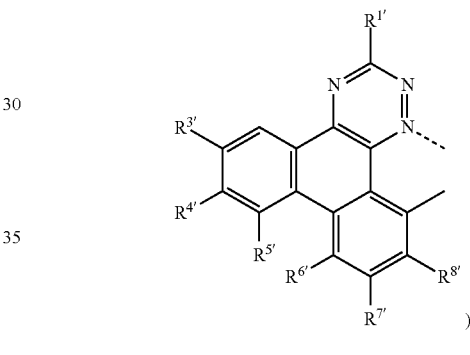

comprises reacting commercially available iridium trichloride hydrate with an excess of $L^aH$ in the presence of 3 equivalents silver trifluoroacetate and optionally in the presence of a solvent (such as halogen based solvents, alcohol based solvents, ether based solvents, ester based solvents, ketone based solvents, nitrile based solvents, and water). The tris-cyclometalated iridium complexes are isolated and purified by conventional methods. In some cases mixtures of isomers are obtained. Often the mixture can be used without isolating the individual isomers. The iridium metal complexes of formula $Ir(L^a)_2L$ can, for example, be prepared by first preparing an intermediate iridium dimer of formula

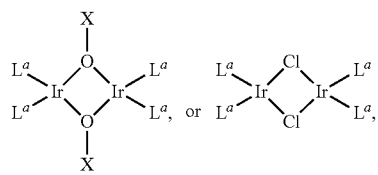

wherein X is H, methyl, or ethyl, and $L^a$ is as defined above, and then addition of HL. The iridium dimers can generally be prepared by first reacting iridium trichloride hydrate with $HL^a$ and adding NaX and by reacting iridium trichloride hydrate with HL$^a$ in a suitable solvent, such as 2-ethoxyethanol. The compounds of formula

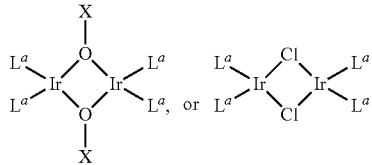

are new and form a further aspect of the present invention.

Accordingly, the present invention relates to compounds of formula

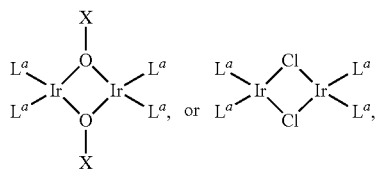

wherein X is H, methyl, or ethyl, and L$^a$ is

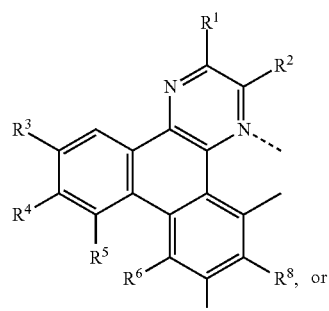

is wherein R$^1$, R$^2$, R$^{1'}$, R$^3$, R$^4$, R$^{3'}$, R$^{4'}$, R$^5$, R$^6$, R$^{5'}$, R$^{6'}$, R$^7$, R$^8$, R$^{7'}$ and R$^{8'}$ are as defined above, with the proviso that at least one of R$^1$, R$^2$, R$^3$, R$^8$, R$^4$, R$^7$, R$^8$ and R$^6$ is different from H and the further proviso that a compound of formula

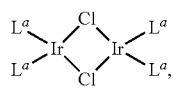

wherein L$^a$ is

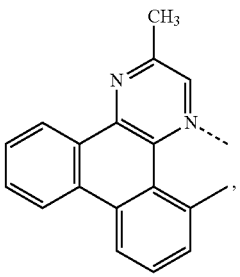

a compound of formula

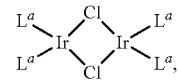

wherein L$^a$ is

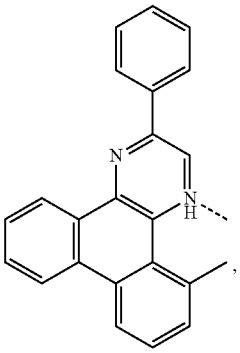

and a compound of formula

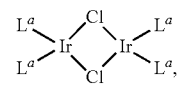

wherein L$^a$ is

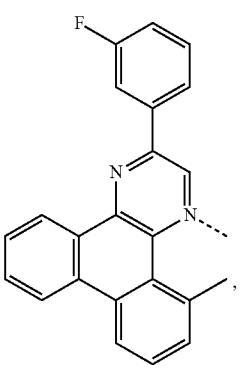

are excluded.

Compounds of formula VIIIa, or VIIb can be synthesized, for example, as outlined in FIGS. 7 and 8 of U.S. Pat. No. 7,166,368.

Halogen is fluorine, chlorine, bromine and iodine.

$C_1$-$C_{24}$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

$C_1$-$C_{24}$ perfluoroalkyl is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

$C_1$-$C_{24}$alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$-$C_{24}$alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_4$-$C_{18}$cycloalkyl, especially $C_5$-$C_{12}$cycloalkyl, is preferably $C_5$-$C_{12}$cycloalkyl or said cycloalkyl substituted by one to three $C_1$-$C_4$alkyl groups, such as, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred.

Examples of $C_4$-$C_{18}$cycloalkyl, which is interrupted by S, O, or $NR^{25}$, are piperidyl, piperazinyl and morpholinyl.

$C_2$-$C_{24}$alkenyl is for example vinyl, allyl, butenyl, pentenyl, hexenyl, heptenyl, or octenyl.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, biphenylyl, 2-fluorenyl, phenanthryl, anthryl, tetracyl, pentacyl, hexacyl, terphenylyl or quadphenylyl; or phenyl substituted by one to three $C_1$-$C_4$alkyl groups, for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_{24}$aralkyl radicals are preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl. or 3-methyl-5-(1',1',3',3'-tetramethyl-butyl)-benzyl.

Heteroaryl is typically $C_2$-$C_{26}$heteroaryl, i.e. a ring with five to seven ring atoms or a condensed rig system, wherein nitrogen, oxygen or sulfur are the possible hetero atoms, and is typically an unsaturated heterocyclic radical with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, which can be unsubstituted or substituted.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. $C_1$-$C_{24}$alkylselenium and $C_1$-$C_{24}$alkyltellurium are $C_1$-$C_{24}$alkylSe— and $C_1$-$C_{24}$alkylTe—, respectively.

Examples of a five or six membered ring formed by $R^9$ and $R^{10}$ and $R^{25}$ and $R^{26}$, respectively are heterocycloalkanes or heterocycloalkenes having from 3 to 5 carbon atoms which can have one additional hetero atom selected from nitrogen, oxygen and sulfur, for example

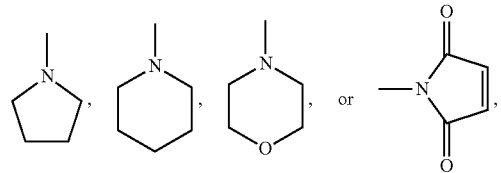

which can be part of a bicyclic system, for example

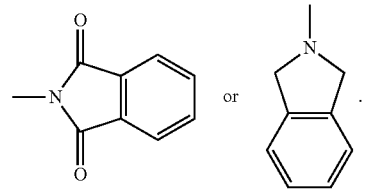

Possible substituents of the above-mentioned groups are $C_1$-$C_8$alkyl, a hydroxyl group, a mercapto group, $C_1$-$C_8$alkoxy, $C_1$-$C_8$alkylthio, halogen, especially fluorine, halo-$C_1$-$C_8$alkyl, especially fluoro-$C_1$-$C_8$alkyl, a cyano group, an aldehyde group, a ketone group, a carboxyl group, an ester group, a carbamoyl group, an amino group, a nitro group or a silyl group.

The term "haloalkyl" means groups given by partially or wholly substituting the above-mentioned alkyl group with halogen, such as trifluoromethyl etc. The term "silyl group" means a group of formula —$SiR^{105'}R^{106'}R^{107'}$, wherein $R^{105'}$, $R^{106'}$ and $R^{107'}$ are independently of each other a $C_1$-$C_8$alkyl group, in particular a $C_1$-$C_4$ alkyl group, a $C_6$-$C_{24}$aryl group or a $C_7$-$C_{12}$aralkylgroup, such as a trimethylsilyl group.

If a substituent, such as, for example, $R^{41}$, occurs more than one time in a group, it can be different in each occurrence.

The present invention is also directed to an electronic device comprising the metal complex and its fabrication process. The electronic device can comprise at least one organic active material positioned between two electrical contact layers, wherein at least one of the layers of the device includes the metallic complex compound. The electronic device can comprise an anode layer (a), a cathode layer (e), and an active layer (c). Adjacent to the anode layer (a) is an optional hole-injecting/transport layer (b), and adjacent to the cathode layer (e) is an optional electron-injection/transport layer (d). Layers (b) and (d) are examples of charge transport layers.

The active layer (c) can comprise at least approximately 1 weight percent of metal complex previously described.

In some embodiments, the active layer (c) may be substantially 100% of the metal complex because a host charge transporting material, such as $Alq_3$ is not needed. By "substantially 100%" it is meant that the metal complex is the only material in the layer, with the possible exception of impurities or adventitious by-products from the process to form the layer. Still, in some embodiments, the metal complex may be a dopant within a host material, which is typically used to aid charge transport within the active layer (c). The active layer (c), including any of the metal complexes, can be a small molecule active material.

The device may include a support or substrate (not shown) adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process. Chemical vapor deposition may be performed as a plasma-enhanced chemical vapor deposition ("PECVD") or metal organic chemical vapor deposition ("MOCVD").

Physical vapor deposition can include all forms of sputtering (e.g., ion beam sputtering), e-beam evaporation, and resistance evaporation.

Specific forms of physical vapor deposition include rf magnetron sputtering or inductively-coupled plasma physical vapor deposition ("ICP-PVD"). These deposition techniques are well-known within the semiconductor fabrication arts.

A hole-transport layer (b) may be adjacent the anode. Both hole transporting small molecule compounds and polymers can be used.

Commonly used hole transporting molecules, in addition to N,N'-diphenyl-N,N'-bis(3-methylphenyl)-[1,1'-biphenyl]-4,4'-diamine (TPD) and bis[4-(N,N-diethylamino)-2-methylphenyl](4-methylphenyl)methane (MPMP), include: polyvinyl-carbazol, 1,1-bis[(di-4-tolylamino)phenyl]cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); a-phenyl-4-N,N-diphenylaminostyrene (TPS); p-(diethylamino)benzaldehyde diphenylhydrazone (DEH); triphenylamine (TPA); 1-phenyl-3-[p-(diethylamino)styryl]-5-[p-(diethylamino)phenyl]pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-di-α-naphthyl-N,N'-diphenyl-4,4'-diphenyldiamine (-NPD), and porphyrinic compounds, such as copper phthalocyanine.

Commonly used hole transporting polymers are polyvinylcarbazole, (phenylmethyl) polysilane, poly(3,4-ethylendioxythiophene) (PEDOT), and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical, or physical vapor deposition.

Usually, the anode layer (a) and the hole-injection/transport layer (b) are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction.

The active layer (c) may comprise the metal complexes described herein. The particular material chosen may depend on the specific application, potentials used during operation, or other factors. The active layer (c) may comprise a host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material is a dopant or a major constituent, the active layer may comprise other materials, such as dopants that tune the emission of the emissive material. Active layer (c) may include a plurality of emissive materials capable of, in combination, emitting a desired spectrum of light. Examples of phosphorescent emissive materials include the metal complexes of the present invention. Examples of fluorescent emissive materials include DCM and DMQA. Examples of host materials include $Alq_3$, BAlq, $BAlq_2$ (Appl. Phys. Lett. 89 (2006) 061111), CBP and mCP. Examples of emissive and host materials are disclosed in U.S. Pat. No. 6,303,238, which is incorporated by reference in its entirety.

The active layer (c) can be applied from solutions by any conventional technique, including spin coating, casting, and printing. The active organic materials can be applied directly by vapor deposition processes, depending upon the nature of the materials.

Optional layer (d) can function both to facilitate electron injection/transport, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metal-cheated oxinoid compounds (e.g., $Alq_3$ or the like); phenanthroline-based compounds (e.g., 2,9-dimethyl-4,7-diphenyl-1,10-phenanthroline ("DDPA"), 4,7-diphenyl-1,10-phenanthroline ("DPA"), or the like; azole compounds (e.g., 2-(4-biphenylyl)-5-(4-t-butylphenyl)-1,3,4-oxadiazole ("PBD") or the like, 3-(4-biphenylyl)-4-phenyl-5-(4-t-butylphenyl)-1,2,4-triazole ("TAZ") or the like; other similar compounds; or any one or more combinations thereof. Alternatively, optional layer (d) may be inorganic and comprise BaO, LiF, $Li_2O$, or the like. Preferred electrontransporting materials are tris(8-hydroxyquinolato)aluminium ($Alq_3$), bis(2-methyl-8-hydroxyquinaolato)(p-phenylphenolato) aluminium (BAlq), tetrakis(8-hydroxyquinolato)zirconium (ZrQ) and mixtures thereof.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e.g., Li, Na, K, Rb, Cs), the Group 2 (alkaline earth) metals, the Group 12 metals, the rare earths, the lanthanides (e.g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer (s) may be present within organic electronic devices. For example, a layer (not shown) between the hole injecting layer (b) and the active layer (c) may facilitate positive charge transport, band-gap matching of the layers, function as a protective layer, or the like. Similarly, additional layers (not shown) between the electron injecting layer (d) and the cathode layer (e) may facilitate negative charge transport, band-gap matching between the layers, function as a protective layer, or the like. Layers that are known in the art can be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The charge transport layers (b) and (d) are generally of the same type as the active layer (c). More specifically, if the active layer (c) has a small molecule compound, then the charge transport layers (b) and (d), if either or both are present, can have a different small molecule compound. If the active layer (c) has a polymer, the charge transport layers (b) and (d), if either or both are present, can also have a different polymer. Still, the active layer (c) may be a small molecule compound, and any of its adjacent charge transport layers may be polymers.

Each functional layer may be made up of more than one layer. For example, the cathode layer may comprise a layer of a Group 1 metal and a layer of aluminum. The Group 1 metal may lie closer to the active layer (c), and the aluminum may help to protect the Group 1 metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. For example, when a potential light-emitting compound, such as $Alq_3$ is used in the electron transport layer (d), the electron-hole recombination zone can lie within the $Alq_3$ layer.

The emission would then be that of $Alq_3$, and not a desired sharp emission. Thus, the thickness of the electron-transport layer should be chosen so that the electron-hole recombination zone lies within the light-emitting layer (i.e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material (s) that for their particular applications.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source (s) may be electrically connected to the electronic device as part of a circuit.

In other embodiments, the metal complex compound can be used as a charge transport material in layer (b) or (d).

The compound does not need to be in a solid matrix diluent (e.g., host charge transport material) when used in layer (b) (c), or (d) in order to be effective. A layer greater than approximately 1% by weight of the metal complex compound, based on the total weight of the layer, and up to substantially 100% of the complex compound can be used as the active layer (c). Additional materials can be present in the active layer (c) with the complex compound. For example, a fluorescent dye may be present to alter the color of emission.

A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

The metallic complexes may be used in applications other than electronic devices. For example, the complexes may be used as catalysts or indicators (e.g., oxygen-sensitive indicators, phosphorescent indicators in bioassays, or the like).

The following examples illustrate certain features and advantages of the present invention. They are intended to be illustrative of the invention, but not limiting. All percentages are by weight, unless otherwise indicated.

EXAMPLES

Example 1

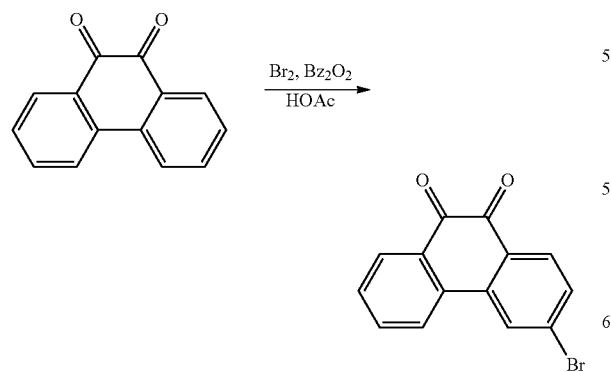

a) 41.6 g (0.20 mol) of 9,10-dioxophenanthrene are suspended under nitrogen in 500 ml of acetic acid and treated at 106° C. with 2.4 g (0.01 mol) of dibenzoyl peroxide, followed by dropwise addition of 35.2 g (0.22 mol) of bromine during 75 min. An additional 35.2 g (0.22 mol) of bromine are added dropwise during 75 min, followed by another 25.6 g (0.16 mol) of bromine during 45 min. The reaction mixture is further heated for 3 h at 106° C., followed by stirring at room temperature for 20 h. The yellow suspension is filtered, washed with a small amount of acetic acid, followed by washing with 500 ml of water and 500 ml of ethanol. The remaining yellow solid (80 g) is dissolved in hot N,N-dimethylformamide (DMF), and the solution cooled down to room temperature, until precipitation started. Precipitation is completed by stirring at room temperature for one hour. The precipitated solid is filtered off, washed with a small amount of DMF, and additional amounts of methanol and hexane. The title product is obtained as a yellow powder after drying under vacuum at 50° C. (yield: 34.8 g (61%)).

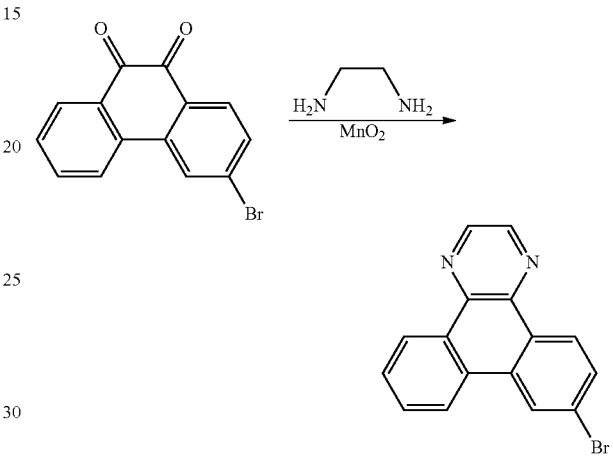

b) 1.6 g (26.8 mmol) of 1,2-diaminoethane are added under nitrogen to a suspension of 6.4 g (22.3 mmol) of the product of example 1a in 100 ml of toluene. The yellow suspension is heated under reflux for 24 h using a water separator. The resulting brownish suspension is treated with 10.0 g of manganese(IV)oxide at 104° C. Heating is continued under reflux until no intermediate product is visible anymore on the TLC (after 10 min reaction time). The hot black suspension is filtered and the solid residue rinsed with 100 ml of toluene. The filtrate is concentrated and further dried under vacuum, giving the title product as yellow solid (yield: 6.3 g (91%)).

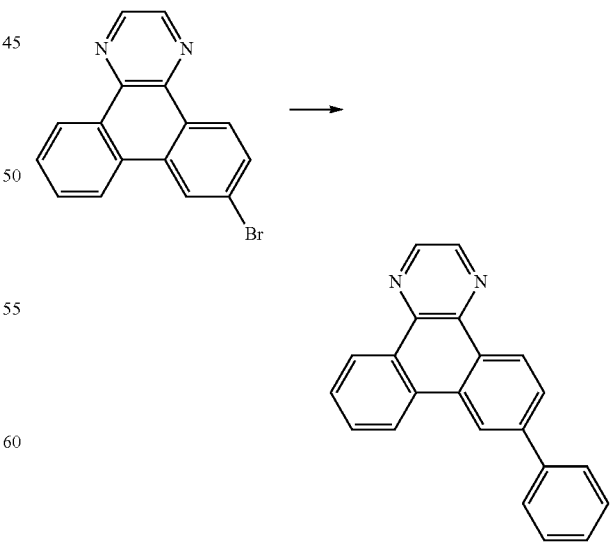

c) 3.1 g (0.01 mol) of the product of example 1b, and 1.34 g (0.011 mol) of phenylboronic acid are suspended under argon in 100 ml of dioxane and 350 ml of toluene. 0.02 g (0.09 mmol) of palladium(II) acetate and 0.25 g (0.61 mmol) of 2-dicyclohexyl-phosphino-2',6'-dimethoxybiphenyl are added, and the reaction mixture is degassed with argon. A degassed solution of 11.5 g (0.05 mol) of potassium phosphate hydrate in 25 ml of water is added. The yellow suspension is heated under reflux for 6 h. The resulting grey biphasic solution is filtered through Hyflo and the filter cake washed with toluene. The filtrate is further extracted with water (3×50 ml), and the organic phase concentrated and dried under vacuum, giving the title product as a light yellow solid (yield: 3.0 g (quantitative)). Melting point: 176-178° C.

Example 2

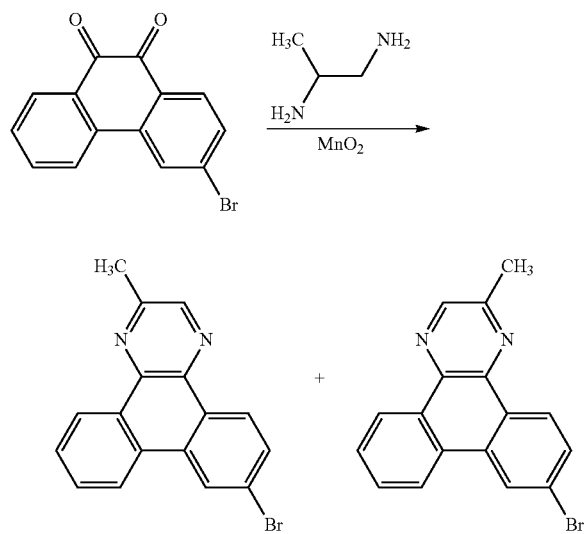

a) The title product isomer mixture is prepared according to the procedure of example 1b, with 1,2-diaminopropane. The $^1$H-NMR spectra shows two product isomers formed in a 1:1-ratio.

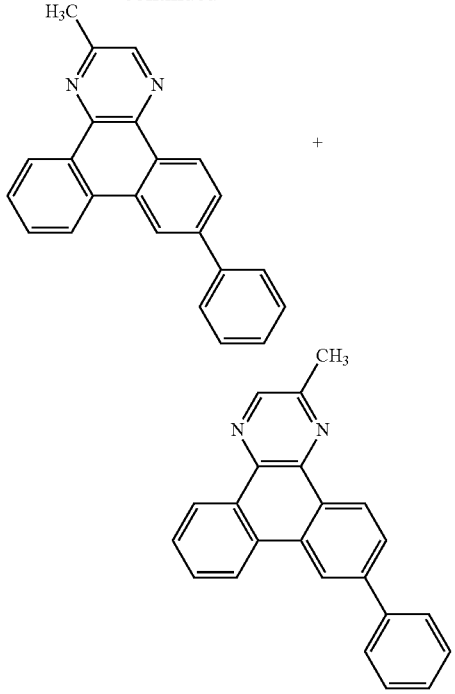

b) 16.2 g (0.05 mol) of the product isomer mixture of example 2a, and 6.7 g (0.055 mol) of phenylboronic acid are suspended under argon in 100 ml of dioxane and 300 ml of toluene. 0.11 g (0.49 mmol) of palladium(II) acetate and 1.23 g (3.0 mmol) of 2-dicyclohexyl-phosphino-2',6'-dimethoxybiphenyl are added, and the reaction mixture is degassed with argon. A degassed solution of 57.6 g (0.25 mol) of potassium phosphate hydrate in 100 ml of water is added. The yellow suspension is heated under reflux for 2 h. The resulting grey biphasic solution is filtered through Hyflo and the filter cake washed with toluene. The filtrate is further extracted with water (3×150 ml), the organic phase concentrated, and the resulting solid recrystallized from 700 ml of acetone. The solid is filtered off and dried under vacuum at 50° C., giving the title product isomer mixture as a light yellow solid (yield: 8.2 g (51%)). Melting point: 158-162° C.

Example 3

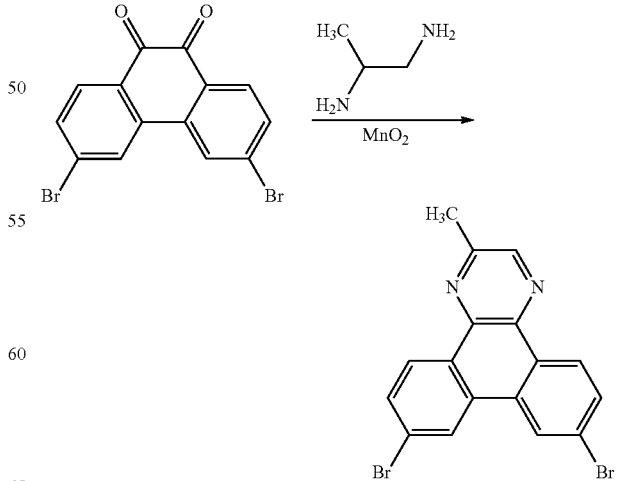

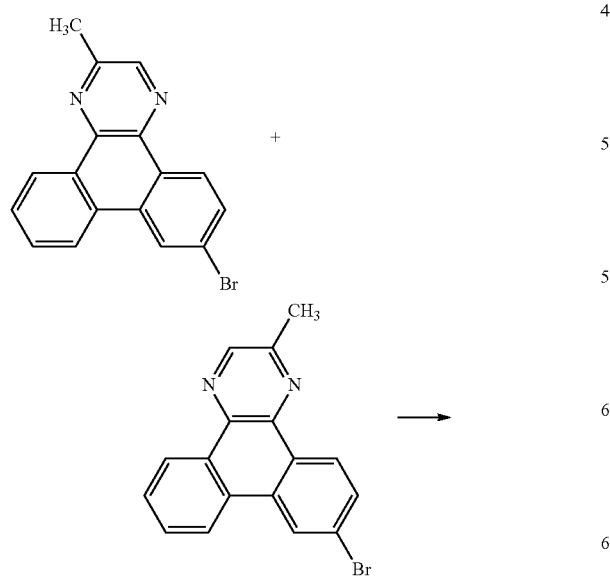

a) 5.4 g (72 mmol) of 1,2-diaminopropane are added to a suspension of 22.0 g (0.06 mol) of 3,6-dibromo-9,10-dioxophenanthrene in 600 ml of toluene. The brown suspension is heated under reflux for 24 h using a water separator. The resulting brownish suspension is treated with 30.0 g of manganese(IV)oxide at 93° C., followed by the addition of 600 ml of toluene. Heating is continued under reflux until no intermediate product is visible anymore on the TLC (after 45 min reaction time). The hot black suspension is filtered and the solid residue rinsed with 400 ml of hot toluene. The filtrate is cooled down until precipitation of a white solid started. The solid is separated and further dried under vacuum giving a light beige solid (yield: 22.2 g (92%)).

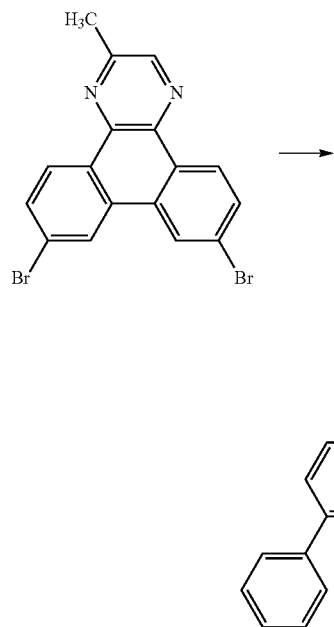

b) 20.1 g (0.05 mol) of the product of example 3a, and 13.4 g (0.11 mol) of phenylboronic acid are suspended under argon in 100 ml of dioxane and 350 ml of toluene. 0.11 g (0.49 mmol) of palladium(II) acetate and 1.23 g (3 mmol) of 2-dicyclohexyl-phosphino-2',6'-dimethoxybiphenyl are added, and the reaction mixture is degassed with argon. A degassed solution of 57.6 g (0.25 mol) of potassium phosphate hydrate in 70 ml of water is added. The yellow suspension is heated under reflux for 90 min. The resulting grey biphasic solution is filtered through Hyflo and the filter cake washed with hot toluene, followed by washing with ethanol. The filtrate is suspended with water, followed by filtration, suspension with water, filtration, and washing with ethanol. The resulting solid is dried under vacuum at 55° C. giving a light pink solid (yield: 17.8 g (90%)). Melting point: 197-199° C.

Example 4

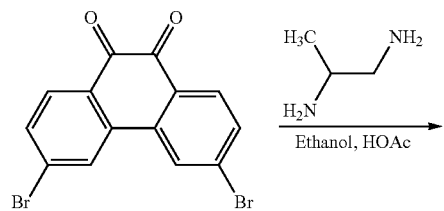

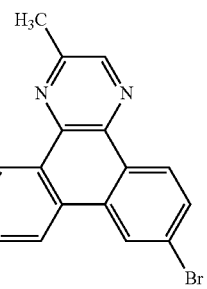

a) 4.86 g (65.6 mmol) of 1,2-diaminopropane are added to a suspension of 20.0 g (54.6 mmol) of 3,6-dibromo-9,10-dioxophenanthrene in 300 ml of ethanol (99%). The reaction mixture is heated under reflux for 6 h. 400 ml of acetic acid are added to the reaction mixture and heating under reflux is continued for 19 h. The resulting beige suspension is cooled down to room temperature, filtered, and washed with ethanol, followed by washing with saturated aqueous sodium bicarbonate, water, and ethanol. 20.2 g of a beige solid are obtained after filtration and drying under vacuum. The solid is further soxhlet extracted with toluene giving the title compound as a light beige solid (yield: 13.0 g (59%)).

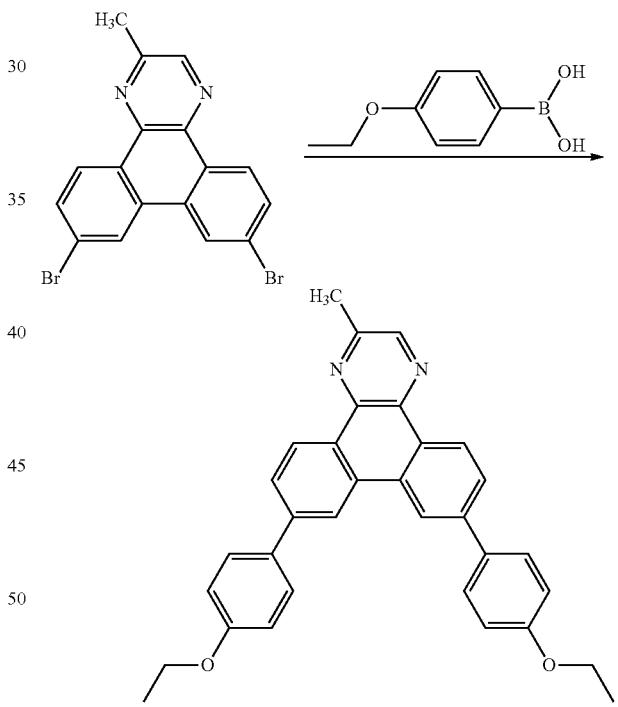

b) 1.00 g (2.49 mmol) of the product of example 4a, and 1.03 g (6.22 mmol) of 4-ethoxyphenyl-boronic acid and 61 mg (0.15 mmol) of 2-dicyclohexyl-phosphino-2',6'-dimethoxybiphenyl are dissolved in 30 ml of toluene and 30 ml of dioxane. The reaction mixture is degassed with argon. 5.6 mg (0.025 mmol) of palladium(II) acetate are added and the reaction mixture is degassed with argon. A degassed solution of 2.86 g (12.4 mmol) of potassium phosphate hydrate in 5 ml of water is added. The reaction mixture is heated under reflux for 3 h. 30 ml of a 1% aqueous NaCN solution is added and the reaction mixture is stirred for 2 h at room temperature. The solution is poured into 150 ml of methanol and the product is filtered off. The product is washed with water and methanol giving the title compound as a light yellow solid (yield: 0.92 g (76%)). Melting point: 249.0-251.5° C.

Example 5

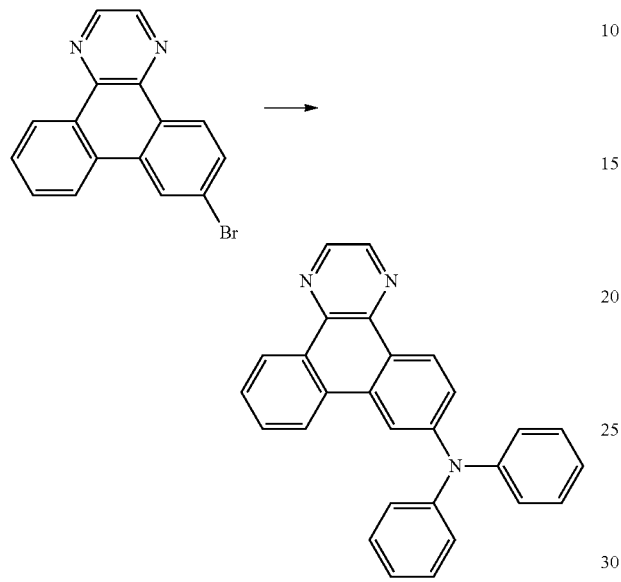

4.2 g (0.044 mol) of sodium tert-butylate are added to 12.4 g (0.04 mol) of the product of example 1b in 300 ml of toluene. The reaction mixture is degassed with argon and 0.45 g (2 mmol) of palladium(II) acetate and 4.0 ml (4 mmol) of a 1.0M solution of tri-tert-butylphosphine in toluene are added, followed by degassing with argon, and addition of 6.8 g (0.04 mol) of diphenylamine. The reaction mixture is stirred for 30 min at 110° C., cooled down to room temperature and stirred together with 1 g of activated charcoal. The mixture is filtered over silica gel and the silica gel washed with 200 ml of ethyl acetate. The collected organic phases are extracted with water (2×200 ml) and concentrated under vacuum, providing a yellow-brownish resin. The resin is dissolved with 50 ml of hot dichloromethane, and cooled down to room temperature. A precipitate is formed which is filtered off, washed with a 20 ml of acetone, and dried under vacuum, giving the title product as a yellow solid (yield: 13.0 g (82%)). Melting point: 179-181° C.

Example 6

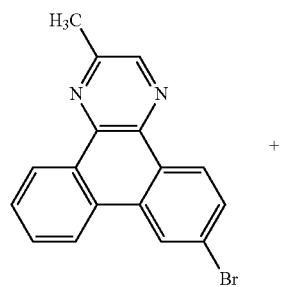

+

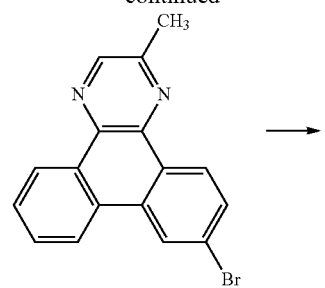

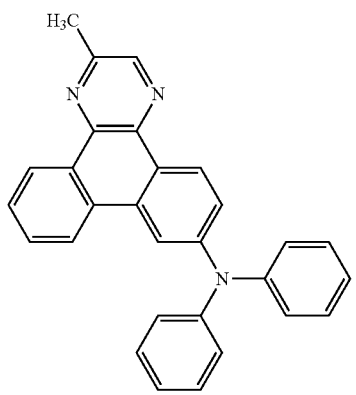

+

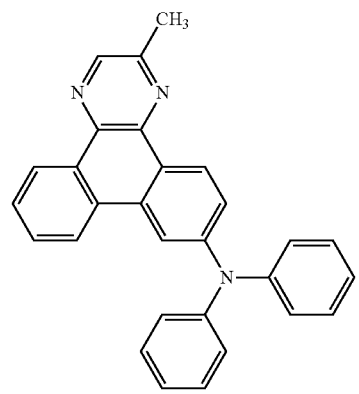

3.2 g (0.033 mol) of sodium tert-butylate are added to 9.7 g (0.03 mol) of the product of example 2a in 300 ml of toluene. The reaction mixture is degassed with argon and 0.34 g (1.5 mmol) of palladium(II) acetate and 3.0 ml (3 mmol) of a 1.0M solution of tri-tert-butylphosphine in toluene are added, followed by degassing with argon, and addition of 5.1 g (0.03 mol) of diphenylamine. The reaction mixture is stirred for 30 min at 110° C., cooled down to room temperature and stirred together with 1 g of activated charcoal. The mixture is filtered over silica gel and the silica gel washed with 200 ml of ethyl acetate. The collected organic phases are extracted with water (2×200 ml) and concentrated under vacuum. The product is recrystallized from acetone, the solid filtered off, and washed with cold acetone, giving the title product isomer mixture as a yellow solid (yield: 9.6 g (78%)). The $^1$H-NMR spectra shows two product isomers formed in a 1:1-ratio. Melting point: 165-168° C.

Example 7

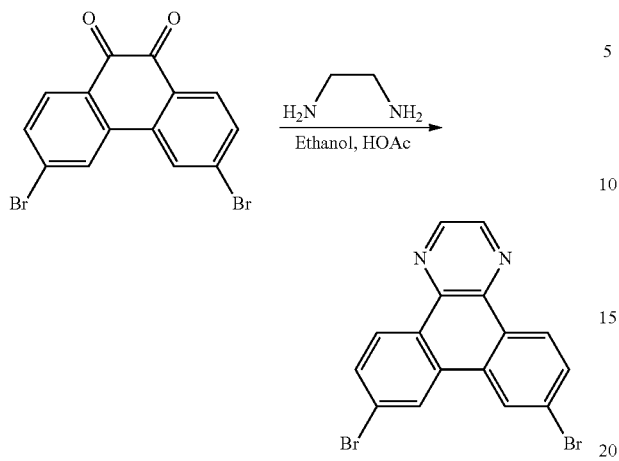

a) 3.94 g (65.6 mmol) of 1,2-diaminoethane are added under nitrogen to 20.0 g (54.6 mmol) of 3,6-dibromo-9,10-dioxophenanthrene in 350 ml of water free ethanol. The reaction mixture is refluxed for 8 h. 400 ml of glacial acetic acid are added and reflux is continued for additional 9 h under air. The reaction mixture is cooled to 25° C., the product is filtered off, washed with ethanol and dried under vacuum at 50° C. The crude product is further soxhlet extracted with toluene giving the title compound as a light beige solid (yield: 16.0 g (76%). Melting point: 278.0-282.0° C.

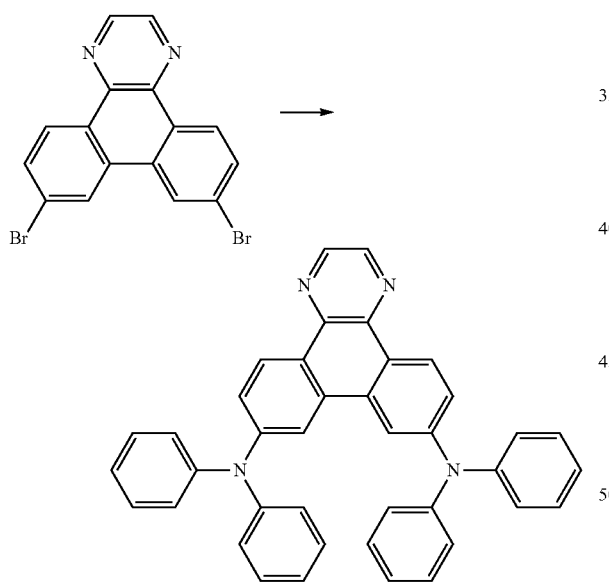

b) 2.27 g (23.6 mmol) of sodium tert-butylate are added to 4.36 g (11.2 mmol) of the product of example 7a in 44 ml of toluene. The reaction mixture is degassed with argon and 0.13 g (0.56 mmol) of palladium(II) acetate and 0.23 g (1.12 mmol) of tri-tert-butylphosphine are added, followed by degassing with argon. A degassed solution of 3.80 g (22.5 mmol) of diphenylamine in 15 ml toluene is added. The reaction mixture is stirred for 1 h at 110° C. under argon, cooled down to room temperature and extracted with $CH_2Cl_2$/water. The organic phase is concentrated and the resulting crude product dissolved in $CH_2Cl_2$, filtered over silica gel and the silica gel is washed with a small amount of $CH_2Cl_2$. The filtrate is concentrated, and the resulting solid dried under vacuum giving the title compound (yield: 5.52 g (87%)). Melting point: 204° C.

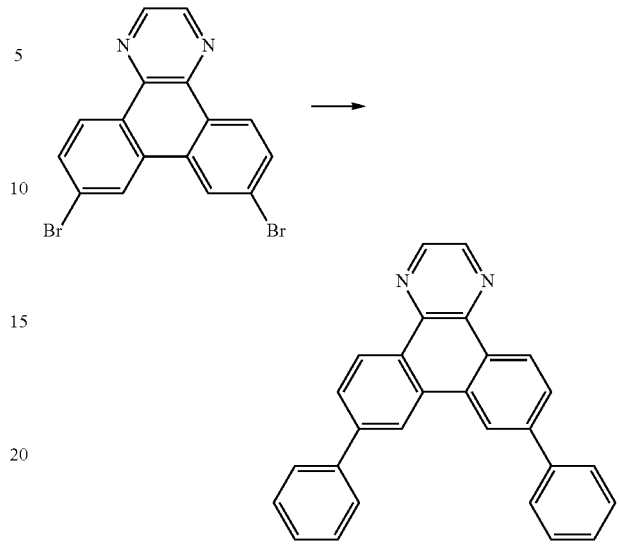

c) 12.9 g (0.033 mol) of the product of example 7a, and 8.94 g (0.073 mol) of phenylboronic acid are suspended under argon in 75 ml of dioxane and 250 ml of toluene. 0.075 g (0.33 mmol) of palladium(II) acetate and 0.82 g (2 mmol) of 2-dicyclohexyl-phosphino-2',6'-dimethoxybiphenyl are added, and the reaction mixture is degassed with argon. A degassed solution of 46 g (0.2 mol) of potassium phosphate hydrate in 70 ml of water is added. The yellow suspension is heated under reflux for 4 h. The resulting grey biphasic solution is filtered through Hyflo and the filter cake washed with hot toluene, followed by washing with ethanol. The filtrate is suspended with water, followed by filtration, suspension with water, filtration, and washing with ethanol. The resulting solid is dried under vacuum at 55° C. giving a light yellow solid (yield: 8.6 g (68%)). Melting point: 254-256° C.

Example 8

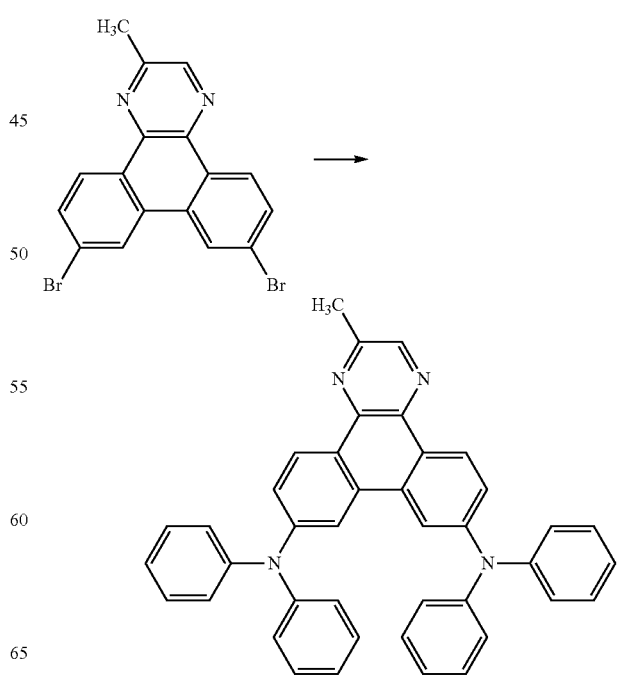

6.2 g (0.065 mol) of sodium tert-butylate are added to 12.1 g (0.03 mol) of the product of example 3a in 240 ml of toluene. The reaction mixture is degassed with argon and 0.34 g (1.5 mmol) of palladium(II) acetate and 3.0 ml (3 mmol) of a 1.0M solution of tri-tert-butylphosphine in toluene are added, followed by degassing with argon. The reaction mixture is heated up to 90° C., treated with 10.7 g (0.063 mol) of diphenylamine in 60 ml of toluene, and heating continued for 3 h at 90° C. The reaction mixture is cooled down to room temperature, two times filtered over silica gel followed by washing of the silica gel with toluene. The collected organic phases are concentrated, giving a dark brown viscous oil, which solidifies upon standing at room temperature. The crude solid is decocted two times in 150 ml of isopropanol, giving the title product as a dark yellow solid (yield: 12.3 g (80%)).

b) 46.0 g (0.2 mol) of the product of example 9a are suspended under argon in 700 ml of THF and cooled down to 0-5° C. The resulting light brownish suspension is dropwise treated at 0-5° C. over one hour with 126.0 g (0.2 mol) of a 1.9M phenyl lithium solution in dibutyl ether. Stirring is continued at the same temperature for 10 min, and for an additional 20 min up to room temperature. 15 ml of water are added first at room temperature giving a dark yellow suspension, followed by the addition of 200 ml of ethyl acetate and 70 g of manganese(IV) oxide. The black suspension is stirred at room temperature overnight, filtered, and the solid residue first washed with ethyl acetate, followed by extensive washing with dichloromethane (3×2000 ml). The combined dichloromethane eluents are concentrated under vacuum giving the title product as a white solid (yield: 46.3 g (76%)). Melting point: 204-206° C.

Example 9

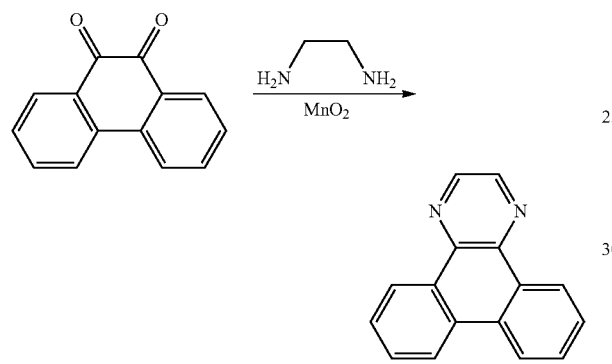

a) 18.6 g (0.31 mol) of 1,2-diaminoethane are added under nitrogen to 55.0 g (0.26 mol) of 9,10-dioxophenanthrene in 1000 ml of toluene. The red suspension is heated under reflux for 24 h using a water separator (amount of water separated: ca. 1 ml). The resulting brownish suspension is treated with 50.0 g of manganese(IV)oxide at 84° C., and heating continued under reflux until no intermediate product is visible anymore on the TLC. The hot black suspension is filtered and the solid residue rinsed with 200 ml of toluene. The solution is concentrated and the resulting solid further dried under vacuum, giving the title compound as a light yellowish solid (yield: 58.0 g (97%)).

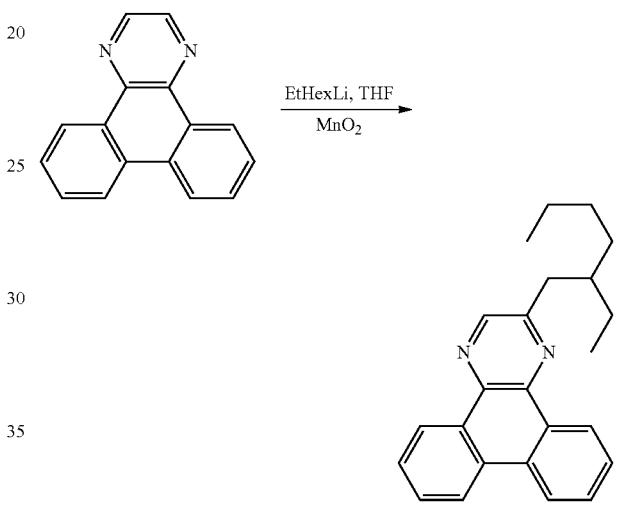

c) 10.0 g (43.4 mmol) of the product of example 9a are suspended under argon in 100 ml of THF and cooled down to −75° C. The resulting light brown suspension is dropwise treated over 30 min with 25 ml (48 mmol) of a 30-35% 2-ethylhexyllithium solution in heptane and stirring continued at the same temperature for 15 min, and for an additional 70 min up to room temperature. 100 ml of ethyl acetate and 10 g of manganese(IV) oxide are added and the black suspension stirred at 65° C. during 23 h. The suspension is filtered and the solid residue washed with 50 ml of ethyl acetate, followed by concentration of the filtrate. The residue is further eluted over silica gel using toluene as eluent. The combined fractions are concentrated under vacuum giving a light pink solid. The solid is further stirred in hot methanol, cooled down to room temperature, filtered, and washed with methanol. The resulting solid is dried under vacuum at 50° C., giving the title product as a white solid (yield: 4.5 g (31%)). Melting point: 58-59° C.

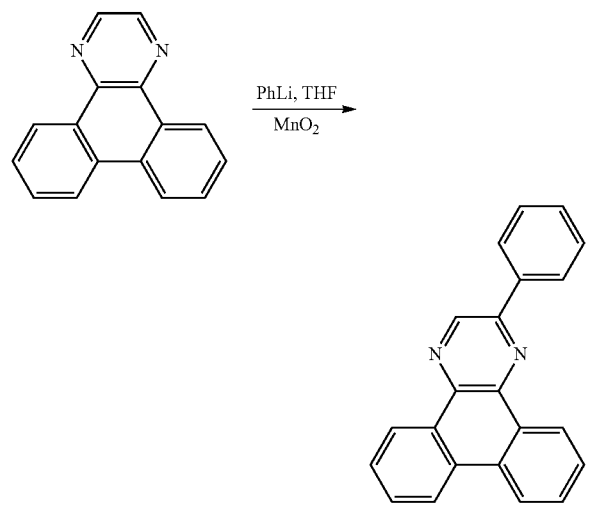

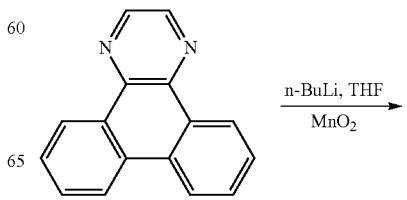

-continued

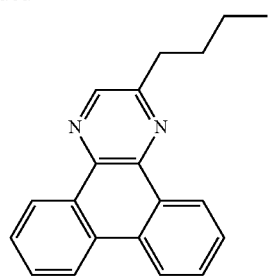

d) The title product is prepared according to the procedure of example 9c, with the product of example 9a, and with a 2.5M solution of n-butyllithium in hexane, giving the title product as a white solid in 49% yield after recrystallization from ethanol. Melting point: 66-67° C.

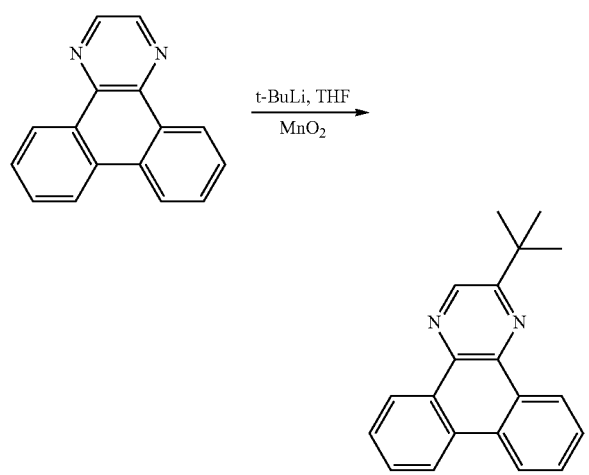

e) The title product is prepared according to the procedure of example 9c, with the product of example 9a, and with a 1.5M solution of tert-butyllithium in pentane, giving the title product as a light beige solid in 16% yield. Melting point: 61-62° C.

f) The title product is prepared according to the procedure of example 9a, using 1,2-diaminocyclohexane, and with a 2.5M solution of n-butyllithium in hexane, giving the title product as a white solid in 49% yield. Melting point: 210° C.

Example 10

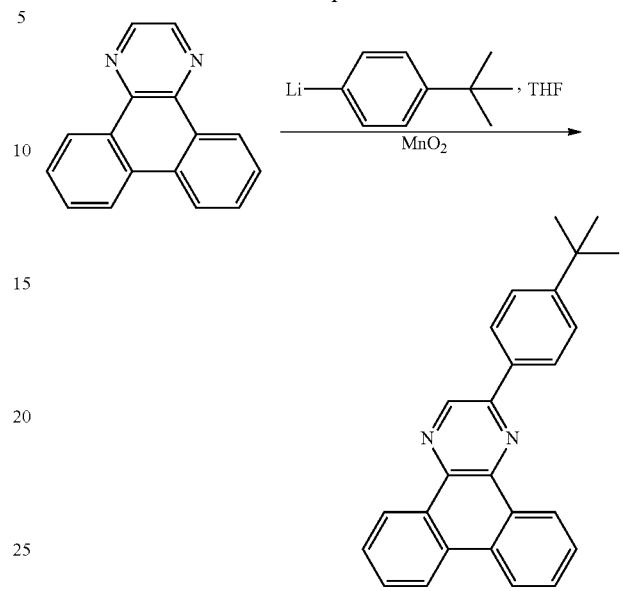

13.3 g (62.5 mmol) of 4-bromo-4-tert-butyl-benzene in 60 ml of diethyl ether are slowly treated under argon with 40 ml of a 1.5M tert-butyl lithium solution in pentane during 30 min at −75° C., followed by the addition of 30 ml of THF, giving a light yellow solution (=solution A). 11.5 g (0.05 mol) of the product of example 9a are dissolved in 250 ml of THF and slowly treated with solution A at −35° C. during one hour. The cooling bath is removed, and 250 ml of ethyl acetate and 40 g of manganese(IV) oxide added as soon as room temperature has been reached. The dark suspension is stirred during 24 h at room temperature, filtered, washed with dichloromethane, and concentrated under vacuum. The residue is suspended in ethanol, then filtered, and further dried under vacuum, giving the title product as a white solid (yield: 10.1 g (56%)). Melting point: 186-187° C.

Example 11

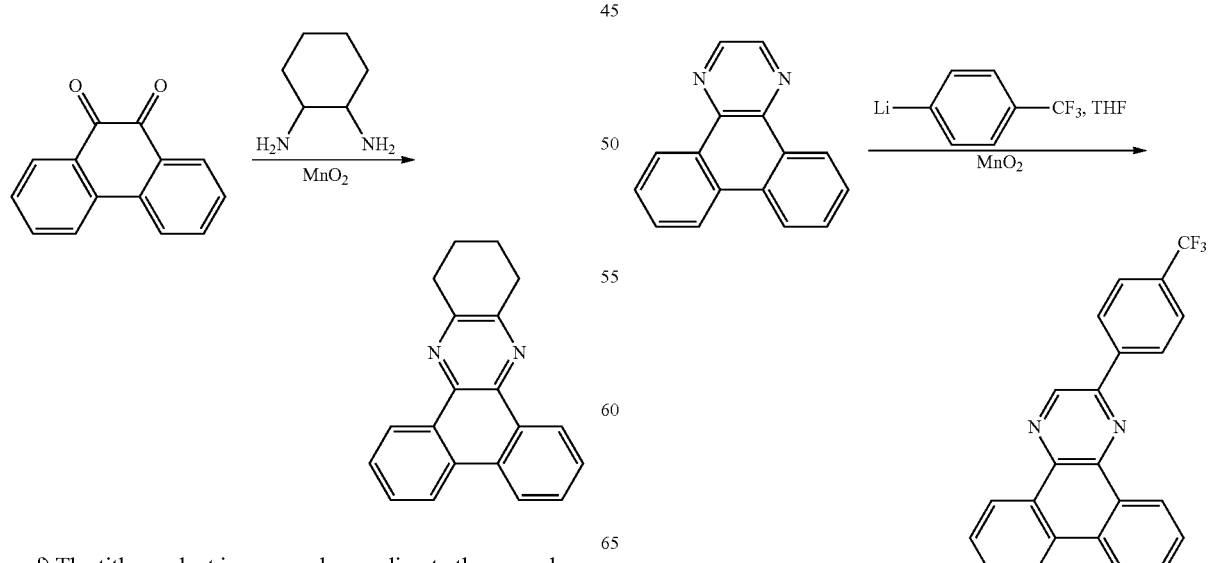

6.3 g (28 mmol) of 4-bromobenzotrifluoride in 30 ml of diethyl ether are slowly treated under argon with 15 ml of a 1.5M tert-butyl lithium solution in pentane during 30 min at −75° C., giving a yellow solution (=solution A). 4.3 g (18.7 mmol) of the product of example 9a are dissolved in 50 ml of THF and slowly treated with solution A at −15° C. during 30 min, followed by the addition of 100 ml of ethyl acetate, and subsequent warming up to 18° C. Manganese(IV) oxide (20 g) is added and the dark suspension stirred during 24 h at room temperature. An additional 20 g of manganese(IV) oxide are added and stirring continued until no more intermediate product is visible by TLC. The dark suspension is filtered, washed with ethyl acetate, concentrated, and stirred with hot hexane until a solid formed. The solid is separated and suspended in ethyl acetate, followed by filtration over silica gel using ethyl acetate as eluent. The combined eluents are concentrated and dried under vacuum giving the title product as a white solid (yield: 4.2 g (74%)). Melting point: 222-224° C.

Example 12

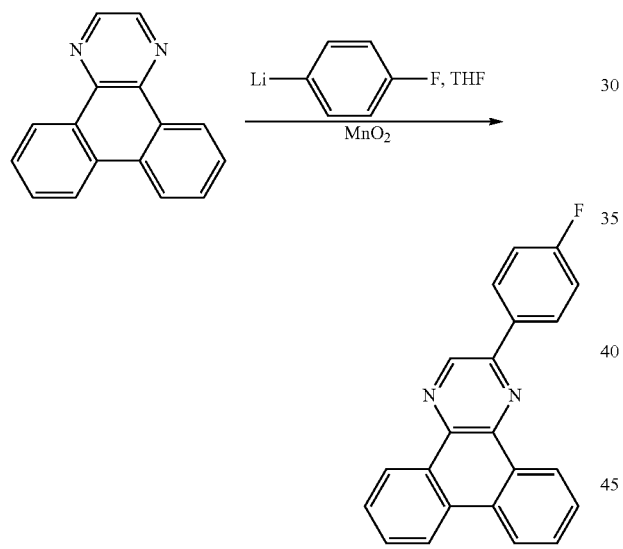

10.95 g (62.5 mmol) of 1-bromo-fluorobenzene in 60 ml of THF are slowly treated under argon with 40 ml of a 1.5M tert-butyl lithium solution in pentane during 30 min at −75° C., followed by the addition of 30 ml of THF, giving a light yellow solution (=solution A). 11.5 g (0.05 mol) of the product of example 9a are dissolved in 250 ml of THF and slowly treated with solution A at −35° C. during one hour. The cooling bath is removed, and 250 ml of ethyl acetate and 40 g of manganese(IV) oxide added as soon as room temperature has been reached. The dark suspension is stirred during 24 h at room temperature, filtered through a filter aid (2 cm of Hyflo). The solid is washed with ethyl acetate first, followed by washing with 500 ml of dichloromethane and 500 ml of acetone. The ethyl acetate fraction is concentrated under vacuum, giving the title product containing side products (12.3 g isolated solid). The dichloromethane and acetone fractions are combined and concentrated under vacuum, giving the title product in high purity as a white solid (yield: 5.0 g (28%)). Melting point: 206-208° C.

Example 13

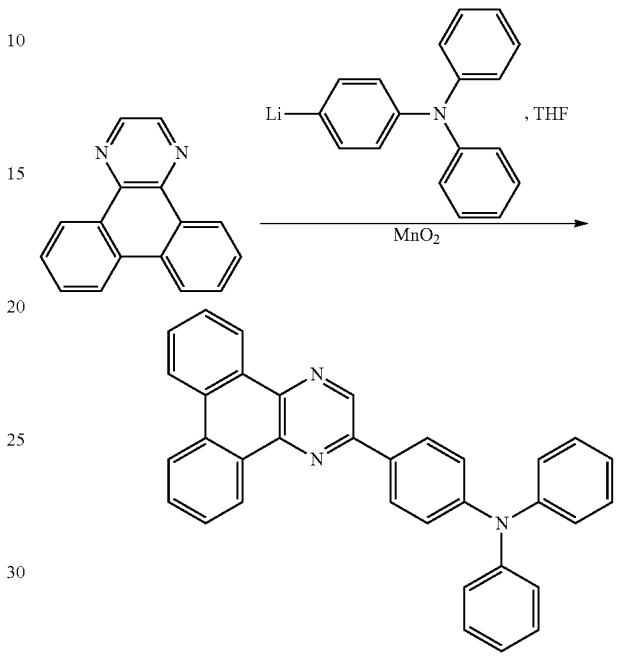

9.7 g (0.03 mol) of 1-bromo-triphenylamine in 60 ml of THF are slowly treated under argon with 24 ml of a 1.5M tert-butyl lithium solution in pentane during 45 min at −75° C., giving a brown solution (=solution A). 6.9 g (0.03 mol) of the product of example 9a are dissolved in 150 ml of THF and slowly treated with solution A at −50° C. during one hour. The cooling bath is removed, and 1 ml of water and 15 g of manganese(IV) oxide added as soon as room temperature has been reached. The dark suspension is stirred during 2 h at room temperature, filtered through Hyflo, and the filtrate concentrated under vacuum. The resulting solid is recrystallized from isopropanol first, washed with acetone, and recrystallized from acetone. The solid is filtered off, dried under vacuum, giving the title product as a light yellow solid (yield: 2.5 g (18%)). Melting point: 216-218° C.

Example 14

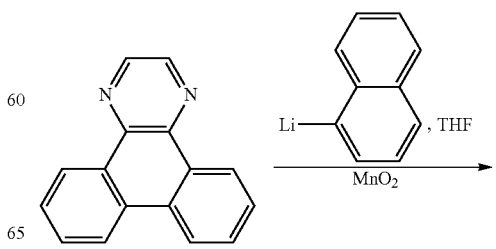

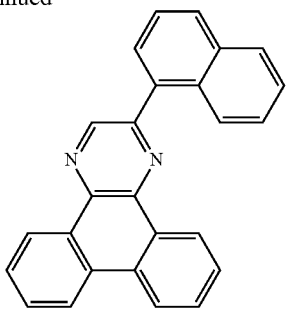

13.0 g (62.5 mmol) of 1-bromonaphthalene in 60 ml of THF are slowly treated under argon with 40 ml of a 1.5M tert-butyl lithium solution in pentane during 40 min at −75° C., giving a yellow solution (=solution A). 11.5 g (50 mmol) of the product of example 9a are dissolved in 250 ml of THF and slowly treated with solution A at −30° C. during 30 min, followed by warming up to room temperature. Manganese (IV) oxide (20 g) is added and the dark suspension stirred during 24 h at room temperature. An additional 20 g of manganese(IV) oxide are added and stirring continued until no more intermediate product is visible by TLC. The dark suspension is filtered, washed with dichloromethane, and concentrated under vacuum. The resulting yellow solid is suspended in hot ethyl acetate, filtered, rinsed with ethyl acetate, and dried under vacuum, giving a beige solid (yield: 7.7 g (43%)). Melting point: 205-206° C.

Example 15

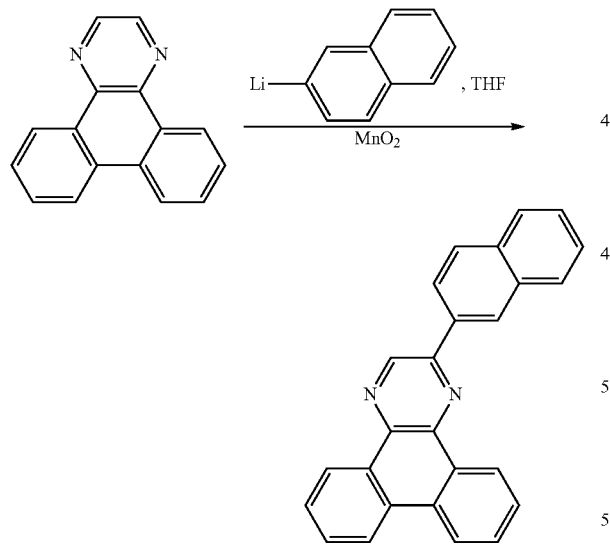

13.0 g (62.5 mmol) of 2-bromonaphthalene in 60 ml of THF are slowly treated under argon with 40 ml of a 1.5M tert-butyl lithium solution in pentane at −75° C. during 30 min, giving a yellow solution (=solution A). 11.5 g (50 mmol) of the product of example 9a are dissolved in 250 ml of THF and slowly treated with solution A at −30° C. during 40 min, followed by warming up to room temperature. Manganese (IV) oxide (20 g) is added and the dark suspension stirred during 24 h at room temperature. The dark suspension is filtered, washed with dichloromethane, and concentrated under vacuum. The resulting yellow solid is suspended in hot ethyl acetate, filtered, rinsed with ethyl acetate, and dried under vacuum, giving a light beige solid (yield: 8.3 g (47%)). Melting point: 216-217° C.

Example 16

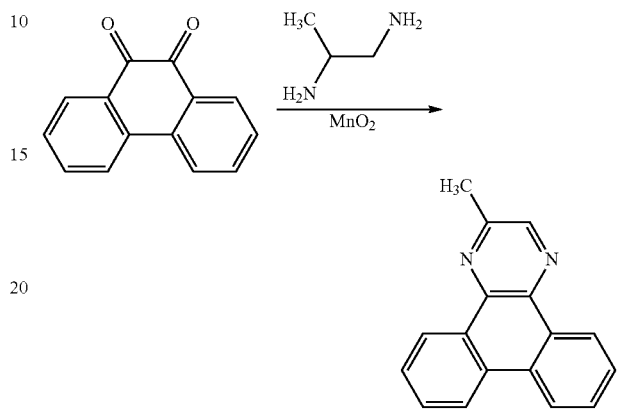

a) 44.5 g (0.6 mol) of 1,2-diaminopropane are added under nitrogen to 104 g (0.5 mol) of 9,10-dioxophenanthrene in 2000 ml of toluene. The red suspension is heated under reflux for 24 h using a water separator. The resulting brownish suspension is treated with 200 g of manganese(IV)oxide at 88° C., and heating continued under reflux until no intermediate product is visible anymore on the TLC. The hot black suspension is filtered through silica gel (5 cm layer), and the silica gel layer rinsed with 200 ml of hot toluene. The collected eluents are concentrated and dried under vacuum, giving the title product as a colorless solid (yield: 103 g (92%)).

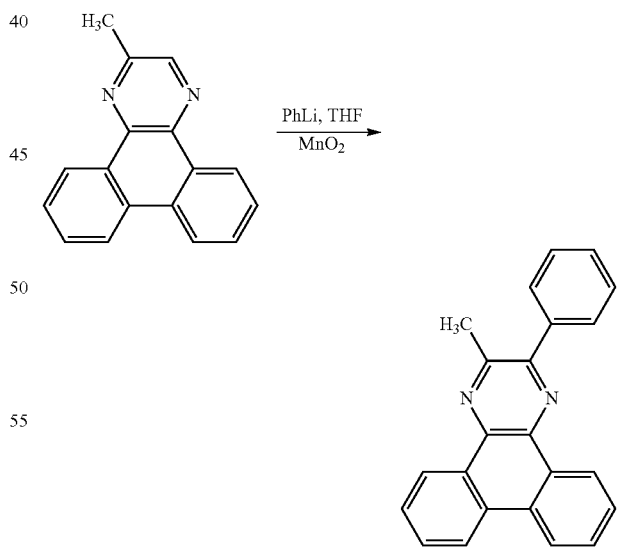

b) The title product is prepared according to the procedure of example 9b, with 12.2 g (0.05 mol) of the product of example 16a, 31.2 ml of a 1.6M phenyl lithium solution in dibutyl ether at 0-5° C., followed by an additional 8 ml of phenyl lithium solution at 22° C., and 15 g of manganese(IV) oxide. The resulting black suspension is filtered, and the solid residue washed with dichloromethane. The collected eluents are concentrated and dried under vacuum giving the title product as yellow solid (yield: 16.0 g (quantitative)). Melting point: 164-166° C.

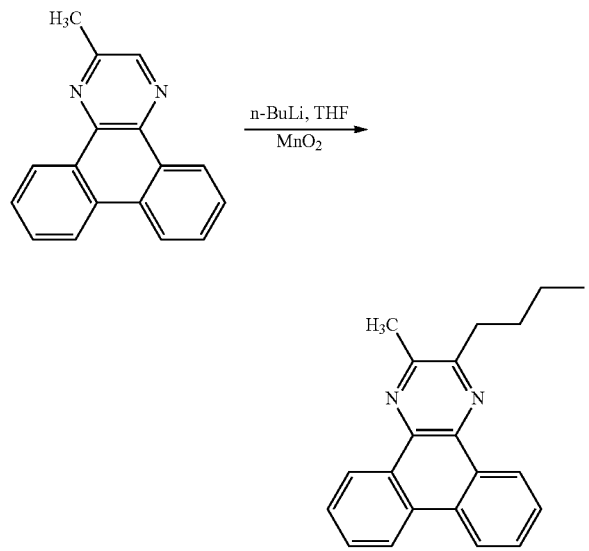

c) The title product is prepared according to the procedure of example 9c, with the product of example 16a, and with a 2.5M solution of n-butyllithium in hexane, giving the title product as a white solid in 57% yield. Melting point: 103° C.

Example 17

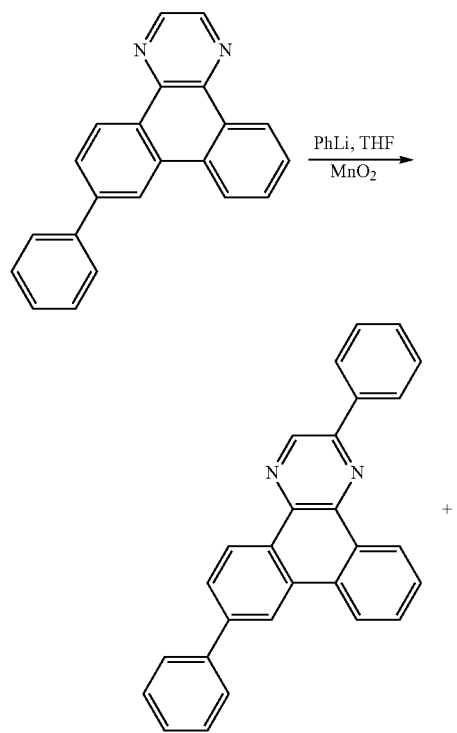

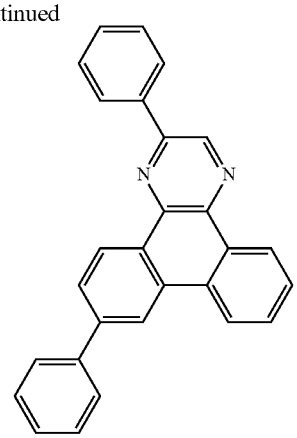

The title product isomer mixture is prepared according to the procedure of example 9b, with the product of example 1c as starting material. The $^1$H-NMR spectra shows two product isomers formed in a 1:1-ratio. Melting point: 215-216° C.

Example 18

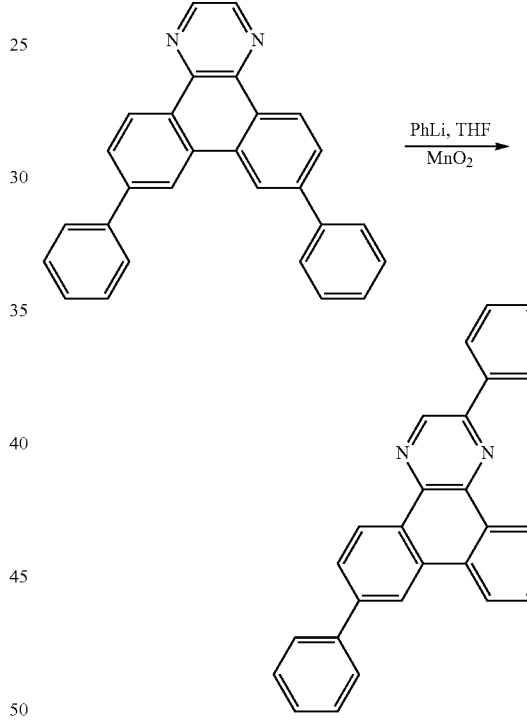

3.8 g (0.01 mol) of the product of example 7c are suspended under argon in 50 ml of diethyl ether and cooled down to 0° C. The resulting light yellow suspension is dropwise treated at 2° C. over 20 min with 5.3 ml (0.01 mol) of a 1.9M phenyl lithium solution in dibutyl ether. Stirring is continued up to room temperature for 35 min. An additional 2 ml of phenyl lithium solution are added and stirring continued for 15 min. The resulting dark suspension is treated with 5 g of manganese(IV) oxide and stirred at room temperature for 30 min. The black suspension is filtered, and the remaining solid washed with 300 ml of ethyl acetate, followed by 300 ml of toluene, and 200 ml of dichloromethane, and further decocting in 300 ml of toluene. All toluene and dichloromethane washings are combined and concentrated under vacuum. The residue is decocted in 200 ml of toluene first, the resulting yellow suspension filtered, and the remaining solid dried under vacuum, giving the product as a yellow solid. Melting point: 275-276° C.

Example 19

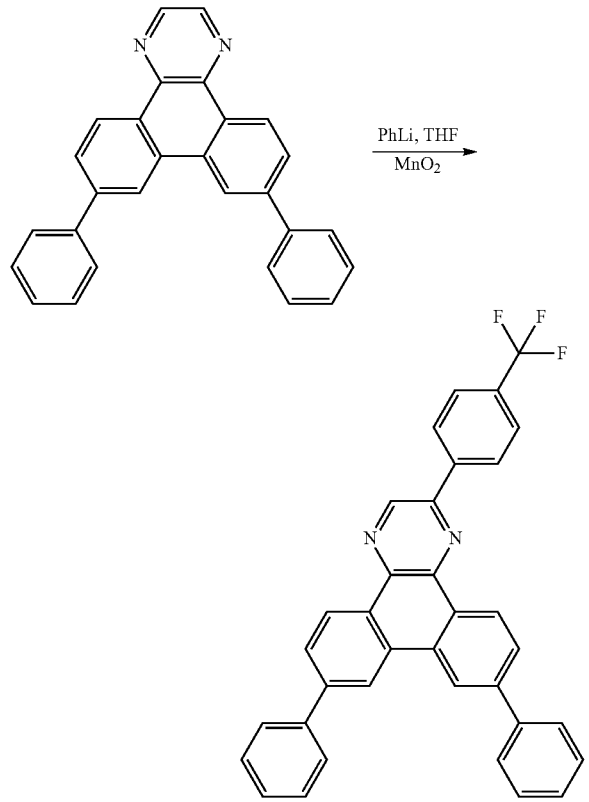 [SMILES: c1ccc(-c2ccc3c(c2)c2cc(-c4ccccc4)ccc2c2nccnc32)cc1 ; "MnO2" ; c1ccc(-c2ccc3c(c2)c2cc(-c4ccccc4)ccc2c2nc(-c4ccccc4)cnc32)cc1]

5.4 g (24 mmol) of 4-bromobenzotrifluoride in 30 ml of diethyl ether are slowly treated under argon with 14.7 ml of a 1.5M tert-butyl lithium solution in pentane during 30 min at −75° C., giving a yellow solution (=solution A). 7.65 g (0.02 mol) of the product of example 7c are dissolved in 250 ml of THF and slowly treated with solution A during 30 min at −35° C., and subsequent warming up to room temperature. Manganese(IV) oxide (20 g) is added and the dark suspension stirred during 24 h at room temperature. The dark suspension is filtered, washed with ethyl acetate and concentrated. The solid is suspended in ethyl acetate, filtered, and dried under vacuum giving the title product as a light yellow solid (yield: 5.0 g (48%)). Melting point: 279-283° C.

Example 20

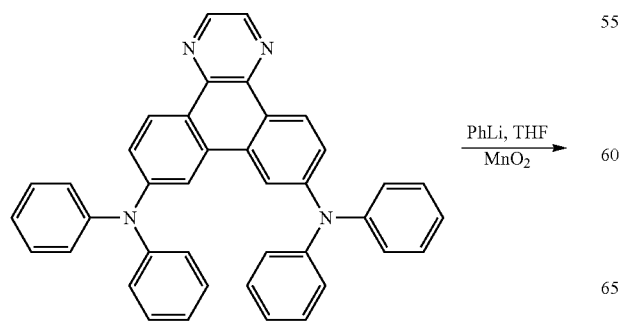

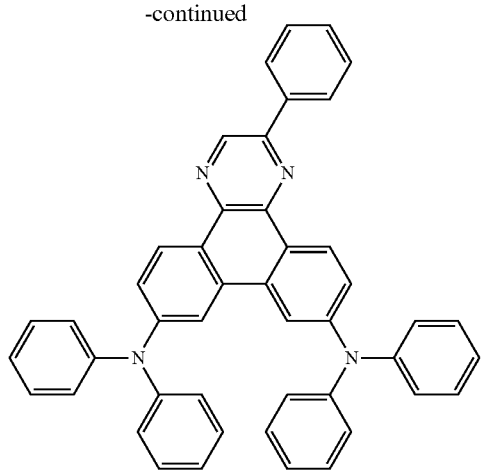

5.6 g (0.01 mol) of the product of example 7b are suspended under argon in 100 ml of diethyl ether and cooled down to 0° C. The resulting yellow suspension is dropwise treated over 20 min at 2° C. with 6.3 ml of a 1.6M phenyl lithium solution in diethyl ether. Stirring is continued for 20 min at 2° C., and then up to room temperature for 15 min. An additional 3 ml of phenyl lithium solution are added and stirring continued for 25 min. The resulting red suspension is diluted with 100 ml of ethyl acetate, treated with 15 g of manganese(IV) oxide and stirred for 24 h at room temperature. The black suspension is filtered, the remaining solid washed with ethyl acetate, and concentrated under vacuum. The dark resin is taken up in 50 ml of ethyl acetate, providing a precipitate by heating the mixture under relux. The suspension is filtered, the solid decocted in 50 ml of ethyl acetate, filtered, and dried under vacuum at 50° C., giving the title product as a yellow solid (yield: 3.9 g (61%)). Melting point: 256-259° C.

Example 21

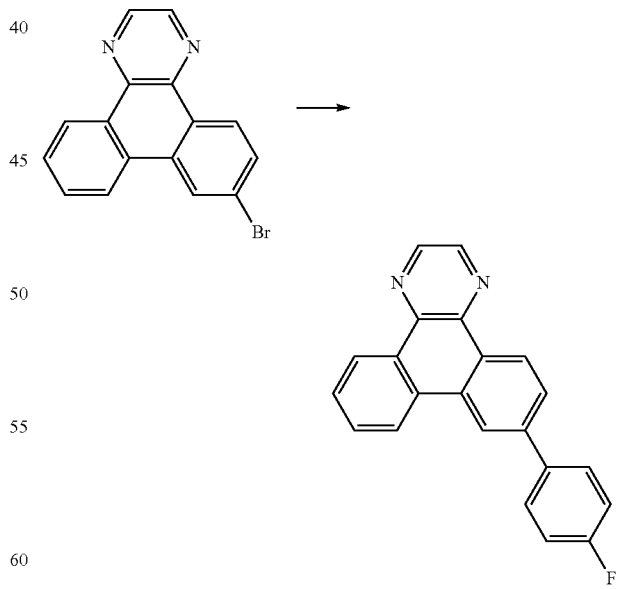

6.2 g (0.02 mol) of the product of example 1b, and 3.1 g (0.022 mol) of 4-fluorobenzeneboronic acid are suspended under argon in 50 ml of dioxane and 150 ml of toluene. 0.04 g (0.18 mmol) of palladium(II) acetate and 0.5 g (1.2 mmol) of 2-dicyclohexyl-phosphino-2',6'-dimethoxybiphenyl are added, and the reaction mixture is degassed with argon. A degassed solution of 23.0 g (0.1 mol) of potassium phosphate hydrate in 50 ml of water is added. The yellow suspension is heated under reflux for 2 h. The resulting grey biphasic solution is filtered through Hyflo and the filter cake washed with toluene. The filtrate is further extracted with water (3×50 ml), and the organic phase concentrated. The resulting solid is recrystallized from 250 ml of ethyl acetate, filtered, washed with a small amount of cold ethyl acetate, and dried under vacuum, giving the title product as a light yellow solid (yield: 4.7 g (63%)). Melting point: 200-201° C.

Example 22

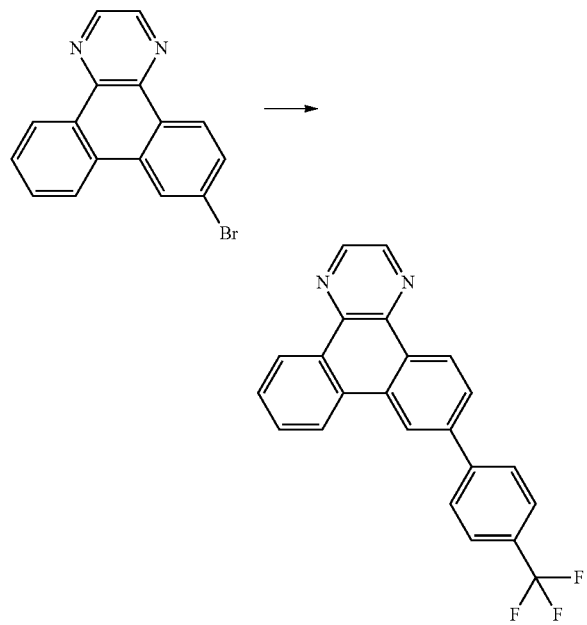

6.2 g (0.02 mol) of the product of example 1b, and 4.1 g (0.022 mol) of 4-(trifluoromethyl)-benzeneboronic acid are suspended under argon in 50 ml of dioxane and 150 ml of toluene. 0.04 g (0.18 mmol) of palladium(II) acetate and 0.5 g (1.2 mmol) of 2-dicyclohexyl-phosphino-2',6'-dimethoxybiphenyl are added, and the reaction mixture is degassed with argon. A degassed solution of 23.0 g (0.1 mol) of potassium phosphate hydrate in 50 ml of water is added. The yellow suspension is heated under reflux for 2 h. The resulting grey biphasic solution is filtered through Hyflo and the filter cake washed with toluene. The filtrate is further extracted with water (3×50 ml), and the organic phase concentrated. The resulting solid is recrystallized from 250 ml of ethyl acetate, filtered, washed with a small amount of cold ethyl acetate, and dried under vacuum, giving the title product as a light yellow solid (yield: 4.7 g (63%)). Melting point: 207-208° C.

Example 23

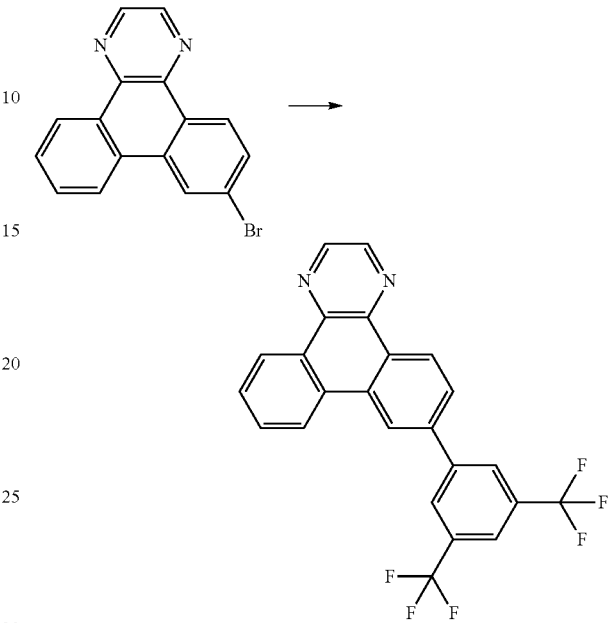

6.2 g (0.02 mol) of the product of example 1b, and 5.67 g (0.022 mol) of 3,5-bis(trifluoromethyl)-benzeneboronic acid are suspended under argon in 50 ml of dioxane and 150 ml of toluene. 0.04 g (0.18 mmol) of palladium(II) acetate and 0.5 g (1.2 mmol) of 2-dicyclohexyl-phosphino-2',6'-dimethoxybiphenyl are added, and the reaction mixture is degassed with argon. A degassed solution of 23.0 g (0.1 mol) of potassium phosphate hydrate in 50 ml of water is added. The yellow suspension is heated under reflux for 2 h. The resulting grey biphasic solution is filtered through Hyflo and the filter cake washed with toluene. The filtrate is further extracted with water (3×50 ml), and the organic phase concentrated. The resulting solid is recrystallized from 250 ml of acetone, filtered, washed with a small amount of cold acetone, and dried under vacuum, giving the title product as a light yellow solid (yield: 6.8 g (77%)). Melting point: 213-214° C.

Example 24

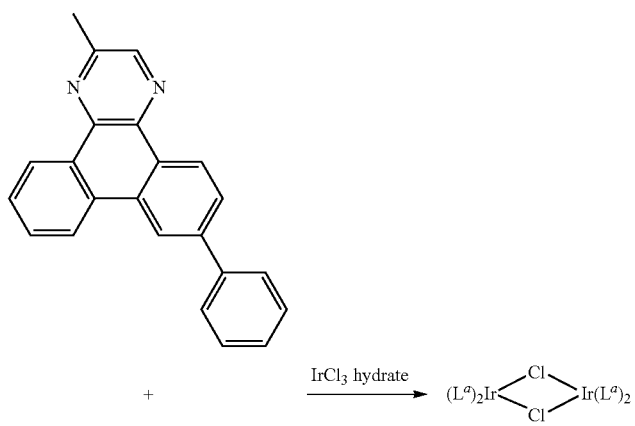

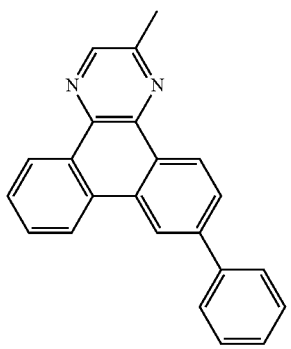

$L^a$ is 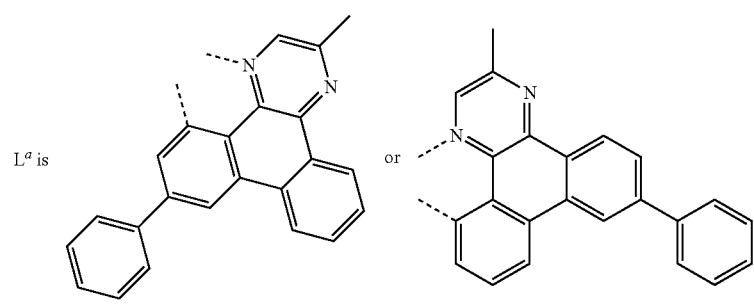

7.2 g (22.5 mmol) of the product isomer mixture of example 2b and 3.9 g (10.7 mmol) of iridium(III)chloride hydrate (52.84% iridium-content) are suspended at room temperature under nitrogen in 100 ml of 2-ethoxyethanol. The grey-black suspension is heated up to 116° C. and kept at this temperature for 19 h. The orange red suspension is filtered, washed with 2-ethoxyethanol first, followed by ethanol, and further dried under vacuum, giving the title product as an orange powder (yield: 8.2 g (88%)).

Example 25

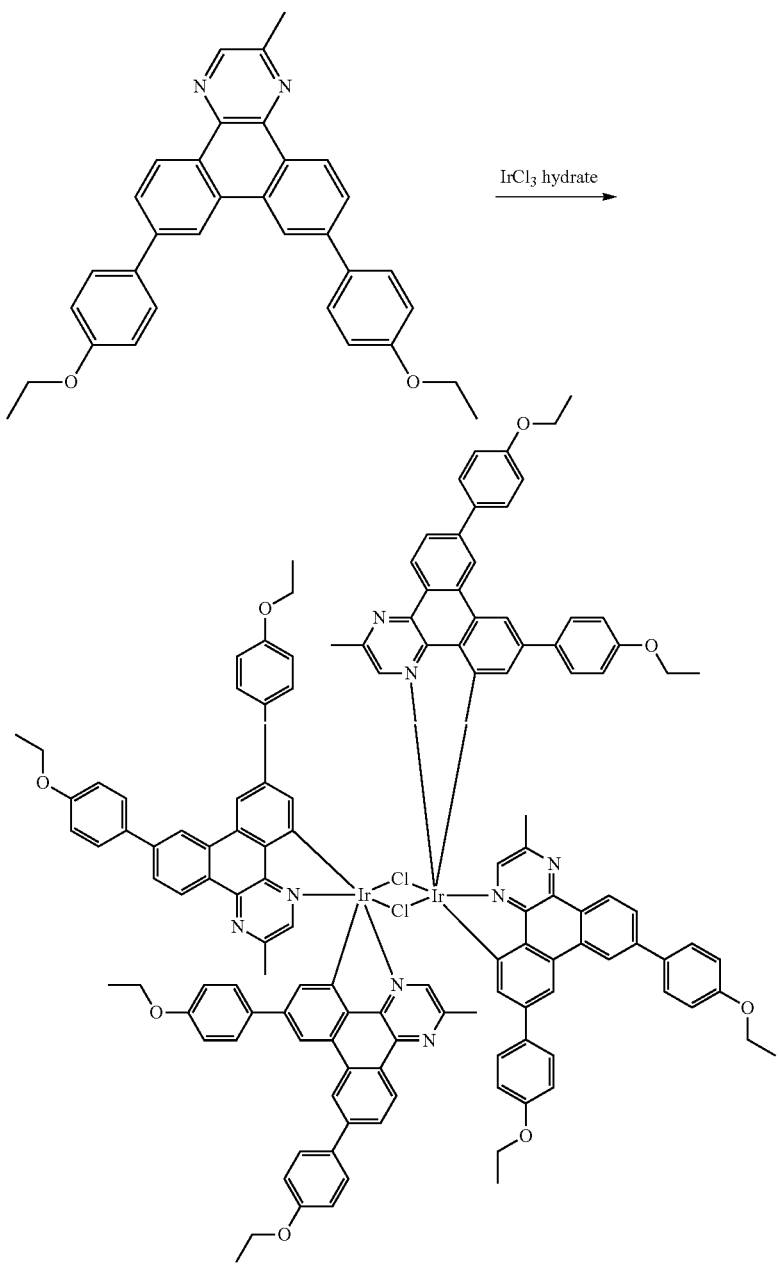

0.96 g (1.99 mmol) of the product of example 4b and 0.32 g (0.90 mmol) of iridium(III)chloride hydrate are suspended under argon in 80 ml of 2-ethoxyethanol and 6 ml of water. The reaction mixture is heated under reflux for 22 h. The reaction mixture is cooled down to 20° C., the product is filtered off, followed by washing several times with water and ethanol. The isolated solid is further dried under vacuum giving the title compound as a dark red powder (yield: 0.69 g (68%)).

Example 26

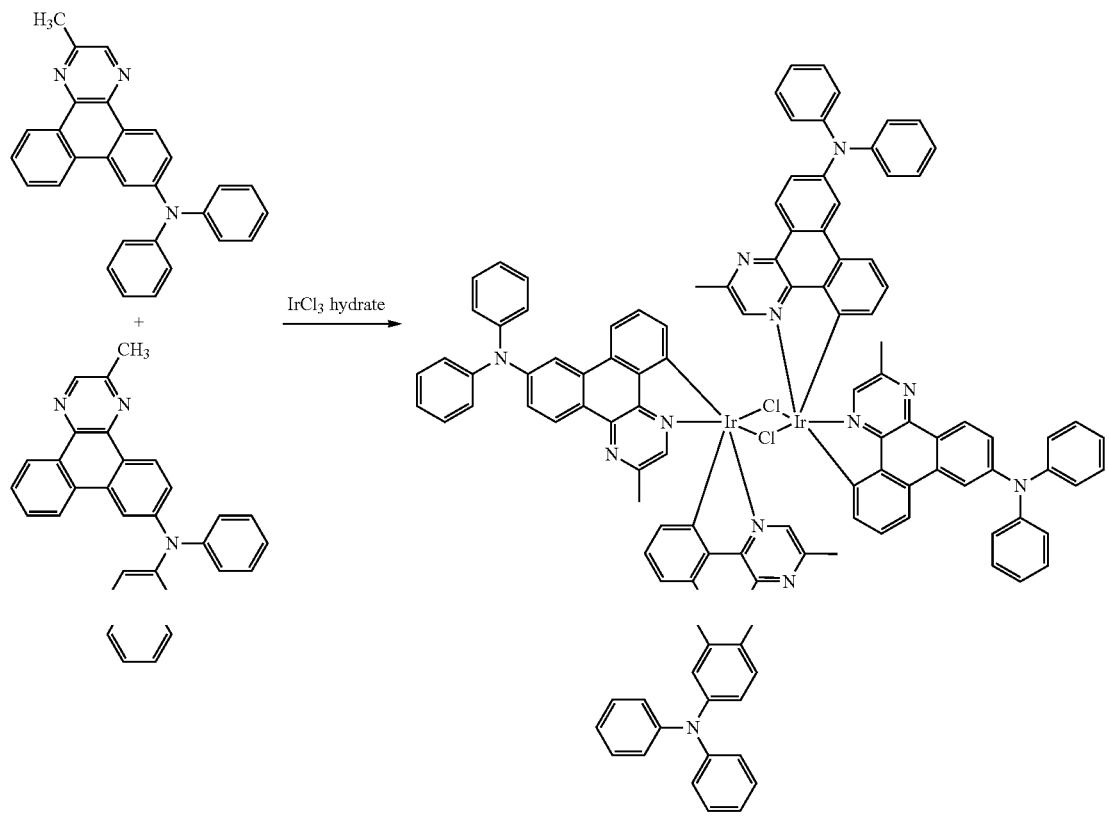

6.6 g (16 mmol) of the product isomer mixture of example 6 and 2.77 g (7.6 mmol) of iridium(III)chloride hydrate (52.84% iridium-content) are suspended at room temperature under nitrogen in 70 ml of 2-ethoxyethanol. The grey-black suspension is heated up to 114° C. and kept at this temperature for 17 h. The dark red suspension is cooled down to room temperature, diluted with 50 ml of ethanol, filtered, washed with ethanol, and further dried under vacuum. The title product is obtained as an orange-red powder (yield: 7.1 g (89%)).

Example 27

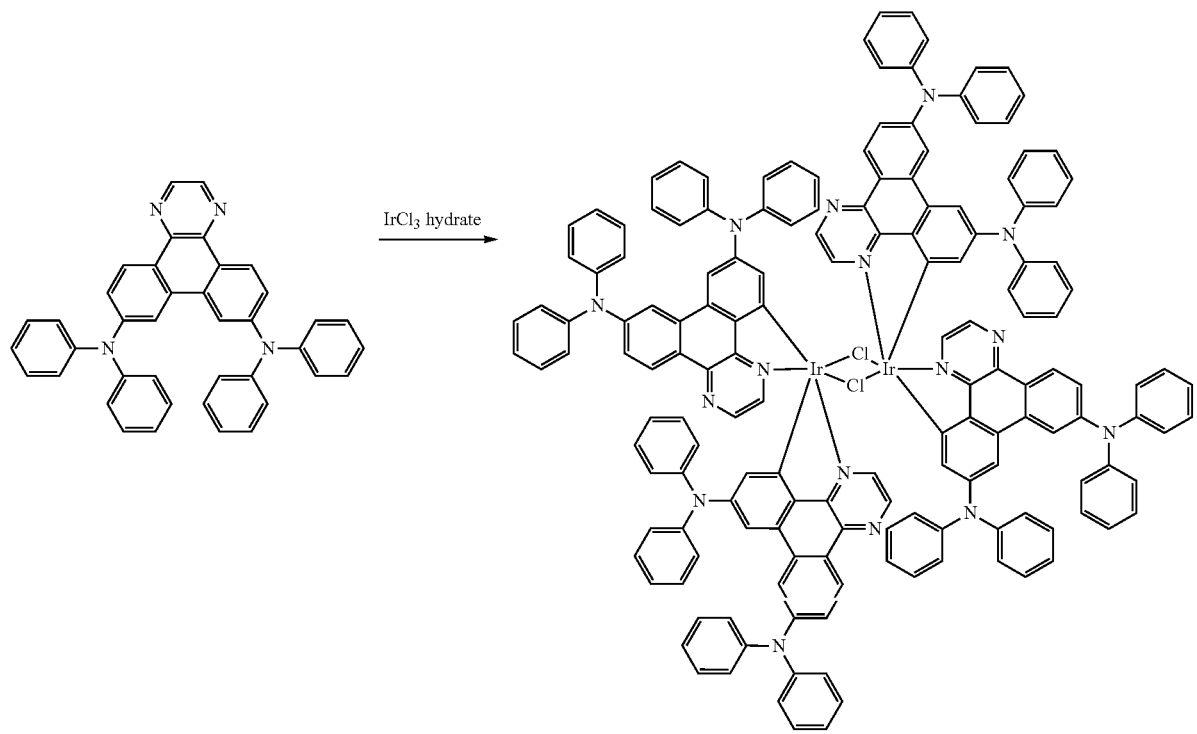

1.0 g (1.77 mmol) of the product of example 7b and 0.31 g (0.84 mmol) of iridium(III)chloride hydrate are suspended under argon in a mixture of 20 ml of 2-ethoxyethanol and 7 ml of water. The reaction mixture is heated under reflux for 19 h. The black reaction mixture is filtered, and then suspended/filtered three times with hot ethanol. The resulting solid is further dried under vacuum giving a brownish black powder (yield: 0.93 g (82%)).

Example 28

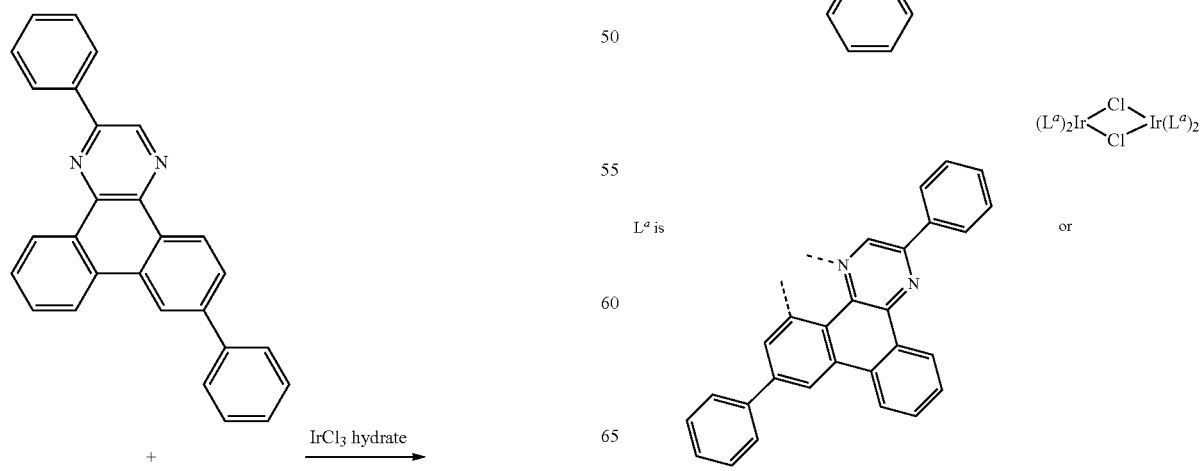

-continued

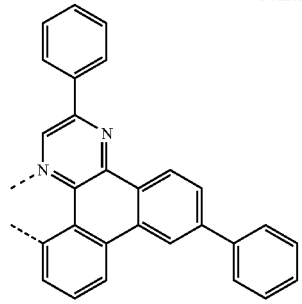

5.5 g (13 mmol) of the product isomer mixture of example 17 and 2.25 g (6.2 mmol) of iridium(III)chloride hydrate (52.84% iridium-content) are suspended at room temperature under nitrogen in 70 ml of 2-ethoxyethanol. The yellow suspension is heated up to 116° C. and kept at this temperature for 18 h. The red suspension is filtered, washed with 2-ethoxyethanol first, followed by ethanol, and further dried under vacuum, giving the title product as an orange red powder (yield: 5.4 g (89%)).

Examples 24-45

The following diiridium complexes are prepared according to the procedure reported for example 24-28, giving the products of examples 29-45. The respective m/z-values of the product structures have been detected by HPLC-MS measurements.

| Example | Ligand | Diiridium complex |
|---|---|---|
| 29 | 1c | $(L^a)_2Ir\underset{Cl}{\overset{Cl}{\rightleftarrows}}Ir(L^a)_2$ <br><br> $L^a$ is <br><br> or |
| 30 | 3b | |

| Example | Ligand | Diiridium complex |
|---|---|---|
| | | 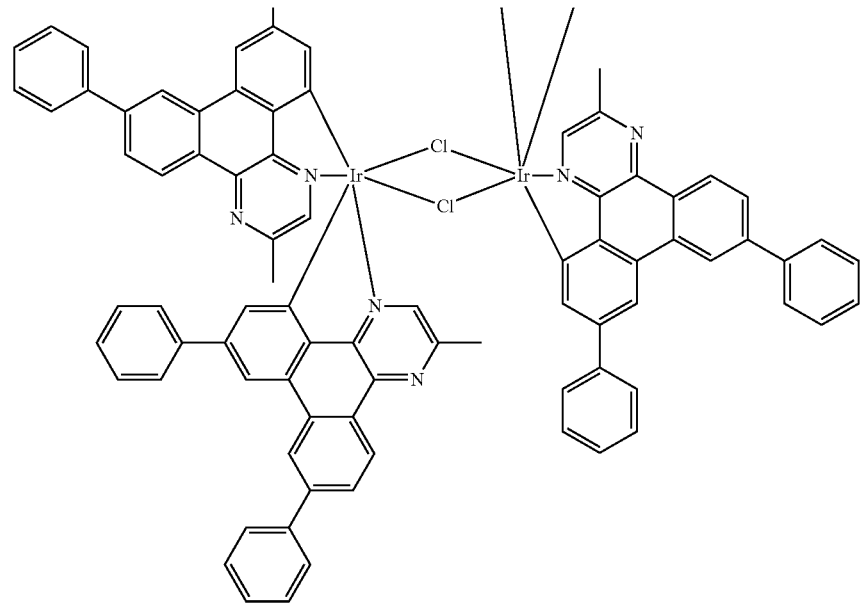 |
| 31 | 5 | 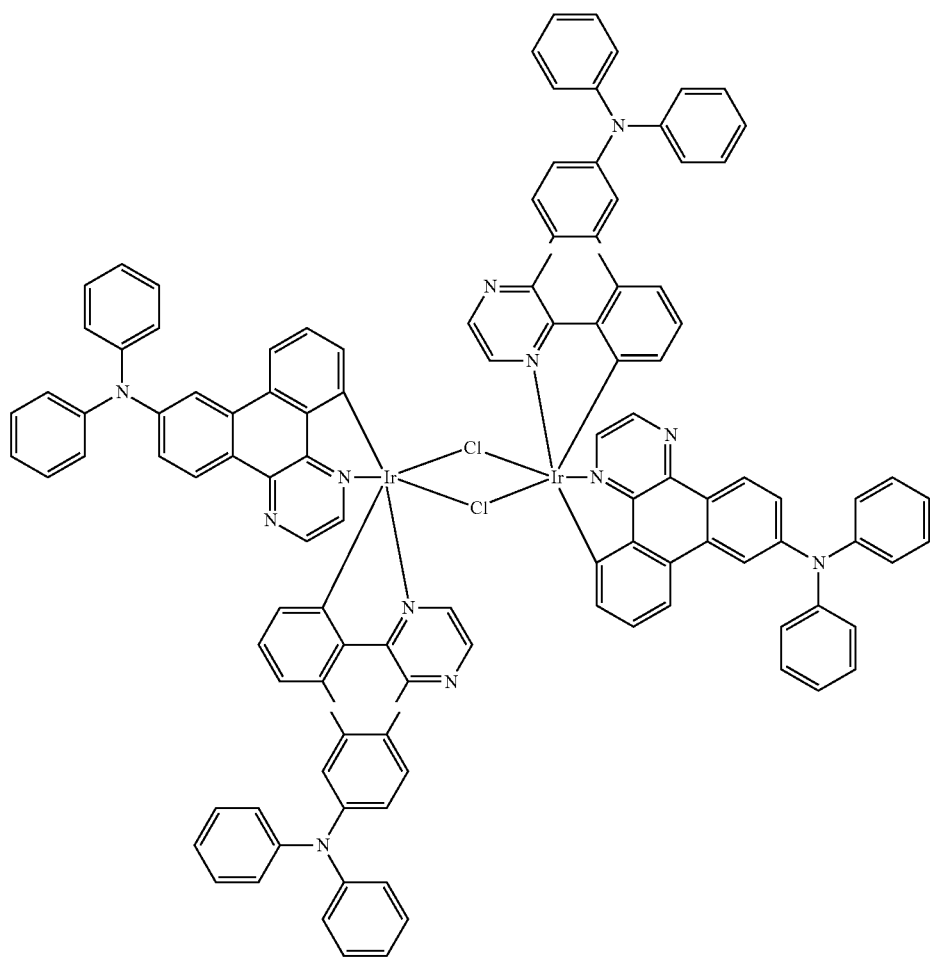 |

-continued
| Example | Ligand | Diiridium complex |
|---|---|---|
| 32 | 8 | 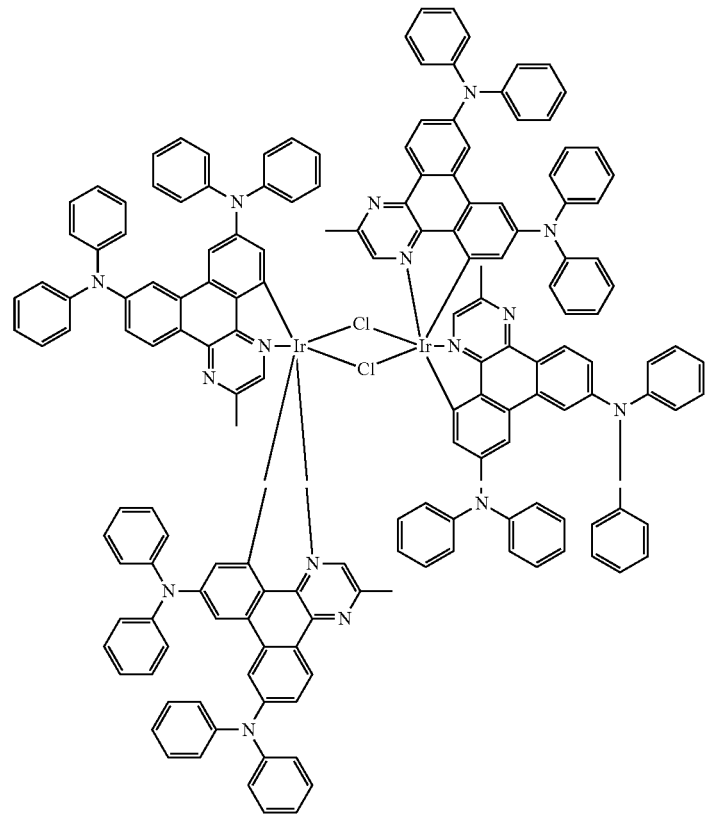 |
| 33 | 9b | 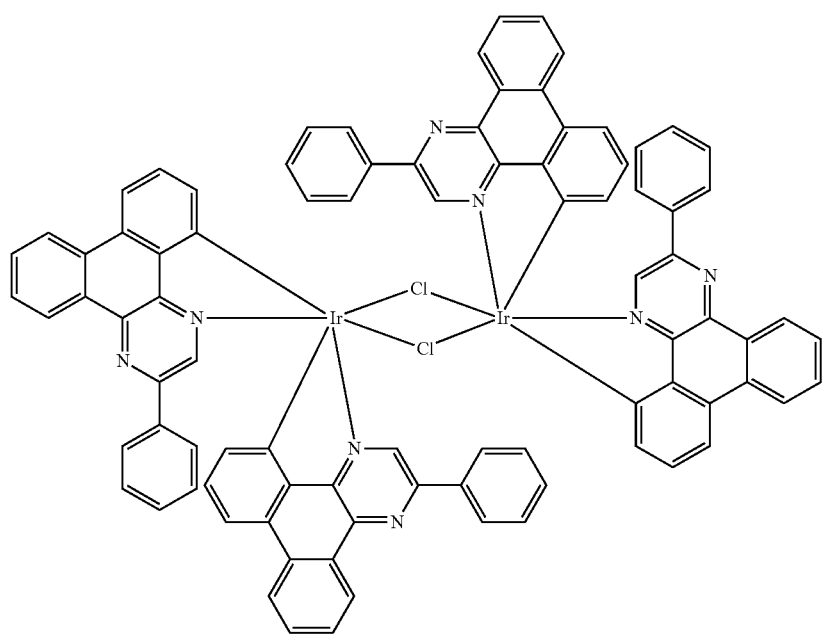 |

-continued
| Example | Ligand | Diiridium complex |
|---|---|---|
| 34 | 10 | 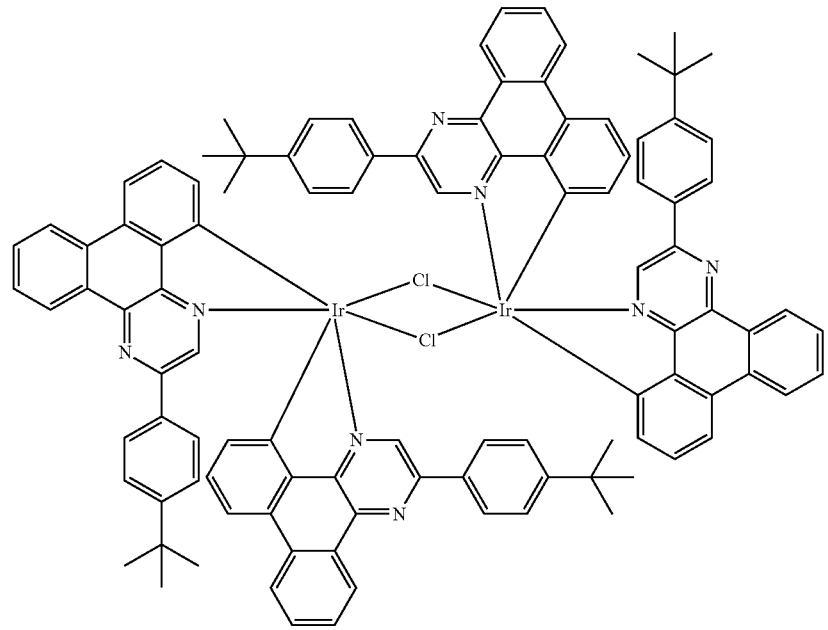 |
| 35 | 11 | 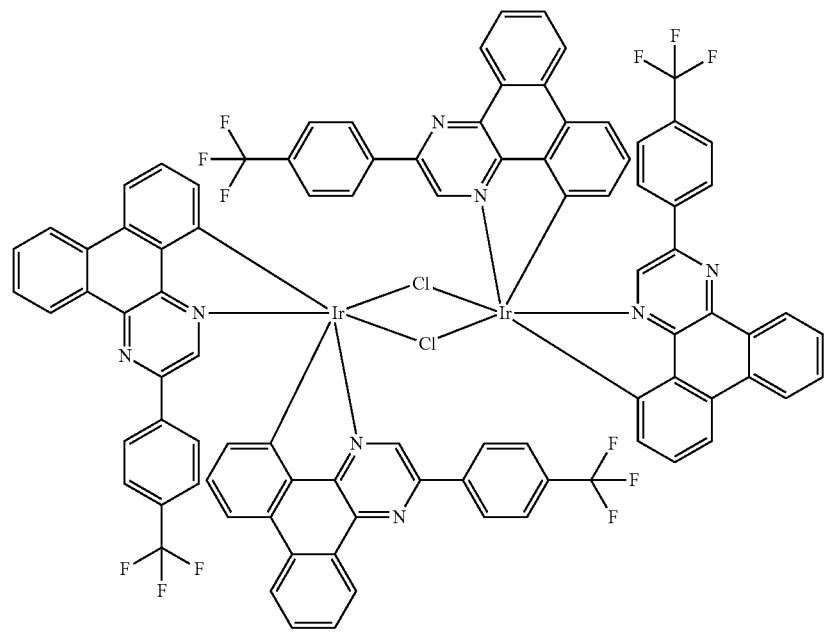 |

| Example | Ligand | Diiridium complex |
|---|---|---|
| 36 | 12 | 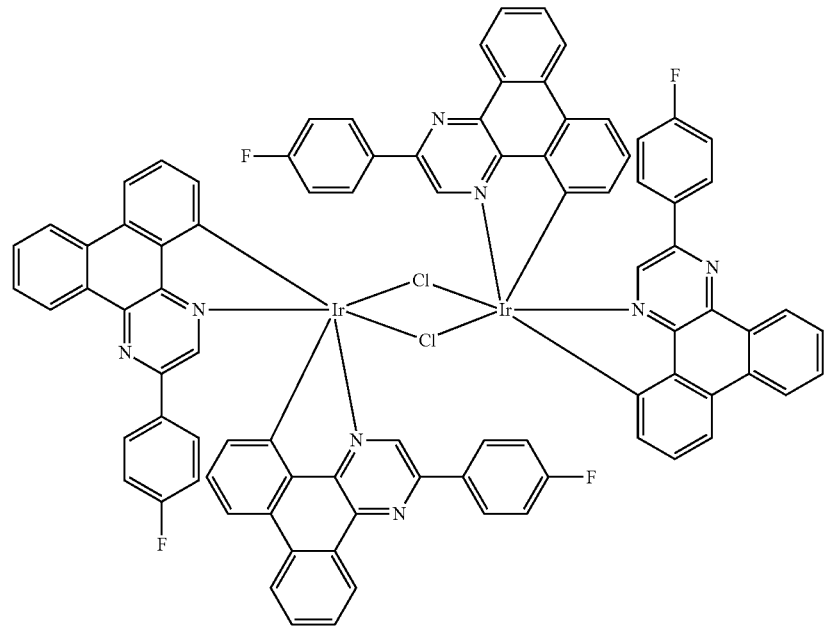 |
| 37 | 13 | 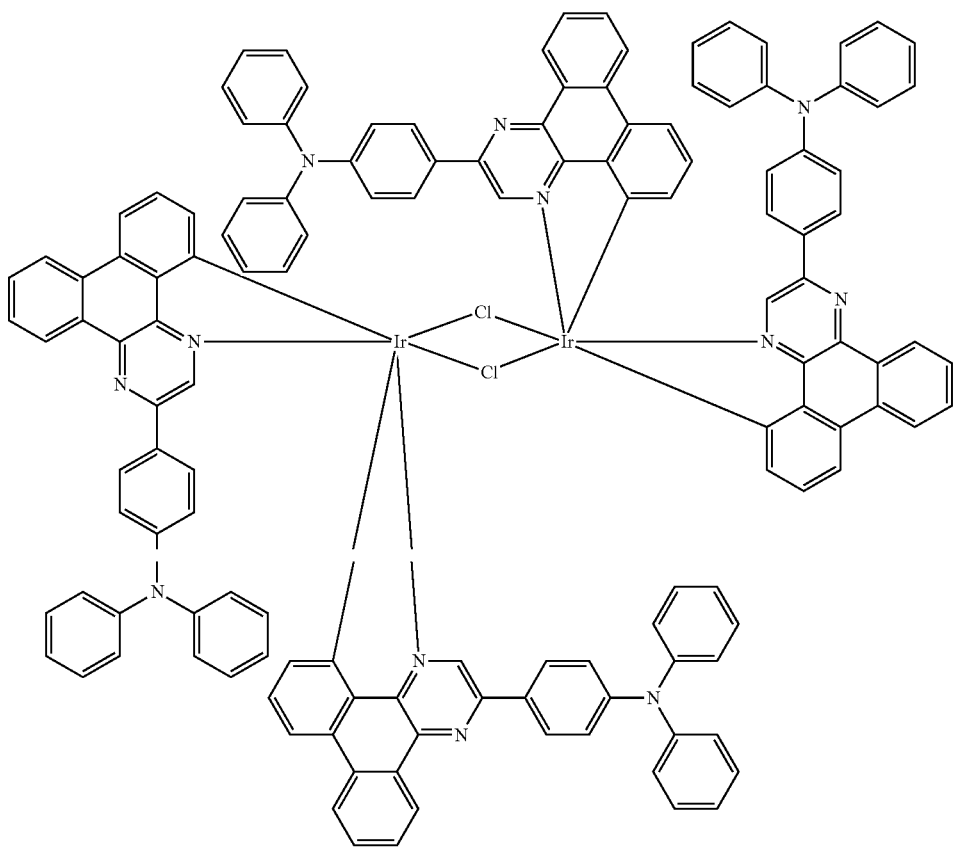 |

-continued
| Example | Ligand | Diiridium complex |
|---|---|---|
| 38 | 14 | 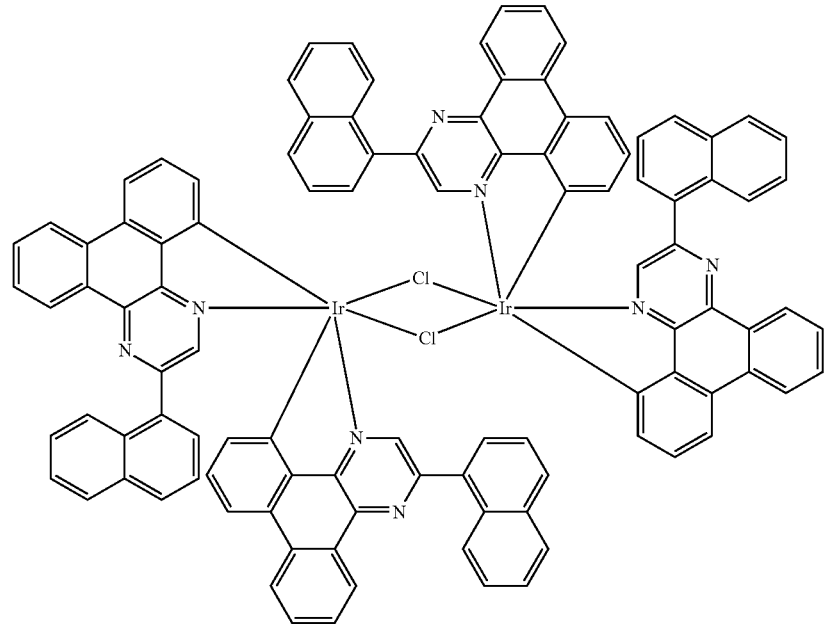 |
| 39 | 15 | 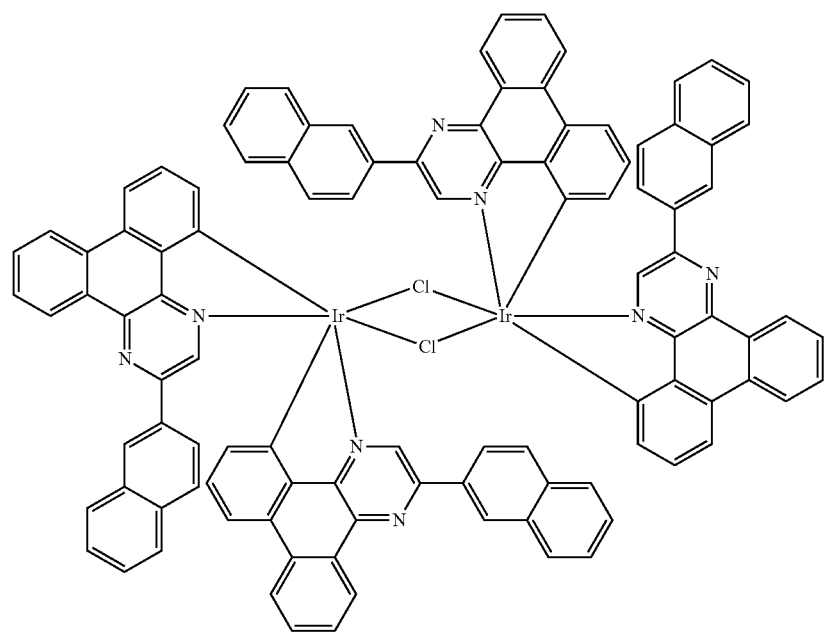 |

-continued
| Example | Ligand | Diiridium complex |
|---|---|---|
| 40 | 16b | 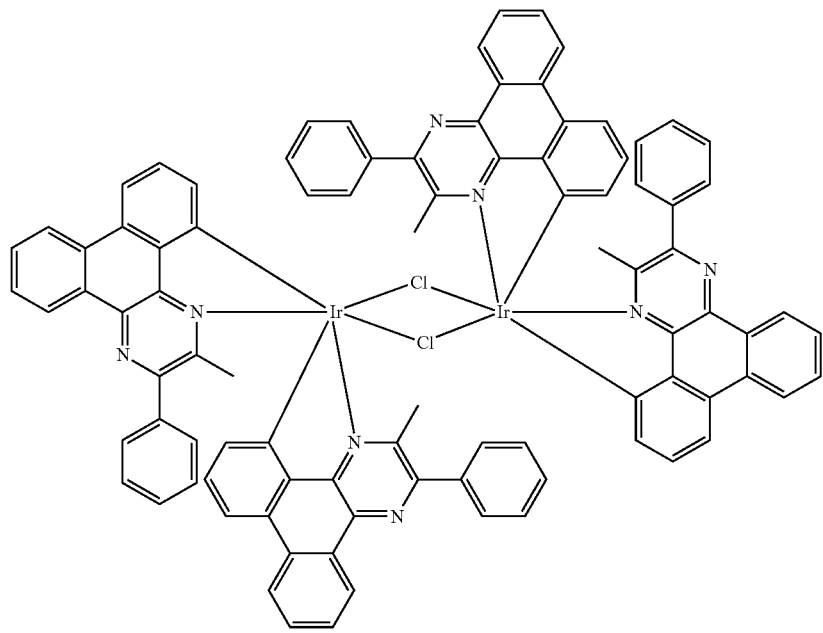 |
| 41 | 19 | 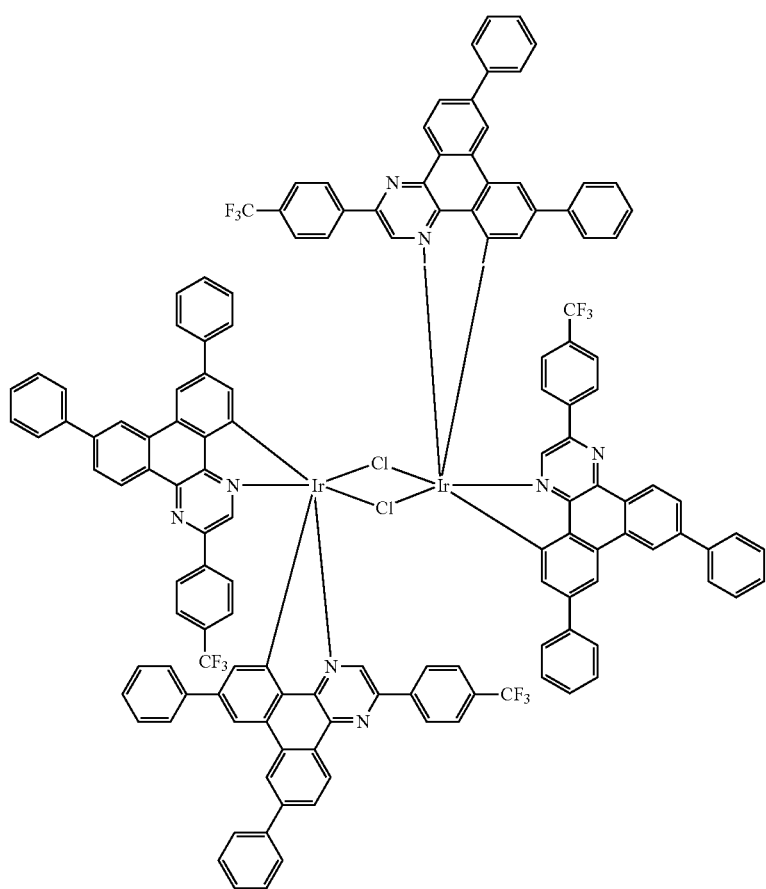 |

-continued
| Example | Ligand | Diiridium complex |
|---|---|---|
| 42 | 20 | 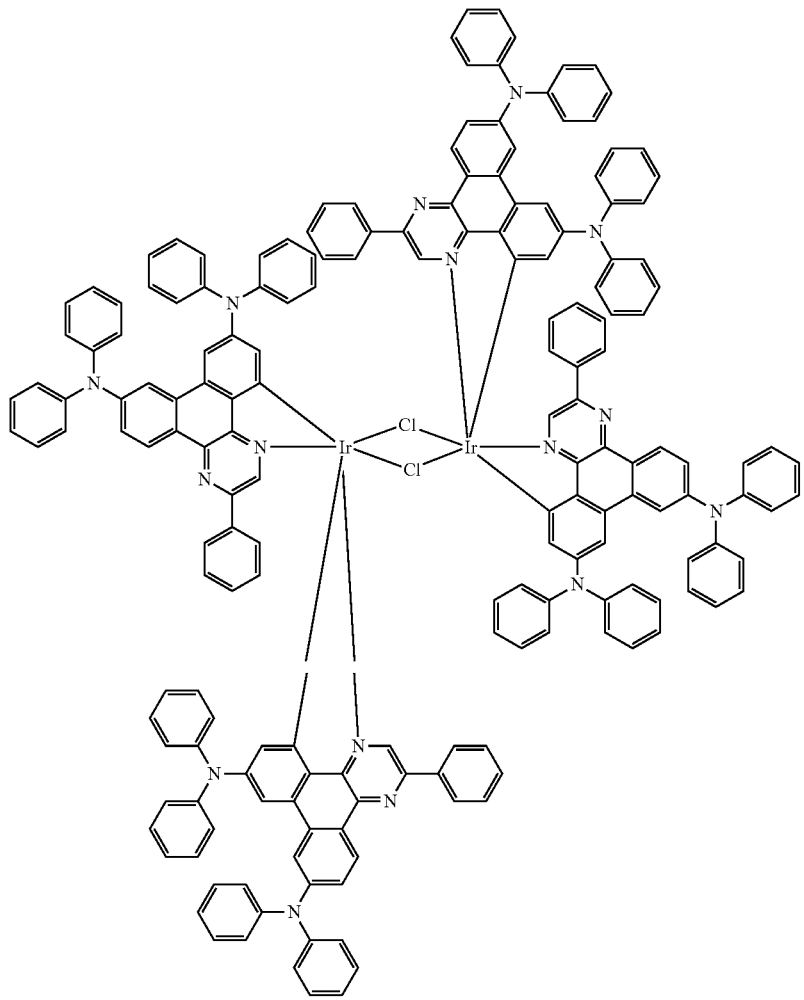 |
| 43 | 21 | 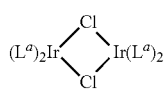<br>$L^a$ is<br>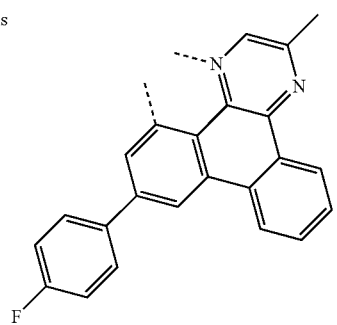 |

| Example | Ligand | Diiridium complex |
|---|---|---|
| | | or 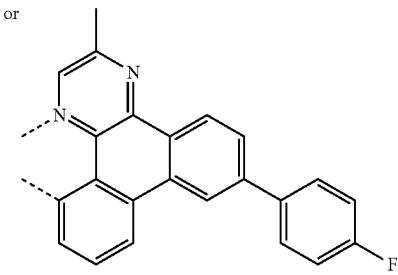 |
| 44 | 22 | 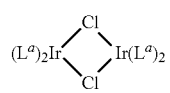<br>$L^a$ is<br>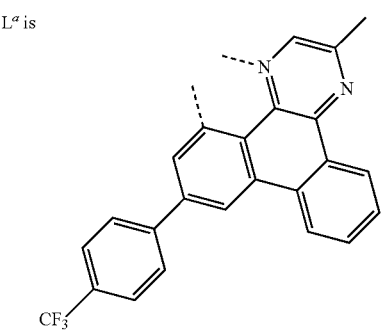<br>or<br>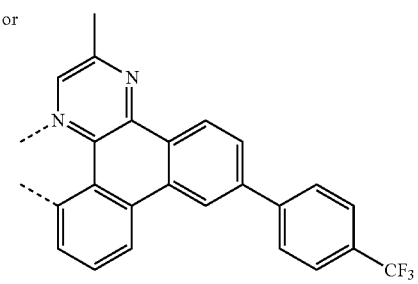 |

| Example | Ligand | Diiridium complex |
|---|---|---|
| 45 | 23 | 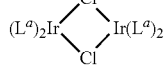<br>$L^a$ is<br>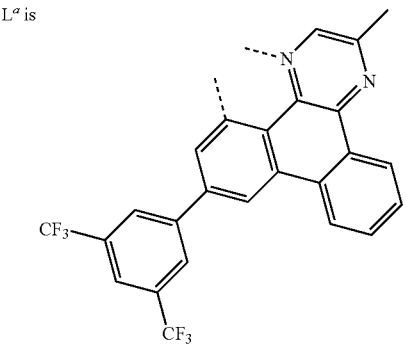<br>or<br>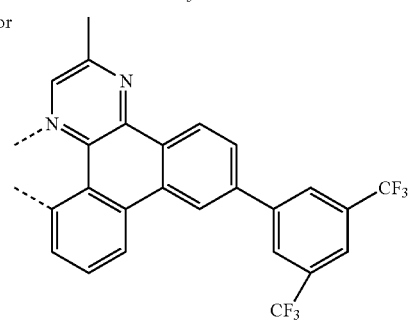 |

Example 46

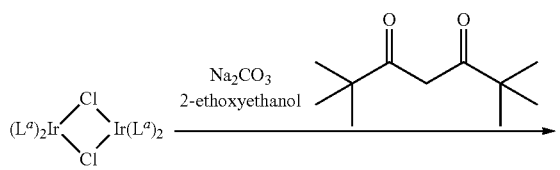

$L^a$ is

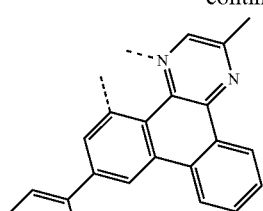  or

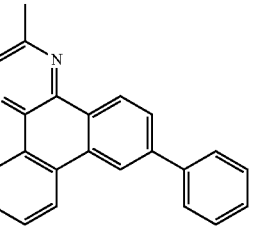

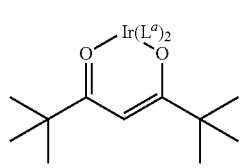

4.3 g (2.5 mmol) of the product of example 24, and 2.65 g (25 mmol) of sodium carbonate are suspended under nitrogen in 100 ml of ethoxyethanol. The dark suspension is treated with 2.3 g (12.5 mmol) of 2,2,6,6-tetramethyl-3,5-heptanedione and stirred at 115° C. until no more starting material is visible by TLC. The resulting dark suspension is filtered, the remaining solid washed with ethanol and suspended in water. The suspension is filtered, washed with water and a small amount of ethanol. The solid is dried under vacuum giving the title product as a red powder (yield: 4.2 g (83%)).

Example 47

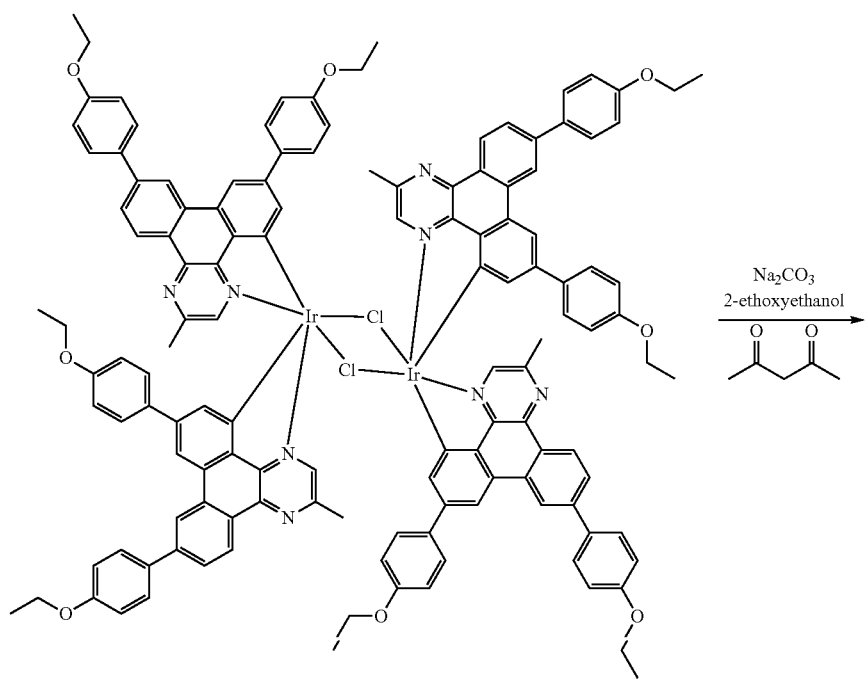

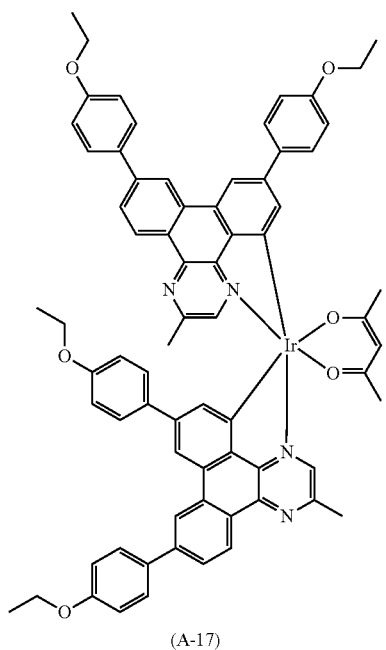

(A-17)

0.60 g (0.25 mmol) of the product of example 25, and 0.18 g (1.66 mmol) of sodium carbonate are suspended under argon in 20 ml of ethoxyethanol. The dark suspension is treated with 65 mg (0.65 mmol) of acetyl acetone and stirred at 120° C. for 16 h. The resulting dark red suspension is cooled down to 20° C. and the product is filtered off. After repeated washing with ethanol and water a dark red powder is obtained (yield: 0.55 g (87%)).

Example 48

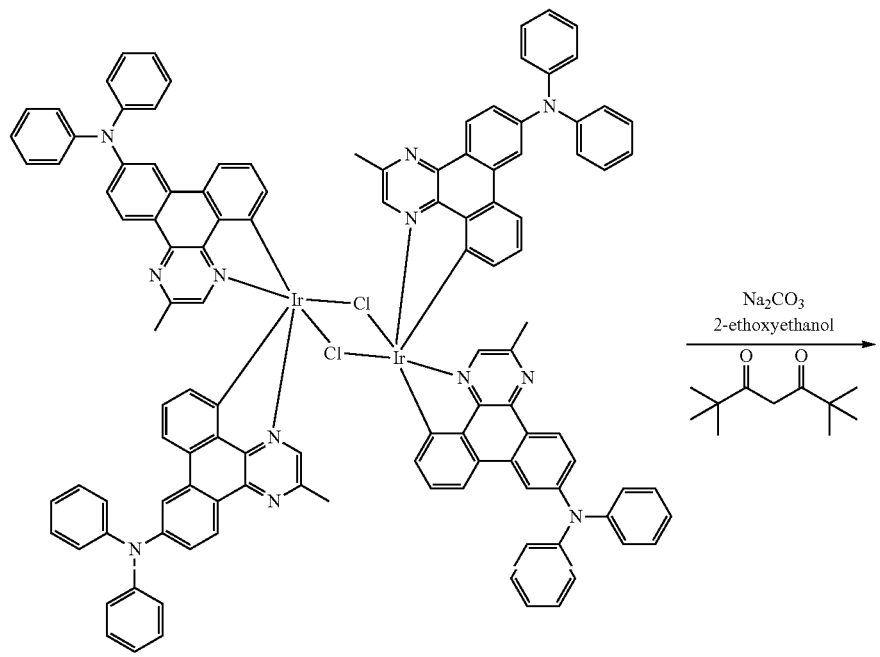

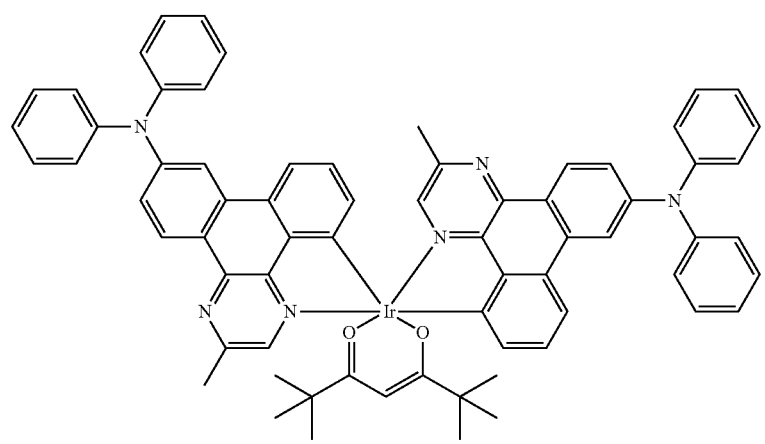

3.15 g (1.5 mmol) of the product of example 26, and 1.6 g (15 mmol) of sodium carbonate are suspended under nitrogen in 70 ml of ethoxyethanol. The red suspension is treated with 1.4 g (7.5 mmol) of 2,2,6,6-tetramethyl-3,5-heptanedione and stirred during 75 min at 108° C. The resulting dark red suspension is filtered and the filtrate treated with water. The resulting suspension is filtered, followed by washing with water and ethanol. The remaining solid is suspended in ethanol, filtered, washed with ethanol, and dried under vacuum at 50° C. The title product is obtained as a red powder (yield: 3.2 g (89%)).

Example 49

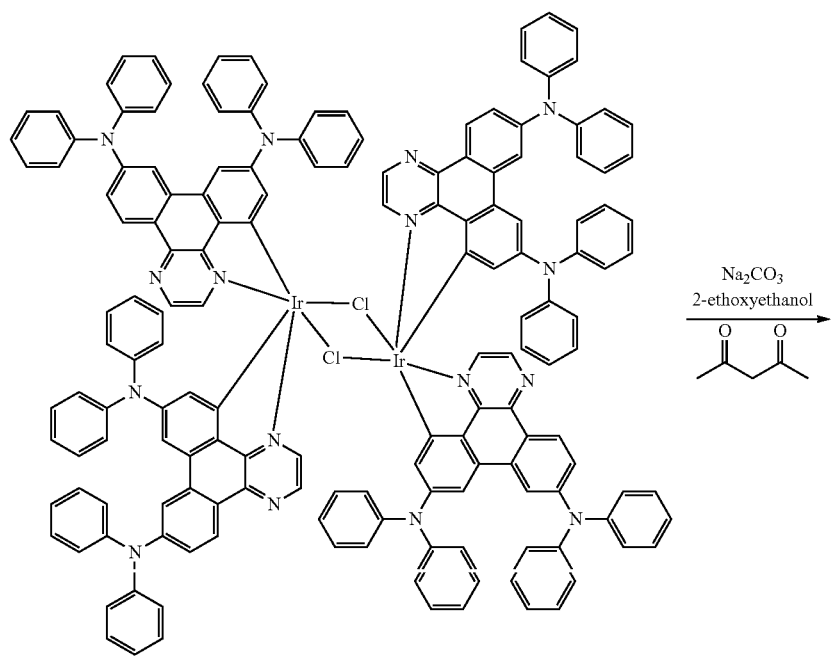

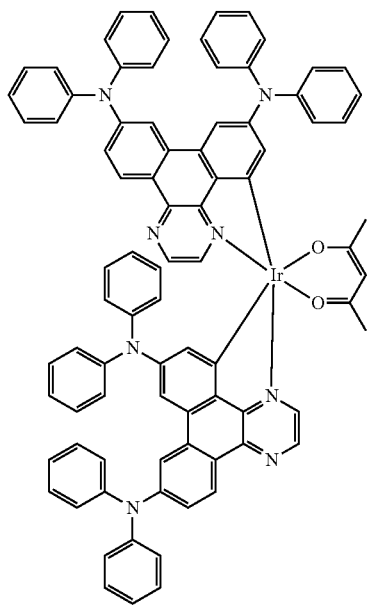

(A-19)

0.9 g (0.37 mmol) of the product of example 27, and 0.26 g (2.44 mmol) of sodium carbonate are suspended under argon in 10 ml of 2-ethoxyethanol. The black suspension is treated with 0.2 g (1.9 mmol) of acetyl acetone and stirred at 100° C. for 21 h. The resulting orange suspension is cooled down to room temperature, diluted with 50 ml of water, filtered, and then washed with 50 ml of ethanol. Washing with water and ethanol is repeated, and the resulting solid dried under vacuum, giving the title compound as a brownish solid (yield: 0.5 g (50%)).

Example 50

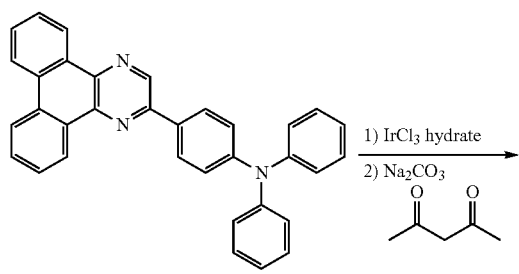

(A-151)

2.3 g (4.9 mmol) of the product of example 13 and 0.85 g (2.31 mmol) of iridium(III)chloride hydrate (52.84% iridium-content) are suspended at room temperature under nitrogen in 30 ml of DMF. The yellow suspension is heated up to 160-165° C. oil bath temperature and kept at this temperature for 4 h. The dark solution is treated at room temperature with 1.2 g (11.6 mmol) of sodium carbonate and 0.85 g (9.3 mmol) of acetylacetone, and heating continued at 140° C. oil bath temperature one hour. The resulting dark suspension is diluted with 200 ml of ethanol, filtered, and the residue washed with 100 ml of ethanol. The solid is suspended in 200 ml of water, filtered, washed with 200 ml of water, followed by washing with 100 ml of ethanol, and 100 ml of hexane. The remaining solid is dried under vacuum and further purified via a flash chromatography over silica gel using dichloromethane as eluent. The title product is obtained as a red solid (yield: 0.8 g (29%)).

Example 51

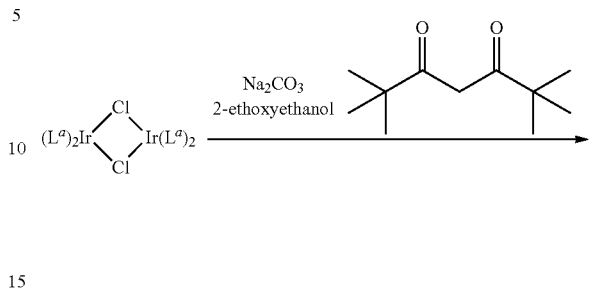

(D-79)

$L^a$ is 5.0 g (2.5 mmol) of the product of example 28, and 3.0 g (27.7 mmol) of sodium carbonate are suspended under nitrogen in 100 of ethoxyethanol. The red suspension is treated at room temperature with 2.33 g (12.6 mmol) of 2,2,6,6-tetramethyl-3,5-heptanedione and stirred during 30 min at 105° C. The resulting dark red suspension is diluted with 100 ml of ethanol, filtered and washed with ethanol. The remaining solid is suspended in water, filtered, and washed with water.

The residue is further washed with ethanol and dried under vacuum at 50° C. The title product is obtained as a red powder (yield: 4.0 g (70%)).
Example 52
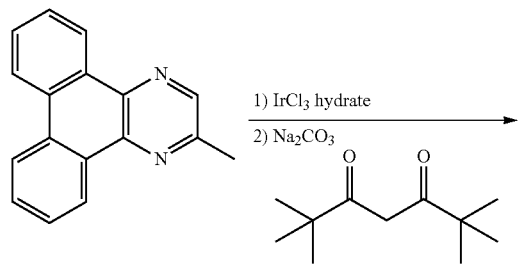
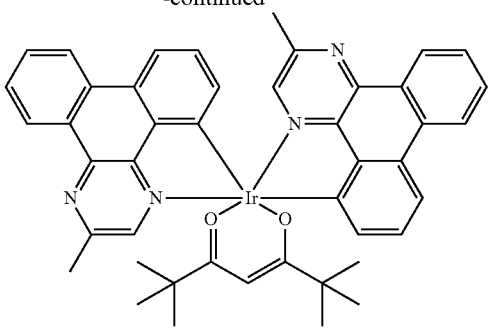
The title product is prepared according to the procedure of example 50, with the product of example 16a, and with 2,2,6,6-tetramethyl-3,5-heptanedione instead of acetylacetone, giving the product as a red solid in 27% yield.
Example 53
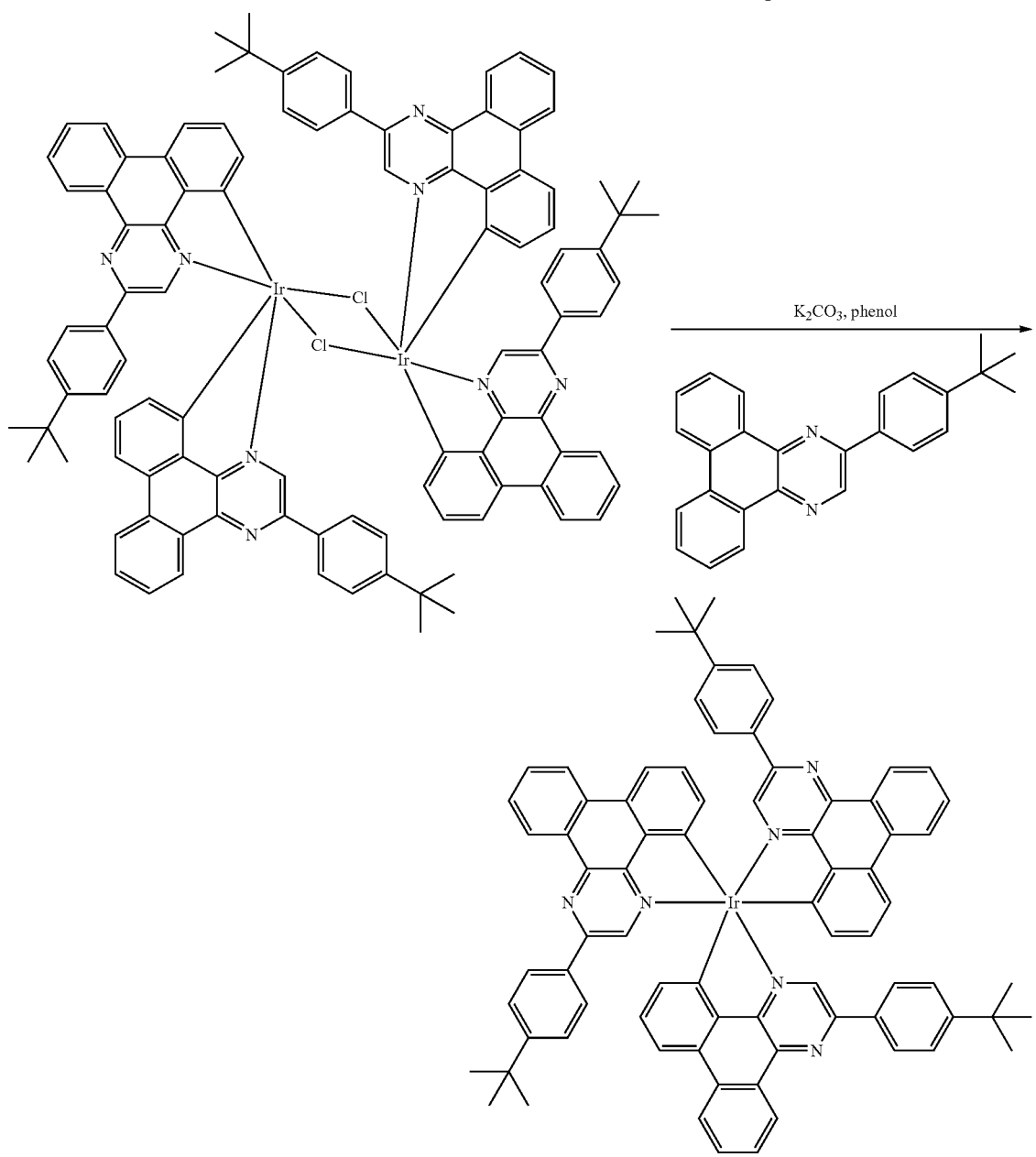
(E-1)

2.0 g (1.1 mmol) of the product of example 34, and 1.52 g (11 mmol) of potassium carbonate are suspended under nitrogen in 15 g of phenol. The orange red suspension is treated with 0.84 g (2.3 mmol) of the product of example 10 and stirred at 200° C. bath temperature for 30 min. The red suspension is cooled down to room temperature and treated with 100 ml of methanol, filtered, and further washed with 200 ml of methanol. The remaining solid is suspended in water, filtered, and washed with water and methanol. The solid is taken up in 200 ml of ethyl acetate and stirred for 15 min, filtered, and washed with ethyl acetate. The last step is repeated, followed by drying the solid under vacuum. The title product is obtained as a red powder (yield: 2.4 g (85%)).

Examples 46-78

The iridium complexes are prepared according to examples 46-51, starting from the products of examples 24-45. Iridium complexes of examples 75-78 are prepared according to the same procedures as described above, starting from the corresponding products of examples 9 and 16, preparing the diiridium complex according to the procedure of example 24 first, followed by preparation of the final iridium complex according to the procedure of example 46. The respective m/z-values of the product structures have been detected by HPLC-MS measurements. All photoluminescence (PL) spectra were measured with a Perkin Elmer Luminance Spectrometer LS 50 B. Materials were dissolved in toluene, and the solution purged with nitrogen in a sealed cuvette. Excitation of the solutions was done at various wavelengths dependent on the absorption characteristics which were measured before PL measurement was carried out using the same cuvettes and solutions. The spectrometer is equipped with two different lamps and covers a wavelength range from 250-800 nm. Colour coordinates CIE x,y were determined from PL spectra and calculated by a software provided with the spectrometer. The PL quantum efficiency is given relative to $Ir(MDQ)_2$ (acac), described in J.-P. Duan et al., Adv. Mat. 2003, 15, 224, with the PL value of $Ir(MDQ)_2(acac)$ given as 100%.

| Example | Iridium complex | Rel. PL Q.E. | CIE x,y ($\lambda_{max}$) |
|---|---|---|---|
| 54 | 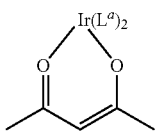 $Ir(L^a)_2$ | 106% | 0.61, 0.39 (604 nm) |

$L^a$ is

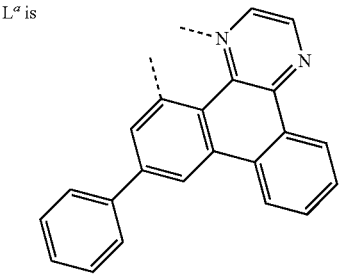

or

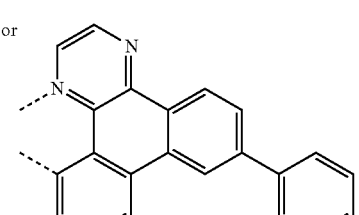

(C-80)

-continued
| Example | Iridium complex | Rel. PL Q.E. | CIE x,y ($\lambda_{max}$) |
|---|---|---|---|
| 55 | 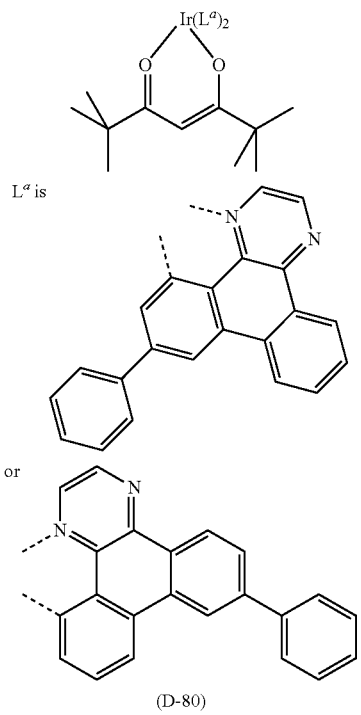 (D-80) | n.d. | n.d. |
| 46 | 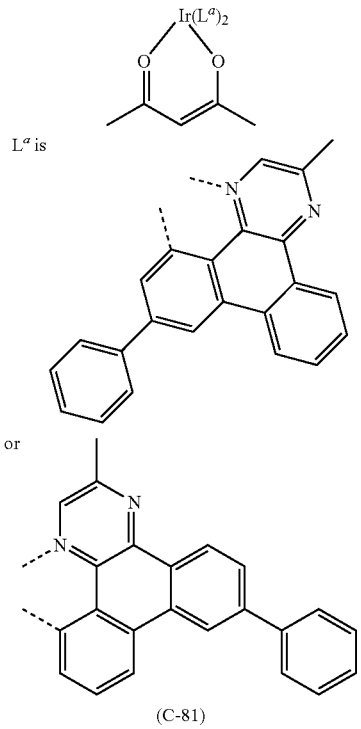 (C-81) | 137% | 0.60, 0.40 (599 nm) |

-continued

| Example | Iridium complex | Rel. PL Q.E. | CIE x,y ($\lambda_{max}$) |
|---|---|---|---|
| 56 | Ir(L$^a$)$_2$ (diketonate shown)<br><br>L$^a$ is (structure) or (D-81) | 107% | 0.61, 0.38 (606 nm) |
| 57 | (A-156) | 124% | 0.60, 0.40 (599 nm) |

-continued
| Example | Iridium complex | Rel. PL Q.E. | CIE x,y ($\lambda_{max}$) |
|---|---|---|---|
| 58 | (B-156) | n.d. | 0.61, 0.38 (607 nm) |
| 47 | (A-17) | 91% | 0.60, 0.40 (604 nm) |
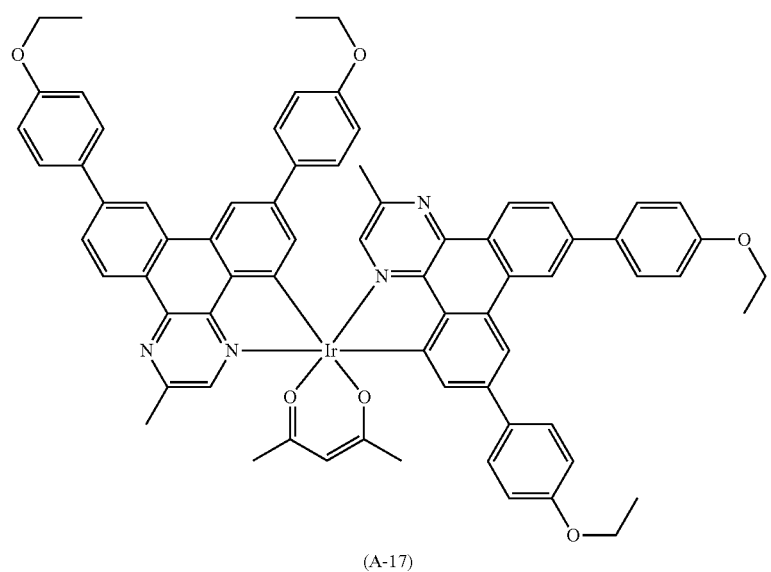

-continued
| Example | Iridium complex | Rel. PL Q.E. | CIE x,y (λ_max) |
|---|---|---|---|
| | | n.d. | |
| 59 | Ir(L^a)_2 with acac; L^a is (C-10) | n.d. | |
| 60 | Ir(L^a)_2 with di-tert-butyl acac; L^a is (D-10) | n.d. | n.d. |
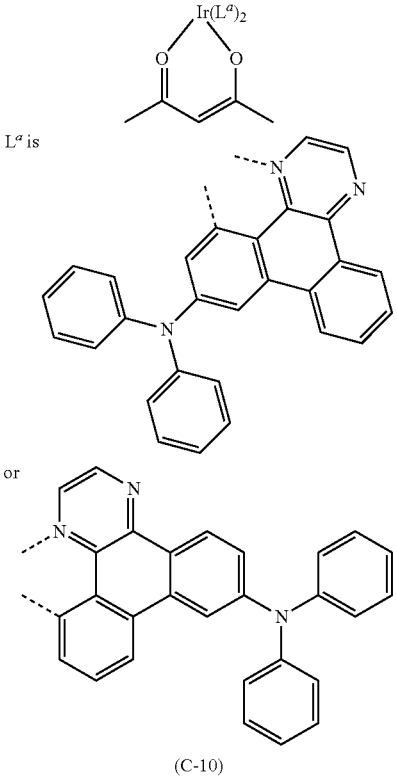
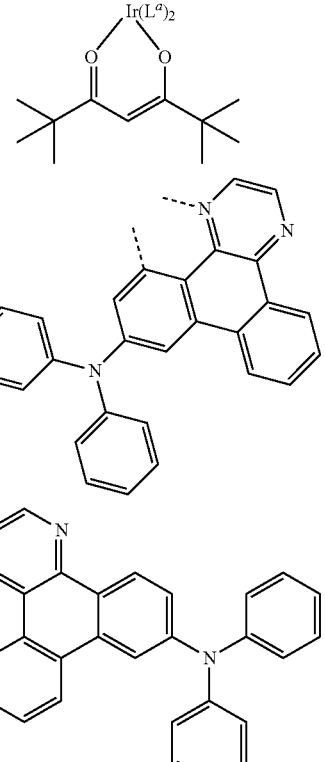

-continued
| Example | Iridium complex | Rel. PL Q.E. | CIE x,y ($\lambda_{max}$) |
|---|---|---|---|
| 61 | Ir(L$^a$)$_2$ 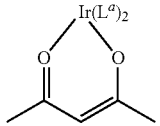 L$^a$ is 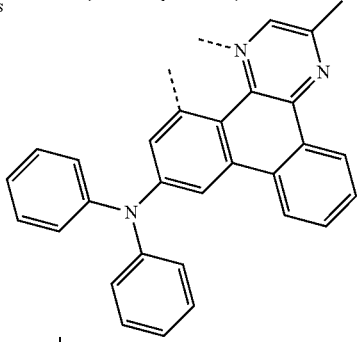 or 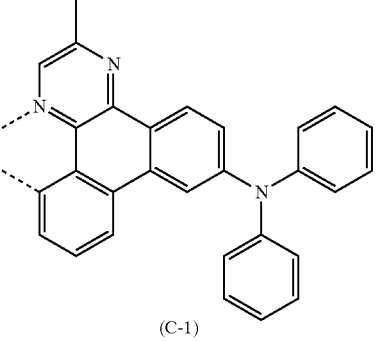 (C-1) | 80% | 0.62, 0.38 (610 nm) |
| 48 | Ir(L$^a$)$_2$ 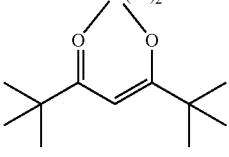 L$^a$ is 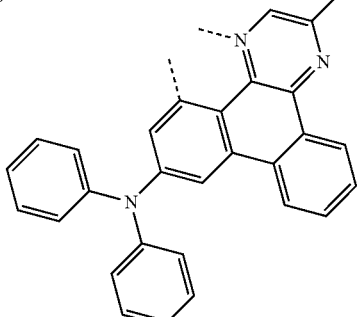 or 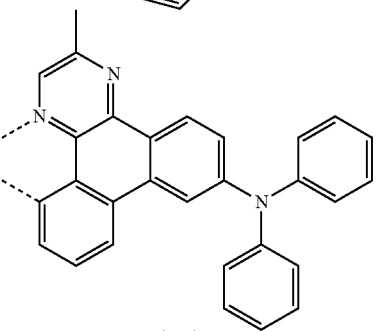 (D-1) | 90% | (611 nm) |

-continued
| Example | Iridium complex | Rel. PL Q.E. | CIE x,y ($\lambda_{max}$) |
|---|---|---|---|
| 49 | 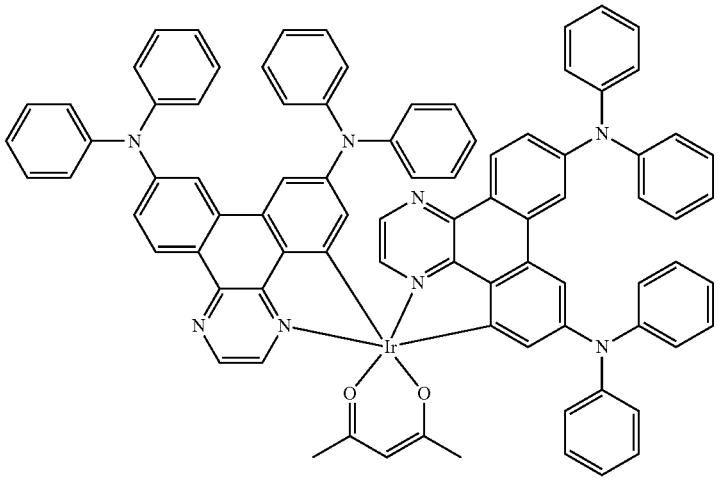<br>(A-19) | n.d. | 0.64, 0.36 (614 nm) |
| 62 | 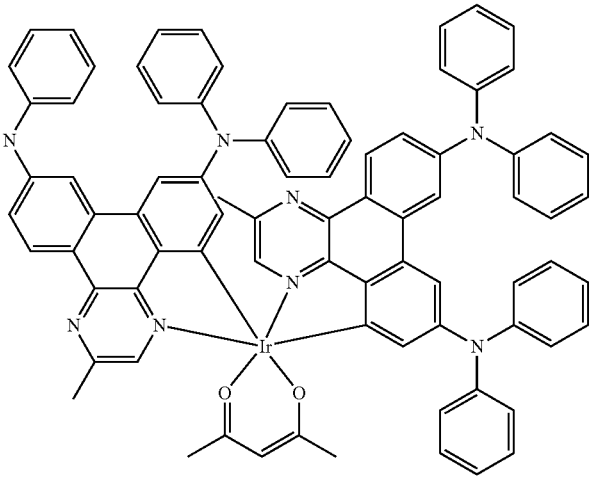<br>(A-1) | 67% | 0.64, 0.36 (614 nm) |
| 65 | 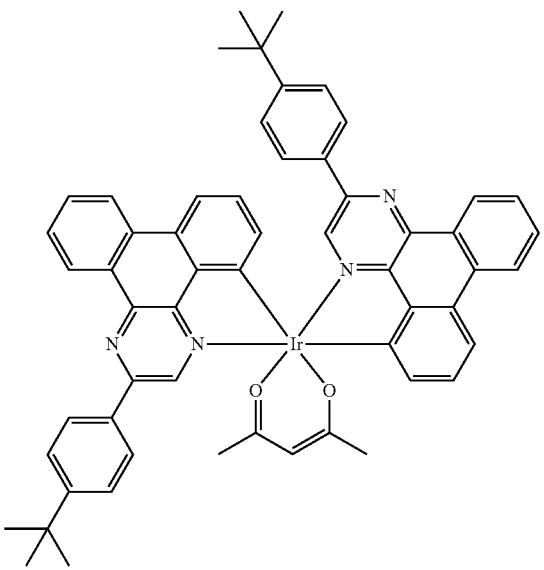<br>(A-157) | 98% | 0.64, 0.35 (614 nm) |

-continued
| Example | Iridium complex | Rel. PL Q.E. | CIE x,y ($\lambda_{max}$) |
|---|---|---|---|
| 66 | 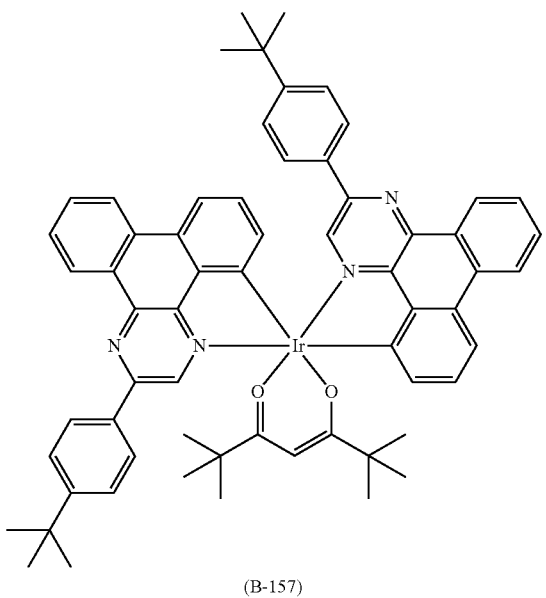 (B-157) | 102% | 0.63, 0.37 (608 nm) |
| 67 | 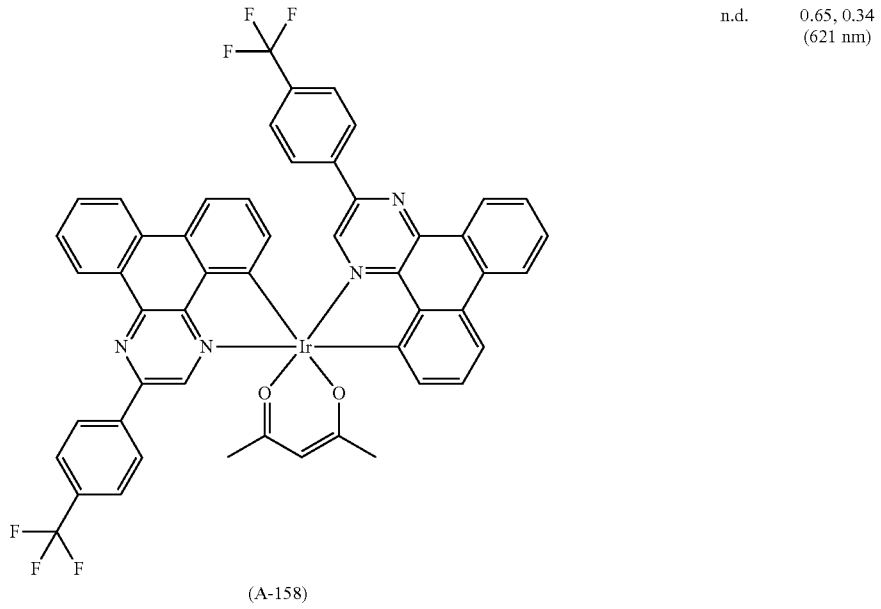 (A-158) | n.d. | 0.65, 0.34 (621 nm) |

-continued
| Example | Iridium complex | Rel. PL Q.E. | CIE x,y ($\lambda_{max}$) |
|---|---|---|---|
| 68 | 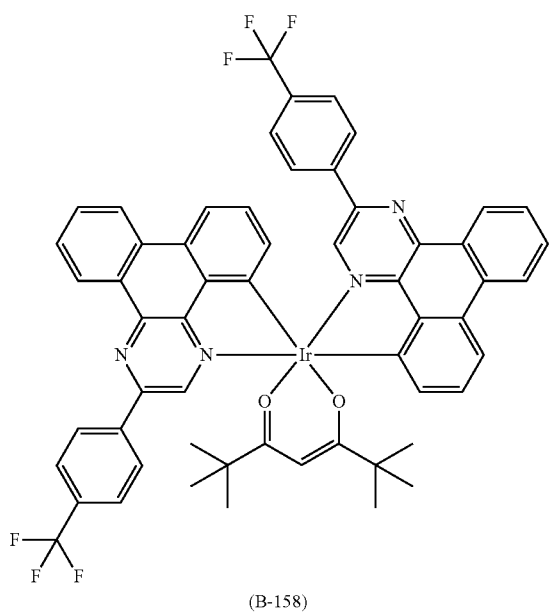<br>(B-158) | 65% | 0.67, 0.33 (626 nm) |
| 69 | 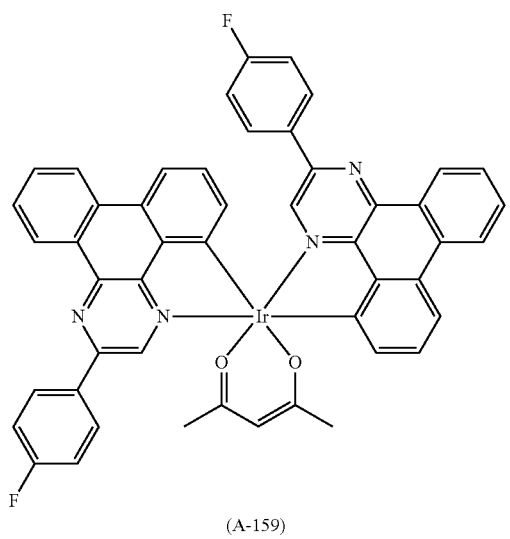<br>(A-159) | n.d. | n.d. |

| Example | Iridium complex | Rel. PL Q.E. | CIE x,y ($\lambda_{max}$) |
|---|---|---|---|
| 70 | (B-159) | 74% | 0.65, 0.35 (618 nm) |
| 50 | (A-151) | 76% | 0.64, 0.35 (612 nm) |
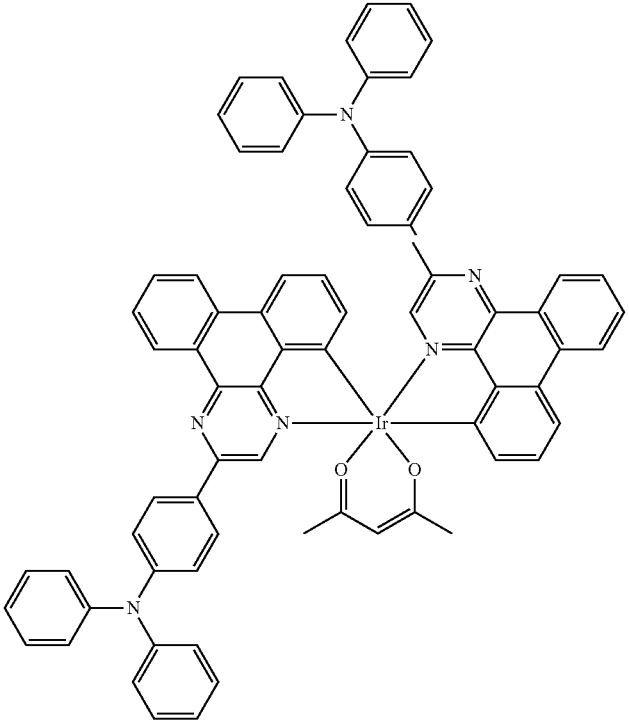

-continued
| Example | Iridium complex | Rel. PL Q.E. | CIE x,y ($\lambda_{max}$) |
|---|---|---|---|
| 71 | 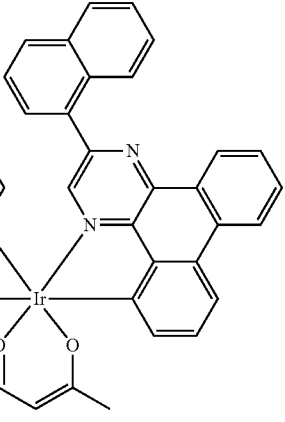<br>(A-160) | 92% | 0.62, 0.37<br>(606 nm) |
| 72 | 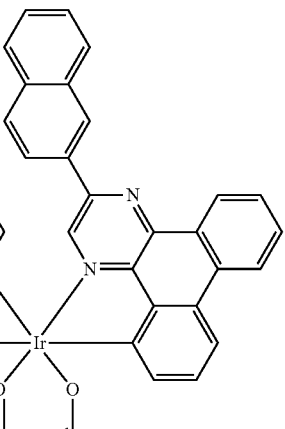<br>(A-161) | 96% | 0.63, 0.36<br>(611 nm) |
| 73 | 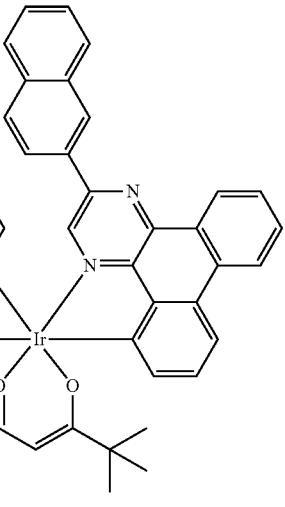<br>(B-161) | n.d. | n.d. |

-continued
| Example | Iridium complex | Rel. PL Q.E. | CIE x,y (λ$_{max}$) |
|---|---|---|---|
| 74 | 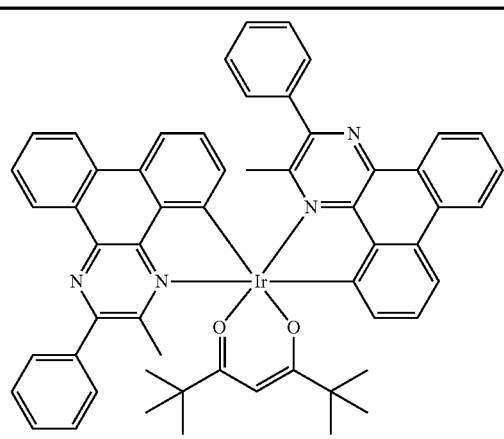<br>(B-162) | 142% | 0.61, 0.39<br>(602 nm) |
| 51 | Ir(L$^a$)$_2$<br>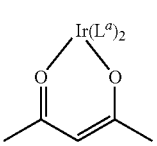<br>L$^a$ is<br>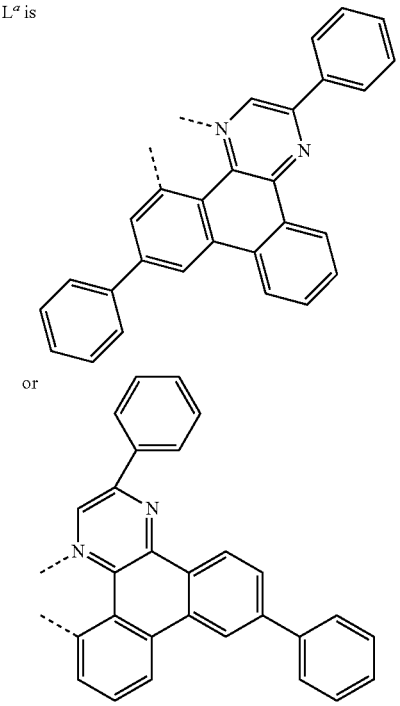<br>or<br>(D-79) | 83% | 0.64, 0.35<br>(616 nm) |

-continued

| Example | Iridium complex | Rel. PL Q.E. | CIE x,y ($\lambda_{max}$) |
|---|---|---|---|
| 52 | | 104% | 0.61, 0.39 (607 nm) |
| 75 | (A-163) | 141% | 0.58, 0.41 (600 nm) |
| 76 | (A-164) | 120% | 0.59, 0.41 (601 nm) |

| Example | Iridium complex | Rel. PL Q.E. | CIE x,y ($\lambda_{max}$) |
|---|---|---|---|
| 77 | (A-166) | n.d. | n.d. |
| 78 | (A-175) | n.d. | n.d. | n.d. = not determined.

APPLICATION EXAMPLES a) Product of example 62 of the present invention:

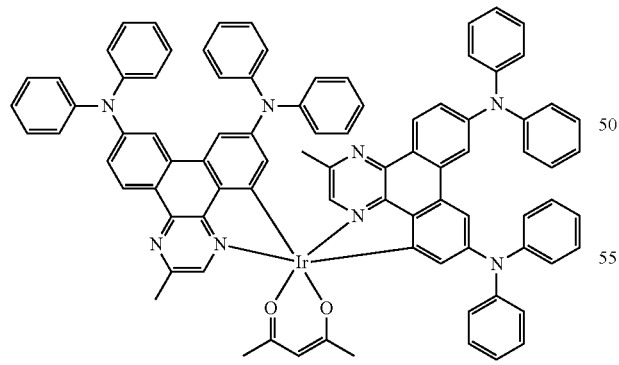

(A-1)

7.7 mg of the compound of example 62 (A-1) are dissolved in 50 ml of toluene (spectroscopic quality), and an aliquot of 0.19 ml further diluted in 5 ml of toluene.

The solution is filled in a quarz cuvette, capped with a stopper containing a membrane and purged during 10 minutes with nitrogen through a needle syringe. The photoluminescence spectrum (Perkin Elmer LS 50 B) is measured using an excitation wavelength of 460 nm. In the emission spectrum only a single band is observed. The maximum emission is observed at a wavelength of 614 nm, displaying a red emission. The resultant CIE coordinates are (0.64, 0.36).

b) Product of example 51 of the present invention:

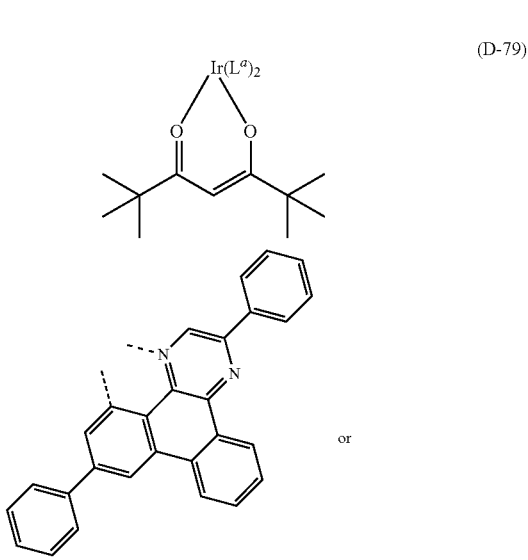

(D-79)

$L^a$ is or

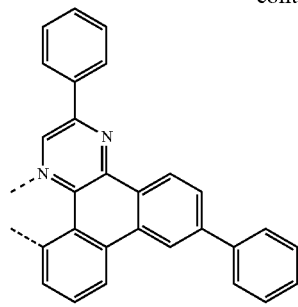

(A-151)

The PL spectrum of the compound of example 51 is measured with the same procedure, giving a single band emission, with a maximum emission of 616 nm, and CIE coordinates of (0.64, 0.35).

c) product of example 50 of the present invention:

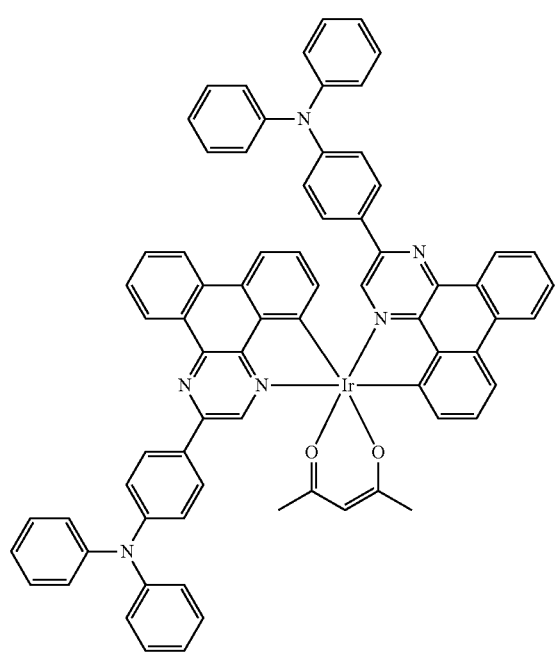

The PL spectrum of the compound of example 50 is measured with the same procedure, giving a single band emission, with a maximum emission of 612 nm, and CIE coordinates of (0.64, 0.35).

d) Product of example 61 of the present invention:

(C-1)

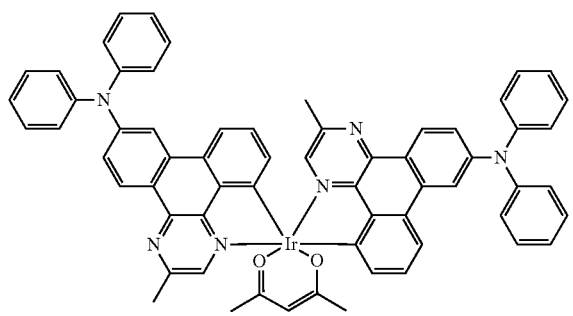

The PL spectrum of the compound of example 61 is measured with the same procedure, giving a single band emission, with a maximum emission of 610 nm, and CIE coordinates of (0.62, 0.38).

e) Product of example 58 of the present invention:

(B-156)

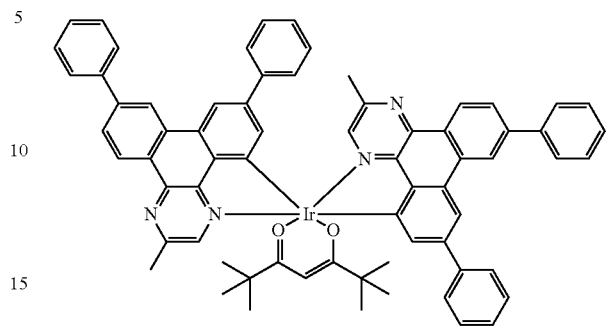

The PL spectrum of the compound of example 58 is measured with the same procedure, giving a single band emission, with a maximum emission of 607 nm, and CIE coordinates of (0.61, 0.38).

f) Product of example 56 of the present invention:

(D-81)

$L^a$ is

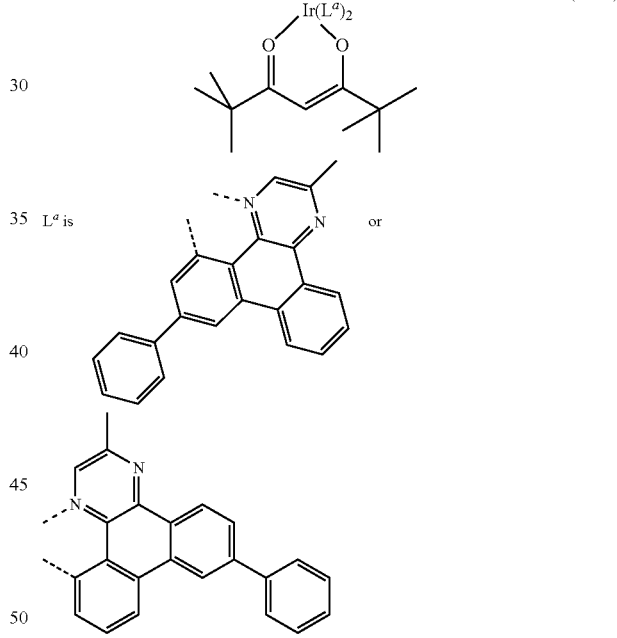

or

The PL spectrum of the compound of example 56 is measured with the same procedure, giving a single band emission, with a maximum emission of 606 nm, and CIE coordinates of (0.61, 0.38).

COMPARATIVE APPLICATION EXAMPLE

In a similar manner the compound described in J.-P. Duan et al., Adv. Mat. 2003, 15, 224 as $Ir(MDQ)_2$ (acac) available from American Dye Source Inc (=ADS076RE). is prepared and measured. The photoluminescence spectrum exhibits a strong emission at 601 nm, displaying an orange-red emission. In the emission spectrum only a single band is observed. The resultant CIE coordinates are at (0.59, 0.41).

The invention claimed is:
1. A compound of the formula

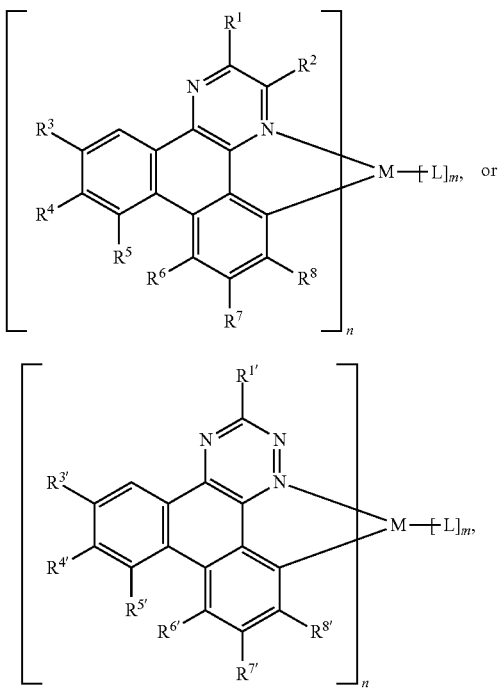

wherein
R$^1$, R$^2$ and R$^{1'}$ are independently of each other H, C$_1$-C$_{18}$alkyl, C$_1$-C$_{18}$alkyl which is substituted by E and/ or interrupted by D, C$_1$-C$_{18}$ perfluoroalkyl, C$_5$-C$_{12}$cycloalkyl, which can optionally be substituted by one to three C$_1$-C$_4$alkyl groups, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$arylalkyl, CN,

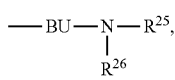

or —CO—R$^{28}$, or
R$^1$ and R$^2$ together form a ring,
R$^3$, R$^8$, R$^{3'}$ and R$^{8'}$ are independently of each other H, C$_1$-C$_{18}$alkyl, C$_1$-C$_{18}$alkyl which is substituted by E and/ or interrupted by D, C$_1$-C$_{18}$ perfluoroalkyl, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$arylalkyl, CN, or —CO—R$^{28}$,

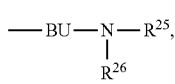

—NR$^{25}$R$^{26}$, —SR$^{29}$, or Si(R$^{30}$)$_3$,
R$^4$, R$^7$, R$^{4'}$ and R$^{7'}$ are independently of each other H, C$_1$-C$_{18}$alkyl, C$_1$-C$_{18}$alkyl which is substituted by E and/ or interrupted by D, C$_1$-C$_{18}$perfluoroalkyl, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$arylalkyl, CN, or —CO—R$^{28}$,

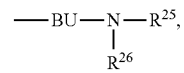

—NR$^{25}$R$^{26}$, —SR$^{29}$, or Si(R$^{30}$)$_3$,
R$^5$, R$^6$, R$^{5'}$ and R$^{6'}$ are independently of each other H, C$_1$-C$_{18}$alkyl, C$_1$-C$_{18}$alkyl which is substituted by E and/ or interrupted by D, C$_1$-C$_{18}$perfluoroalkyl, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$arylalkyl, CN, or —CO—R$^{28}$,

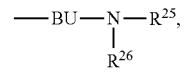

—NR$^{25}$R$^{26}$, —SR$^{29}$, Si(R$^{30}$)$_3$,
R$^{25}$ and R$^{26}$ are independently of each other C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, or
R$^{25}$ and R$^{26}$ together with the nitrogen atom to which they are bonded form a heteroaromatic ring, or ring system, which may optionally be substituted,
BU is a bridging unit,
D is —CO—; —COO—; —S—; —SO—; —SO$_2$—; —O—; —NR$^{25'}$—; —SiR$^{30}$R$^{31}$—; —POR$^{32}$—; —CR$^{23}$=CR$^{24}$—; or —C≡C—;
E is —OR$^{29}$; —SR$^{29}$; —NR$^{25}$R$^{26'}$; —COR$^{28}$; —COOR$^{27}$; —CONR$^{25}$R$^{26'}$; —CN; or halogen; G is E, C$_1$-C$_{18}$alkyl, C$_1$-C$_{18}$alkyl which is interrupted by D, C$_1$-C$_{18}$ perfluoroalkyl, C$_1$-C$_{18}$alkoxy, or C$_1$-C$_{18}$alkoxy which is substituted by E and/or interrupted by D, or C$_2$-C$_{18}$alkenyl,
R$^{23}$, R$^{24}$, R$^{25'}$ and R$^{26'}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—;
R$^{27}$ and R$^{28}$ are independently of each other H; C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—,
R$^{29}$ is H; C$_6$-C$_{18}$aryl; C$_6$-C$_{18}$aryl, which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—,
R$^{30}$ and R$^{31}$ are independently of each other C$_1$-C$_{18}$alkyl, C$_6$-C$_{18}$aryl, or C$_6$-C$_{18}$aryl, which is substituted by C$_1$-C$_{18}$alkyl, and
R$^{32}$ is C$_1$-C$_{18}$alkyl, C$_6$-C$_{18}$aryl, or C$_6$-C$_{18}$aryl, which is substituted by C$_1$-C$_{18}$alkyl,
M is Pd, Rh, Re, Pt, or Ir,
L is a mono-, or bi-dentate ligand,
if L is a monodentate ligand,
m is 0, or 2, and n is 1, or 2, if M is Pd, or Pt,
m is 0, 2, or 4, and n is 1, 2, or 3, if M is Rh, Ir or Re, if L is a bidentate ligand,
m is 0, or 1, and n is 1, or 2, if M is Pd, or Pt,
m is 0, 1, or 2, and n is 1, 2, or 3, if M is Rh, Ir or Re,
with the proviso that at least one of $R^1$, $R^2$, $R^3$, $R^8$, $R^4$, $R^7$, $R^5$ and $R^6$ is different from H and the further proviso that

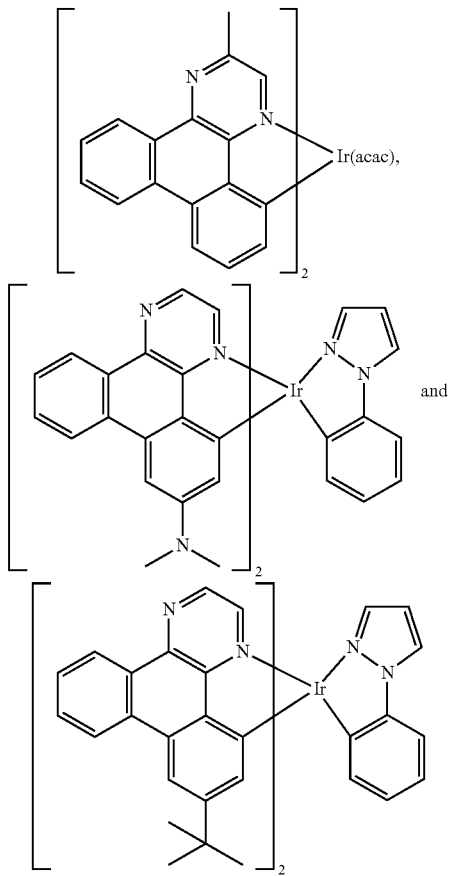

are excluded; and with the further proviso that organometallic complexes having a structure represented by the general formula

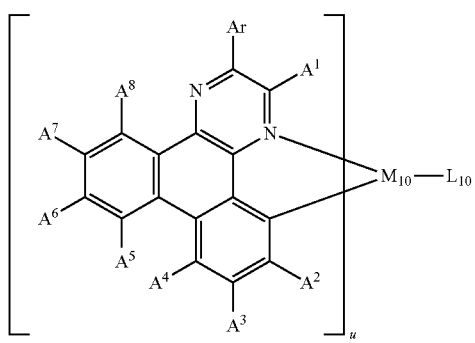

(G1)

are excluded,
wherein Ar represents an aryl group having 6 to 25 carbon atoms;
$A^1$ represents any one of hydrogen, an alkyl group having 1 to 4 carbon atoms, and an alkoxy group having 1 to 4 carbon atoms;

$A^2$ to $A^8$ each represent any one of hydrogen, an alkyl group having 1 to 4 carbon atoms, an alkoxy group having 1 to 4 carbon atoms, and a halogen group;
$M_{10}$ represents a metal of Group 9 elements and Group 10 elements;
$L_{10}$ represents a monoanionic ligand; and
u is 2 when the metal is a Group 9 element, and u is 1 when the metal is a Group 10 element.

2. The compound of the formula I, or II according to claim 1, wherein
$R^1$, $R^{1'}$ and $R^2$ are independently of each other H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G,

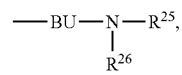

or CN, or
$R^1$ and $R^2$ together form a group

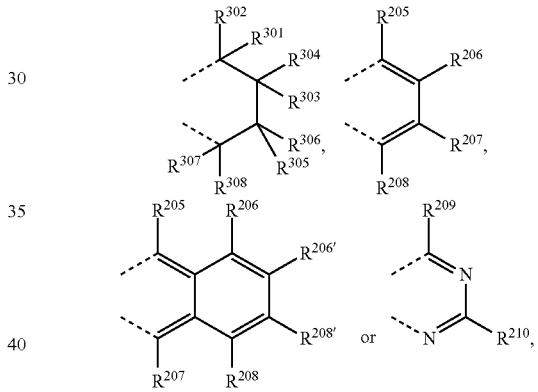

$R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkoxy, or $C_6$-$C_{24}$aryl, $C_6$-$C_{24}$aryl which is substituted by $C_1$-$C_{18}$alkyl or $C_1$-$C_{18}$alkoxy;
$R^{301}$, $R^{302}$, $R^{303}$, $R^{304}$, $R^{305}$, $R^{306}$, $R^{307}$ and $R^{308}$ are independently of each other H, or $C_1$-$C_{18}$alkyl, $R^3$, $R^8$, $R^{3'}$ and $R^{8'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy, $C_1$-$C_{18}$alkoxy which is substituted by E and/or interrupted by —O—, $C_7$-$C_{25}$arylalkyl, CN, or —$NR^{25}R^{26}$;
$R^4$, $R^7$, $R^{4'}$ and $R^{7'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy which is substituted by E and/or interrupted by —O—, $C_7$-$C_{25}$arylalkyl, CN, —$NR^{25}R^{26}$;
$R^5$, $R^6$, $R^{5'}$ and $R^{6'}$ are H,
$R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together with the nitrogen atom to which they are bonded form a heteroaromatic ring system

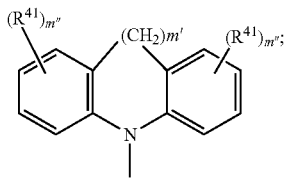

m' is 0, 1, or 2;

m" can be the same or different at each occurence and is 0, 1, 2, or 3;

$R^{41}$ can be the same or different at each occurence and is Cl, F, CN, $N(R^{45})_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —$NR^{45}$—, —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, or two or more groups $R^{41}$ form a ring system;

$R^{45}$ is H, a $C_1$-$C_{25}$alkyl group, a $C_4$-$C_{18}$cycloalkyl group, in which one or more carbon atoms which are not in neighbourhood to each other could be replaced by —$NR^{45"}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{41}$, and $R^{45"}$ is H, a $C_1$-$C_{25}$alkyl group, or a $C_4$-$C_{18}$cycloalkyl group, E is —$OR^{29}$; —$SR^{29}$; —$NR^{25'}R^{26'}$, CN, or F; G is E, $CF_3$, $C_1$-$C_{18}$alkyl, or $C_2$-$C_{18}$alkenyl, M is Pd, Rh, Re, Pt, or Ir, L is a bidentate ligand, m is 0, or 1, and n is 1, or 2, if M is Pd, or Pt, m is 0, 1, or 2, and n is 1, 2, or 3, if M is Rh, Ir or Re, and $R^{29}$; $R^{29'}$; $R^{25'}$ and $R^{26'}$ are as defined in claim 1, with the proviso that at least one of $R^3$, $R^8$, $R^4$ and $R^7$ is different from H.

3. The compound of the formula I according to claim 1, wherein at least one of the substituents $R^1$, $R^4$ and $R^7$ is a group —$NR^{25}R^{26}$, or $C_6$-$C_{24}$aryl, which is substituted by —$NR^{25}R^{26}$, wherein $R^{25}$ and $R^{26}$ are independently of each other

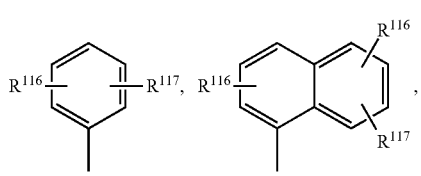

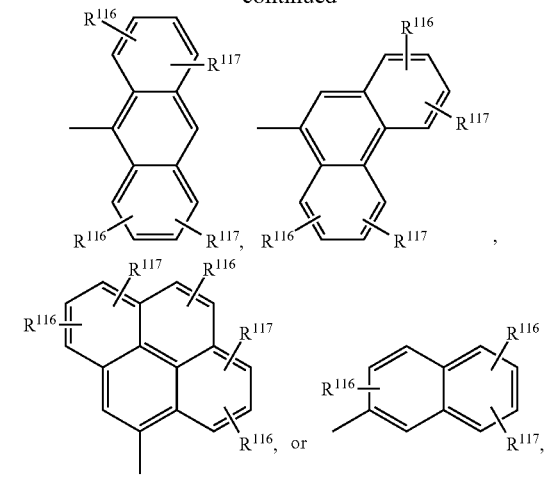

wherein $R^{116}$ and $R^{117}$ are independently of each other $C_1$-$C_{25}$alkyl, which may optionally be interrupted by —O—, or $C_1$-$C_{25}$alkoxy; or $R^{25}$ and $R^{26}$ together with the nitrogen atom to which they are bonded form a group of formula

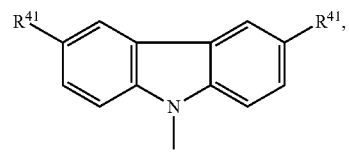

$R^{41}$ is H, or $C_1$-$C_{25}$alkyl.

4. The compound of claim 1 having a structure (Va), (Vb), (Vc), (VIa), (VIb), or (VIc) below:

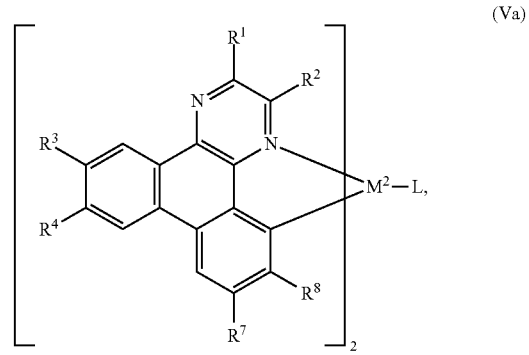

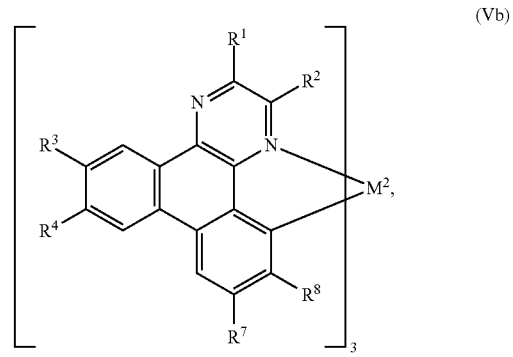

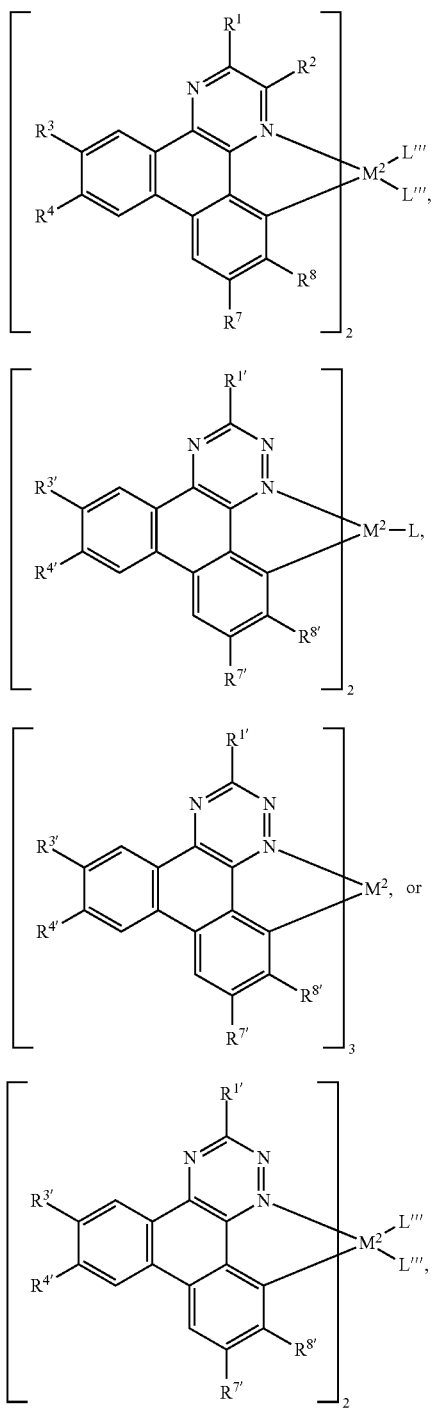

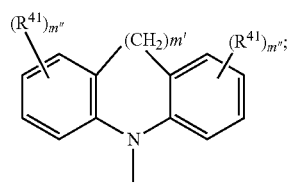

which is substituted by G, $C_2$-$C_{18}$alkenyl, $C_1$-$C_{18}$alkoxy, $C_1$-$C_{18}$alkoxy which is substituted by E and/or interrupted by —O—, $C_7$-$C_{25}$arylalkyl, CN, or —NR$^{25}$R$^{26}$;

R$^4$, R$^7$, R$^{4'}$ and R$^{7'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_1$-$C_{18}$alkoxy which is substituted by E and/or interrupted by —O—, $C_7$-$C_{25}$arylalkyl, CN, —NR$^{25}$R$^{26}$;

R$^{25}$ and R$^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or R$^{25}$ and R$^{26}$ together with the nitrogen atom to which they are bonded form a heteroaromatic ring system m' is 0, 1, or 2;

m'' can be the same or different at each occurence and is 0, 1, 2, or 3;

R$^{41}$ can be the same or different at each occurence and is Cl, F, CN, N(R$^{45}$)$_2$, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —NR$^{45}$—, —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups R$^{41}$, or two or more groups R$^{41}$ form a ring system;

R$^{45}$ is H, a $C_1$-$C_{25}$alkyl group, a $C_4$-$C_{18}$cycloalkyl group, in which one or more carbon atoms which are not in neighbourhood to each other can be replaced by —NR$^{45''}$—, —O—, —S—, —C(=O)—O—, or, —O—C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups R$^{41}$, and R$^{45''}$ is H, a $C_1$-$C_{25}$alkyl group, or a $C_4$-$C_{18}$cycloalkyl group, wherein R$^1$, R$^{1'}$ and R$^2$ are independently of each other H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G, or CN, R$^3$, R$^8$, R$^{3'}$ and R$^{8'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl E is —OR$^{29}$; —SR$^{29}$; —NR$^{25'}$R$^{26'}$, CN or F; G is E, $C_1$-$C_{18}$alkyl, CF$_3$, or $C_2$-$C_{18}$alkenyl, R$^{29}$; R$^{29'}$; R$^{25'}$ and R$^{26'}$ are as defined in claim 1, M$^2$ is Rh, Re or Ir, L is a bidentate ligand, and L''' is a monodentate ligand, or a compound of claim 1 having a structure (VIIa), (VIIb), (VIIIa), or (VIIIb) below:

(VIIa)

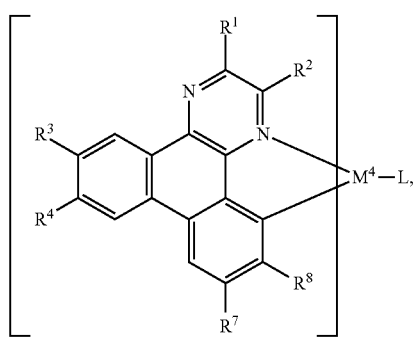

(VIIb)

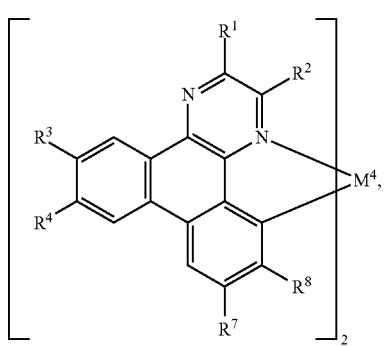

(VIIIa)

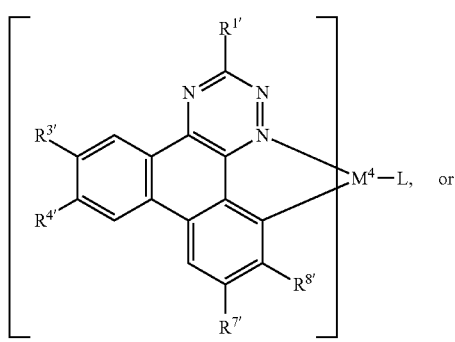

(VIIIb)

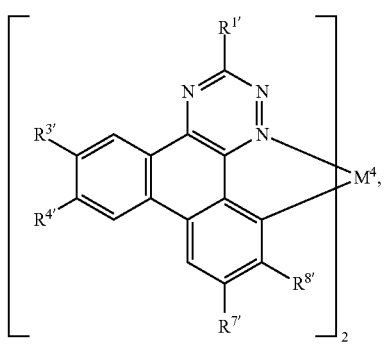

wherein $M^4$ is Pd, or Pt, and L, $R^1$, $R^2$, $R^{1'}$, $R^3$, $R^4$, $R^{3'}$, $R^{4'}$, $R^7$, $R^8$, $R^{7'}$ and $R^{8'}$ are as defined above.

5. The compound of formula I according to claim 1, wherein $R^2$ is H, or $CH_3$, $R^1$ and $R^{1'}$ are H, $C_1$-$C_{18}$alkyl, $C_5$-$C_{12}$cycloalkyl, which can optionally be substituted by one to three $C_1$-$C_4$alkyl groups, $C_6$-$C_{24}$aryl, $C_6$-$C_{24}$aryl which is substituted by G, $C_2$-$C_{20}$heteroaryl, $C_2$-$C_{20}$heteroaryl which is substituted by G,

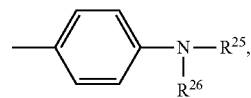

or CN, $R^3$, $R^8$, $R^{3'}$ and $R^{8'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by $C_1$-$C_{18}$alkyl, or $C_1$-$C_{18}$alkoxy; $C_1$-$C_{18}$alkyl; or $C_1$-$C_{18}$alkoxy which are interrupted by —O—; $C_1$-$C_{18}$alkoxy, or $C_1$-$C_{18}$alkoxy which is interrupted by —O—; or —$NR^{25}R^{26}$;

$R^4$, $R^7$, $R^{4'}$ and $R^{7'}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by $C_1$-$C_{18}$alkyl, or $C_1$-$C_{18}$alkoxy; $C_1$-$C_{18}$alkyl, or $C_1$-$C_{18}$alkoxy which are interrupted by —O—; $C_1$-$C_{18}$alkoxy, or $C_1$-$C_{18}$alkoxy which is interrupted by —O—; or —$NR^{25}R^{26}$;

$R^{25}$ and $R^{26}$ are independently of each other; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkoxy which are interrupted by —O—; or $R^{25}$ and $R^{26}$ together with the nitrogen atom to which they are bonded form a heteroaromatic ring system

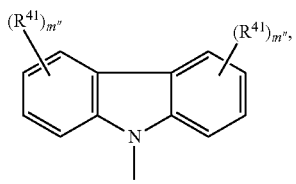

wherein $R^{41}$ is H, or $C_1$-$C_{25}$alkyl;

$M^2$ is Ir, and $M^4$ is Pd or Pt, and

L is a bidentate ligand.

6. The compound of claim 1, wherein the bidentate ligand L is a compound of formula

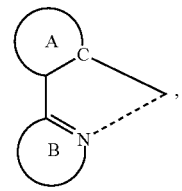

wherein the ring A,

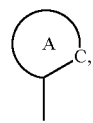

represents an optionally substituted aryl group which can optionally contain heteroatoms, the ring B,

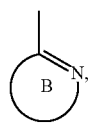

represents an optionally substituted nitrogen containing aryl group, which can optionally contain further heteroatoms, or the ring A may be taken with the ring B binding to the ring A to form a ring group of formula

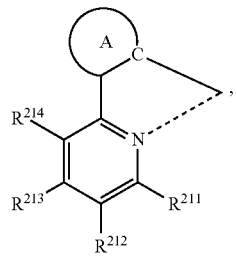

wherein $R^{211}$, $R^{212}$, $R^{213}$, and $R^{214}$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^{211}$, $R^{212}$, $R^{213}$, and $R^{214}$ may be substituted; or $R^{213}$ and $R^{214}$ or $R^{212}$ and $R^{213}$ are a group of formula

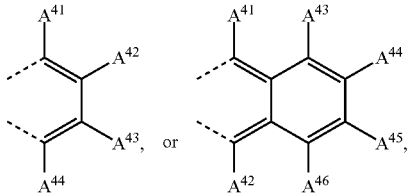

wherein $A^{41}$, $A^{42}$, $A^{43}$, $A^{44}$, $A^{45}$, and $A^{46}$ are independently of each other H, halogen, CN, $C_1$-$C_{24}$alkyl, $C_1$-$C_{24}$ perfluoroalkyl, $C_1$-$C_{24}$alkoxy, $C_1$-$C_{24}$alkylthio, $C_6$-$C_{18}$aryl, which may optionally be substituted by G', —$NR^{25'}R^{26'}$, —$CONR^{25'26'}$, or —$COOR^{27'}$, or $C_2$-$C_{10}$heteroaryl; wherein $R^{25'}$ and $R^{26'}$ are independently of each other $C_6$-$C_{18}$aryl, $C_7$-$C_{18}$aralkyl, or $C_1$-$C_{24}$alkyl, $R^{27'}$ is $C_1$-$C_{24}$alkyl, $C_6$-$C_{18}$aryl, or $C_7$-$C_{18}$aralkyl;

G' is $C_1$-$C_{18}$alkyl, —$OR^{305}$, —$SR^{305}$, —$NR^{305}R^{306}$, —$CONR^{305}R^{306}$, or —CN, wherein $R^{305}$ and $R^{306}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—;

$R^{305}$ is $C_1$-$C_{18}$alkyl, or $C_6$-$C_{18}$aryl, and $R^{306}$ is $C_1$-$C_{18}$alkyl, or $C_6$-$C_{18}$aryl; or L is a bidentate ligand L' selected from

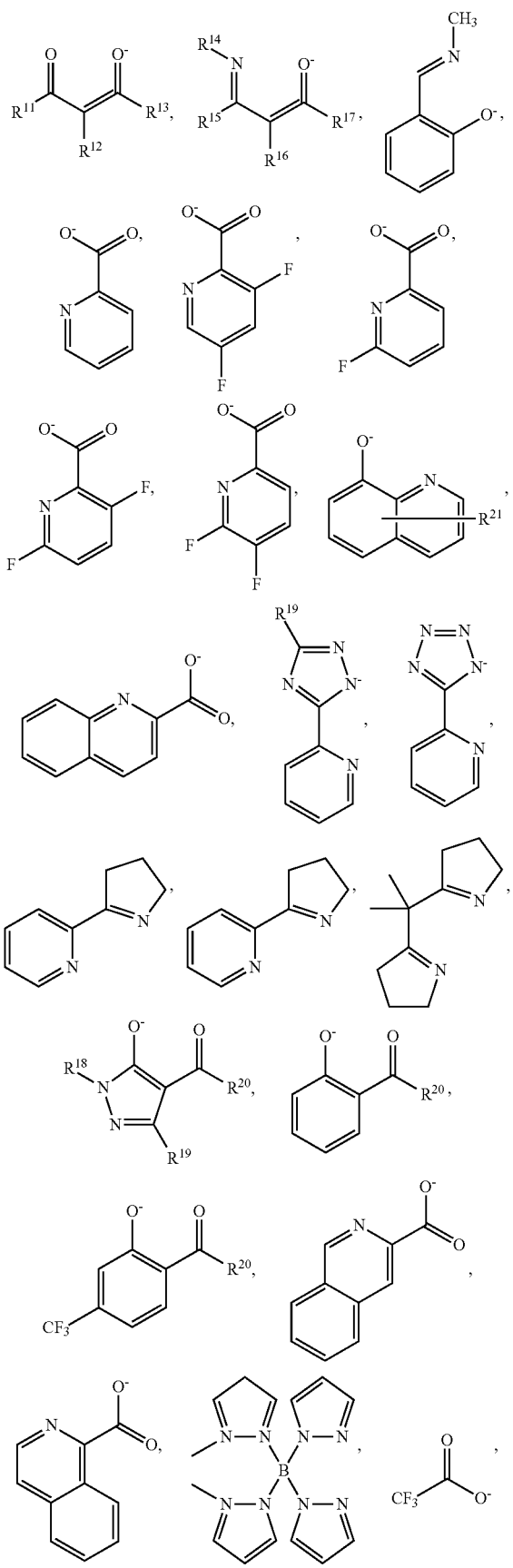

169
-continued
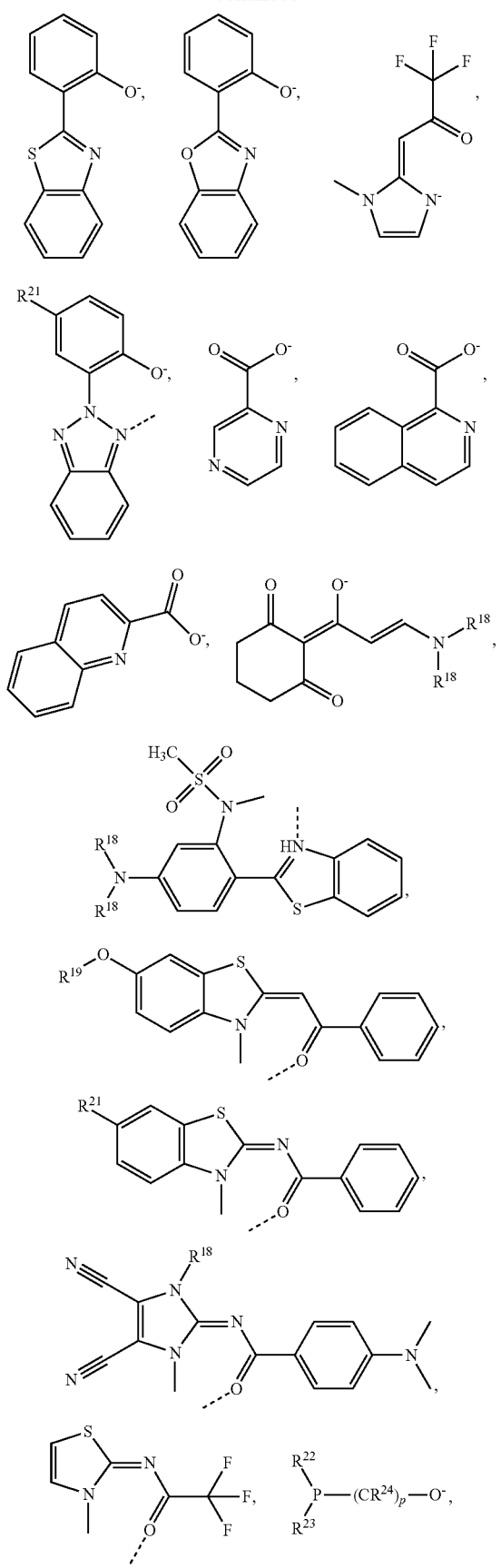
170
-continued
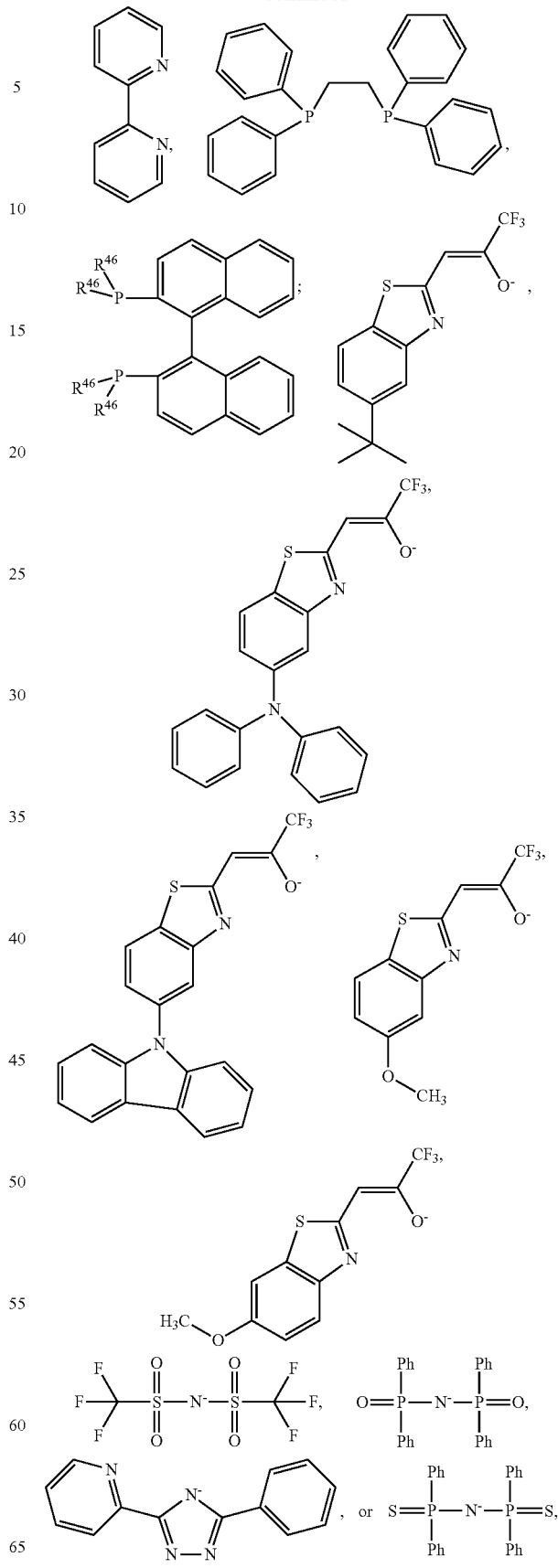

wherein $R^{11}$ and $R^{15}$ are independently of each other hydrogen, $C_1$-$C_8$alkyl, $C_6$-$C_{18}$aryl, $C_2$-$C_{10}$heteroaryl, or $C_1$-$C_8$perfluoroalkyl, $R^{12}$ and $R^{16}$ are independently of each other hydrogen, $C_6$-$C_{18}$aryl, or $C_1$-$C_8$alkyl, and $R^{13}$ and $R^{17}$ are independently of each other hydrogen, $C_1$-$C_8$alkyl, $C_6$-$C_{18}$aryl, $C_2$-$C_{10}$heteroaryl, $C_1$-$C_8$ perfluoroalkyl, or $C_1$-$C_8$alkoxy, and $R^{14}$ is $C_1$-$C_8$alkyl, $C_6$-$C_{10}$aryl, or $C_7$-$C_{11}$aralkyl, $R^{18}$ is $C_6$-$C_{10}$aryl, $R^{19}$ is $C_1$-$C_8$alkyl, or $C_1$-$C_8$ perfluoroalkyl, $R^{20}$ is hydrogen, $C_1$-$C_8$alkyl, or $C_6$-$C_{10}$aryl, $R^{21}$ is hydrogen, $C_1$-$C_8$alkyl, or $C_1$-$C_8$alkoxy, which may be partially or fully fluorinated, $R^{22}$ and $R^{23}$ are independently of each other $C_q(H+F)_{2q+1}$, or $C_6(H+F)_5$, $R^{24}$ can be the same or different at each occurrence and is selected from H, or $C_q(H+F)_{2q+1}$, $R^{46}$ is $C_1$-$C_8$alkyl, $C_6$-$C_{18}$aryl, or $C_6$-$C_{18}$aryl, which is substituted by $C_1$-$C_8$alkyl, q is an integer of 1 to 24, p is 2, or 3, or L is a bidentate ligand L" selected from

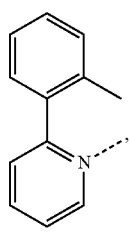
(X-1)

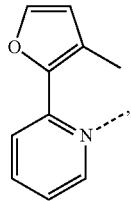
(X-2)

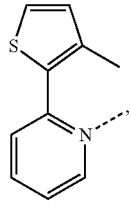
(X-3)

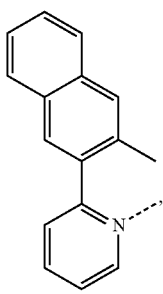
(X-4)

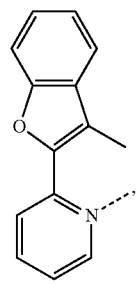
(X-5)

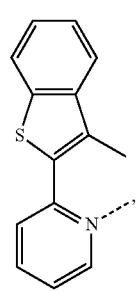
(X-6)

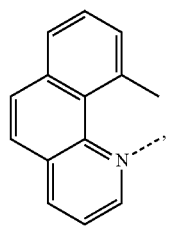
(X-7)

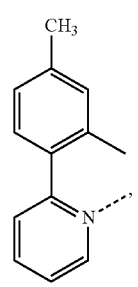
(X-8)

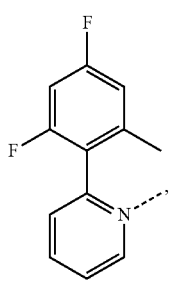
(X-9)

(X-10) 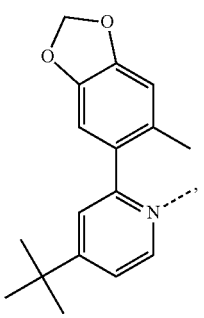
(X-11) 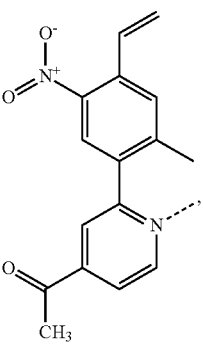
(X-12) 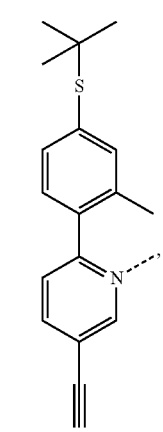
(X-13) 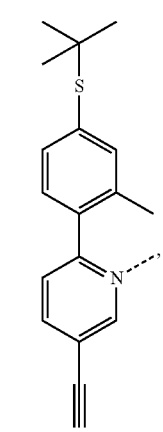
(X-14) 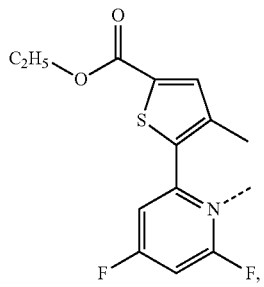
(X-15) 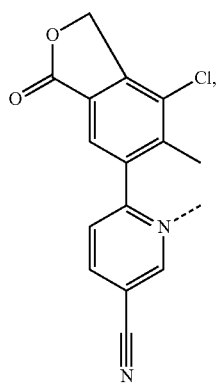
(X-16) 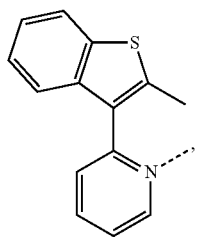
(X-17) 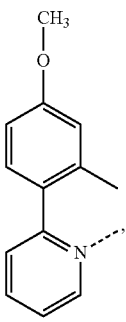
(X-18) 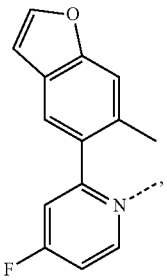

-continued
(X-19) 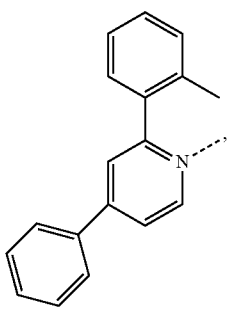
(X-20) 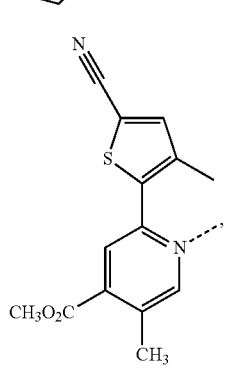
(X-21) 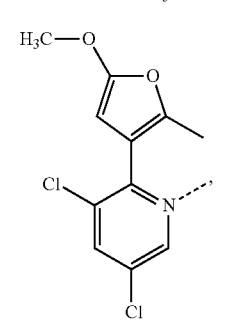
(X-22) 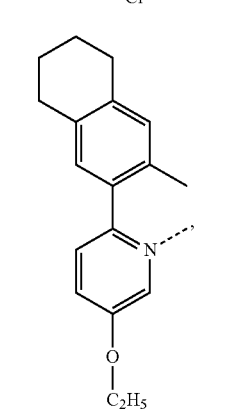
(X-23) 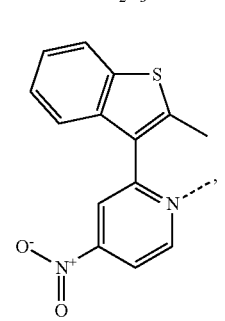
-continued
(X-24) 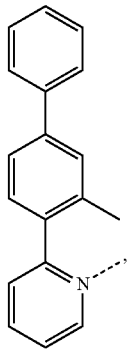
(X-25) 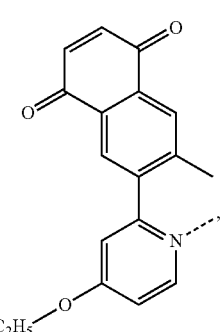
(X-26) 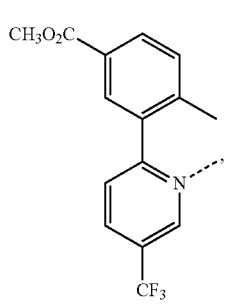
(X-27) 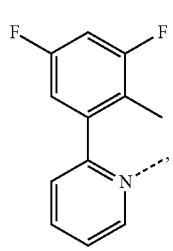
(X-28)

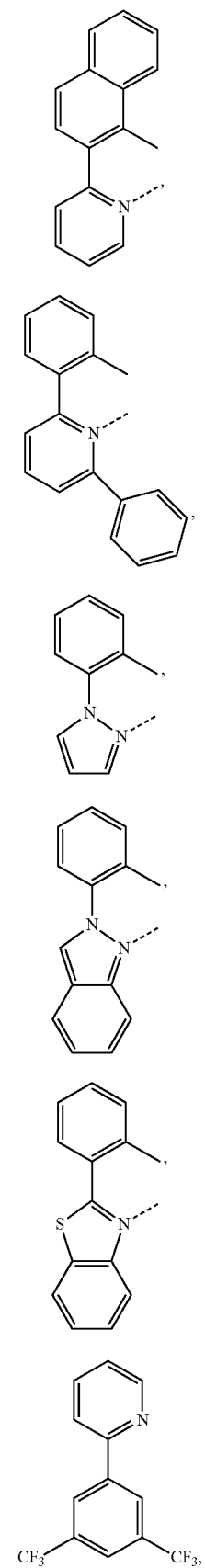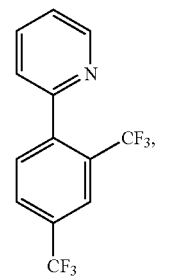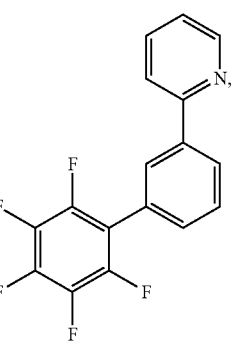

-continued
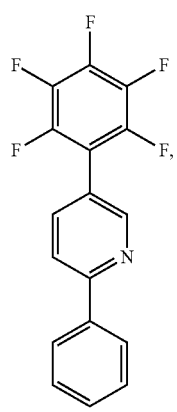
(X-38)
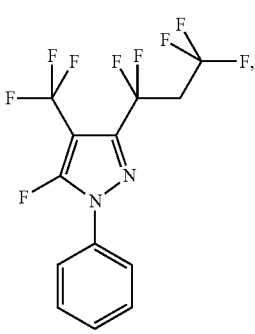
(X-39)
(X-40)
(X-41)
(X-42)
-continued
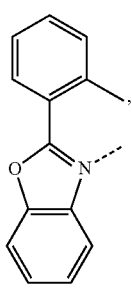
(X-43)
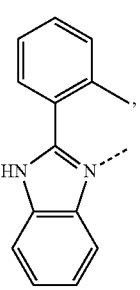
(X-44)
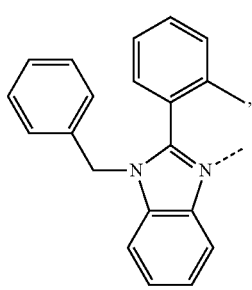
(X-45)
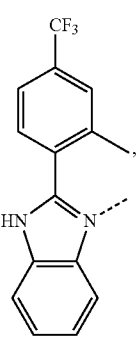
(X-46)
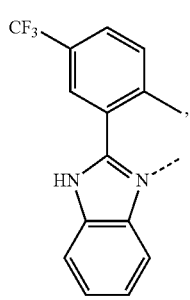
(X-47)

(X-48) 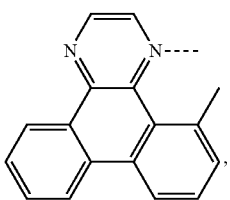
(X-49) 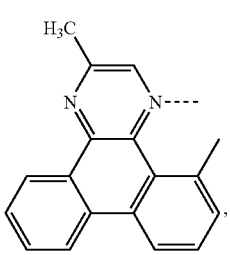
(X-50) 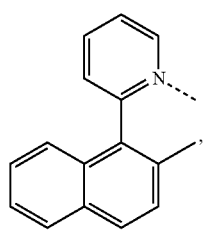
(X-51) 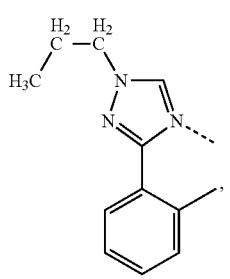
(X-52) 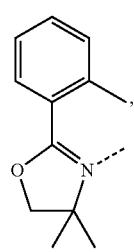
(X-53) 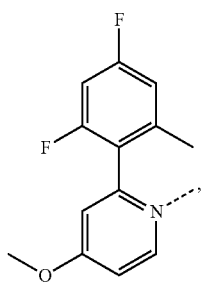
(X-54) 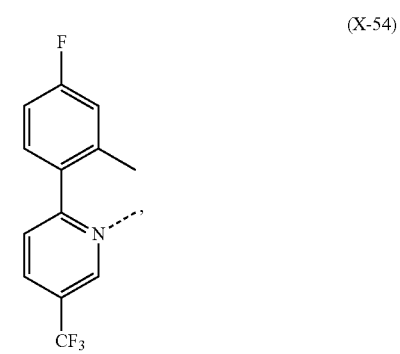
(X-55) 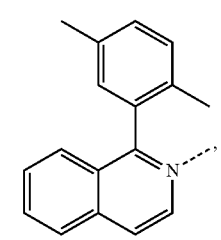
(X-56) 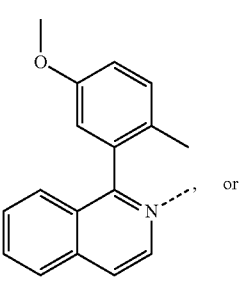 or
(X-57) 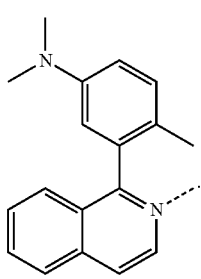

7. The compound of claims 6:
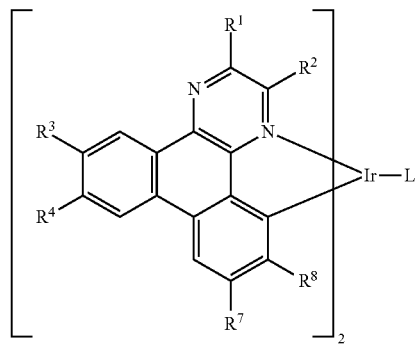
| Cpd. | L | R¹ | R² | R³ and R⁸ | R⁴ and R⁷ |
|---|---|---|---|---|---|
| A-1 | A$^{1)}$ | —CH₃ | H | H | N(C₆H₅)₂ |
| A-2 | A$^{1)}$ | —CH₃ | H | N(C₆H₅)₂ | H |
| A-3 | A$^{1)}$ | —CH₃ | H | H | N(naphthyl)(C₆H₅) |
| A-4 | A$^{1)}$ | —CH₃ | H | N(naphthyl)(C₆H₅) | H |

-continued
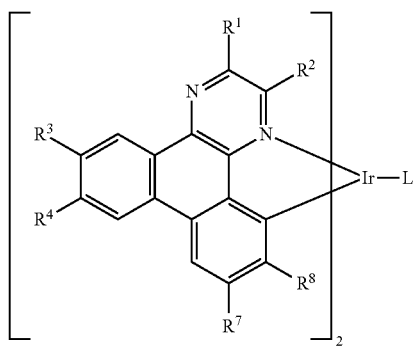
| Cpd. | L | R¹ | R² | R³ and R⁸ | R⁴ and R⁷ |
|---|---|---|---|---|---|
| A-5 | A[1)] | —CH₃ | H | H | 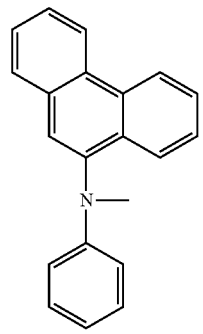 |
| A-6 | A[1)] | —CH₃ | H | 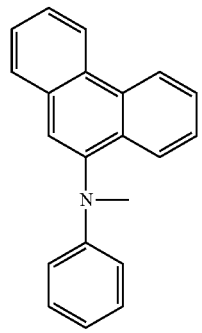 | H |
| A-7 | A[1)] | —CH₃ | H | H | 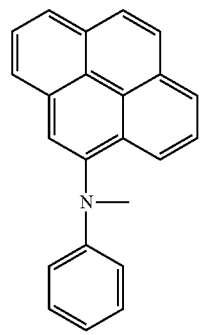 |

-continued
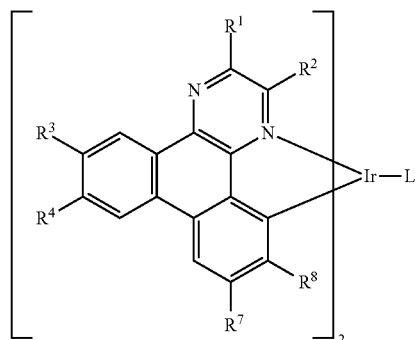
| Cpd. | L | R¹ | R² | R³ and R⁸ | R⁴ and R⁷ |
|---|---|---|---|---|---|
| A-8 | A[1)] | —CH₃ | H | ![pyrene-N(Me)(Ph)] | H |
| A-9 | A[1)] | —CH₃ | H | H | ![anthracene-N(Me)(Ph)] |
| A-10 | A[1)] | —CH₃ | H | ![anthracene-N(Me)(Ph)] | H |
| A-11 | A[1)] | —CH₃ | H | H | ![N-methylcarbazole] |

-continued
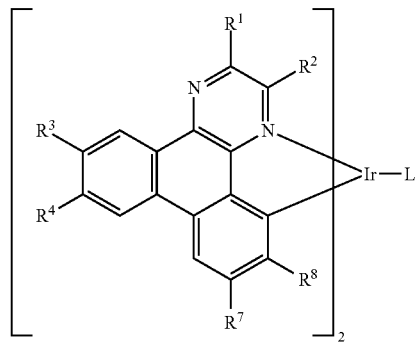
| Cpd. | L | R¹ | R² | R³ and R⁸ | R⁴ and R⁷ |
|---|---|---|---|---|---|
| A-12 | A[1)] | —CH₃ | H | 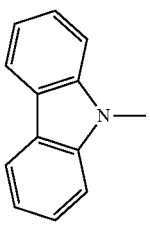 | H |
| A-13 | A[1)] | —CH₃ | H | H | 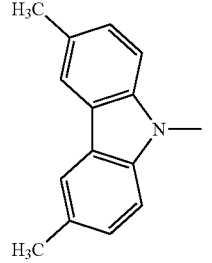 |
| A-14 | A[1)] | —CH₃ | H | 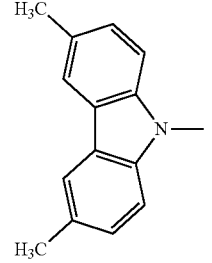 | H |
| A-15 | A[1)] | —CH₃ | H | H | 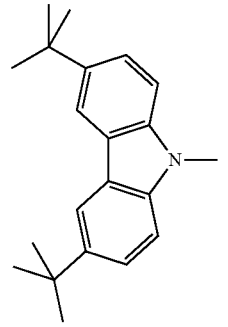 |

-continued
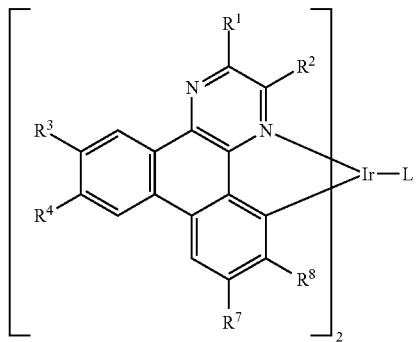
| Cpd. | L | R¹ | R² | R³ and R⁸ | R⁴ and R⁷ |
|---|---|---|---|---|---|
| A-16 | A[1)] | —CH₃ | H | 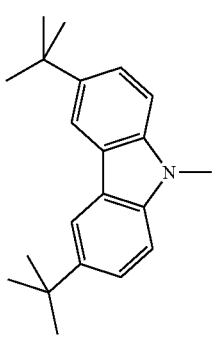 | H |
| A-17 | A[1)] | —CH₃ | H | H | 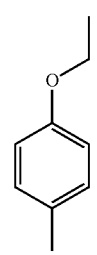 |
| A-18 | A[1)] | —CH₃ | H | 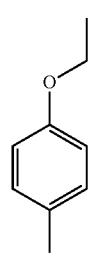 | H |
| A-19 | A[1)] | H | H | H | 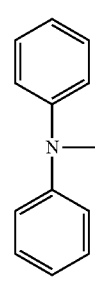 |

-continued
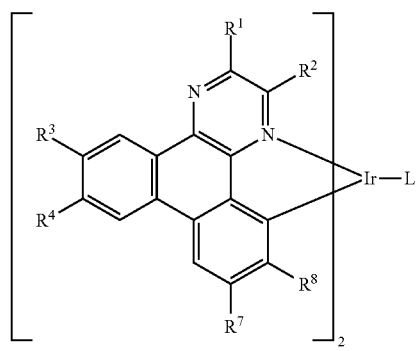
| Cpd. | L | R¹ | R² | R³ and R⁸ | R⁴ and R⁷ |
|---|---|---|---|---|---|
| A-20 | A[1)] | H | H | ![N,N-diphenylamino] | H |
| A-21 | A[1)] | H | H | H | ![N-naphthyl-N-phenylamino] |
| A-22 | A[1)] | H | H | ![N-naphthyl-N-phenylamino] | H |
| A-23 | A[1)] | H | H | H | ![N-(phenanthrenyl)-N-phenylamino] |

-continued
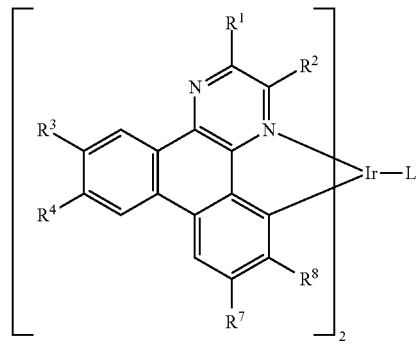
| Cpd. | L | R¹ | R² | R³ and R⁸ | R⁴ and R⁷ |
|---|---|---|---|---|---|
| A-24 | A[1)] | H | H | 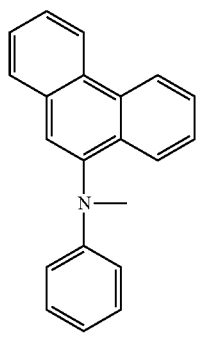 | H |
| A-25 | A[1)] | H | H | H | 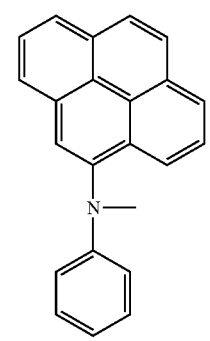 |
| A-26 | A[1)] | H | H | 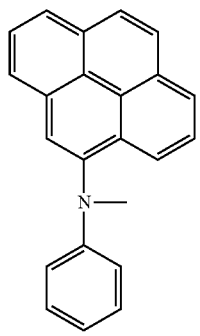 | H |

-continued
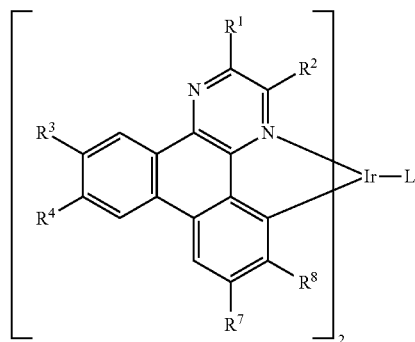
| Cpd. | L | R¹ | R² | R³ and R⁸ | R⁴ and R⁷ |
|---|---|---|---|---|---|
| A-27 | A[1)] | H | H | H | 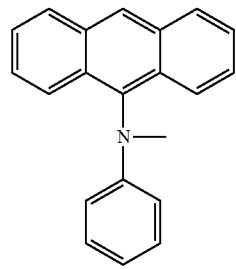 |
| A-28 | A[1)] | H | H | 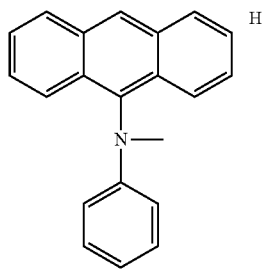 | H |
| A-29 | A[1)] | H | H | H | 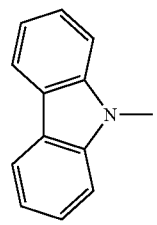 |
| A-30 | A[1)] | H | H | 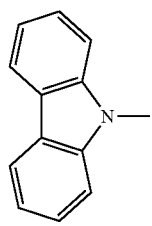 | H |

-continued
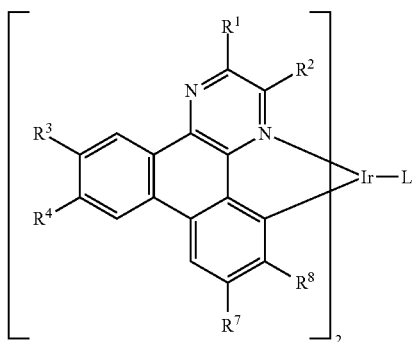
| Cpd. | L | R¹ | R² | R³ and R⁸ | R⁴ and R⁷ |
|------|---|----|----|-----------|-----------|
| A-31 | A¹⁾ | H | H | H | 3,6-dimethyl-9-methylcarbazol-N-yl |
| A-32 | A¹⁾ | H | H | 3,6-dimethyl-9-methylcarbazol-N-yl | H |
| A-33 | A¹⁾ | H | H | H | 3,6-di-tert-butyl-9-methylcarbazol-N-yl |
| A-34 | A¹⁾ | H | H | H | 3,6-di-tert-butyl-9-methylcarbazol-N-yl |

-continued
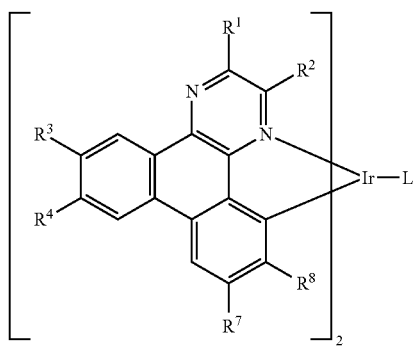
| Cpd. | L | R¹ | R² | R³ and R⁸ | R⁴ and R⁷ |
|---|---|---|---|---|---|
| A-35 | A[1)] | H | H | H | 4-ethoxyphenyl (p-tolyl ether) |
| A-36 | A[1)] | H | 4-ethoxyphenyl | H | H |
| A-37 | A[1)] | Ph | H | H | N,N-diphenylamino |
| A-38 | A[1)] | Ph | N,N-diphenylamino | H | H |

-continued
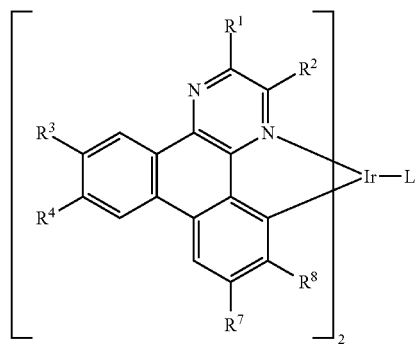
| Cpd. | L | R¹ | R² | R³ and R⁸ | R⁴ and R⁷ |
|---|---|---|---|---|---|
| A-39 | A¹⁾ | Ph | H | H | ![N-methyl-N-phenyl-1-naphthylamine] |
| A-40 | A¹⁾ | Ph | H | ![N-methyl-N-phenyl-1-naphthylamine] | H |
| A-41 | A¹⁾ | Ph | H | H | ![N-methyl-N-phenyl-9-phenanthrylamine] |
| A-42 | A¹⁾ | Ph | H | ![N-methyl-N-phenyl-9-phenanthrylamine] | H |

-continued
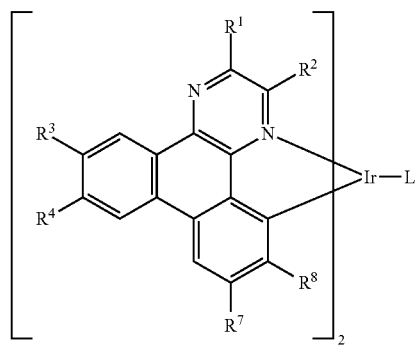
| Cpd. | L | R¹ | R² | R³ and R⁸ | R⁴ and R⁷ |
|---|---|---|---|---|---|
| A-43 | A[1)] | Ph | H | H | 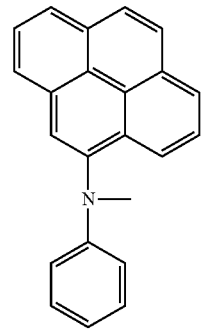 |
| A-44 | A[1)] | Ph | H | 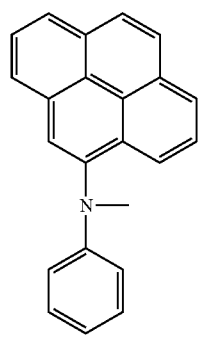 | H |
| A-45 | A[1)] | Ph | H | H | 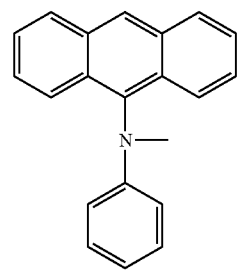 |
| A-46 | A[1)] | Ph | H | 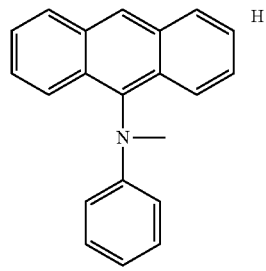 | H |

-continued
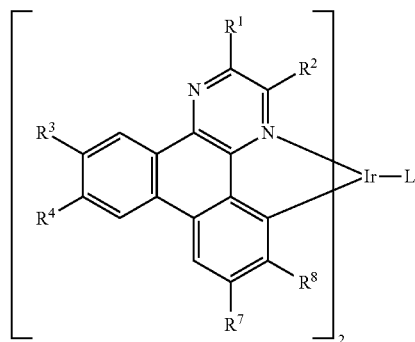
| Cpd. | L | R¹ | R² | R³ and R⁸ | R⁴ and R⁷ |
|---|---|---|---|---|---|
| A-47 | A[1)] | Ph | H | H | 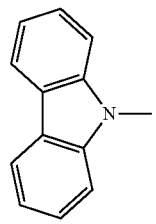 |
| A-48 | A[1)] | Ph | H | (carbazole structure) | H |
| A-49 | A[1)] | Ph | H | H | (3,6-dimethyl carbazole) |
| A-50 | A[1)] | Ph | H | (3,6-dimethyl carbazole) | H |

-continued
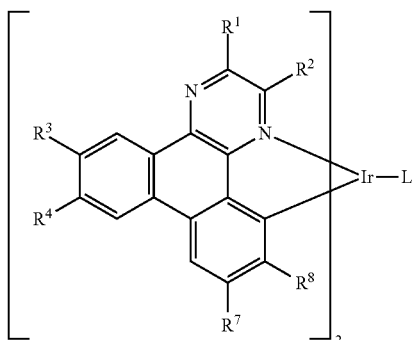
| Cpd. | L | R¹ | R² | R³ and R⁸ | R⁴ and R⁷ |
|---|---|---|---|---|---|
| A-51 | A¹⁾ | Ph | H | H | 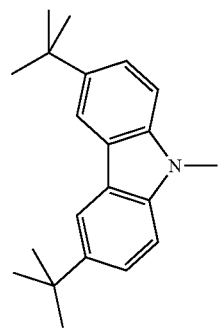 |
| A-52 | A¹⁾ | Ph | H | 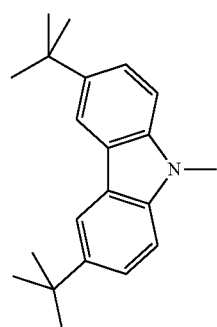 | H |
| A-53 | A¹⁾ | Ph | H | H | 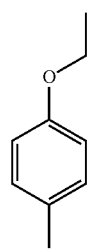 |
| A-54 | A¹⁾ | Ph | H | 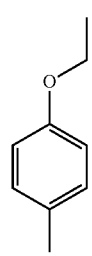 | H |

-continued
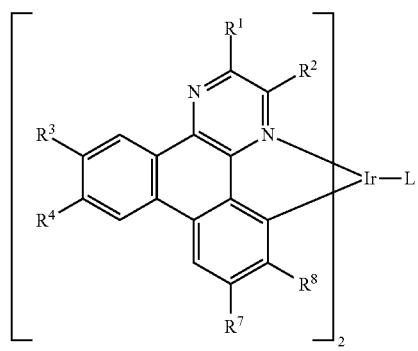
| Cpd. | L | R¹ | R² | R³ and R⁸ | R⁴ and R⁷ |
|---|---|---|---|---|---|
| A-55 | A[1)] | F-C₆H₄- (4-fluorophenyl) | H | H | N,N-diphenylamino |
| A-56 | A[1)] | F-C₆H₄- (4-fluorophenyl) | H | N,N-diphenylamino | H |
| A-57 | A[1)] | F-C₆H₄- (4-fluorophenyl) | H | H | N-naphthyl-N-phenylamino |
| A-58 | A[1)] | F-C₆H₄- (4-fluorophenyl) | H | N-naphthyl-N-phenylamino | H |

-continued
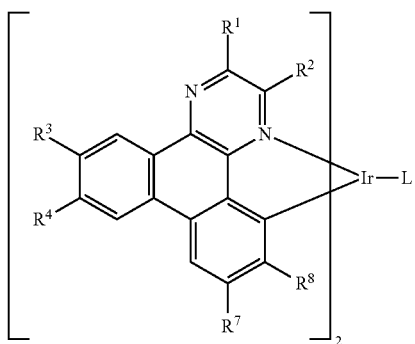
| Cpd. | L | R¹ | R² | R³ and R⁸ | R⁴ and R⁷ |
|---|---|---|---|---|---|
| A-59 | A[1)] | 4-F-C₆H₄ | H | H | N-methyl-N-phenyl-phenanthren-9-amine |
| A-60 | A[1)] | 4-F-C₆H₄ | H | N-methyl-N-phenyl-phenanthren-9-amine | H |
| A-61 | A[1)] | 4-F-C₆H₄ | H | H | N-methyl-N-phenyl-pyren-1-amine |

-continued
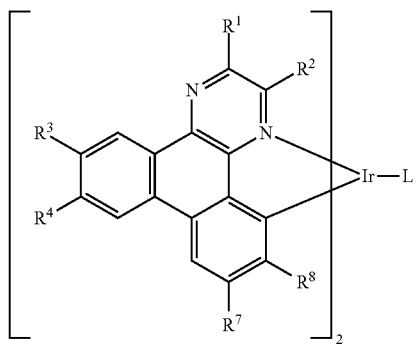
| Cpd. | L | R¹ | R² | R³ and R⁸ | R⁴ and R⁷ |
|---|---|---|---|---|---|
| A-62 | A¹⁾ | ![F-phenyl] | H | ![N-methyl-N-phenyl-pyrenylamine] | H |
| A-63 | A¹⁾ | ![F-phenyl] | H | H | ![N-methyl-N-phenyl-anthracenylamine] |
| A-64 | A¹⁾ | ![F-phenyl] | H | ![N-methyl-N-phenyl-anthracenylamine] | H |
| A-65 | A¹⁾ | ![F-phenyl] | H | H | ![N-methyl-carbazole] |

-continued
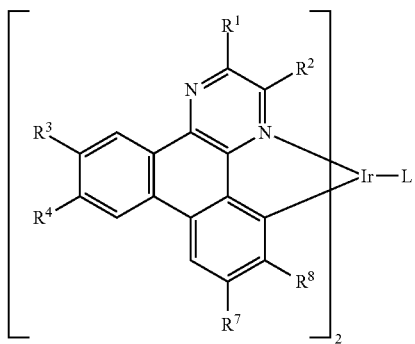
| Cpd. | L | R¹ | R² | R³ and R⁸ | R⁴ and R⁷ |
|---|---|---|---|---|---|
| A-66 | A[1)] | 4-F-C₆H₄ | H | N-methylcarbazol-3-yl | H |
| A-67 | A[1)] | 4-F-C₆H₄ | H | H | 3,6-dimethyl-N-methylcarbazol-2-yl |
| A-68 | A[1)] | 4-F-C₆H₄ | H | 3,6-dimethyl-N-methylcarbazol-2-yl | H |
| A-69 | A[1)] | 4-F-C₆H₄ | H | H | 3,6-di-tert-butyl-N-methylcarbazol-2-yl |

-continued
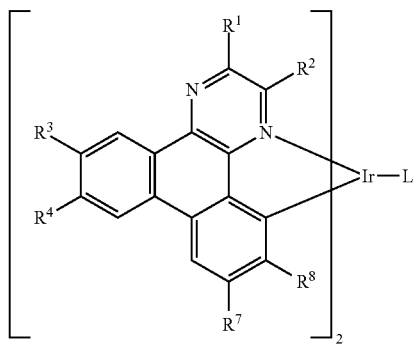
| Cpd. | L | R¹ | R² | R³ and R⁸ | R⁴ and R⁷ |
|---|---|---|---|---|---|
| A-70 | A¹⁾ | 4-fluorophenyl | H | 3,6-di-tert-butyl-9-methylcarbazol-yl | H |
| A-71 | A¹⁾ | 4-fluorophenyl | H | H | 4-ethoxyphenyl |
| A-72 | A¹⁾ | 4-fluorophenyl | H | 4-ethoxyphenyl | H |
| A-73 | A¹⁾ | 3,5-difluorophenyl | H | H | N,N-diphenylamino |

-continued
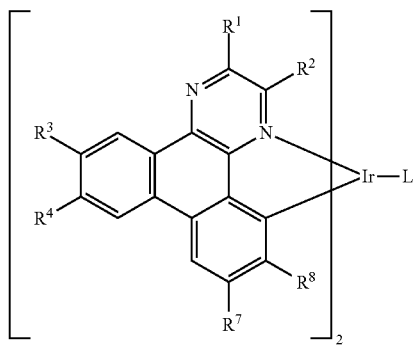
| Cpd. | L | R¹ | R² | R³ and R⁸ | R⁴ and R⁷ |
|---|---|---|---|---|---|
| A-74 | A[1)] | 3,5-difluorophenyl | H | N,N-diphenylamino | H |
| A-75 | A[1)] | 3,5-difluorophenyl | H | H | N-naphthyl-N-phenylamino |
| A-76 | A[1)] | 3,5-difluorophenyl | H | N-naphthyl-N-phenylamino | H |
| A-77 | A[1)] | 3,5-difluorophenyl | H | H | N-(phenanthren-9-yl)-N-phenylamino |

-continued
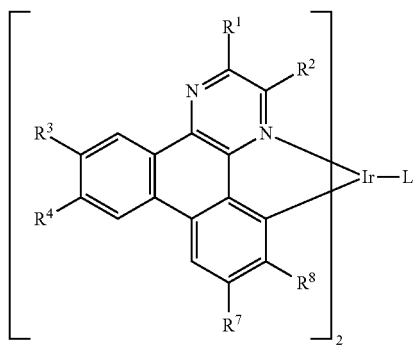
| Cpd. | L | R¹ | R² | R³ and R⁸ | R⁴ and R⁷ |
|---|---|---|---|---|---|
| A-78 | A[1)] | F,F (3,5-difluorophenyl) | H | N-methyl-N-phenyl-phenanthren-9-amine | H |
| A-79 | A[1)] | F,F (3,5-difluorophenyl) | H | H | N-methyl-N-phenyl-pyren-1-amine |
| A-80 | A[1)] | F,F (3,5-difluorophenyl) | H | N-methyl-N-phenyl-pyren-1-amine | H |

-continued
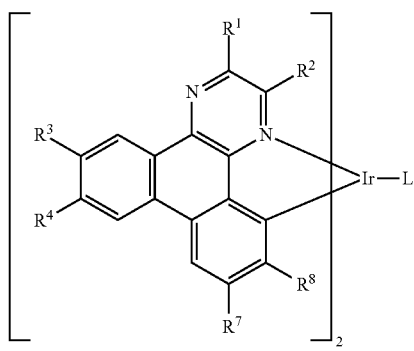
| Cpd. | L | R¹ | R² | R³ and R⁸ | R⁴ and R⁷ |
|---|---|---|---|---|---|
| A-81 | A¹⁾ | 3,5-difluorophenyl | H | H | 9-(N-methyl-N-phenylamino)anthracenyl |
| A-82 | A¹⁾ | 3,5-difluorophenyl | H | 9-(N-methyl-N-phenylamino)anthracenyl | H |
| A-83 | A¹⁾ | 3,5-difluorophenyl | H | H | N-methylcarbazolyl |
| A-84 | A¹⁾ | 3,5-difluorophenyl | H | N-methylcarbazolyl | H |

-continued
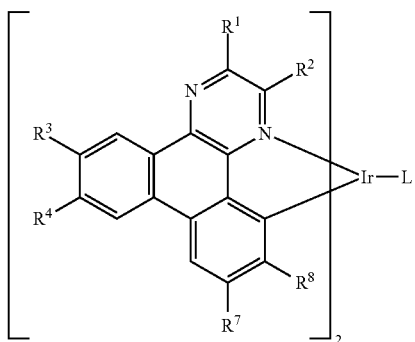
| Cpd. | L | R¹ | R² | R³ and R⁸ | R⁴ and R⁷ |
|---|---|---|---|---|---|
| A-85 | A¹⁾ | 3,5-difluorophenyl | H | H | 3,6-dimethyl-9-methylcarbazol-2-yl |
| A-86 | A¹⁾ | 3,5-difluorophenyl | H | 3,6-dimethyl-9-methylcarbazol-2-yl | H |
| A-87 | A¹⁾ | 3,5-difluorophenyl | H | H | 3,6-di-tert-butyl-9-methylcarbazol-2-yl |
| A-88 | A¹⁾ | 3,5-difluorophenyl | H | 3,6-di-tert-butyl-9-methylcarbazol-2-yl | H |

-continued
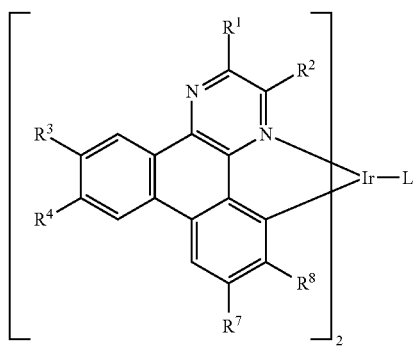
| Cpd. | L | R¹ | R² | R³ and R⁸ | R⁴ and R⁷ |
|---|---|---|---|---|---|
| A-89 | A¹⁾ | 3,5-difluorophenyl | H | H | 4-ethoxyphenyl |
| A-90 | A¹⁾ | 3,5-difluorophenyl | H | 4-ethoxyphenyl | H |
| A-91 | A¹⁾ | pentafluorophenyl | H | H | N,N-diphenylamino |
| A-92 | A¹⁾ | pentafluorophenyl | H | N,N-diphenylamino | H |

-continued
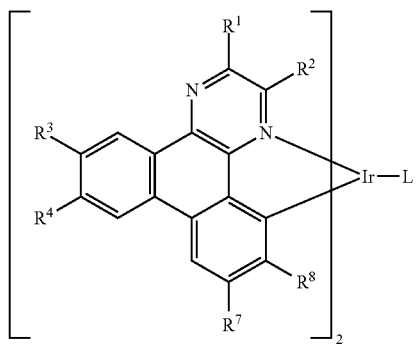
| Cpd. | L | R¹ | R² | R³ and R⁸ | R⁴ and R⁷ |
|---|---|---|---|---|---|
| A-93 | A[1)] | pentafluorophenyl | H | H | N-methyl-N-phenyl-naphthalen-1-amine |
| A-94 | A[1)] | pentafluorophenyl | H | N-methyl-N-phenyl-naphthalen-1-amine | H |
| A-95 | A[1)] | pentafluorophenyl | H | H | N-methyl-N-phenyl-phenanthren-9-amine |
| A-96 | A[1)] | pentafluorophenyl | H | N-methyl-N-phenyl-phenanthren-9-amine | H |

-continued
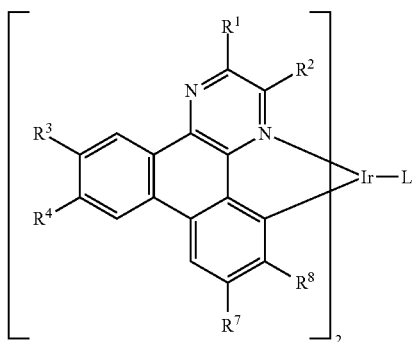
| Cpd. | L | R¹ | R² | R³ and R⁸ | R⁴ and R⁷ |
|---|---|---|---|---|---|
| A-97 | A[1)] | pentafluorophenyl | H | H | N-methyl-N-phenyl-pyrenyl |
| A-98 | A[1)] | pentafluorophenyl | H | N-methyl-N-phenyl-pyrenyl | H |
| A-99 | A[1)] | pentafluorophenyl | H | H | N-methyl-N-phenyl-anthracenyl |
| A-100 | A[1)] | pentafluorophenyl | H | N-methyl-N-phenyl-anthracenyl | H |

-continued
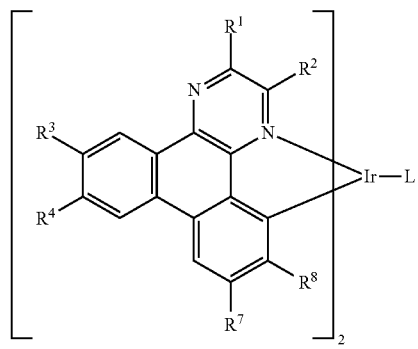
| Cpd. | L | R¹ | R² | R³ and R⁸ | R⁴ and R⁷ |
|------|---|----|----|-----------|-----------|
| A-101 | A[1)] | pentafluorophenyl | H | H | N-methylcarbazolyl |
| A-102 | A[1)] | pentafluorophenyl | H | N-methylcarbazolyl | H |
| A-103 | A[1)] | pentafluorophenyl | H | H | 3,6-dimethyl-N-methylcarbazolyl |
| A-104 | A[1)] | pentafluorophenyl | H | 3,6-dimethyl-N-methylcarbazolyl | H |

-continued
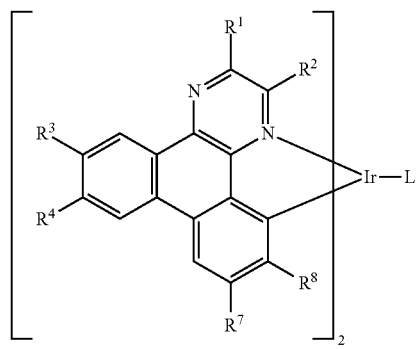
| Cpd. | L | R¹ | R² | R³ and R⁸ | R⁴ and R⁷ |
|---|---|---|---|---|---|
| A-105 | A[1)] | 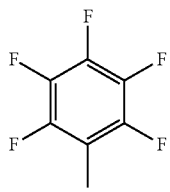 | H | H | 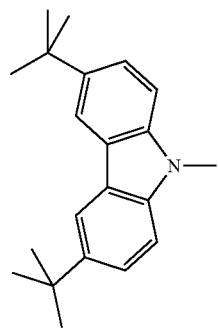 |
| A-106 | A[1)] | 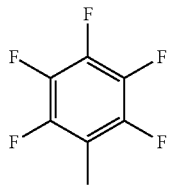 | H | 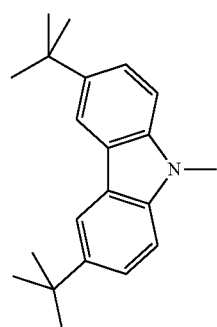 | H |
| A-107 | A[1)] | 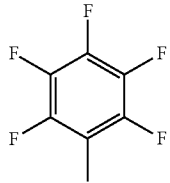 | H | H | 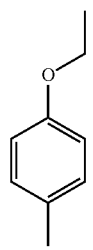 |
| A-108 | A[1)] | 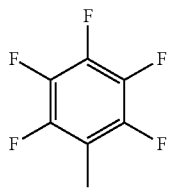 | H | 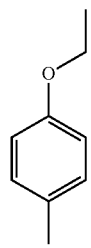 | H |

-continued
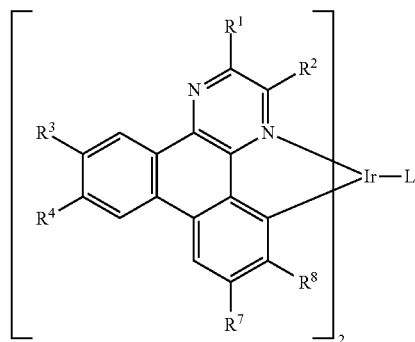
| Cpd. | L | R¹ | R² | R³ and R⁸ | R⁴ and R⁷ |
|---|---|---|---|---|---|
| A-109 | A[1)] | CF₃-C₆H₄- | H | H | N(C₆H₅)₂ |
| A-110 | A[1)] | CF₃-C₆H₄- | H | N(C₆H₅)₂ | H |
| A-111 | A[1)] | CF₃-C₆H₄- | H | H | N(naphthyl)(C₆H₅) |
| A-112 | A[1)] | CF₃-C₆H₄- | H | N(naphthyl)(C₆H₅) | H |

-continued
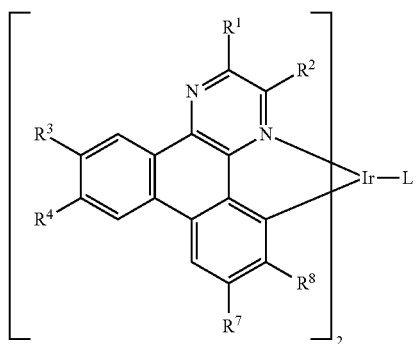
| Cpd. | L | R¹ | R² | R³ and R⁸ | R⁴ and R⁷ |
|---|---|---|---|---|---|
| A-113 | A[1)] | CF₃–C₆H₄– (p-tolyl with CF₃) | H | H | N-methyl-N-phenyl-phenanthren-9-amine |
| A-114 | A[1)] | CF₃–C₆H₄– | H | N-methyl-N-phenyl-phenanthren-9-amine | H |
| A-115 | A[1)] | CF₃–C₆H₄– | H | H | N-methyl-N-phenyl-pyren-1-amine |

-continued
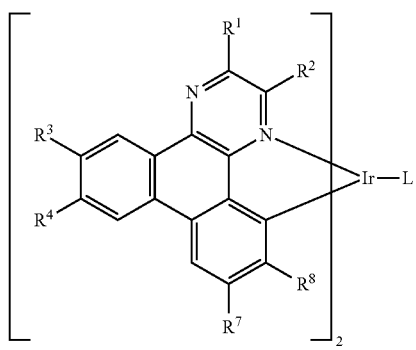
| Cpd. | L | R¹ | R² | R³ and R⁸ | R⁴ and R⁷ |
|---|---|---|---|---|---|
| A-116 | A[1)] | CF₃–C₆H₄– (p-tolyl position) | H | N-phenyl-N-methyl-pyrenyl-amine | H |
| A-117 | A[1)] | CF₃–C₆H₄– | H | H | N-phenyl-N-methyl-anthracenyl-amine (9-position) |
| A-118 | A[1)] | CF₃–C₆H₄– | H | N-phenyl-N-methyl-anthracenyl-amine | H |
| A-119 | A[1)] | CF₃–C₆H₄– | H | H | N-methyl-carbazolyl |

-continued
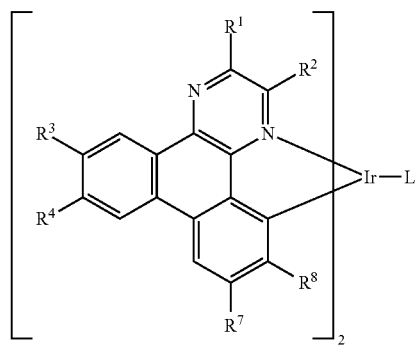
| Cpd. | L | R¹ | R² | R³ and R⁸ | R⁴ and R⁷ |
|---|---|---|---|---|---|
| A-120 | A[1)] | CF₃-C₆H₄- (p-tolyl with CF₃) | H | N-methylcarbazol-3-yl | H |
| A-121 | A[1)] | CF₃-C₆H₄- | H | H | 3,6-dimethyl-N-methylcarbazol-? |
| A-122 | A[1)] | CF₃-C₆H₄- | H | 3,6-dimethyl-N-methylcarbazol-? | H |
| A-123 | A[1)] | CF₃-C₆H₄- | H | H | 3,6-di-tert-butyl-N-methylcarbazol-? |

-continued
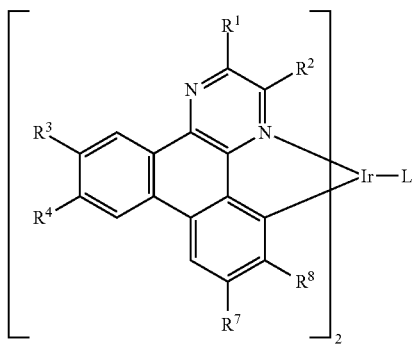
| Cpd. | L | R¹ | R² | R³ and R⁸ | R⁴ and R⁷ |
|---|---|---|---|---|---|
| A-124 | A[1)] | CF₃–C₆H₄–CH₃ | H | 3,6-di-tert-butyl-9-methylcarbazolyl | H |
| A-125 | A[1)] | CF₃–C₆H₄–CH₃ | H | H | 4-ethoxyphenyl-methyl |
| A-126 | A[1)] | CF₃–C₆H₄–CH₃ | H | 4-ethoxyphenyl-methyl | H |
| A-127 | A[1)] | N(C₆H₅)₂(C₆H₄CH₃) | H | H | N(C₆H₅)₂CH₃ |

-continued
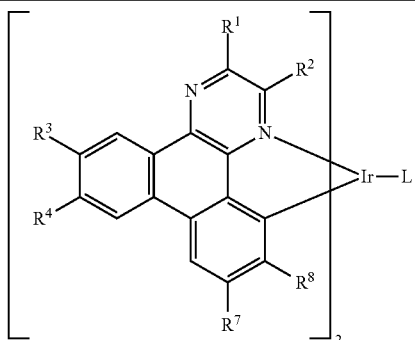
| Cpd. | L | R¹ | R² | R³ and R⁸ | R⁴ and R⁷ |
|---|---|---|---|---|---|
| A-128 | A¹⁾ | (4-methylphenyl)diphenylamine | H | N,N-diphenylamine | H |
| A-129 | A¹⁾ | (4-methylphenyl)diphenylamine | H | H | N-methyl-N-phenyl-1-naphthylamine |
| A-130 | A¹⁾ | (4-methylphenyl)diphenylamine | H | N-phenyl-1-naphthylamine | H |
| A-131 | A¹⁾ | (4-methylphenyl)diphenylamine | H | H | N-phenyl-phenanthren-9-amine |

-continued
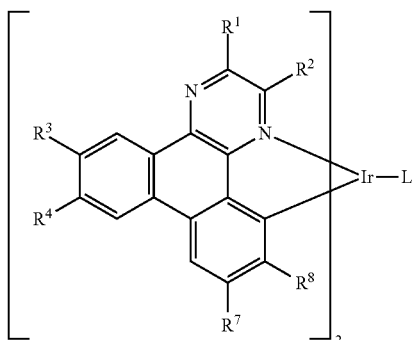
| Cpd. | L | R¹ | R² | R³ and R⁸ | R⁴ and R⁷ |
|---|---|---|---|---|---|
| A-132 | A¹⁾ | [N,N-diphenyl-4-methylaniline] | H | [N-methyl-N-phenyl-phenanthren-9-amine] | H |
| A-133 | A¹⁾ | [N,N-diphenyl-4-methylaniline] | H | H | [N-methyl-N-phenyl-pyren-1-amine] |
| A-134 | A¹⁾ | [N,N-diphenyl-4-methylaniline] | H | [N-methyl-N-phenyl-pyren-1-amine] | H |

-continued
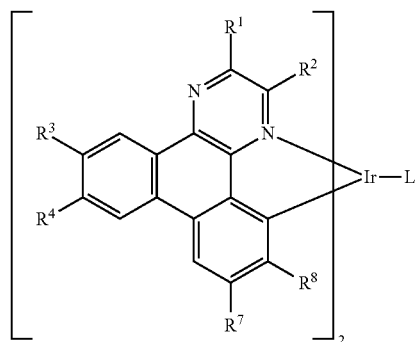
| Cpd. | L | R¹ | R² | R³ and R⁸ | R⁴ and R⁷ |
|---|---|---|---|---|---|
| A-135 | A¹⁾ | ![N(Ph)(Ph)(tolyl)] | H | H | ![N(anthracenyl)(Me)(Ph)] |
| A-136 | A¹⁾ | ![N(Ph)(Ph)(tolyl)] | H | ![N(anthracenyl)(Me)(Ph)] | H |
| A-137 | A¹⁾ | ![N(Ph)(Ph)(tolyl)] | H | H | ![N-methylcarbazole] |
| A-138 | A¹⁾ | ![N(Ph)(Ph)(tolyl)] | H | ![N-methylcarbazole] | H |

-continued
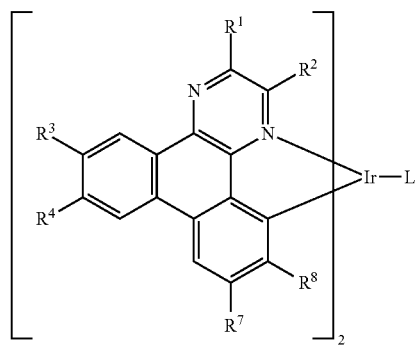
| Cpd. | L | R¹ | R² | R³ and R⁸ | R⁴ and R⁷ |
|---|---|---|---|---|---|
| A-139 | A[1)] | *N,N-diphenyl-4-methylaniline (triphenylamine with p-tolyl)* | H | H | *3,6-dimethyl-9-methylcarbazole* |
| A-140 | A[1)] | *N,N-diphenyl-4-methylaniline* | H | *3,6-dimethyl-9-methylcarbazole* | H |
| A-141 | A[1)] | *N,N-diphenyl-4-methylaniline* | H | H | *3,6-di-tert-butyl-9-methylcarbazole* |
| A-142 | A[1)] | *N,N-diphenyl-4-methylaniline* | H | *3,6-di-tert-butyl-9-methylcarbazole* | H |

-continued
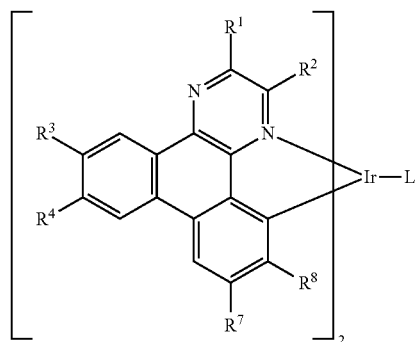
| Cpd. | L | R¹ | R² | R³ and R⁸ | R⁴ and R⁷ |
|---|---|---|---|---|---|
| A-143 | A¹⁾ | N(Ph)(Ph)(C₆H₄-CH₃) | H | H | C₆H₄-O-CH₂CH₃ (p-ethoxyphenyl) |
| A-144 | A¹⁾ | N(Ph)(Ph)(C₆H₄-CH₃) | H | p-ethoxyphenyl | H |
| A-145 | A¹⁾ | N(Ph)(Ph)(C₆H₄-CH₃) | H | H | C₆H₄-CF₃ |
| A-146 | A¹⁾ | N(Ph)(Ph)(C₆H₄-CH₃) | H | C₆H₄-CF₃ | H |

-continued
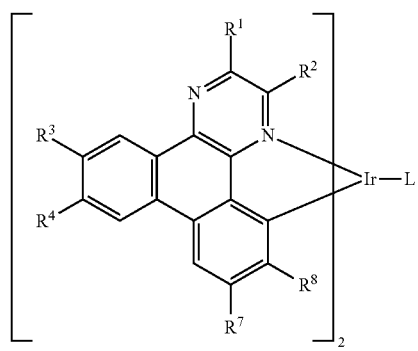
| Cpd. | L | R¹ | R² | R³ and R⁸ | R⁴ and R⁷ |
|---|---|---|---|---|---|
| A-147 | A¹⁾ | N(Ph)(Ph)(p-tolyl) | H | H | 4-tert-butylphenyl |
| A-148 | A¹⁾ | N(Ph)(Ph)(p-tolyl) | H | 4-tert-butylphenyl | H |
| A-149 | A¹⁾ | N(Ph)(Ph)(p-tolyl) | H | H | p-tolyl |
| A-150 | A¹⁾ | N(Ph)(Ph)(p-tolyl) | H | p-tolyl | H |

-continued
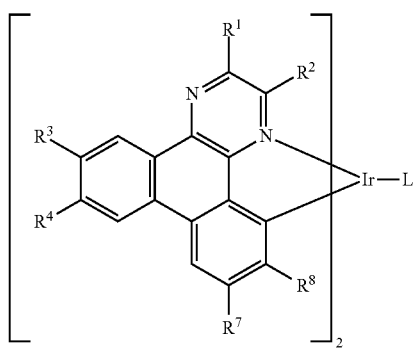
| Cpd. | L | R¹ | R² | R³ and R⁸ | R⁴ and R⁷ |
|---|---|---|---|---|---|
| A-151 | A[1)] | (N,N-diphenyl-4-methylaniline) | H | H | H |
| A-152 | A[1)] | (N-phenyl-N-(4-methylphenyl)-1-naphthylamine) | H | H | H |
| A-153 | A[1)] | (9-(4-methylphenyl)carbazole) | H | H | H |
| A-154 | A[1)] | (3,6-dimethyl-9-(4-methylphenyl)carbazole) | H | H | H |

-continued
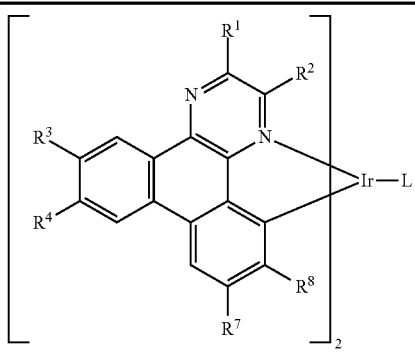
| Cpd. | L | R¹ | R² | R³ and R⁸ | R⁴ and R⁷ |
|---|---|---|---|---|---|
| A-155 | A¹⁾ | 3,6-di-tert-butyl-9-(p-tolyl)carbazol-N-yl | H | H | H |
| A-156 | A¹⁾ | $CH_3$ | H | phenyl | phenyl |
| A-157 | A¹⁾ | 4-tert-butylphenyl | H | H | H |
| A-158 | A¹⁾ | 4-(trifluoromethyl)phenyl | H | H | H |
| A-159 | A¹⁾ | 4-fluorophenyl | H | H | H |
| A-160 | A¹⁾ | 1-naphthyl | H | H | H |
| A-161 | A¹⁾ | 2-naphthyl | H | H | H |
| A-162 | A¹⁾ | phenyl | $CH_3$ | H | H |
| A-163 | A¹⁾ | 2-ethylhexyl | H | H | H |
| A-164 | A¹⁾ | n-butyl | H | H | H |
| A-165 | A¹⁾ | tert-butyl | H | H | H |

-continued
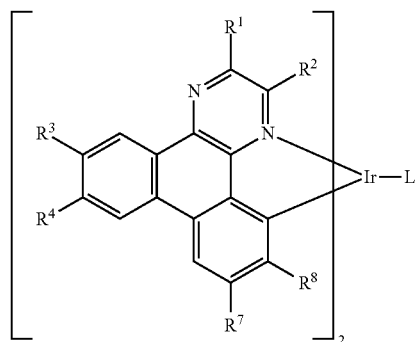
| Cpd. | L | R¹ | R² | R³ and R⁸ | R⁴ and R⁷ |
|---|---|---|---|---|---|
| A-166 | A[1)] | —(CH₂)₄— | H | H | |
| A-167 | A[1)] | 2-ethylhexyl | CH₃ | H | H |
| A-168 | A[1)] | n-butyl | CH₃ | H | H |
| A-169 | A[1)] | tert-butyl | CH₃ | H | H |
| A-170 | A[1)] | 2-ethylhexyl | H | H | propyl |
| A-171 | A[1)] | n-butyl | H | H | propyl |
| A-172 | A[1)] | tert-butyl | H | H | propyl |
| A-173 | A[1)] | —(CH₂)₄— | —(CH₂)₄— | H | propyl |
| A-174 | A[1)] | 2-ethylhexyl | CH₃ | H | propyl |
| A-175 | A[1)] | n-butyl | CH₃ | H | propyl |
| A-176 | A[1)] | tert-butyl | CH₃ | H | propyl |
| B-1 | B[1)] | —CH₃ | H | H | 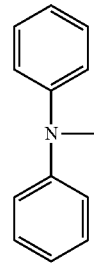 |
| B-2 | B[1)] | —CH₃ | H | 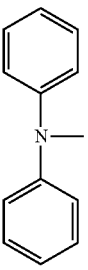 | H |
| B-3 | B[1)] | —CH₃ | H | H | 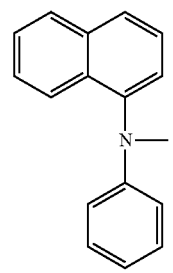 |

-continued
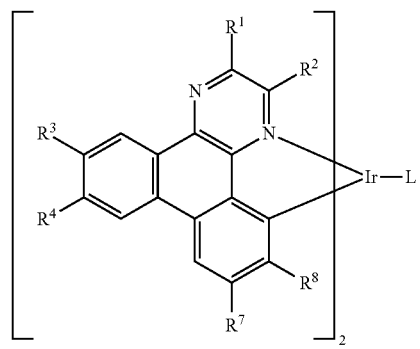
| Cpd. | L | R¹ | R² | R³ and R⁸ | R⁴ and R⁷ |
|------|---|-----|-----|-----------|-----------|
| B-4 | B¹⁾ | —CH₃ | H | 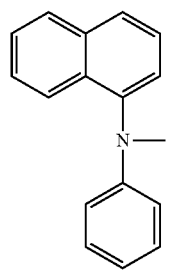 | H |
| B-5 | B¹⁾ | —CH₃ | H | H | 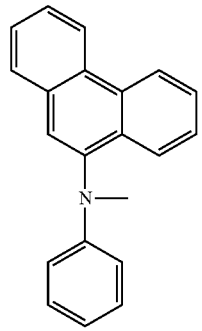 |
| B-6 | B¹⁾ | —CH₃ | H | 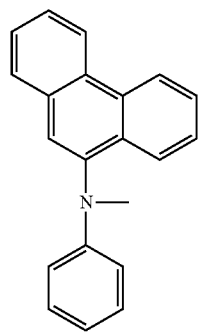 | H |

-continued
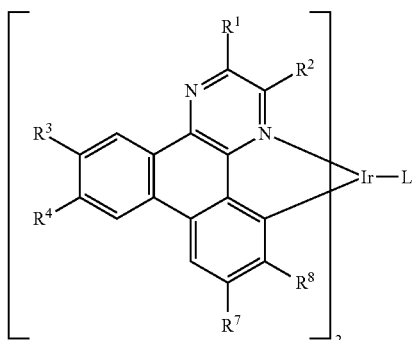
| Cpd. | L | R¹ | R² | R³ and R⁸ | R⁴ and R⁷ |
|---|---|---|---|---|---|
| B-7 | B[1)] | —CH₃ | H | H | ![pyrene-N(Me)(Ph) substituent] |
| B-8 | B[1)] | —CH₃ | H | ![pyrene-N(Me)(Ph) substituent] | H |
| B-9 | B[1)] | —CH₃ | H | H | ![anthracene-N(Me)(Ph) substituent] |
| B-10 | B[1)] | —CH₃ | H | ![anthracene-N(Me)(Ph) substituent] | H |

-continued
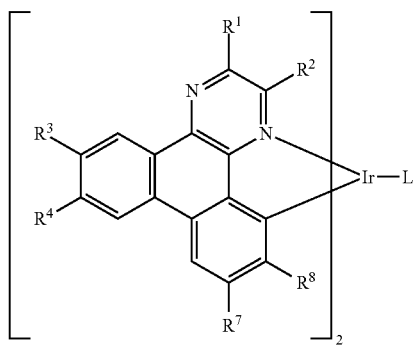
| Cpd. | L | R¹ | R² | R³ and R⁸ | R⁴ and R⁷ |
|---|---|---|---|---|---|
| B-11 | B¹⁾ | —CH₃ | H | H | 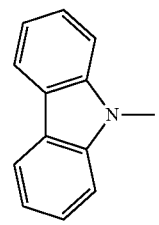 |
| B-12 | B¹⁾ | —CH₃ | H | 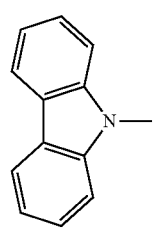 | H |
| B-13 | B¹⁾ | —CH₃ | H | H | 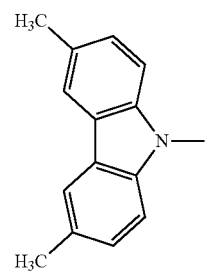 |
| B-14 | B¹⁾ | —CH₃ | H | 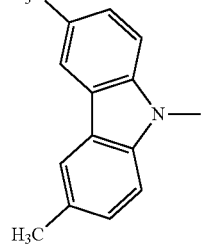 | H |

-continued
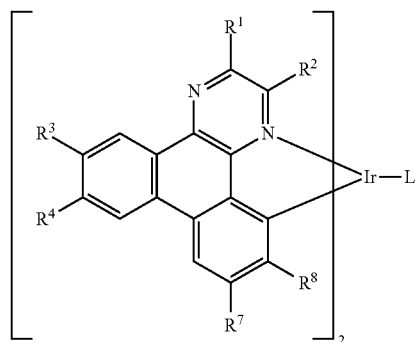
| Cpd. | L | R¹ | R² | R³ and R⁸ | R⁴ and R⁷ |
|---|---|---|---|---|---|
| B-15 | B[1)] | —CH$_3$ | H | H | 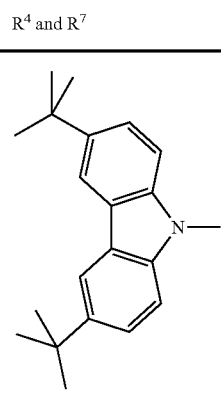 |
| B-16 | B[1)] | —CH$_3$ | H | 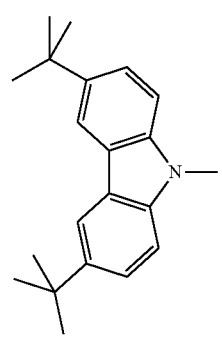 | H |
| B-17 | B[1)] | —CH$_3$ | H | H | 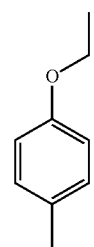 |
| B-18 | B[1)] | —CH$_3$ | H | 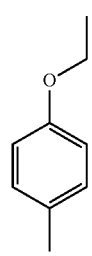 | H |

-continued
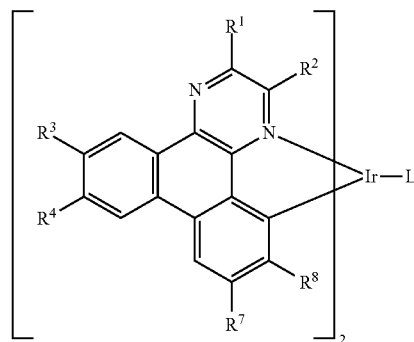
| Cpd. | L | R¹ | R² | R³ and R⁸ | R⁴ and R⁷ |
|---|---|---|---|---|---|
| B-19 | B¹⁾ | H | H | H | ![N,N-diphenylamino] |
| B-20 | B¹⁾ | H | ![N,N-diphenylamino] | H | H |
| B-21 | B¹⁾ | H | H | H | ![N-naphthyl-N-phenylamino] |
| B-22 | B¹⁾ | H | ![N-naphthyl-N-phenylamino] | H | H |

-continued
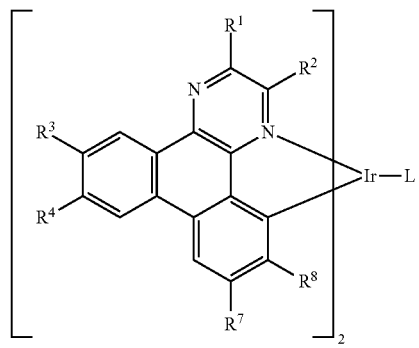
| Cpd. | L | R¹ | R² | R³ and R⁸ | R⁴ and R⁷ |
|---|---|---|---|---|---|
| B-23 | B[1)] | H | H | H | 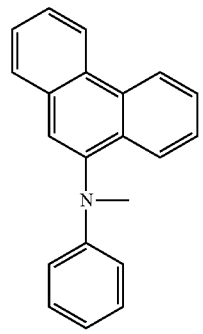 |
| B-24 | B[1)] | H | H | 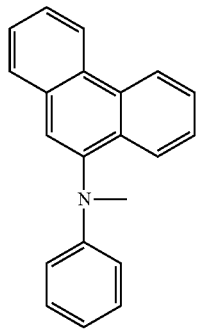 | H |
| B-25 | B[1)] | H | H | H | 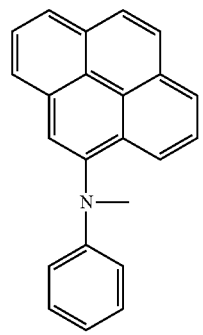 |

-continued
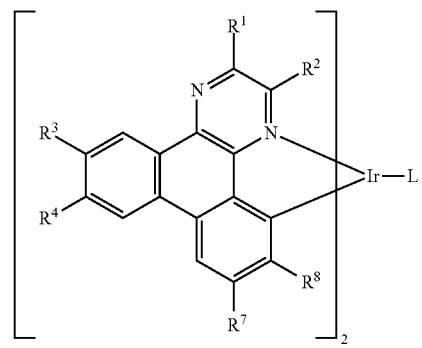
| Cpd. | L | R¹ | R² | R³ and R⁸ | R⁴ and R⁷ |
|---|---|---|---|---|---|
| B-26 | B¹⁾ | H | H | 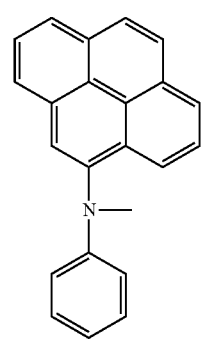 | H |
| B-27 | B¹⁾ | H | H | H | 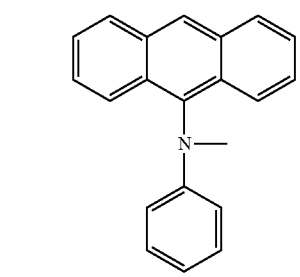 |
| B-28 | B¹⁾ | H | H | 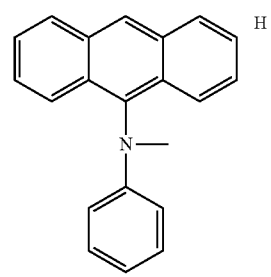 | H |
| B-29 | B¹⁾ | H | H | H | 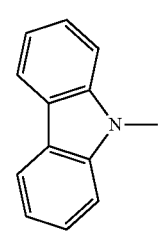 |

-continued
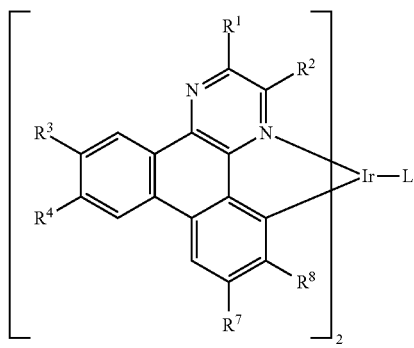
| Cpd. | L | R¹ | R² | R³ and R⁸ | R⁴ and R⁷ |
|---|---|---|---|---|---|
| B-30 | B¹⁾ | H | H | 9-methylcarbazol-3-yl | H |
| B-31 | B¹⁾ | H | H | H | 3,6-dimethyl-9-methylcarbazol-... |
| B-32 | B¹⁾ | H | H | 3,6-dimethyl-9-methylcarbazol-... | H |
| B-33 | B¹⁾ | H | H | H | 3,6-di-tert-butyl-9-methylcarbazol-... |

-continued
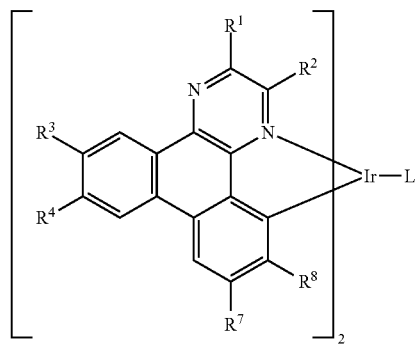
| Cpd. | L | R¹ | R² | R³ and R⁸ | R⁴ and R⁷ |
|---|---|---|---|---|---|
| B-34 | B[1)] | H | H | 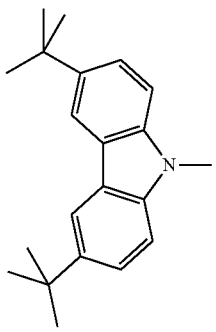 | H |
| B-35 | B[1)] | H | H | H | 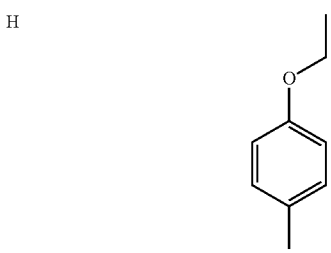 |
| B-36 | B[1)] | H | H | 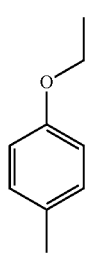 | H |
| B-37 | B[1)] | Ph | H | H |  |

-continued
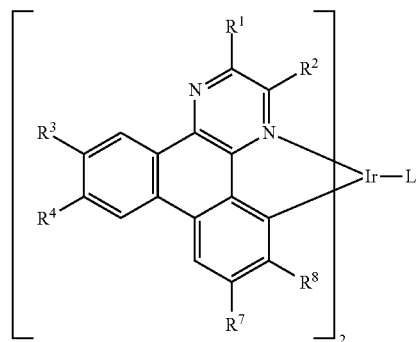
| Cpd. | L | R¹ | R² | R³ and R⁸ | R⁴ and R⁷ |
|---|---|---|---|---|---|
| B-38 | B[1)] | Ph | H | ![N,N-diphenyl-N-methylamine] | H |
| B-39 | B[1)] | Ph | H | H | ![N-methyl-N-phenyl-1-naphthylamine] |
| B-40 | B[1)] | Ph | H | ![N-methyl-N-phenyl-1-naphthylamine] | H |
| B-41 | B[1)] | Ph | H | H | ![N-methyl-N-phenyl-9-phenanthrylamine] |

-continued
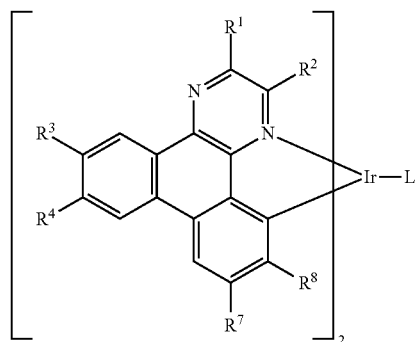
| Cpd. | L | R¹ | R² | R³ and R⁸ | R⁴ and R⁷ |
|---|---|---|---|---|---|
| B-42 | B[1)] | Ph | H | 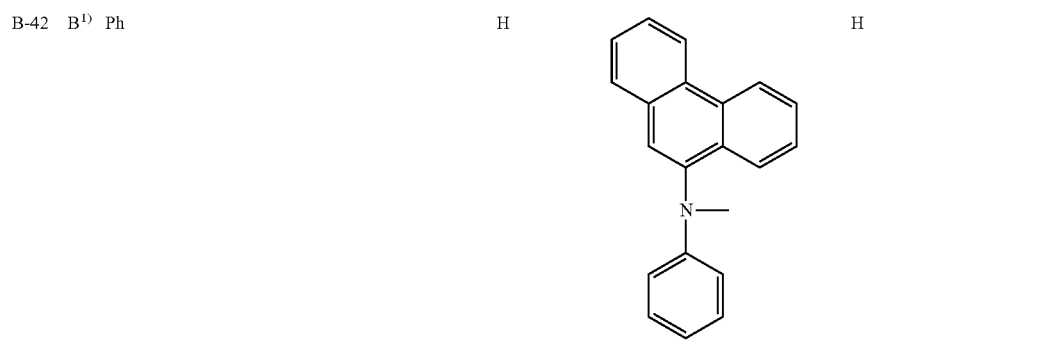 | H |
| B-43 | B[1)] | Ph | H | H | 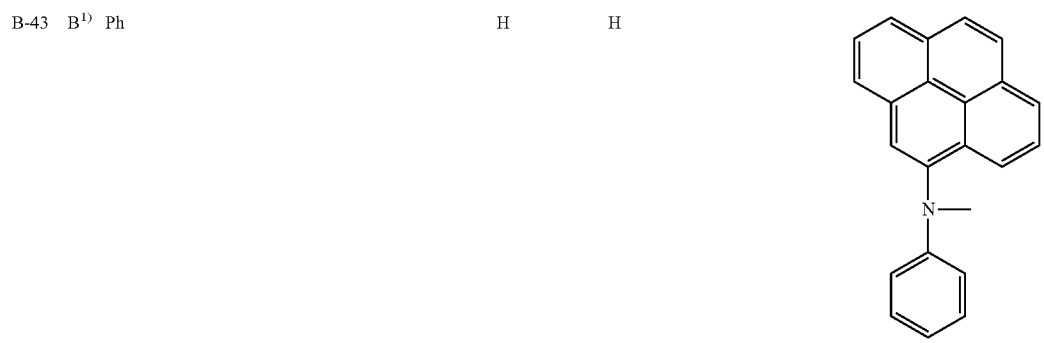 |
| B-44 | B[1)] | Ph | H | 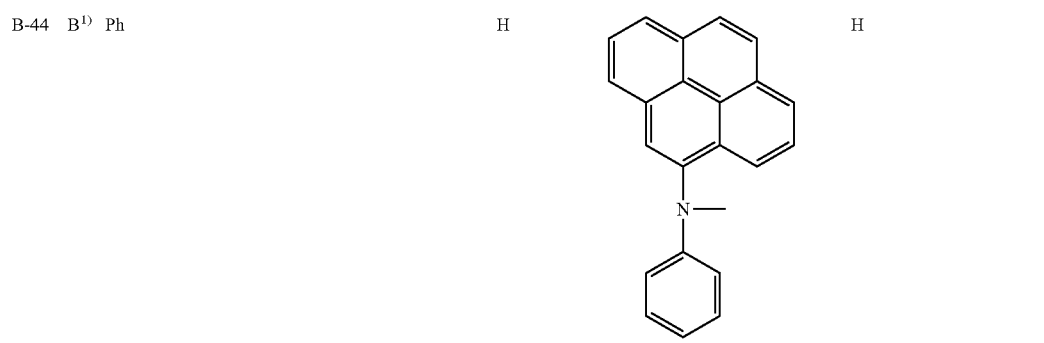 | H |

-continued
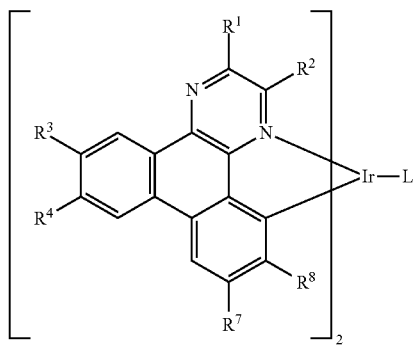
| Cpd. | L | R¹ | R² | R³ and R⁸ | R⁴ and R⁷ |
|---|---|---|---|---|---|
| B-45 | B[1)] | Ph | H | H | 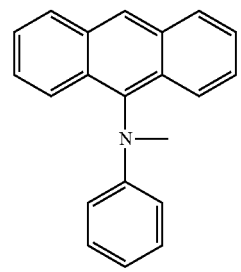 |
| B-46 | B[1)] | Ph | H | 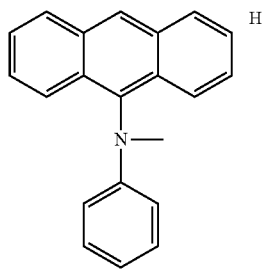 | H |
| B-47 | B[1)] | Ph | H | H | 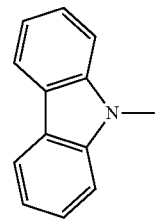 |
| B-48 | B[1)] | Ph | H | 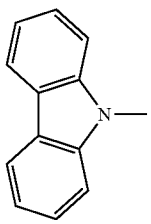 | H |

-continued
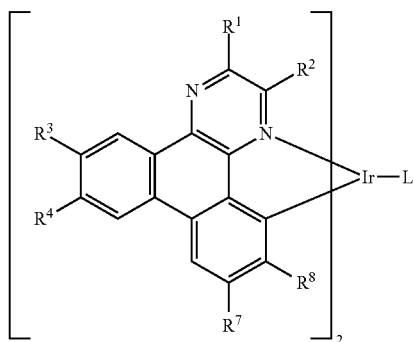
| Cpd. | L | R¹ | R² | R³ and R⁸ | R⁴ and R⁷ |
|---|---|---|---|---|---|
| B-49 | B¹⁾ | Ph | H | H | 3,6-dimethyl-9-methylcarbazol-2-yl |
| B-50 | B¹⁾ | Ph | H | 3,6-dimethyl-9-methylcarbazol-2-yl | H |
| B-51 | B¹⁾ | Ph | H | H | 3,6-di-tert-butyl-9-methylcarbazol-2-yl |
| B-52 | B¹⁾ | Ph | H | H | 3,6-di-tert-butyl-9-methylcarbazol-2-yl |

-continued
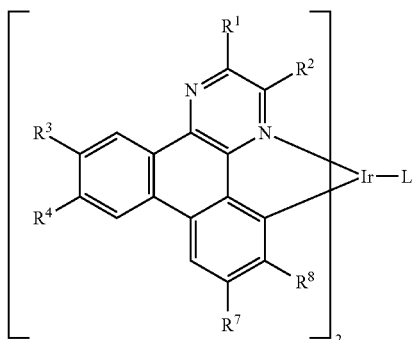
| Cpd. | L | R¹ | R² | R³ and R⁸ | R⁴ and R⁷ |
|---|---|---|---|---|---|
| B-53 | B[1)] | Ph | H | H | 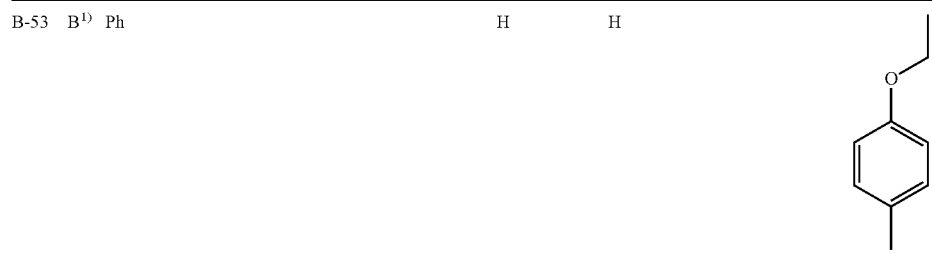 |
| B-54 | B[1)] | Ph | H | 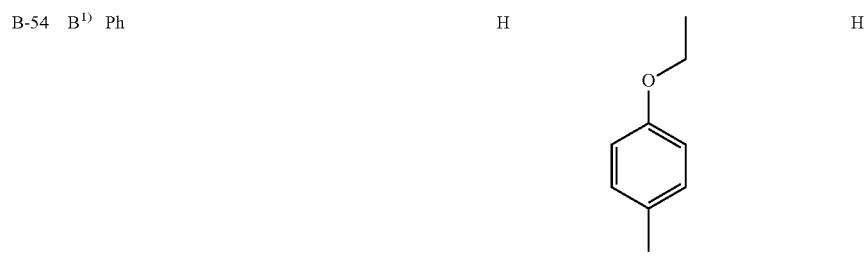 | H |
| B-55 | B[1)] | 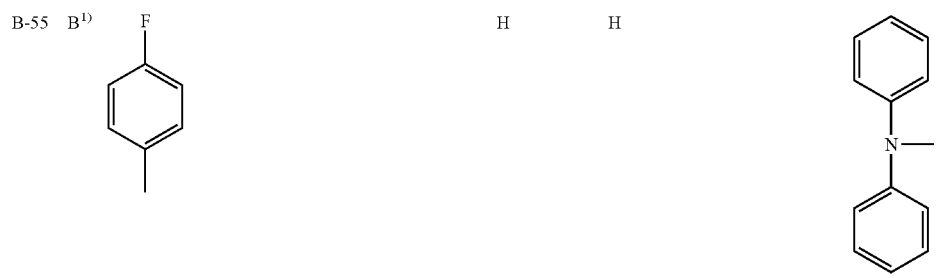 | | H | H |
| B-56 | B[1)] | 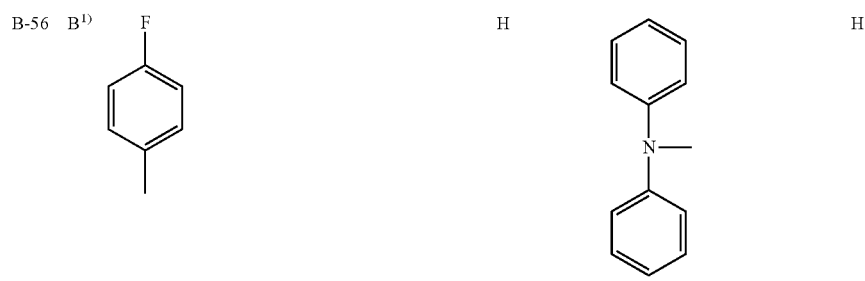 | | H | H |

-continued
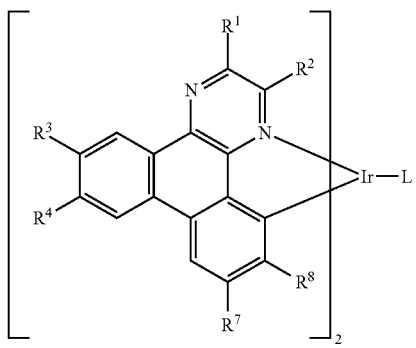
| Cpd. | L | R¹ | R² | R³ and R⁸ | R⁴ and R⁷ |
|---|---|---|---|---|---|
| B-57 | B¹⁾ | 4-F-C₆H₄ | H | H | N-methyl-N-phenyl-naphthalen-1-amine |
| B-58 | B¹⁾ | 4-F-C₆H₄ | H | N-methyl-N-phenyl-naphthalen-1-amine | H |
| B-59 | B¹⁾ | 4-F-C₆H₄ | H | H | N-methyl-N-phenyl-phenanthren-9-amine |
| B-60 | B¹⁾ | 4-F-C₆H₄ | H | N-methyl-N-phenyl-phenanthren-9-amine | H |

-continued
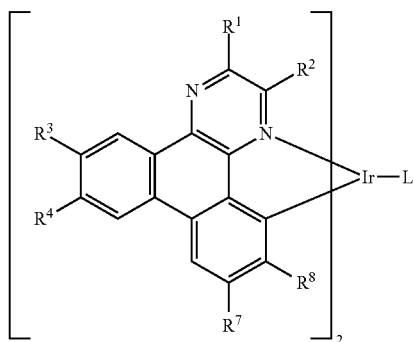
| Cpd. | L | R¹ | R² | R³ and R⁸ | R⁴ and R⁷ |
|---|---|---|---|---|---|
| B-61 | B[1)] | F-phenyl (4-F) | H | H | N-methyl-N-phenyl-pyrenyl |
| B-62 | B[1)] | F-phenyl (4-F) | H | N-methyl-N-phenyl-pyrenyl | H |
| B-63 | B[1)] | F-phenyl (4-F) | H | H | N-methyl-N-phenyl-anthracenyl |
| B-64 | B[1)] | F-phenyl (4-F) | H | N-methyl-N-phenyl-anthracenyl | H |

-continued
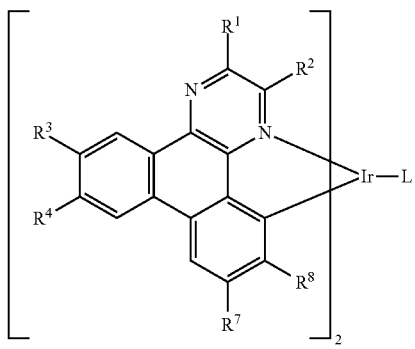
| Cpd. | L | R¹ | R² | R³ and R⁸ | R⁴ and R⁷ |
|---|---|---|---|---|---|
| B-65 | B[1)] | 4-F-C₆H₄ | H | H | N-methylcarbazol-3-yl |
| B-66 | B[1)] | 4-F-C₆H₄ | H | N-methylcarbazol-3-yl | H |
| B-67 | B[1)] | 4-F-C₆H₄ | H | H | 3,6-dimethyl-N-methylcarbazol-3-yl |
| B-68 | B[1)] | 4-F-C₆H₄ | H | 3,6-dimethyl-N-methylcarbazol-3-yl | H |

-continued
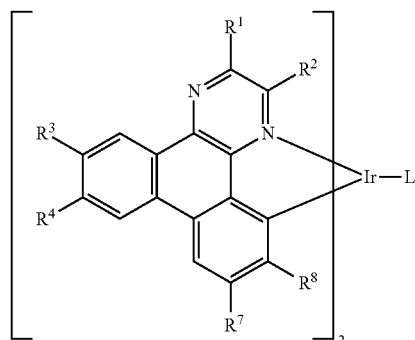
| Cpd. | L | R¹ | R² | R³ and R⁸ | R⁴ and R⁷ |
|---|---|---|---|---|---|
| B-69 | B¹⁾ | 4-F-C₆H₄ | H | H | 3,6-di-tert-butyl-9-methyl-carbazol-2-yl |
| B-70 | B¹⁾ | 4-F-C₆H₄ | H | 3,6-di-tert-butyl-9-methyl-carbazol-2-yl | H |
| B-71 | B¹⁾ | 4-F-C₆H₄ | H | H | 4-ethoxyphenyl |
| B-72 | B¹⁾ | 4-F-C₆H₄ | H | 4-ethoxyphenyl | H |

-continued
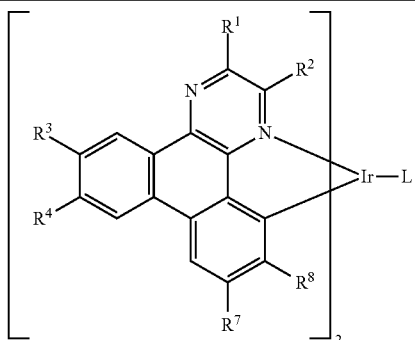
| Cpd. | L | R¹ | R² | R³ and R⁸ | R⁴ and R⁷ |
|---|---|---|---|---|---|
| B-73 | B¹⁾ | 3,5-difluorophenyl | H | H | N,N-diphenylamino |
| B-74 | B¹⁾ | 3,5-difluorophenyl | H | N,N-diphenylamino | H |
| B-75 | B¹⁾ | 3,5-difluorophenyl | H | H | N-naphthyl-N-phenylamino |
| B-76 | B¹⁾ | 3,5-difluorophenyl | H | N-naphthyl-N-phenylamino | H |

-continued
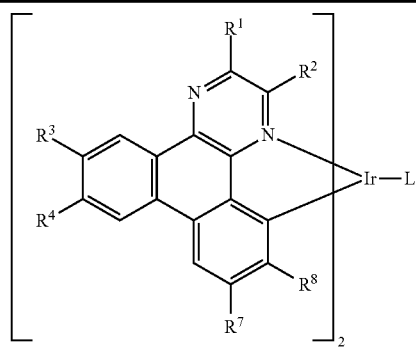
| Cpd. | L | R¹ | R² | R³ and R⁸ | R⁴ and R⁷ |
|---|---|---|---|---|---|
| B-77 | B¹⁾ | 3,5-difluorophenyl | H | H | N-methyl-N-phenyl-phenanthren-9-amine |
| B-78 | B¹⁾ | 3,5-difluorophenyl | H | N-methyl-N-phenyl-phenanthren-9-amine | H |
| B-79 | B¹⁾ | 3,5-difluorophenyl | H | H | N-methyl-N-phenyl-pyren-1-amine |

-continued
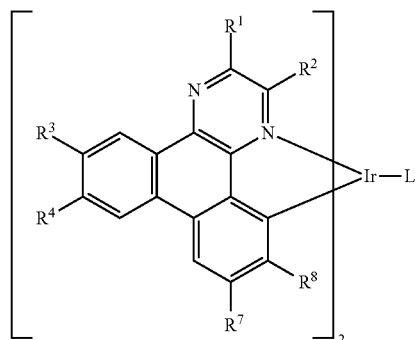
| Cpd. | L | R¹ | R² | R³ and R⁸ | R⁴ and R⁷ |
|---|---|---|---|---|---|
| B-80 | B¹⁾ | 3,5-difluorophenyl | H | N-methyl-N-phenylaminopyrene | H |
| B-81 | B¹⁾ | 3,5-difluorophenyl | H | H | N-methyl-N-phenylaminoanthracene |
| B-82 | B¹⁾ | 3,5-difluorophenyl | H | N-methyl-N-phenylaminoanthracene | H |
| B-83 | B¹⁾ | 3,5-difluorophenyl | H | H | N-methylcarbazole |

-continued
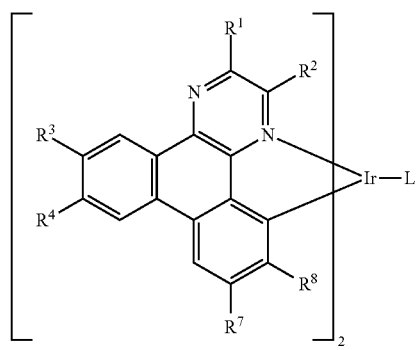
| Cpd. | L | R¹ | R² | R³ and R⁸ | R⁴ and R⁷ |
|---|---|---|---|---|---|
| B-84 | B¹⁾ | 3,5-difluorophenyl | H | 9-methylcarbazol-3-yl | H |
| B-85 | B¹⁾ | 3,5-difluorophenyl | H | H | 3,6-dimethyl-9-methylcarbazol-... |
| B-86 | B¹⁾ | 3,5-difluorophenyl | H | 3,6-dimethyl-9-methylcarbazol-... | H |
| B-87 | B¹⁾ | 3,5-difluorophenyl | H | H | 3,6-di-tert-butyl-9-methylcarbazol-... |

-continued
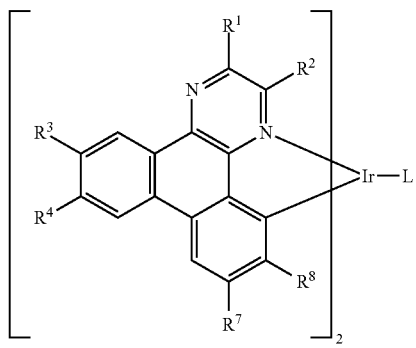
| Cpd. | L | R¹ | R² | R³ and R⁸ | R⁴ and R⁷ |
|---|---|---|---|---|---|
| B-88 | B¹⁾ | 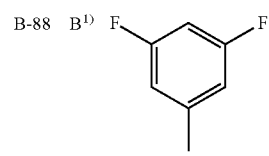 | H | 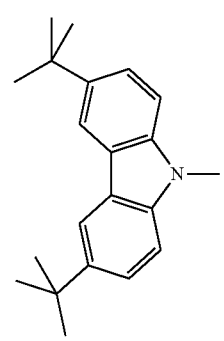 | H |
| B-89 | B¹⁾ | 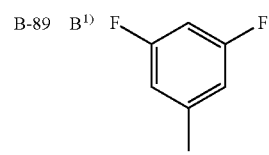 | H | H | 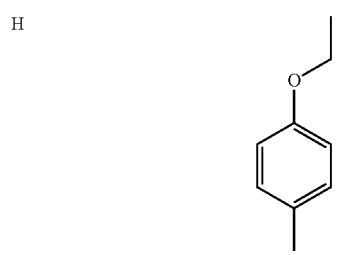 |
| B-90 | B¹⁾ | 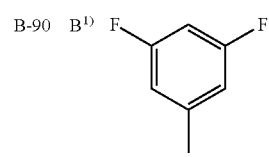 | H | 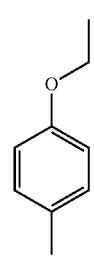 | H |
| B-91 | B¹⁾ | 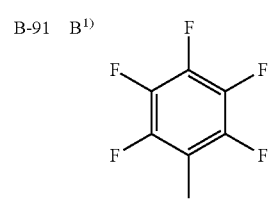 | H | H | 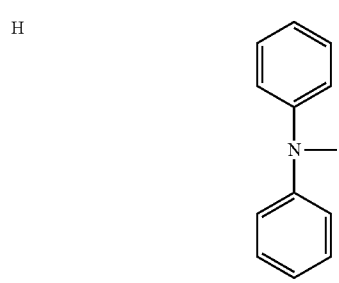 |

-continued
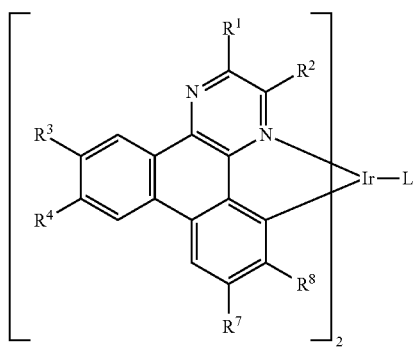
| Cpd. | L | R¹ | R² | R³ and R⁸ | R⁴ and R⁷ |
|---|---|---|---|---|---|
| B-92 | B[1)] | pentafluorophenyl | H | N,N-diphenylamino | H |
| B-93 | B[1)] | pentafluorophenyl | H | H | N-naphthyl-N-phenylamino |
| B-94 | B[1)] | pentafluorophenyl | H | N-naphthyl-N-phenylamino | H |
| B-95 | B[1)] | pentafluorophenyl | H | H | N-phenanthryl-N-phenylamino |

-continued
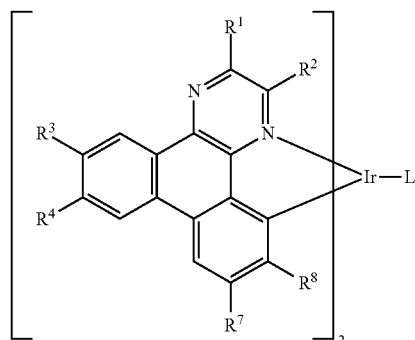
| Cpd. | L | R¹ | R² | R³ and R⁸ | R⁴ and R⁷ |
|---|---|---|---|---|---|
| B-96 | B[1)] | (pentafluorophenyl) | H | (N-methyl-N-phenyl-phenanthren-9-amine) | H |
| B-97 | B[1)] | (pentafluorophenyl) | H | H | (N-methyl-N-phenyl-pyren-1-amine) |
| B-98 | B[1)] | (pentafluorophenyl) | H | (N-methyl-N-phenyl-pyren-1-amine) | H |

-continued
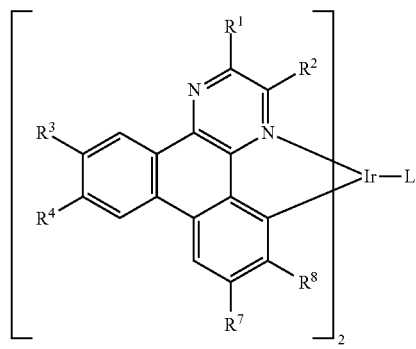
| Cpd. | L | R¹ | R² | R³ and R⁸ | R⁴ and R⁷ |
|---|---|---|---|---|---|
| B-99 | B¹⁾ | pentafluorophenyl | H | H | 9-(N-methyl-N-phenylamino)anthracen-10-yl |
| B-100 | B¹⁾ | pentafluorophenyl | H | 9-(N-methyl-N-phenylamino)anthracen-10-yl | H |
| B-101 | B¹⁾ | pentafluorophenyl | H | H | N-carbazolyl |
| B-102 | B¹⁾ | pentafluorophenyl | H | N-carbazolyl | H |

-continued
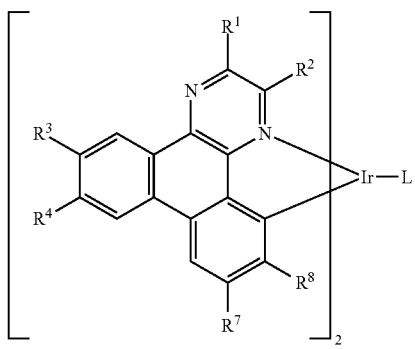
| Cpd. | L | R¹ | R² | R³ and R⁸ | R⁴ and R⁷ |
|---|---|---|---|---|---|
| B-103 | B[1)] | pentafluorophenyl | H | H | 3,6-dimethyl-9-methylcarbazolyl |
| B-104 | B[1)] | pentafluorophenyl | H | 3,6-dimethyl-9-methylcarbazolyl | H |
| B-105 | B[1)] | pentafluorophenyl | H | H | 3,6-di-tert-butyl-9-methylcarbazolyl |
| B-106 | B[1)] | pentafluorophenyl | H | 3,6-di-tert-butyl-9-methylcarbazolyl | H |

-continued
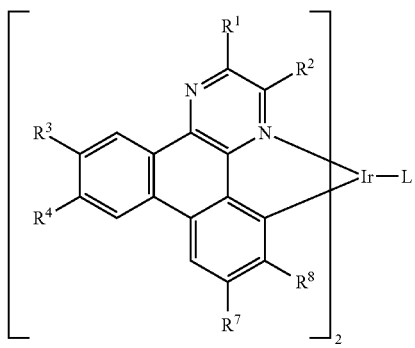
| Cpd. | L | R¹ | R² | R³ and R⁸ | R⁴ and R⁷ |
|---|---|---|---|---|---|
| B-107 | B[1)] | pentafluorophenyl | H | H | 4-methylphenoxy |
| B-108 | B[1)] | pentafluorophenyl | H | 4-methylphenoxy | H |
| B-109 | B[1)] | 4-(trifluoromethyl)phenyl | H | H | diphenylamino |
| B-110 | B[1)] | 4-(trifluoromethyl)phenyl | H | diphenylamino | H |

-continued
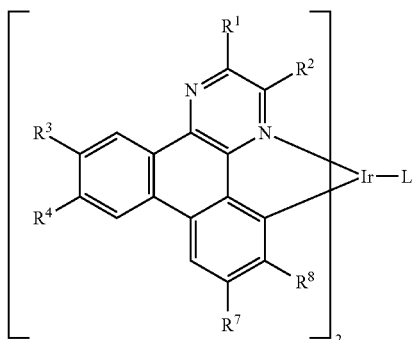
| Cpd. | L | R$^1$ | R$^2$ | R$^3$ and R$^8$ | R$^4$ and R$^7$ |
|---|---|---|---|---|---|
| B-111 | B[1)] | CF$_3$-C$_6$H$_4$- (p-tolyl with CF$_3$) | H | H | N-methyl-N-phenyl-naphthalen-1-amine |
| B-112 | B[1)] | CF$_3$-C$_6$H$_4$- | H | N-methyl-N-phenyl-naphthalen-1-amine | H |
| B-113 | B[1)] | CF$_3$-C$_6$H$_4$- | H | H | N-methyl-N-phenyl-phenanthren-9-amine |
| B-114 | B[1)] | CF$_3$-C$_6$H$_4$- | H | N-methyl-N-phenyl-phenanthren-9-amine | H |

-continued
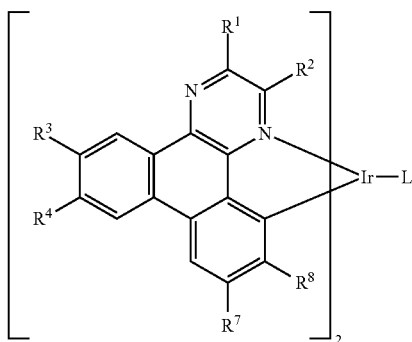
| Cpd. | L | R¹ | R² | R³ and R⁸ | R⁴ and R⁷ |
|---|---|---|---|---|---|
| B-115 | B[1)] | CF₃-C₆H₄- | H | H | N-methyl-N-phenyl-pyrenyl-amine |
| B-116 | B[1)] | CF₃-C₆H₄- | H | N-methyl-N-phenyl-pyrenyl-amine | H |
| B-117 | B[1)] | CF₃-C₆H₄- | H | H | N-methyl-N-phenyl-anthracenyl-amine |
| B-118 | B[1)] | CF₃-C₆H₄- | H | N-methyl-N-phenyl-anthracenyl-amine | H |

-continued
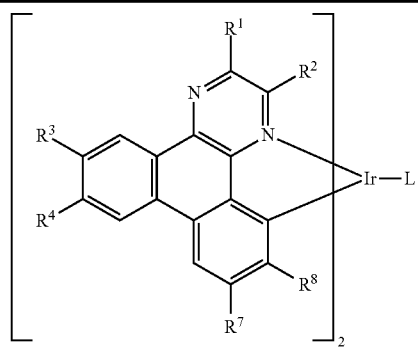
| Cpd. | L | R¹ | R² | R³ and R⁸ | R⁴ and R⁷ |
|---|---|---|---|---|---|
| B-119 | B[1)] | CF₃-C₆H₄- | H | H | N-methylcarbazol-3-yl |
| B-120 | B[1)] | CF₃-C₆H₄- | H | N-methylcarbazol-3-yl | H |
| B-121 | B[1)] | CF₃-C₆H₄- | H | H | 3,6-dimethyl-N-methylcarbazol-3-yl |
| B-122 | B[1)] | CF₃-C₆H₄- | H | 3,6-dimethyl-N-methylcarbazol-3-yl | H |

-continued
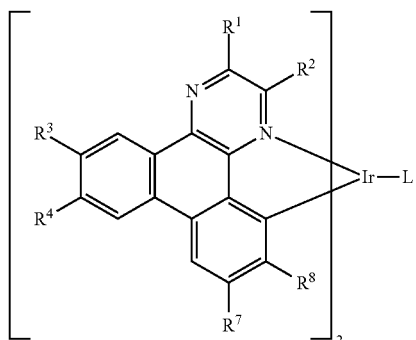
| Cpd. | L | R¹ | R² | R³ and R⁸ | R⁴ and R⁷ |
|---|---|---|---|---|---|
| B-123 | B[1)] | CF₃-C₆H₄- (p-tolyl) | H | H | 3,6-di-tert-butyl-9-methylcarbazolyl |
| B-124 | B[1)] | CF₃-C₆H₄- (p-tolyl) | H | 3,6-di-tert-butyl-9-methylcarbazolyl | H |
| B-125 | B[1)] | CF₃-C₆H₄- (p-tolyl) | H | H | 4-ethoxyphenyl (p-tolyl-O-Et) |
| B-126 | B[1)] | CF₃-C₆H₄- (p-tolyl) | H | 4-ethoxyphenyl | H |

-continued
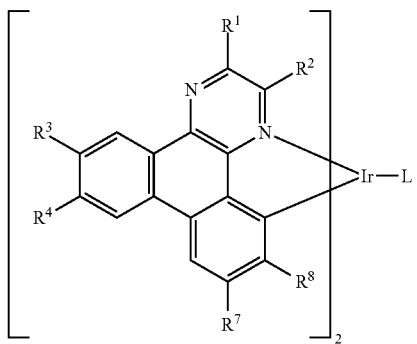
| Cpd. | L | R¹ | R² | R³ and R⁸ | R⁴ and R⁷ |
|---|---|---|---|---|---|
| B-127 | B[1]) | (N,N-diphenyl-4-methylphenylamine) | H | H | (N-methyl-N-phenylaniline) |
| B-128 | B[1]) | (N,N-diphenyl-4-methylphenylamine) | H | (N-methyl-N-phenylaniline) | H |
| B-129 | B[1]) | (N,N-diphenyl-4-methylphenylamine) | H | H | (N-methyl-N-phenyl-1-naphthylamine) |
| B-130 | B[1]) | (N,N-diphenyl-4-methylphenylamine) | H | (N-methyl-N-phenyl-1-naphthylamine) | H |

-continued
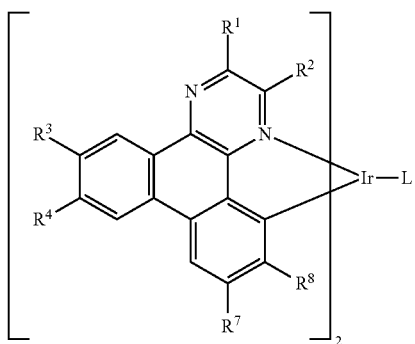
| Cpd. | L | R¹ | R² | R³ and R⁸ | R⁴ and R⁷ |
|---|---|---|---|---|---|
| B-131 | B¹⁾ | (N,N-diphenyl-4-methylphenylamine) | H | H | (N-methyl-N-phenyl-phenanthren-9-amine) |
| B-132 | B¹⁾ | (N,N-diphenyl-4-methylphenylamine) | H | (N-methyl-N-phenyl-phenanthren-9-amine) | H |
| B-133 | B¹⁾ | (N,N-diphenyl-4-methylphenylamine) | H | H | (N-methyl-N-phenyl-pyren-1-amine) |

-continued
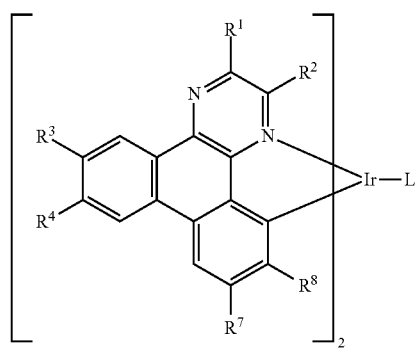
| Cpd. | L | R¹ | R² | R³ and R⁸ | R⁴ and R⁷ |
|---|---|---|---|---|---|
| B-134 | B[1) | triphenylamine with p-tolyl | H | N-methyl-N-phenyl-pyrenyl | H |
| B-135 | B[1) | triphenylamine with p-tolyl | H | H | N-methyl-N-phenyl-anthracenyl |
| B-136 | B[1) | triphenylamine with p-tolyl | H | N-methyl-N-phenyl-anthracenyl | H |
| B-137 | B[1) | triphenylamine with p-tolyl | H | H | N-methylcarbazolyl |

-continued
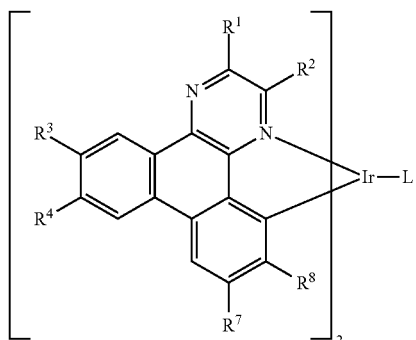
| Cpd. | L | R¹ | R² | R³ and R⁸ | R⁴ and R⁷ |
|---|---|---|---|---|---|
| B-138 | B[1)] | N(Ph)(Ph)(tolyl) | H | N-methylcarbazole | H |
| B-139 | B[1)] | N(Ph)(Ph)(tolyl) | H | H | 3,6-dimethyl-N-methylcarbazole |
| B-140 | B[1)] | N(Ph)(Ph)(tolyl) | H | 3-methyl-N-methylcarbazole | H |
| B-141 | B[1)] | N(Ph)(Ph)(tolyl) | H | H | 3,6-di-tert-butyl-N-methylcarbazole |

-continued
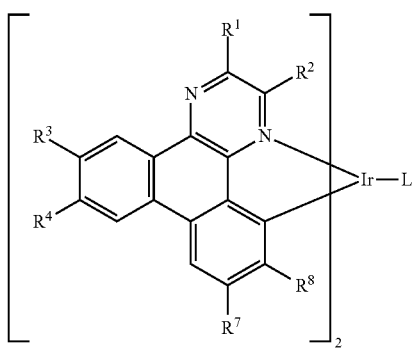
| Cpd. | L | R¹ | R² | R³ and R⁸ | R⁴ and R⁷ |
|---|---|---|---|---|---|
| B-142 | B[1)] | N,N-diphenyl-p-tolylamine | H | 3,6-di-tert-butyl-9-methylcarbazole | H |
| B-143 | B[1)] | N,N-diphenyl-p-tolylamine | H | H | 4-ethoxy-p-tolyl |
| B-144 | B[1)] | N,N-diphenyl-p-tolylamine | H | 4-ethoxy-p-tolyl | H |
| B-145 | B[1)] | N,N-diphenyl-p-tolylamine | H | H | 4-(trifluoromethyl)-p-tolyl |

-continued
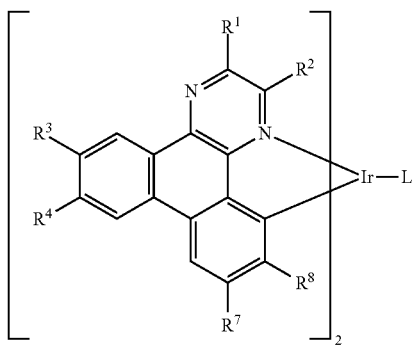
| Cpd. | L | R¹ | R² | R³ and R⁸ | R⁴ and R⁷ |
|---|---|---|---|---|---|
| B-146 | B¹⁾ | N(Ph)(Ph)(p-tolyl) | H | 4-CF₃-phenyl | H |
| B-147 | B¹⁾ | N(Ph)(Ph)(p-tolyl) | H | H | 4-tert-butyl-phenyl |
| B-148 | B¹⁾ | N(Ph)(Ph)(p-tolyl) | H | 4-tert-butyl-phenyl | H |
| B-149 | B¹⁾ | N(Ph)(Ph)(p-tolyl) | H | H | phenyl |

-continued
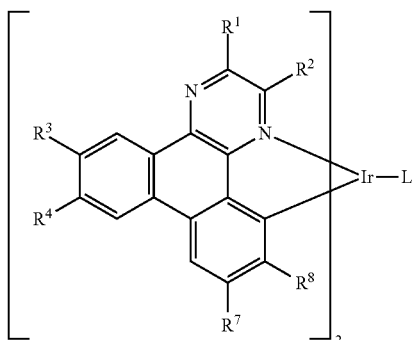
| Cpd. | L | R¹ | R² | R³ and R⁸ | R⁴ and R⁷ |
|---|---|---|---|---|---|
| B-150 | B[1)] | *diphenyl-p-tolylamine* | H | *phenyl* | H |
| B-151 | B[1)] | *diphenyl-p-tolylamine* | H | H | H |
| B-152 | B[1)] | *N-(1-naphthyl)-N-phenyl-p-tolylamine* | H | H | H |
| B-153 | B[1)] | *9-(p-tolyl)carbazole* | H | H | H |

-continued
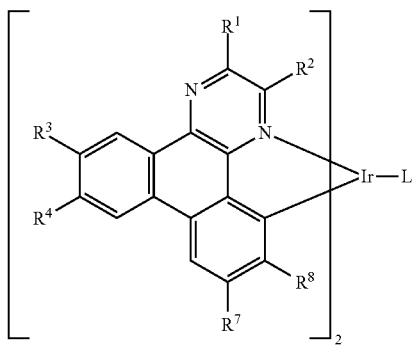
| Cpd. | L | R¹ | R² | R³ and R⁸ | R⁴ and R⁷ |
|---|---|---|---|---|---|
| B-154 | B[1)] | 9-(p-tolyl)-3,6-dimethylcarbazol-N-yl | H | H | H |
| B-155 | B[1)] | 9-(p-tolyl)-3,6-di-tert-butylcarbazol-N-yl | H | H | H |
| B-156 | B[1)] | CH₃ | H | p-tolyl | phenyl |
| B-157 | B[1)] | 4-tert-butylphenyl | H | H | H |
| B-158 | B[1)] | 4-(trifluoromethyl)phenyl | H | H | H |

-continued

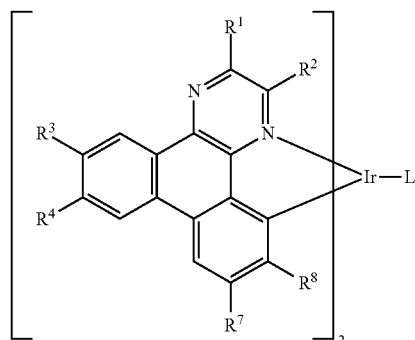

| Cpd. | L | R¹ | R² | R³ and R⁸ | R⁴ and R⁷ |
|---|---|---|---|---|---|
| B-159 | B¹⁾ | 4-fluorophenyl | H | H | H |
| B-160 | B¹⁾ | 1-naphthyl | H | H | H |
| B-161 | B¹⁾ | 2-naphthyl | H | H | H |
| B-162 | B¹⁾ | phenyl | CH₃ | H | H |
| B-163 | B¹⁾ | 2-ethylhexyl | H | H | H |
| B-164 | B¹⁾ | n-butyl | H | H | H |
| B-165 | B¹⁾ | tert-butyl | H | H | H |
| B-166 | B¹⁾ | —(CH₂)₄— | H | H | H |
| B-167 | B¹⁾ | 2-ethylhexyl | CH₃ | H | H |
| B-168 | B¹⁾ | n-butyl | CH₃ | H | H |
| B-169 | B¹⁾ | tert-butyl | CH₃ | H | H |
| B-170 | B¹⁾ | 2-ethylhexyl | H | H | propyl |
| B-171 | B¹⁾ | n-butyl | H | H | propyl |
| B-172 | B¹⁾ | tert-butyl | H | H | propyl |
| B-171 | B¹⁾ | —(CH₂)₄— | H | H | propyl |
| B-174 | B¹⁾ | 2-ethylhexyl | CH₃ | H | propyl |

-continued
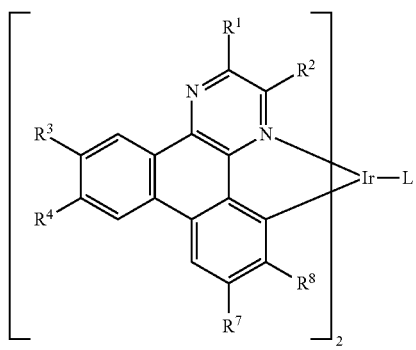
| Cpd. | L | R¹ | R² | R³ and R⁸ | R⁴ and R⁷ |
|---|---|---|---|---|---|
| B-175 | B[1) | n-butyl | CH₃ | H | propyl |
| B-176 | B[1) | tert-butyl | CH₃ | H | propyl |
[1)] A = 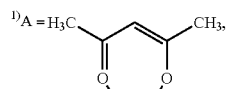
B = 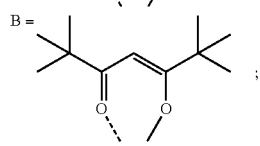
L$^a$ is (L$^a$)₂IrL
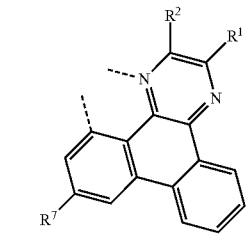
or
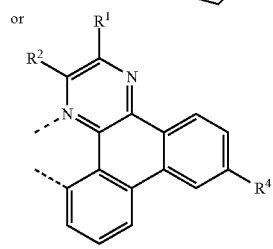
| Cpd. | L | R¹ | R² | R⁷ = R[42) |
|---|---|---|---|---|
| C-1 | A[1) | —CH₃ | H | 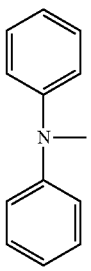 |

-continued
| Cpd. | L | R¹ | R² | R⁷ = R⁴²⁾ |
|---|---|---|---|---|
| C-2 | A¹⁾ | —CH₃ | H | 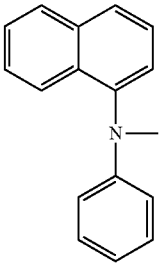 |
| C-3 | A¹⁾ | —CH₃ | H | 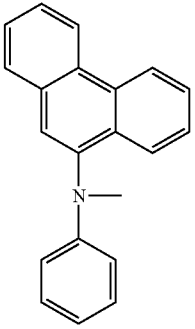 |
| C-4 | A¹⁾ | —CH₃ | H | 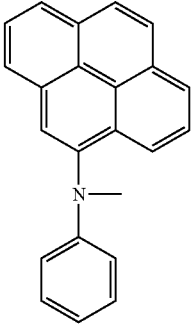 |
| C-5 | A¹⁾ | —CH₃ | H | 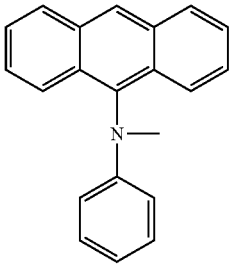 |
| C-6 | A¹⁾ | —CH₃ | H | 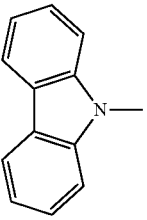 |

-continued
| Cpd. | L | $R^1$ | $R^2$ | $R^7 = R^{42)}$ |
|---|---|---|---|---|
| C-7 | $A^{1)}$ | —CH$_3$ | H | 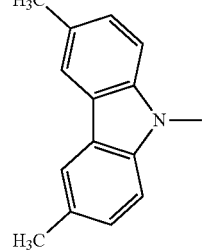 |
| C-8 | $A^{1)}$ | —CH$_3$ | H | 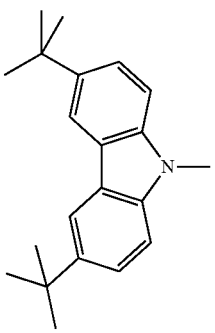 |
| C-9 | $A^{1)}$ | —CH$_3$ | H | 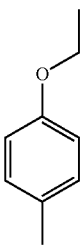 |
| C-10 | $A^{1)}$ | H | H | 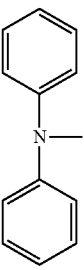 |
| C-12 | $A^{1)}$ | H | H | 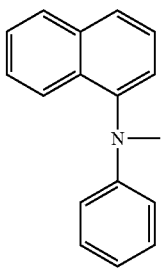 |

-continued
| Cpd. | L | $R^1$ | $R^2$ | $R^7 = R^{42)}$ |
|---|---|---|---|---|
| C-13 | $A^{1)}$ | H | H | 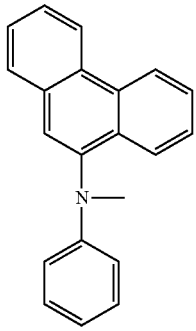 |
| C-14 | $A^{1)}$ | H | H | 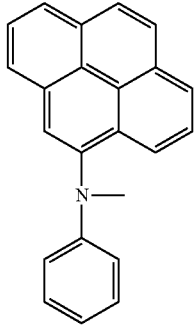 |
| C-15 | $A^{1)}$ | H | H | 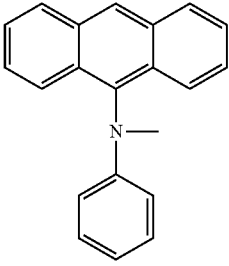 |
| C-16 | $A^{1)}$ | H | H | 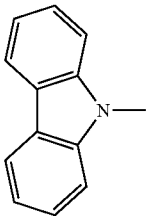 |
| C-17 | $A^{1)}$ | H | H | 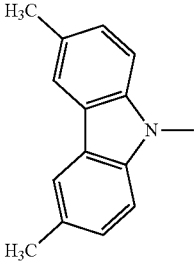 |

-continued
| Cpd. | L | R¹ | R² | R⁷ = R⁴²⁾ |
|---|---|---|---|---|
| C-18 | A¹⁾ | H | H | 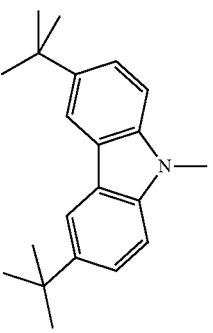 |
| C-19 | A¹⁾ | H | H | 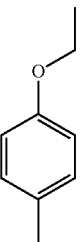 |
| C-20 | A¹⁾ | Ph | H | 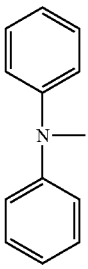 |
| C-21 | A¹⁾ | Ph | H | 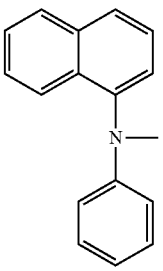 |
| C-22 | A¹⁾ | Ph | H | 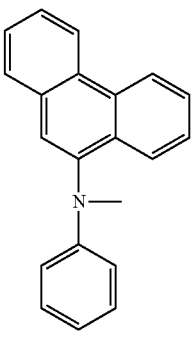 |

-continued
| Cpd. | L | R¹ | R² | R⁷ = R⁴²⁾ |
|---|---|---|---|---|
| C-23 | A¹⁾ | Ph | H | 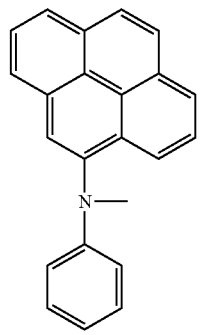 |
| C-24 | A¹⁾ | Ph | H | 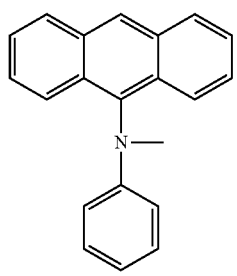 |
| C-25 | A¹⁾ | Ph | H | 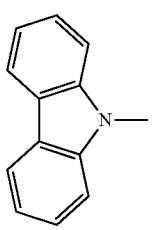 |
| C-26 | A¹⁾ | Ph | H | 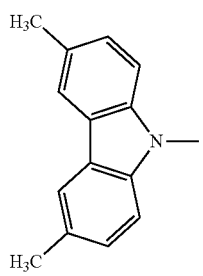 |
| C-27 | A¹⁾ | Ph | H | 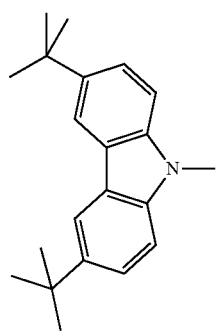 |

-continued
| Cpd. | L | R¹ | R² | R⁷ = R⁴²⁾ |
|---|---|---|---|---|
| C-28 | A¹⁾ | Ph | H | 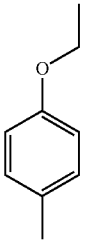 |
| C-29 | A¹⁾ | 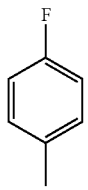 | H | 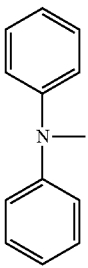 |
| C-30 | A¹⁾ | 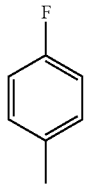 | H | 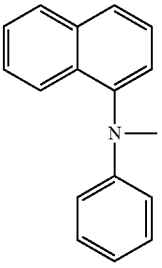 [SMILES: CN(c1ccccc1)c1cccc2ccccc12] |
| C-31 | A¹⁾ | 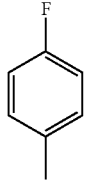 | H | 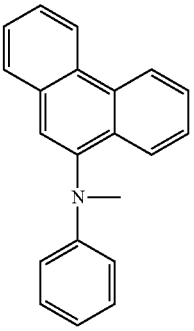 |
| C-32 | A¹⁾ | 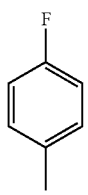 | H | 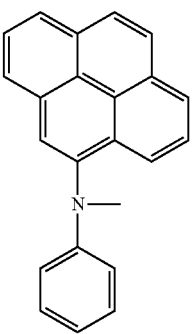 |

-continued

| Cpd. | L | R¹ | R² | R⁷ = R⁴²⁾ |
|---|---|---|---|---|
| C-33 | A¹⁾ | 4-F-C₆H₄- | H | N-methyl-N-phenyl-benz[a]acridin-7-amine substituent |
| C-34 | A¹⁾ | 4-F-C₆H₄- | H | 9-methylcarbazol-3-yl |
| C-35 | A¹⁾ | 4-F-C₆H₄- | H | 3,6-dimethyl-9-methylcarbazol-yl |
| C-36 | A¹⁾ | 4-F-C₆H₄- | H | 3,6-di-tert-butyl-9-methylcarbazol-yl |
| C-37 | A¹⁾ | 4-F-C₆H₄- | H | 4-ethoxy-3-methylphenyl |

-continued
| Cpd. | L | R¹ | R² | R⁷ = R⁴²⁾ |
|---|---|---|---|---|
| C-38 | A¹⁾ | 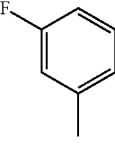 | H | 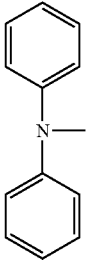 |
| C-39 | A¹⁾ | 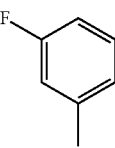 | H | 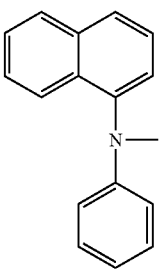 [SMILES: CN(c1ccccc1)c1cccc2ccccc12] |
| C-40 | A¹⁾ | 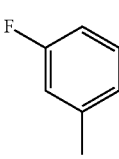 | H | 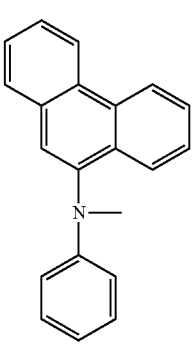 |
| C-41 | A¹⁾ | 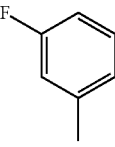 | H | 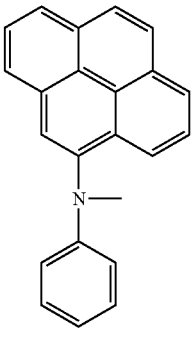 |
| C-42 | A¹⁾ | 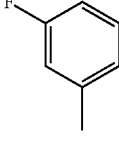 | H | 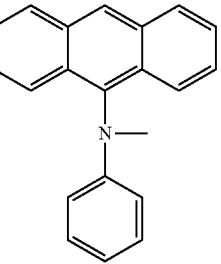 |

-continued
| Cpd. | L | R¹ | R² | R⁷ = R⁴²⁾ |
|---|---|---|---|---|
| C-43 | A¹⁾ | 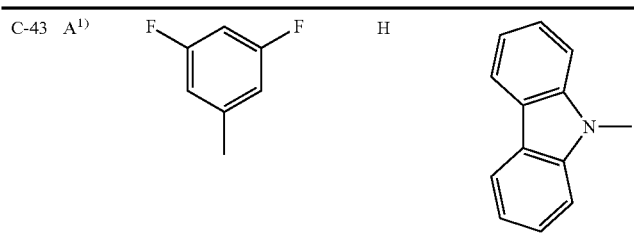 | H | |
| C-44 | A¹⁾ | | H | 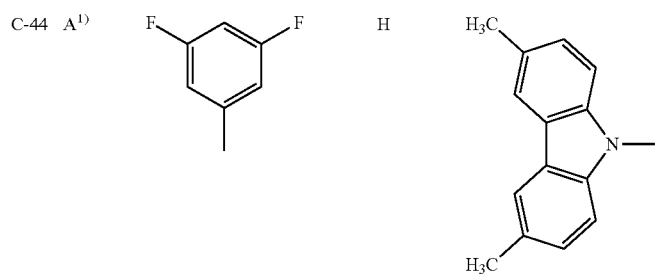 |
| C-45 | A¹⁾ | | H | 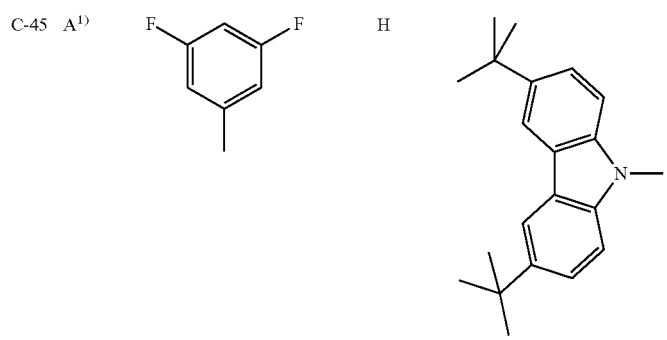 |
| C-46 | A¹⁾ | | H | 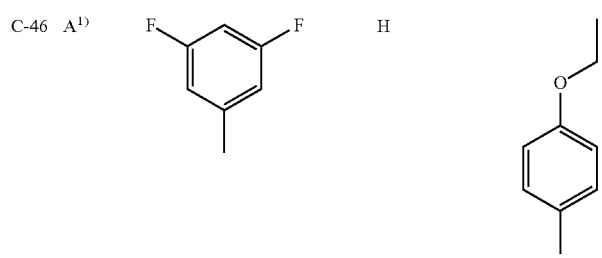 |
| C-47 | A¹⁾ | | H | 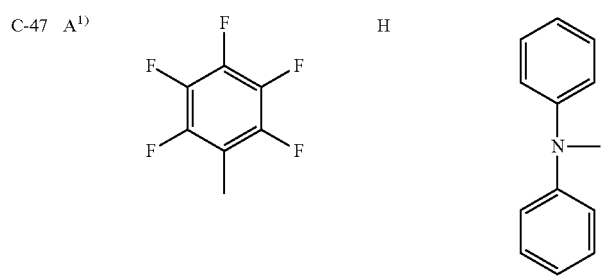 |

-continued
| Cpd. | L | R¹ | R² | R⁷ = R⁴²⁾ |
|---|---|---|---|---|
| C-48 | A¹⁾ | 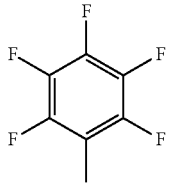 | H | 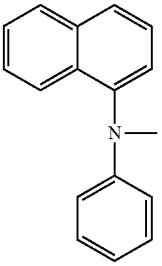 [SMILES: CN(c1ccccc1)c1cccc2ccccc12] |
| C-49 | A¹⁾ | 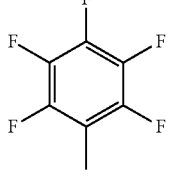 | H | 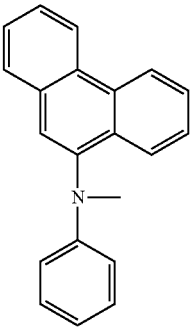 |
| C-50 | A¹⁾ | 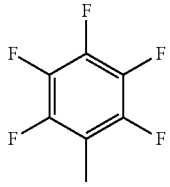 | H | 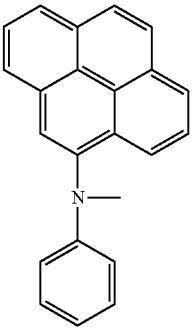 |
| C-51 | A¹⁾ | 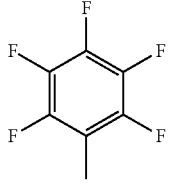 | H | 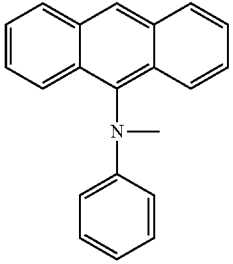 [SMILES: CN(c1ccccc1)c1c2ccccc2cc2ccccc12] |
| C-52 | A¹⁾ | 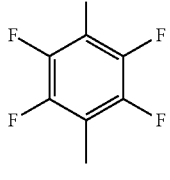 | H | 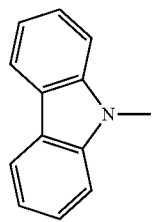 |

-continued
| Cpd. | L | R¹ | R² | R⁷ = R⁴²⁾ |
|---|---|---|---|---|
| C-53 | A¹⁾ | 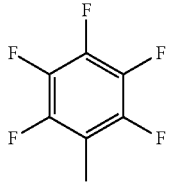 | H | 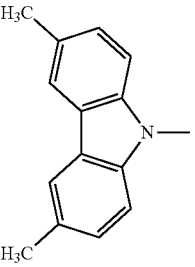 |
| C-54 | A¹⁾ | 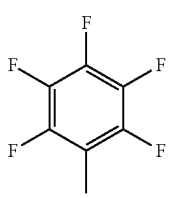 | H | 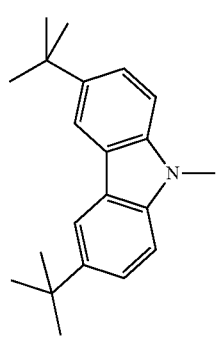 [SMILES: Cn1c2ccc(C(C)(C)C)cc2c2cc(C(C)(C)C)ccc21] |
| C-55 | A¹⁾ | 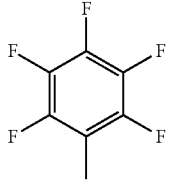 | H | 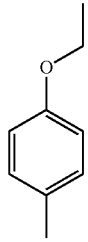 |
| C-56 | A¹⁾ | 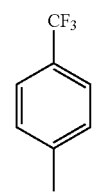 | H | 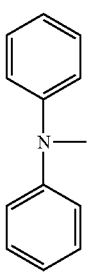 |
| C-57 | A¹⁾ | 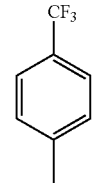 | H | 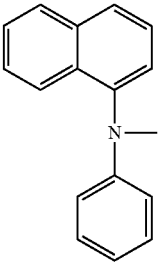 [SMILES: CN(c1ccccc1)c1cccc2ccccc12] |

-continued
| Cpd. | L | R¹ | R² | R⁷ = R⁴²⁾ |
|---|---|---|---|---|
| C-58 | A¹⁾ | 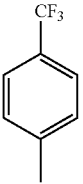 | H | 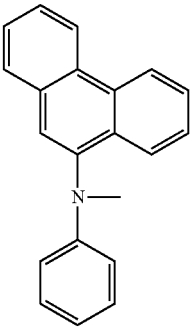 |
| C-59 | A¹⁾ | 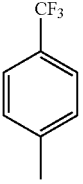 | H | 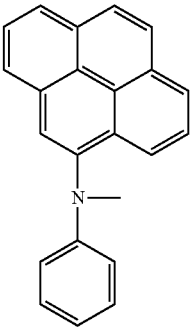 |
| C-60 | A¹⁾ | 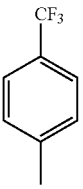 | H | 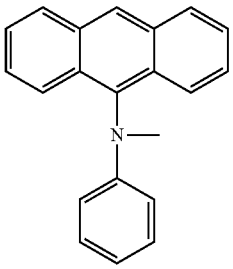 [SMILES: CN(c1ccccc1)c1c2ccccc2cc2ccccc12] |
| C-61 | A¹⁾ | 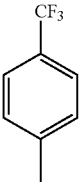 | H | 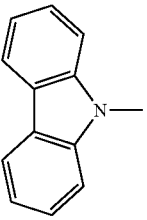 |
| C-62 | A¹⁾ | 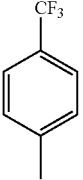 | H | 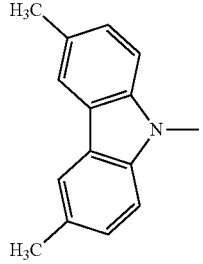 |

-continued
| Cpd. | L | R¹ | R² | R⁷ = R⁴²⁾ |
|---|---|---|---|---|
| C-63 | A¹⁾ | 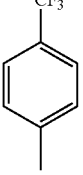 | H | 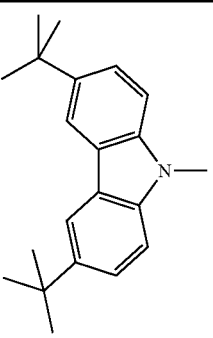 |
| C-64 | A¹⁾ | 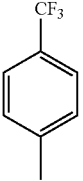 | H | 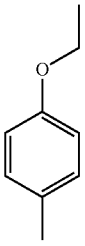 |
| C-65 | A¹⁾ | 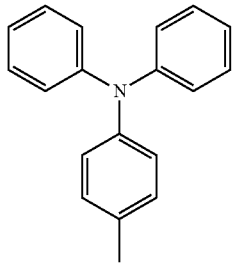 | H | 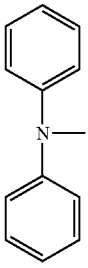 |
| C-66 | A¹⁾ | 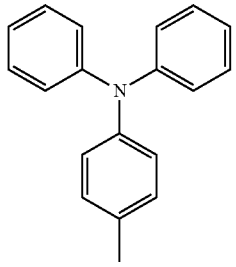 | H | 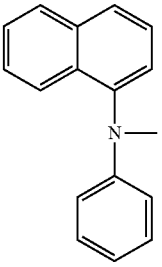 [SMILES: CN(c1ccccc1)c1cccc2ccccc12] |
| C-67 | A¹⁾ | 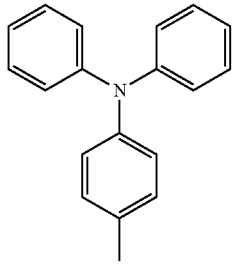 | H | 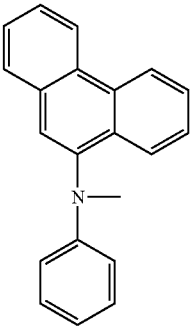 [SMILES: CN(c1ccccc1)c1cc2ccccc2c2ccccc12] |

-continued
| Cpd. | L | R¹ | R² | R⁷ = R⁴²⁾ |
|---|---|---|---|---|
| C-68 | A¹⁾ | 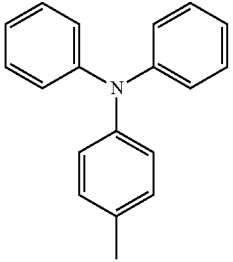 | H | 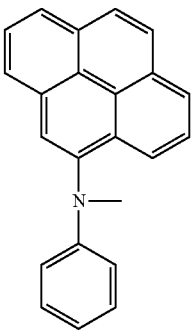 |
| C-69 | A¹⁾ | 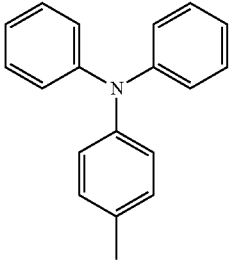 | H | 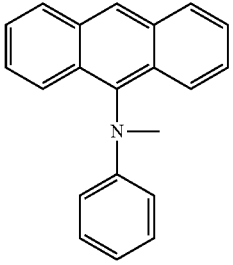 [SMILES: CN(c1ccccc1)c1c2ccccc2cc2ccccc12] |
| C-70 | A¹⁾ | 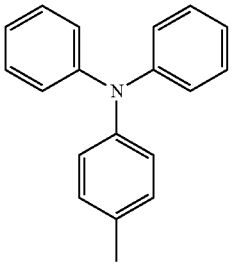 | H | 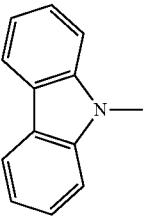 |
| C-71 | A¹⁾ | 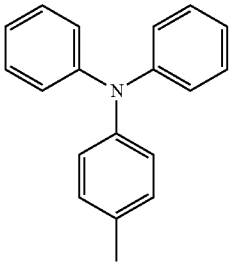 | H | 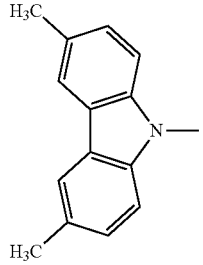 |
| C-72 | A¹⁾ | 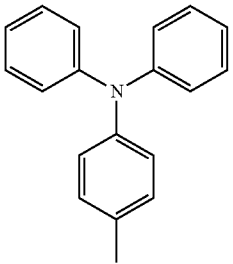 | H | 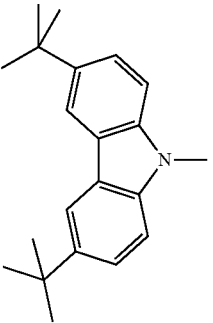 [SMILES: Cn1c2ccc(C(C)(C)C)cc2c2cc(C(C)(C)C)ccc21] |

-continued
| Cpd. | L | R¹ | R² | R⁷ = R⁴²⁾ |
|---|---|---|---|---|
| C-73 | A¹⁾ | 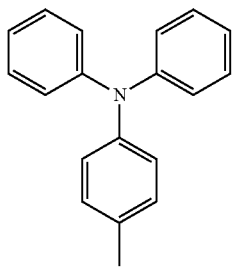 | H | 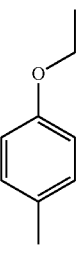 |
| C-74 | A¹⁾ | 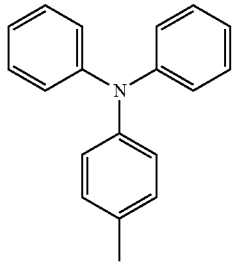 | H | 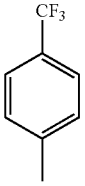 |
| C-76 | A¹⁾ | 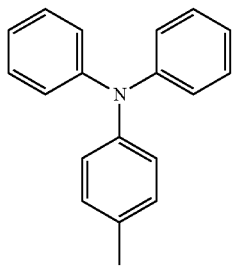 | H | 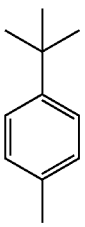 |
| C-78 | A¹⁾ | 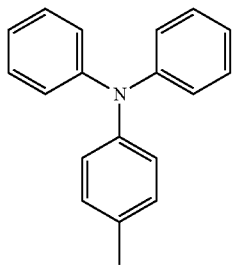 | H | 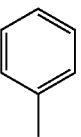 |
| C-79 | A¹⁾ | 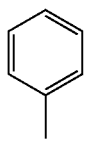 | H | 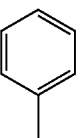 |
| C-80 | A¹⁾ | H | H | 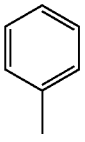 |
| C-81 | A¹⁾ | CH₃ | H | 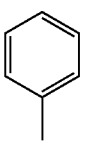 |
| C-82 | A¹⁾ | 2-ethylhexyl | H | H |
| C-83 | A¹⁾ | n-butyl | H | H |

-continued

| Cpd. | L | R$^1$ | R$^2$ | R$^7$ = R$^{4\,2)}$ |
|---|---|---|---|---|
| C-84 | A$^{1)}$ | tert-butyl | H | H |
| C-85 | A$^{1)}$ | —(CH$_2$)$_4$— | H | H |
| C-86 | A$^{1)}$ | 2-ethylhexyl | CH$_3$ | H |
| C-87 | A$^{1)}$ | n-butyl | CH$_3$ | H |
| C-88 | A$^{1)}$ | tert-butyl | CH$_3$ | H |
| C-89 | A$^{1)}$ | 2-ethylhexyl | H | propyl |
| C-90 | A$^{1)}$ | n-butyl | H | propyl |
| C-91 | A$^{1)}$ | tert-butyl | H | propyl |
| C-92 | A$^{1)}$ | —(CH$_2$)$_4$— | H | propyl |
| C-93 | A$^{1)}$ | 2-ethylhexyl | CH$_3$ | propyl |
| C-94 | A$^{1)}$ | n-butyl | CH$_3$ | propyl |
| C-95 | A$^{1)}$ | tert-butyl | CH$_3$ | propyl |
| D-1 | B$^{1)}$ | —CH$_3$ | H | 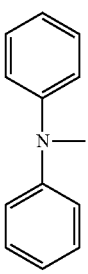 |
| D-2 | B$^{1)}$ | —CH$_3$ | H | 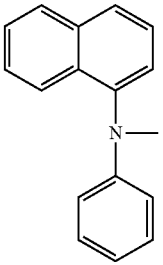 |
| D-3 | B$^{1)}$ | —CH$_3$ | H | 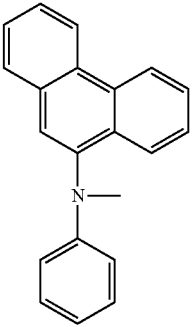 |
| D-4 | B$^{1)}$ | —CH$_3$ | H | 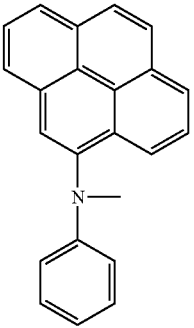 |

-continued
| Cpd. | L | R¹ | R² | R⁷ = R⁴²⁾ |
|---|---|---|---|---|
| D-5 | B¹⁾ | —CH₃ | H | 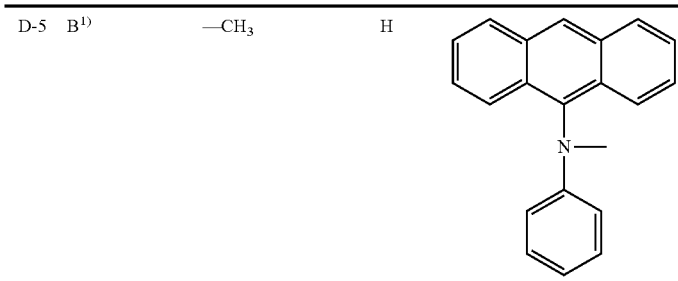 |
| D-6 | B¹⁾ | —CH₃ | H | 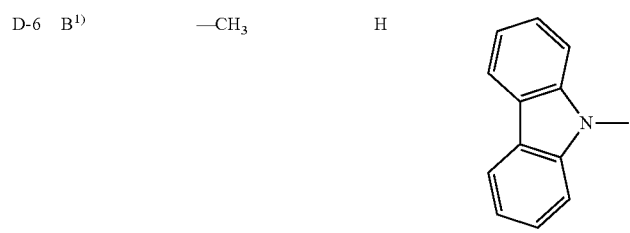 |
| D-7 | B¹⁾ | —CH₃ | H | 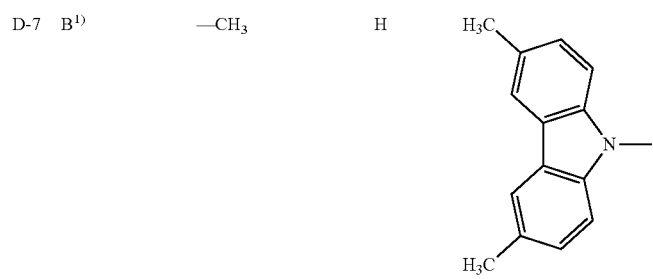 |
| D-8 | B¹⁾ | —CH₃ | H | 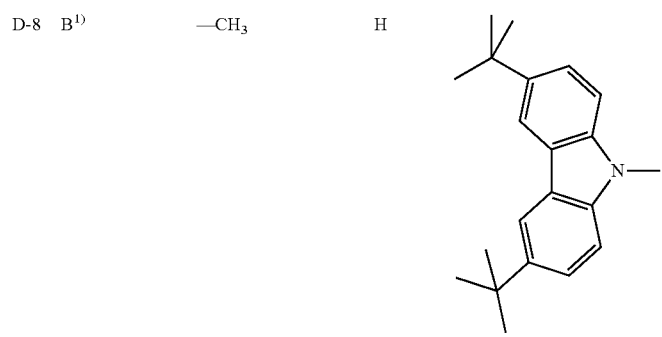 |
| D-9 | B¹⁾ | —CH₃ | H | 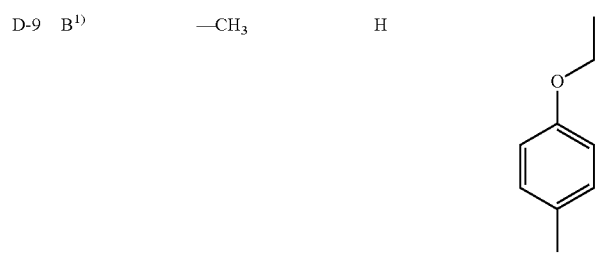 |

-continued
| Cpd. | L | R¹ | R² | R⁷ = R⁴²⁾ |
|---|---|---|---|---|
| D-10 | B¹⁾ | H | H | 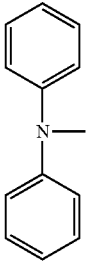 |
| D-12 | B¹⁾ | H | H | 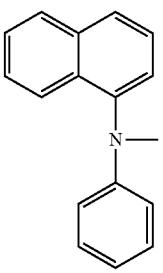 |
| D-13 | B¹⁾ | H | H | 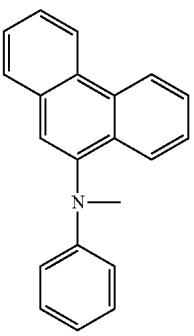 |
| D-14 | B¹⁾ | H | H | 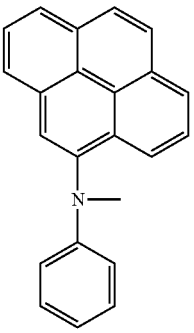 |
| D-15 | B¹⁾ | H | H | 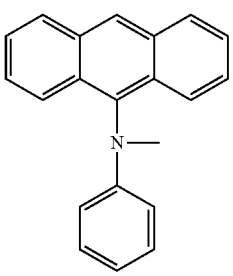 |

-continued
| Cpd. | L | R¹ | R² | R⁷ = R⁴²⁾ |
|---|---|---|---|---|
| D-16 | B¹⁾ | H | H | 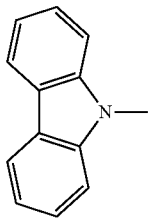 |
| D-17 | B¹⁾ | H | H | 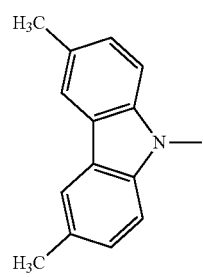 |
| D-18 | B¹⁾ | H | H | 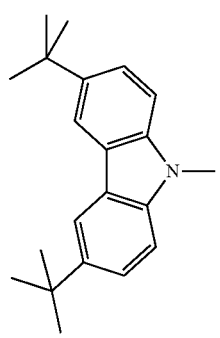 |
| D-19 | B¹⁾ | H | H | 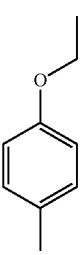 |
| D-20 | B¹⁾ | Ph | H | 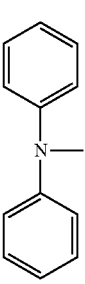 |

-continued
| Cpd. | L | $R^1$ | $R^2$ | $R^7 = R^{42)}$ |
|---|---|---|---|---|
| D-21 | $B^{1)}$ | Ph | H | 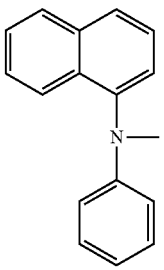 |
| D-22 | $B^{1)}$ | Ph | H | 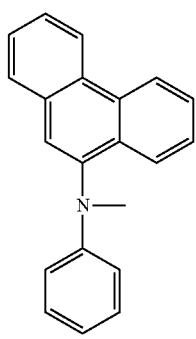 |
| D-23 | $B^{1)}$ | Ph | H | 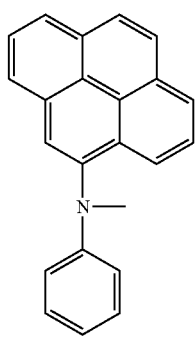 |
| D-24 | $B^{1)}$ | Ph | H | 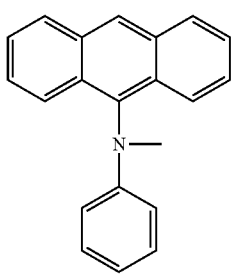 |
| D-25 | $B^{1)}$ | Ph | H | 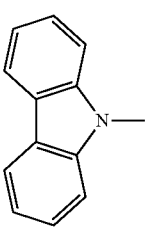 |

-continued
| Cpd. | L | R¹ | R² | R⁷ = R⁴²⁾ |
|---|---|---|---|---|
| D-26 | B¹⁾ | Ph | H | 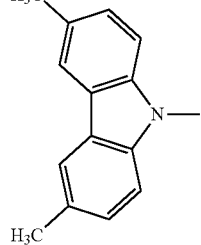 |
| D-27 | B¹⁾ | Ph | H | 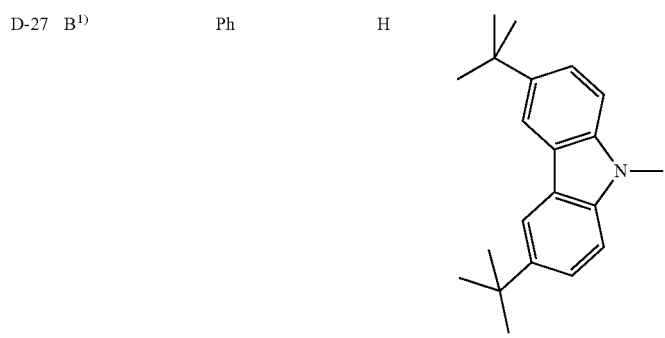 |
| D-28 | B¹⁾ | Ph | H | 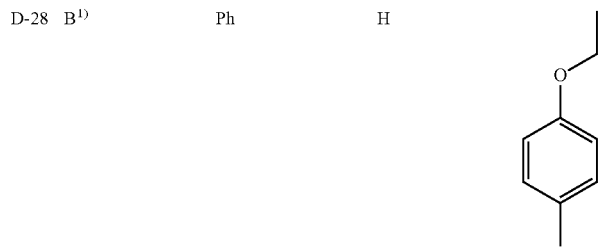 |
| D-29 | B¹⁾ | 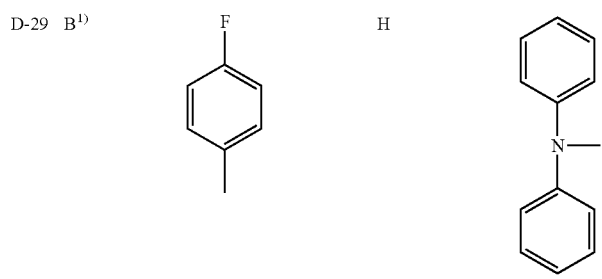 | H | |
| D-30 | B¹⁾ | 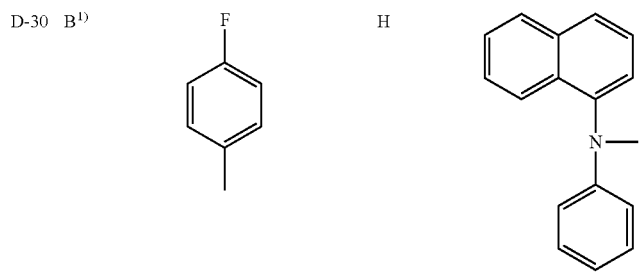 | H | |

-continued

| Cpd. | L | R¹ | R² | R⁷ = R⁴²⁾ |
|---|---|---|---|---|
| D-31 | B¹⁾ | 4-fluorophenyl | H | N-methyl-N-phenyl-phenanthren-9-amine |
| D-32 | B¹⁾ | 4-fluorophenyl | H | N-methyl-N-phenyl-pyren-1-amine |
| D-33 | B¹⁾ | 4-fluorophenyl | H | N-methyl-N-phenyl-anthracen-9-amine |
| D-34 | B¹⁾ | 4-fluorophenyl | H | 9-methyl-carbazole |
| D-35 | B¹⁾ | 4-fluorophenyl | H | 3,6-dimethyl-9-methyl-carbazole |

-continued
| Cpd. | L | R¹ | R² | R⁷ = R⁴²⁾ |
|---|---|---|---|---|
| D-36 | B¹⁾ |  | H | 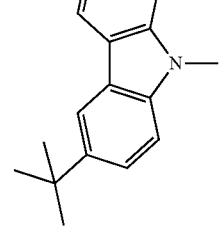 |
| D-37 | B¹⁾ | 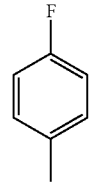 | H | 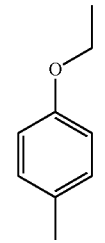 |
| D-38 | B¹⁾ | 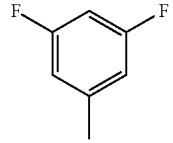 | H | 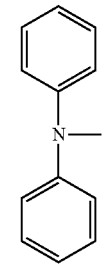 |
| D-39 | B¹⁾ | 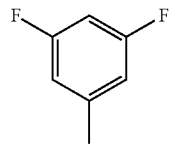 | H | 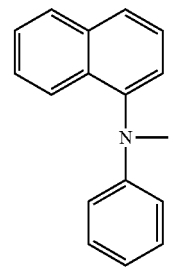 [SMILES: CN(c1ccccc1)c1cccc2ccccc12] |
| D-40 | B¹⁾ | 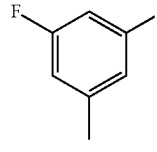 | H | 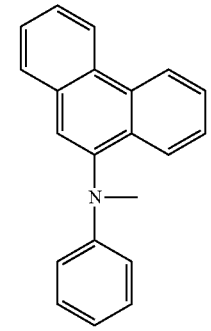 |

-continued

| Cpd. | L | R¹ | R² | R⁷ = R⁴²⁾ |
|---|---|---|---|---|
| D-41 | B¹⁾ | 3,5-difluorophenyl | H | N-methyl-N-phenyl-aminopyrene |
| D-42 | B¹⁾ | 3,5-difluorophenyl | H | N-methyl-N-phenyl-aminoanthracene |
| D-43 | B¹⁾ | 3,5-difluorophenyl | H | 9-methylcarbazole |
| D-44 | B¹⁾ | 3,5-difluorophenyl | H | 2,7-dimethyl-9-methylcarbazole |
| D-45 | B¹⁾ | 3,5-difluorophenyl | H | 2,7-di-tert-butyl-9-methylcarbazole |

| Cpd. | L | R¹ | R² | R⁷ = R⁴²⁾ |
|---|---|---|---|---|
| D-46 | B¹⁾ | 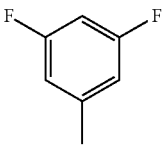 | H | 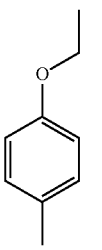 |
| D-47 | B¹⁾ | 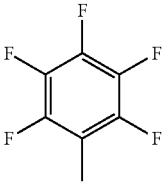 | H | 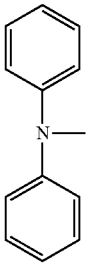 |
| D-48 | B¹⁾ | 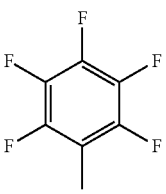 | H | 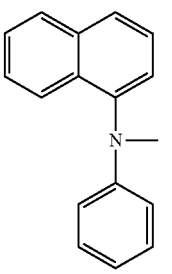 [SMILES: CN(c1ccccc1)c1cccc2ccccc12] |
| D-49 | B¹⁾ | 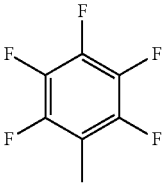 | H | 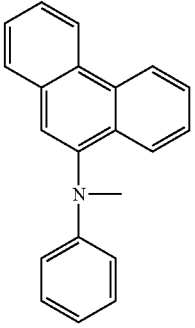 |
| D-50 | B¹⁾ | 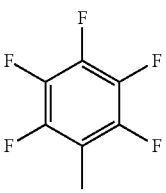 | H | 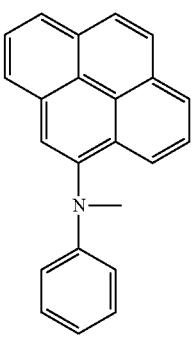 |

-continued
| Cpd. | L | R$^1$ | R$^2$ | R$^7$ = R$^{42)}$ |
|---|---|---|---|---|
| D-51 | B$^{1)}$ | 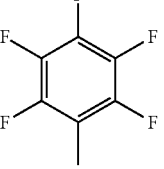 | H | 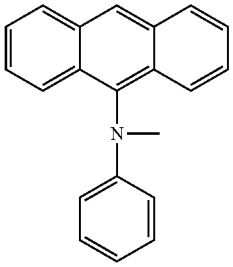 [SMILES: CN(c1ccccc1)c1c2ccccc2cc2ccccc12] |
| D-52 | B$^{1)}$ | 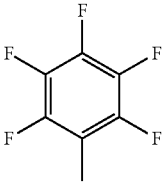 | H | 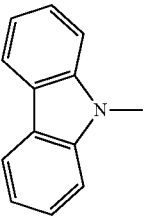 |
| D-53 | B$^{1)}$ | 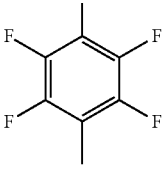 | H | 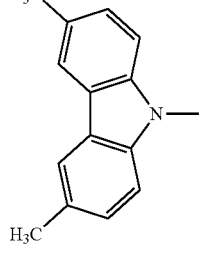 |
| D-54 | B$^{1)}$ | 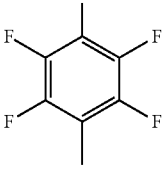 | H | 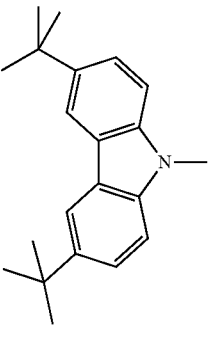 [SMILES: Cn1c2ccc(C(C)(C)C)cc2c2cc(C(C)(C)C)ccc21] |
| D-55 | B$^{1)}$ | 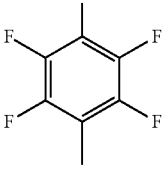 | H | 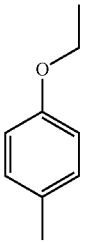 |

-continued
| Cpd. | L | R$^1$ | R$^2$ | R$^7$ = R$^{42}$) |
|---|---|---|---|---|
| D-56 | B$^{1)}$ | 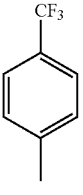 4-CF$_3$-C$_6$H$_4$ | H | 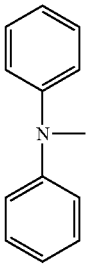 N,N-diphenylamino |
| D-57 | B$^{1)}$ | 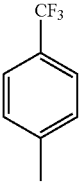 4-CF$_3$-C$_6$H$_4$ | H | 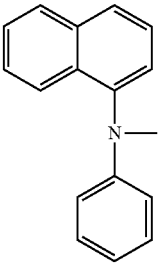 [SMILES: CN(c1ccccc1)c1cccc2ccccc12] N-(1-naphthyl)-N-phenylamino |
| D-58 | B$^{1)}$ | 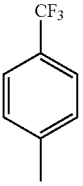 4-CF$_3$-C$_6$H$_4$ | H | 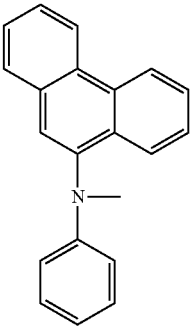 N-(phenanthren-9-yl)-N-phenylamino |
| D-59 | B$^{1)}$ | 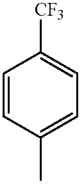 4-CF$_3$-C$_6$H$_4$ | H | 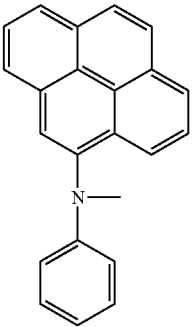 N-(pyren-1-yl)-N-phenylamino |
| D-60 | B$^{1)}$ | 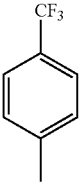 4-CF$_3$-C$_6$H$_4$ | H | 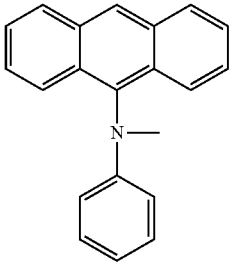 [SMILES: CN(c1ccccc1)c1c2ccccc2cc2ccccc12] N-(anthracen-9-yl)-N-phenylamino |

-continued
| Cpd. | L | R¹ | R² | R⁷ = R⁴²⁾ |
|---|---|---|---|---|
| D-61 | B¹⁾ | | H | |
| D-62 | B¹⁾ | | H | |
| D-63 | B¹⁾ | | H | |
| D-64 | B¹⁾ | | H | |
| D-65 | B¹⁾ | | H | |
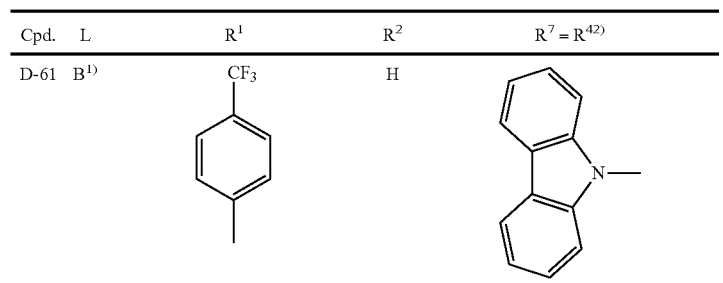
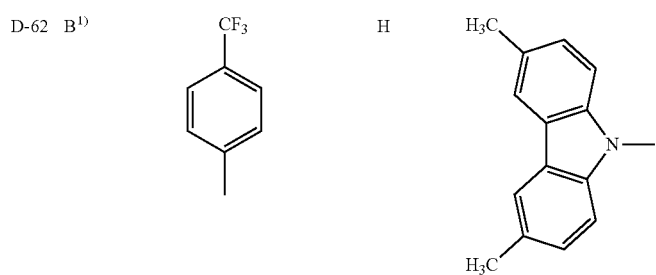
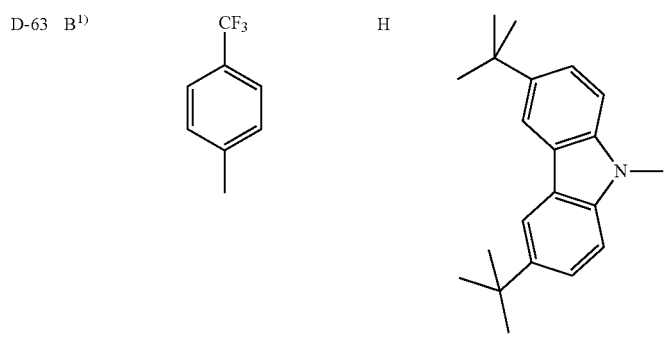
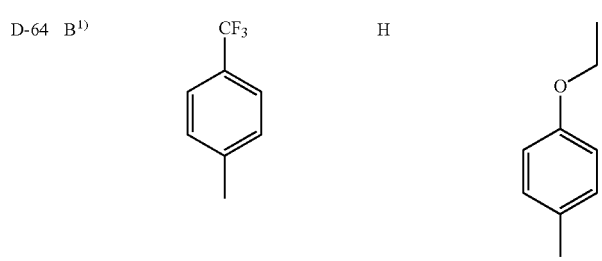
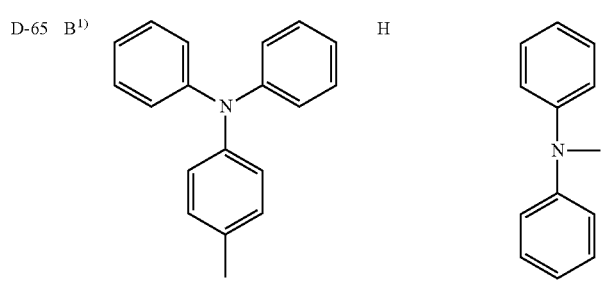

-continued

| Cpd. | L | R$^1$ | R$^2$ | R$^7$ = R$^{42)}$ |
|---|---|---|---|---|
| D-66 | B$^{1)}$ | [N,N-diphenyl-4-methylphenylamine structure] | H | [N-methyl-N-phenyl-1-naphthylamine structure] |
| D-67 | B$^{1)}$ | [N,N-diphenyl-4-methylphenylamine structure] | H | [N-methyl-N-phenyl-phenanthrenylamine structure] |
| D-68 | B$^{1)}$ | [N,N-diphenyl-4-methylphenylamine structure] | H | [N-methyl-N-phenyl-pyrenylamine structure] |
| D-69 | B$^{1)}$ | [N,N-diphenyl-4-methylphenylamine structure] | H | [N-methyl-N-phenyl-anthracenylamine structure] |
| D-70 | B$^{1)}$ | [N,N-diphenyl-4-methylphenylamine structure] | H | [9-methylcarbazole structure] |

-continued
| Cpd. | L | R¹ | R² | R⁷ = R⁴²⁾ |
|---|---|---|---|---|
| D-71 | B¹⁾ | 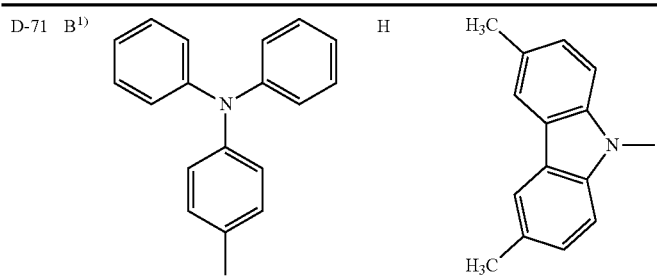 | H | |
| D-72 | B¹⁾ | 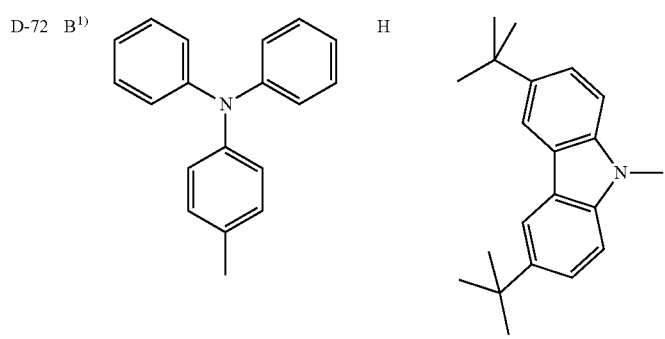 | H | |
| D-73 | B¹⁾ | 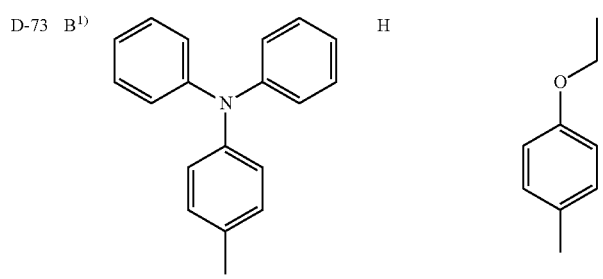 | H | |
| D-74 | B¹⁾ | 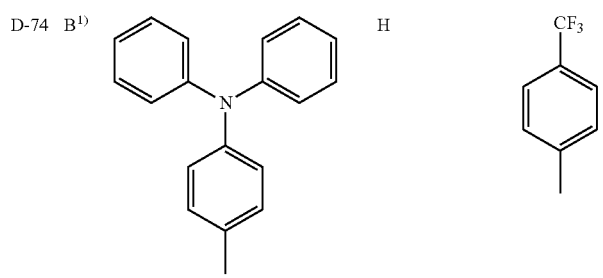 | H | |
| D-76 | B¹⁾ | 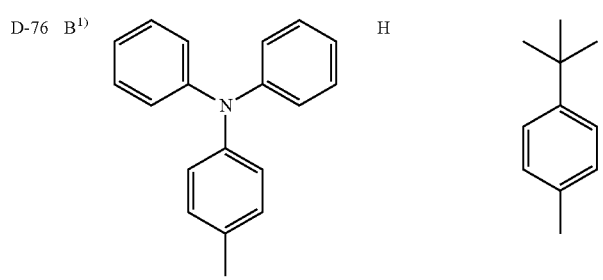 | H | |

-continued

| Cpd. | L | R¹ | R² | R⁷ = R⁴²⁾ |
|---|---|---|---|---|
| D-78 | B¹⁾ | 4-(diphenylamino)phenyl (tolyl-N(Ph)₂) | H | phenyl (tolyl) |
| D-79 | B¹⁾ | tolyl | H | tolyl |
| D-80 | B¹⁾ | H | H | tolyl |
| D-81 | B¹⁾ | CH₃ | H | tolyl |
| D-82 | B¹⁾ | 2-ethylhexyl | H | H |
| D-83 | B¹⁾ | n-butyl | H | H |
| D-84 | B¹⁾ | tert-butyl | H | H |
| D-85 | B¹⁾ | —(CH₂)₄— | H | H |
| D-86 | B¹⁾ | 2-ethylhexyl | CH₃ | H |
| D-87 | B¹⁾ | n-butyl | CH₃ | H |
| D-88 | B¹⁾ | tert-butyl | CH₃ | H |
| D-89 | B¹⁾ | 2-ethylhexyl | H | propyl |
| D-90 | B¹⁾ | n-butyl | H | propyl |
| D-91 | B¹⁾ | tert-butyl | H | propyl |
| D-92 | B¹⁾ | —(CH₂)₄— | H | propyl |
| D-93 | B¹⁾ | 2-ethylhexyl | CH₃ | propyl |
| D-94 | B¹⁾ | n-butyl | CH₃ | propyl |
| D-95 | B¹⁾ | tert-butyl | CH₃ | propyl |

¹⁾ A = acetylacetonate (2,4-pentanedionate), B = 2,2,6,6-tetramethyl-3,5-heptanedionate;

²⁾ The ligand $L^a$ used for the production of comp. C-1 (etc.) is present in form of two isomers:

—R¹ = —CH₃, R² = H, R⁷ = 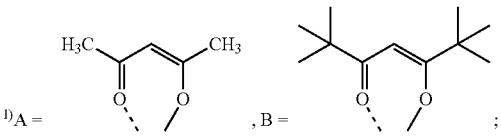 , and

—R¹ = —CH₃, R² = H, R⁴ = 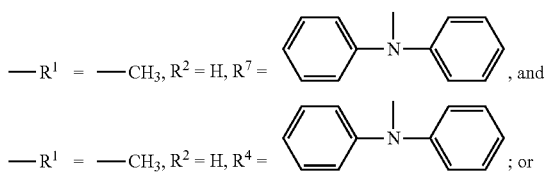 ; or

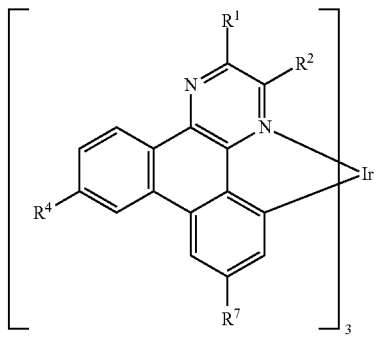
| Cpd. | R¹ | R² | R⁴ | R⁷ |
|---|---|---|---|---|
| E-1 | 4-tert-butylphenyl | H | H | H |
| E-2 | 4-fluorophenyl | H | H | H |
| E-3 | 3,5-difluorophenyl | H | H | H |
| E-4 | pentafluorophenyl | H | H | H |
| E-5 | 4-(trifluoromethyl)phenyl | H | H | H |
| E-6 | 4-(N,N-diphenylamino)-4'-methylphenyl | H | H | H |

-continued
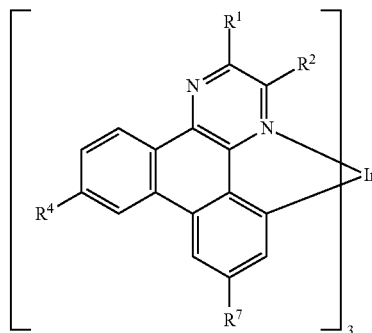
| Cpd. | R¹ | R² | R⁴ | R⁷ |
|---|---|---|---|---|
| E-7 | 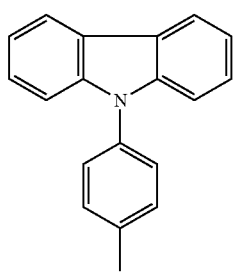 | H | H | H |
| E-8 | 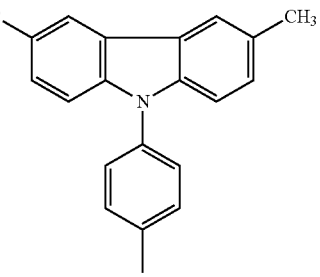 | H | H | H |
| E-9 | 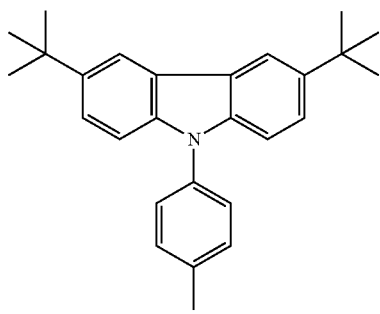 | H | H | H |
| E-10 | 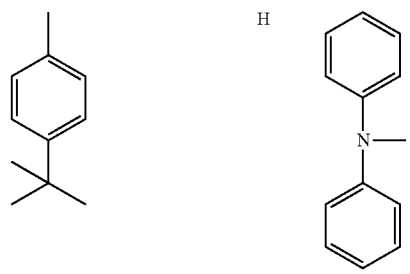 | H | | H |

-continued
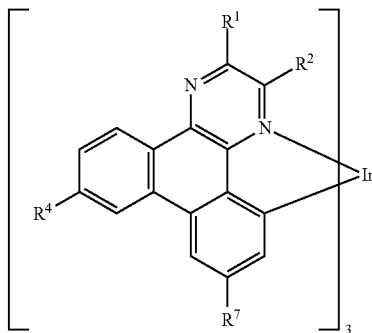
| Cpd. | R¹ | R² | R⁴ | R⁷ |
|---|---|---|---|---|
| E-11 | ![4-fluorophenyl] | H | ![N,N-diphenylamino] | H |
| E-12 | ![3,5-difluorophenyl] | H | ![N,N-diphenylamino] | H |
| E-13 | ![pentafluorophenyl] | H | ![N,N-diphenylamino] | H |
| E-14 | ![4-(trifluoromethyl)phenyl] | H | ![N,N-diphenylamino] | H |

-continued
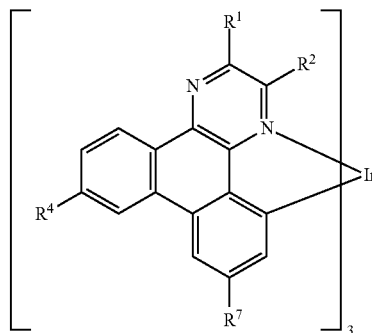
| Cpd. | R¹ | R² | R⁴ | R⁷ |
|---|---|---|---|---|
| E-15 | (triphenylamine with p-tolyl) | H | (diphenylamine) | H |
| E-16 | (9-(p-tolyl)carbazole) | H | (diphenylamine) | H |
| E-17 | (3,6-dimethyl-9-(p-tolyl)carbazole) | H | (diphenylamine) | H |
| E-18 | (3,6-di-tert-butyl-9-(p-tolyl)carbazole) | H | (diphenylamine) | H |

-continued
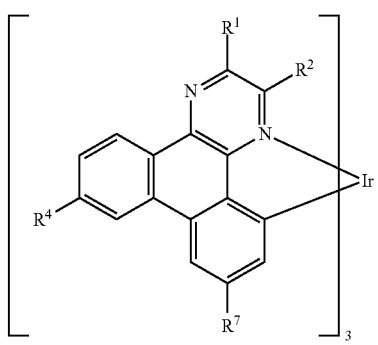
| Cpd. | R¹ | R² | R⁴ | R⁷ |
|---|---|---|---|---|
| E-19 | 4-tert-butylphenyl | H | N-carbazolyl | H |
| E-20 | 4-fluorophenyl | H | N-carbazolyl | H |
| E-21 | 3,5-difluorophenyl | H | N-carbazolyl | H |
| E-22 | pentafluorophenyl | H | N-carbazolyl | H |
| E-23 | 4-(trifluoromethyl)phenyl | H | N-carbazolyl | H |

-continued
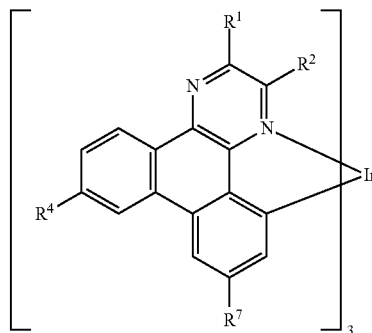
| Cpd. | R¹ | R² | R⁴ | R⁷ |
| --- | --- | --- | --- | --- |
| E-24 | 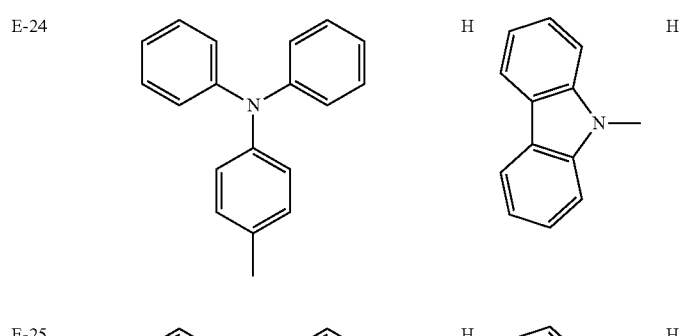 | H | | H |
| E-25 | 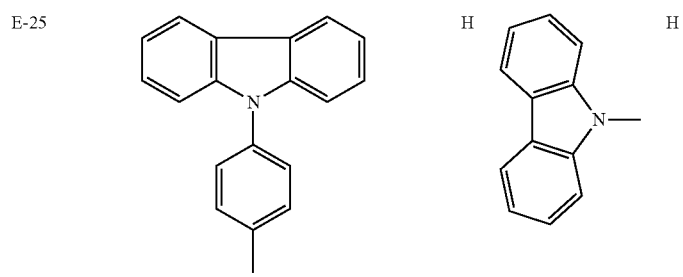 | H | | H |
| E-26 | 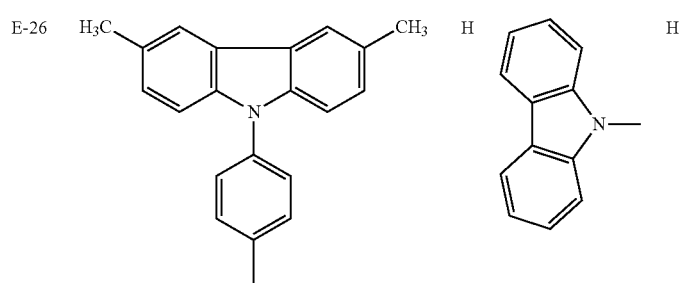 | H | | H |
| E-27 | 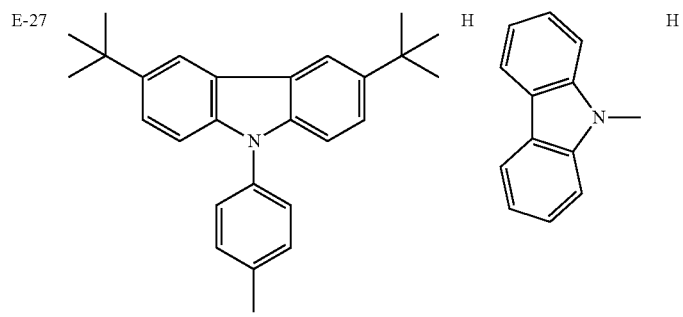 | H | | H |

-continued
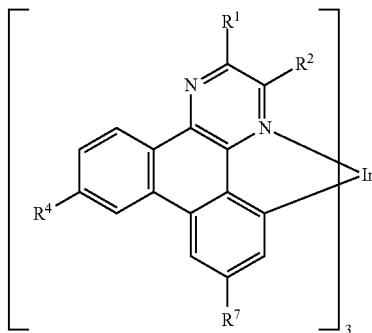
| Cpd. | R¹ | R² | R⁴ | R⁷ |
|---|---|---|---|---|
| E-28 | 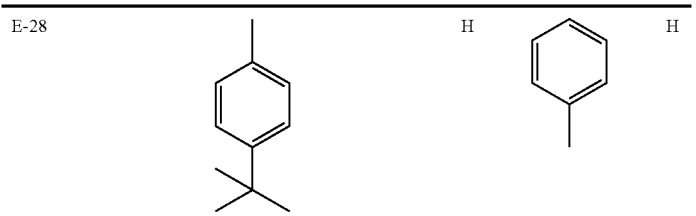 | H | | H |
| E-29 | 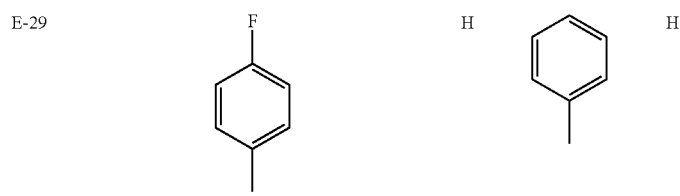 | H | | H |
| E-30 | 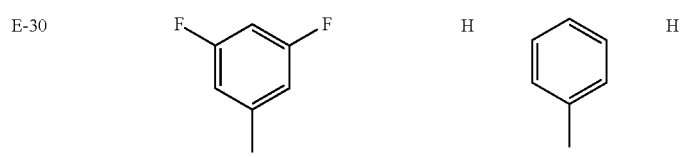 | H | | H |
| E-31 | 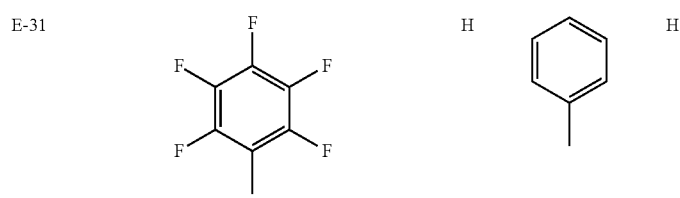 | H | | H |
| E-32 | 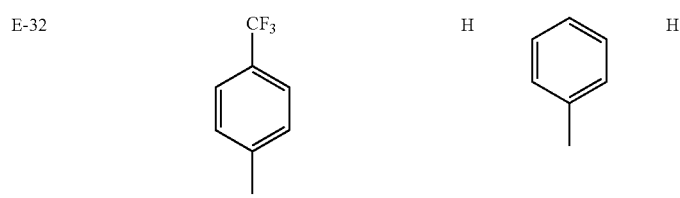 | H | | H |

-continued
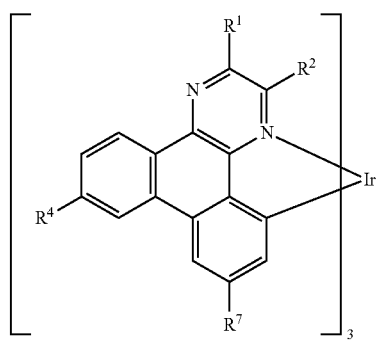
| Cpd. | R¹ | R² | R⁴ | R⁷ |
|---|---|---|---|---|
| E-33 | 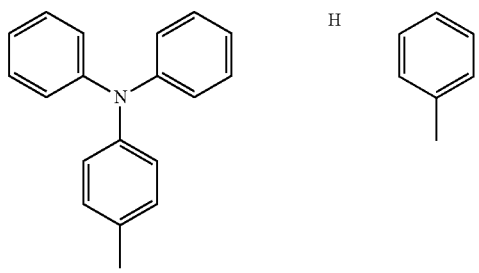 | H | 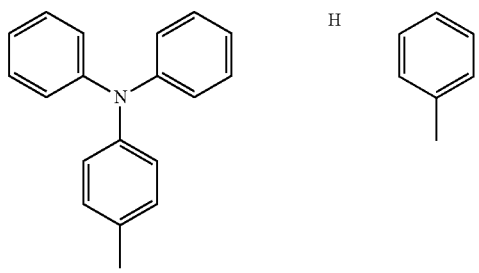 | H |
| E-34 | 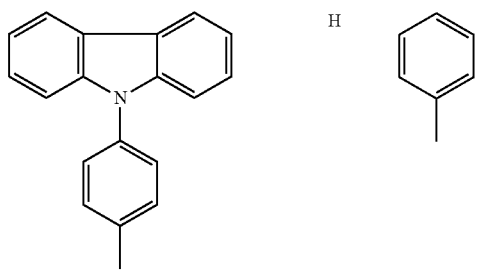 | H | 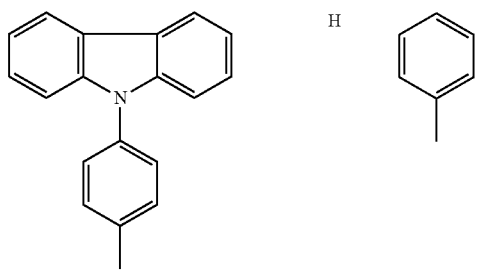 | H |
| E-35 | 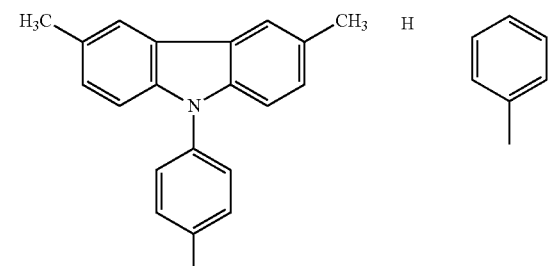 | H | 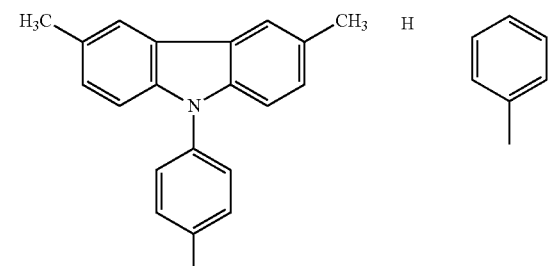 | H |
| E-36 | 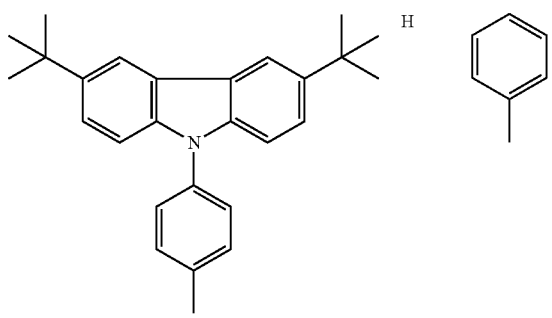 | H | 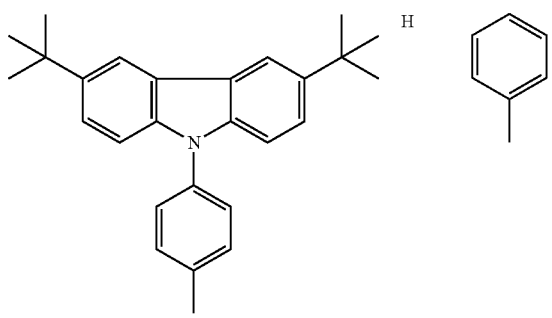 | H. |

8. The compound of the formula I according to claim 1, which is a compound of formula

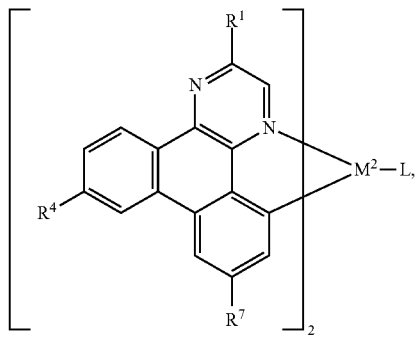

wherein $M^2$ is iridium, $R^1$ is H, cyclohexyl, which can optionally be substituted by one to three $C_1$-$C_4$alkyl groups, $C_1$-$C_{18}$alkyl,

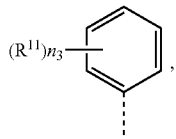

wherein $n_3$ is 0, or an integer 1, 2, 3, 4, or 5, $R^{11}$ can be same, or different in each occurrence and is $C_1$-$C_{25}$alkyl, $C_1$-$C_{25}$alkoxy, —$NR^{25}R^{26}$, F, or $CF_3$, $R^4$ and $R^7$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_1$-$C_{18}$alkoxy, which may be interrupted by —O—, or —$NR^{25}R^{26}$;

$R^{25}$ and $R^{26}$ are independently of each other

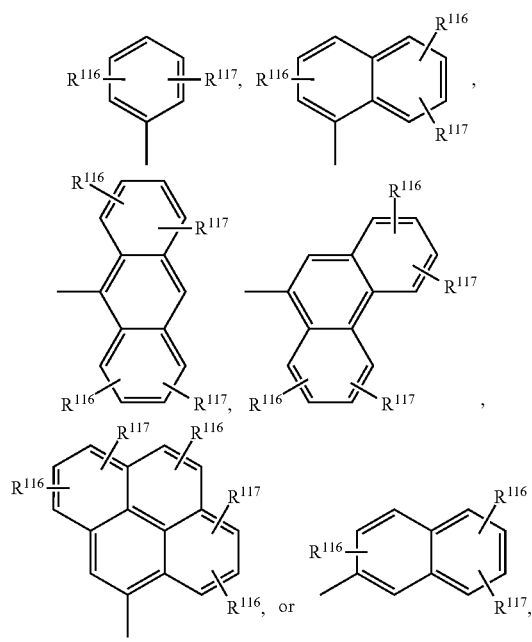

$R^{116}$ and $R^{117}$ are independently of each other $C_1$-$C_{25}$alkyl, which may optionally be interrupted by —O—, or $C_1$-$C_{25}$alkoxy; or $R^{25}$ and $R^{26}$ together with the nitrogen atom to which they are bonded form a group of formula

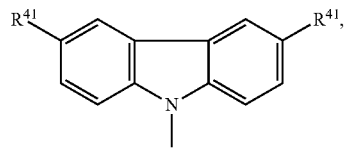

$R^{41}$ is H, or $C_1$-$C_{25}$alkyl, and

L is as defined in claim 1.

9. The compound of the formula I according to claim 1, which is a compound of formula formula $LIr(L^a)_2$, or $Ir(L^a)_3$, wherein $L^a$ is a group of formula

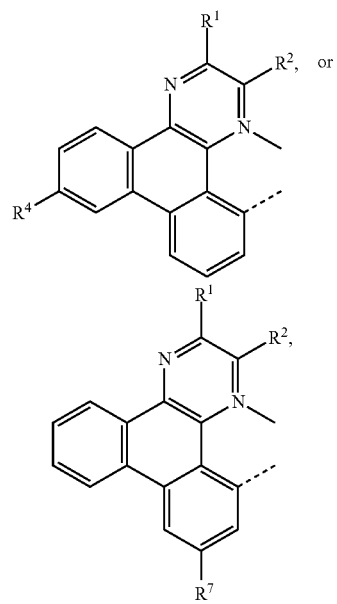

wherein $R^1$ is H, $C_1$-$C_{18}$alkyl, cyclohexyl, which can optionally be substituted by one to three $C_1$-$C_4$alkyl groups,

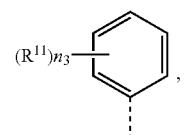

wherein $n_3$ is 0, or an integer 1, 2, 3, 4, or 5, $R^{11}$ can be same, or different in each occurrence and is $C_1$-$C_{25}$alkyl, $C_1$-$C_{25}$alkoxy, —$NR^{25}R^{26}$, F, or $CF_3$, $R^2$ is H, or $CH_3$, $R^4$ and $R^7$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by —$NR^{25}R^{26}$, $C_1$-$C_{18}$alkoxy which may be interrupted by —O—, or —$NR^{25}R^{26}$;

$R^{25}$ and $R^{26}$ are independently of each other

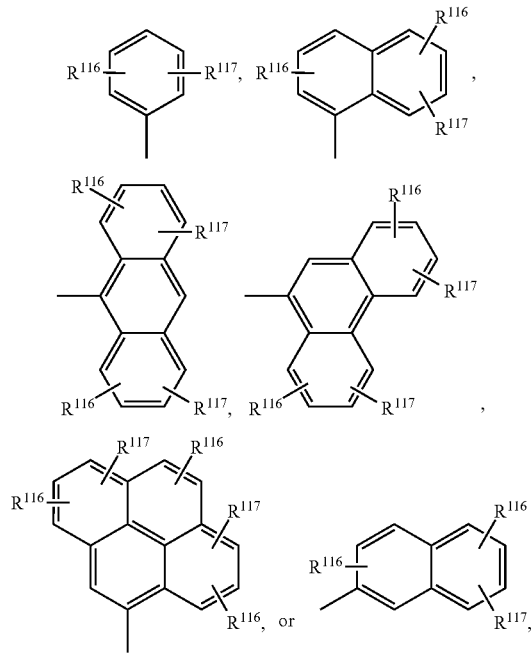

$R^{116}$ and $R^{117}$ are independently of each other $C_1$-$C_{25}$alkyl, which may optionally be interrupted by —O—, or $C_1$-$C_{25}$alkoxy; or $R^{25}$ and $R^{26}$ together with the nitrogen atom to which they are bonded form a group of formula

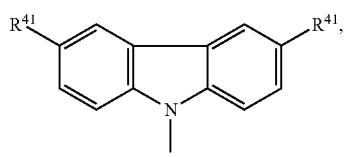

$R^{41}$ is H, or $C_1$-$C_{25}$alkyl, and

L is as defined in claim 1.

10. The compound of the formula I according to claim 1, which is a compound of formula

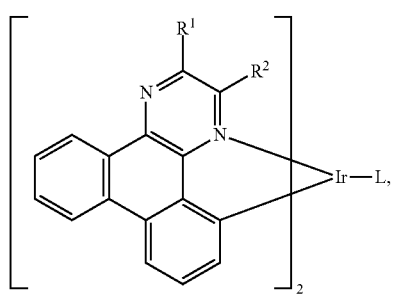

wherein $R^1$ is $C_2$-$C_{10}$alkyl, cyclohexyl, which can optionally be substituted by one to three $C_1$-$C_4$alkyl groups, $R^2$ is H, or $CH_3$, and L is

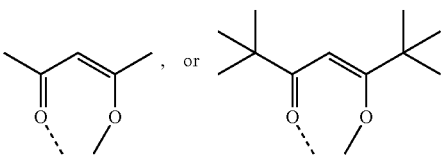

11. An organic electronic device, comprising an emitting layer wherein the emitting layer comprises a compound according to claim 1.

12. The device of claim 11, further comprising a hole transport layer selected from polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-di-α-naphthyl-N,N'-diphenyl-4,4'-diphenyldiamine (α-NPD), porphyrinic compounds, and combinations thereof, or electrontransporting materials, selected from tris(8-hydroxyquinolato)aluminium (Alq3), bis(2-methyl-8-hydroxyquinaolato)(p-phenylphenolato)aluminium (BAlq), tetrakis (8-hydroxyquinolato)zirconium (ZrQ) and mixtures thereof.

13. An electronic device comprising a compound according to claim 1 which electronic device is a organic light emitting diodes (OLEDs), as oxygen sensitive indicators, as phosphorescent indicators in bioassays, or catalysts.

14. Compounds of formula

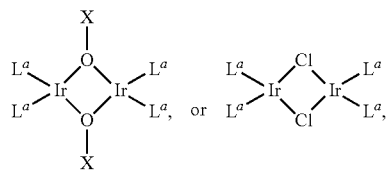

wherein X is H, methyl, or ethyl, and $L^a$ is

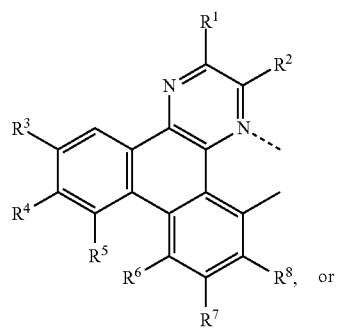

-continued

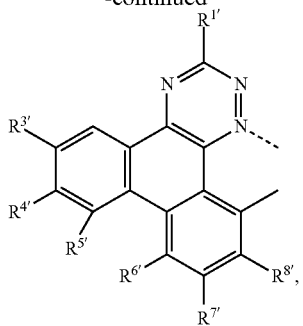

wherein $R_1$, $R_2$, $R_{1'}$, $R^3$, $R^4$, $R^{3'}$, $R^{4'}$, $R^5$, $R^6$, $R^{5'}$, $R^{6'}$, $R^7$, $R^8$, $R^{7'}$ and $R^{8'}$ are as defined in claim 1, with the proviso that at least one of $R^1$, $R^2$, $R^3$, $R^8$, $R^4$, $R^7$, $R^5$ and $R^6$ is different from H and the further proviso that a compound of formula

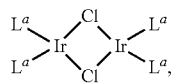

wherein $L^a$ is

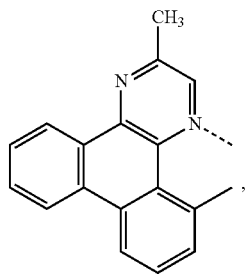

a compound of formula

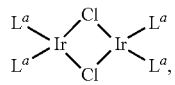

wherein $L^a$ is

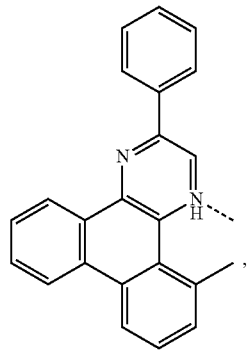

and a compound of formula

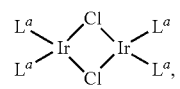

wherein $L^a$ is

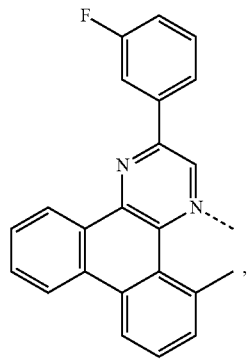

are excluded.

* * * * *